US012029857B2

United States Patent
Campana et al.

(10) Patent No.: US 12,029,857 B2
(45) Date of Patent: Jul. 9, 2024

(54) FLOW SENSOR FOR VENTILATION

(71) Applicant: ZOLL Medical Corporation, Chelmsford, MA (US)

(72) Inventors: Lisa Campana, Waltham, MA (US); Paolo Giacometti, Nashua, NH (US); Gideon Butler, Portsmouth, NH (US); Frederick J. Geheb, Danvers, MA (US); Annemarie Silver, Bedford, MA (US); Gary A. Freeman, Waltham, MA (US); Frederick Faller, Burlington, MA (US); Michael Riley, Groveland, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 17/873,977

(22) Filed: Jul. 26, 2022

(65) Prior Publication Data

US 2022/0355061 A1 Nov. 10, 2022

Related U.S. Application Data

(63) Continuation of application No. 15/461,684, filed on Mar. 17, 2017, now Pat. No. 11,433,211.
(Continued)

(51) Int. Cl.
*A61M 16/10* (2006.01)
*A61B 5/00* (2006.01)
(Continued)

(52) U.S. Cl.
CPC ........... *A61M 16/107* (2014.02); *A61B 5/087* (2013.01); *A61B 5/0871* (2013.01);
(Continued)

(58) Field of Classification Search
CPC .... A61M 16/107; A61B 5/087; A61B 5/0871; A61B 5/4836; A61B 5/486; A61B 5/7275; A61B 5/7282; A61B 5/0876
See application file for complete search history.

(56) References Cited

U.S. PATENT DOCUMENTS

| 3,989,037 A | 11/1976 | Franetzki |
| 4,083,245 A | 4/1978 | Osborn |

(Continued)

OTHER PUBLICATIONS

Berberig et al., "The Prandtl micro flow sensor (PMFS): a novel silicon diaphragm capacitive sensor for flow-velocity measurement", Sensors and Actuators, 1998, pp. 93-98, A66, Elsevier Science S.A.

(Continued)

*Primary Examiner* — Dung T Ulsh
(74) *Attorney, Agent, or Firm* — The Webb Law Firm

(57) ABSTRACT

A flow sensor system for ventilation treatment comprises a flow conduit configured to allow gas flow between a first region and a second region, the flow conduit defining a lumen for the gas flow; a flow restrictor disposed within the lumen of the flow conduit between the first region and the second region; a first absolute pressure sensor disposed adjacent to the first region of the flow conduit and configured to measure a pressure of the gas flow at the first region of the flow conduit; and a second absolute pressure sensor disposed adjacent to the second region of the flow conduit and configured to measure pressure of the gas flow at the second region of the flow conduit.

22 Claims, 61 Drawing Sheets

Related U.S. Application Data

(60) Provisional application No. 62/309,784, filed on Mar. 17, 2016.

(51) Int. Cl.
*A61B 5/087* (2006.01)
*A61B 5/145* (2006.01)
*A61B 5/316* (2021.01)
*A61B 5/349* (2021.01)
*A61H 31/00* (2006.01)
*A61M 16/00* (2006.01)
*G16H 20/40* (2018.01)
*G16H 50/30* (2018.01)

(52) U.S. Cl.
CPC ............ *A61B 5/4836* (2013.01); *A61B 5/486* (2013.01); *A61B 5/7275* (2013.01); *A61B 5/7282* (2013.01); *A61H 31/005* (2013.01); *A61B 5/0876* (2013.01); *A61B 5/14546* (2013.01); *A61B 5/316* (2021.01); *A61B 5/349* (2021.01); *A61B 5/4064* (2013.01); *A61B 5/7455* (2013.01); *A61B 2505/01* (2013.01); *A61B 2562/0247* (2013.01); *A61B 2562/12* (2013.01); *A61H 2201/0228* (2013.01); *A61H 2201/107* (2013.01); *A61H 2201/5058* (2013.01); *A61H 2201/5071* (2013.01); *A61H 2201/5084* (2013.01); *A61H 2201/5087* (2013.01); *A61M 2016/0027* (2013.01); *A61M 2016/0039* (2013.01); *A61M 2205/3368* (2013.01); *G16H 20/40* (2018.01); *G16H 50/30* (2018.01)

(56) References Cited

U.S. PATENT DOCUMENTS

| | | | |
|---|---|---|---|
| 4,197,857 A | 4/1980 | Osborn | |
| 4,993,269 A | 2/1991 | Guillaume et al. | |
| 5,038,621 A | 8/1991 | Stupecky | |
| 5,137,026 A | 8/1992 | Waterson et al. | |
| 5,347,843 A | 9/1994 | Orr et al. | |
| 5,379,650 A | 1/1995 | Kofoed et al. | |
| 5,509,406 A | 4/1996 | Kock et al. | |
| 5,535,663 A | 7/1996 | Yamashita et al. | |
| 5,535,738 A | 7/1996 | Estes et al. | |
| 5,564,432 A | 10/1996 | Thomson | |
| 5,598,838 A | 2/1997 | Servidio et al. | |
| 5,632,269 A | 5/1997 | Zdrojkowski | |
| 5,641,915 A | 6/1997 | Ortiz et al. | |
| 5,660,170 A | 8/1997 | Rajan et al. | |
| 5,685,296 A | 11/1997 | Zdrojkowski et al. | |
| 5,694,923 A | 12/1997 | Hete et al. | |
| 5,704,345 A | 1/1998 | Berthon-Jones | |
| 5,735,287 A | 4/1998 | Thomson | |
| 5,763,787 A | 6/1998 | Gravel et al. | |
| 5,794,615 A | 8/1998 | Estes | |
| 5,827,977 A | 10/1998 | Ortiz et al. | |
| 5,886,267 A | 3/1999 | Ortiz | |
| 5,913,249 A | 6/1999 | Weckstrom | |
| 5,925,831 A | 7/1999 | Storsved | |
| 5,937,855 A | 8/1999 | Zdrojkowski et al. | |
| 5,970,801 A | 10/1999 | Ciobanu et al. | |
| 5,979,247 A | 11/1999 | Kizawa | |
| 6,017,315 A | 1/2000 | Starr et al. | |
| 6,029,665 A | 2/2000 | Berthon-Jones | |
| 6,099,481 A | 8/2000 | Daniels et al. | |
| 6,105,575 A | 8/2000 | Estes et al. | |
| 6,135,106 A | 10/2000 | Dirks et al. | |
| 6,138,675 A | 10/2000 | Berthon-Jones | |
| 6,142,148 A | 11/2000 | Weckstrom et al. | |
| 6,179,784 B1 | 1/2001 | Daniels et al. | |
| 6,184,773 B1 | 2/2001 | Bonne et al. | |
| 6,203,502 B1 | 3/2001 | Hilgendorf et al. | |
| 6,224,560 B1 | 5/2001 | Gazula et al. | |
| 6,305,374 B1 | 10/2001 | Zdrojkowski et al. | |
| 6,342,040 B1 | 1/2002 | Starr et al. | |
| 6,363,933 B1 | 4/2002 | Berthon-Jones | |
| 6,471,658 B1 | 10/2002 | Daniels et al. | |
| 6,471,853 B1 | 10/2002 | Moscaritolo | |
| 6,543,449 B1 | 4/2003 | Woodring et al. | |
| 6,544,192 B2 | 4/2003 | Starr et al. | |
| 6,585,662 B1 | 7/2003 | Jones et al. | |
| 6,591,674 B2 | 7/2003 | Gehman et al. | |
| 6,609,517 B1 | 8/2003 | Estes et al. | |
| 6,662,802 B2 | 12/2003 | Smith et al. | |
| 6,691,579 B2 | 2/2004 | Orr et al. | |
| 6,722,211 B1 | 4/2004 | Ciobanu et al. | |
| 6,742,399 B2 | 6/2004 | Kunz et al. | |
| 6,802,225 B2 | 10/2004 | Shahar et al. | |
| 6,813,964 B1 | 11/2004 | Clark et al. | |
| 6,814,073 B2 | 11/2004 | Wickham | |
| 6,826,966 B1 | 12/2004 | Karbassi et al. | |
| 6,871,535 B2 | 3/2005 | Blakley et al. | |
| 6,910,481 B2 | 6/2005 | Kimmel et al. | |
| 6,917,886 B2 | 7/2005 | Cohen et al. | |
| 6,935,338 B1 | 8/2005 | Triunfo, Jr. | |
| 6,945,123 B1 | 9/2005 | Kuehl et al. | |
| 6,964,204 B2 | 11/2005 | Clark et al. | |
| 6,968,741 B2 | 11/2005 | Orr et al. | |
| 7,000,612 B2 | 2/2006 | Jafari et al. | |
| 7,004,168 B2 | 2/2006 | Mace et al. | |
| 7,013,726 B1 | 3/2006 | Drummond et al. | |
| 7,013,893 B2 | 3/2006 | Wickham | |
| 7,024,945 B2 | 4/2006 | Wallace | |
| 7,028,560 B2 | 4/2006 | Castillon Levano | |
| 7,032,463 B2 | 4/2006 | Misholi et al. | |
| 7,059,195 B1 | 6/2006 | Liu et al. | |
| 7,096,729 B2 | 8/2006 | Repko et al. | |
| 7,159,588 B2 | 1/2007 | Wickham | |
| 7,174,789 B2 | 2/2007 | Orr et al. | |
| 7,258,003 B2 | 8/2007 | Padmanabhan et al. | |
| 7,261,003 B2 | 8/2007 | McDonald et al. | |
| 7,270,143 B2 | 9/2007 | Kohlmann et al. | |
| 7,290,454 B2 | 11/2007 | Liu | |
| 7,296,573 B2 | 11/2007 | Estes et al. | |
| 7,305,988 B2 | 12/2007 | Acker et al. | |
| 7,335,164 B2 | 2/2008 | Mace et al. | |
| 7,337,678 B2 | 3/2008 | Thakre et al. | |
| 7,343,823 B2 | 3/2008 | Speldrich | |
| 7,437,951 B2 | 10/2008 | McDonald et al. | |
| 7,556,039 B1 | 7/2009 | Pierry | |
| 7,603,898 B2 | 10/2009 | Speldrich | |
| 7,607,360 B2 | 10/2009 | Todokoro et al. | |
| 7,647,926 B2 | 1/2010 | Gerder et al. | |
| 7,654,146 B2 | 2/2010 | Orr et al. | |
| 7,654,157 B2 | 2/2010 | Speldrich | |
| 7,662,106 B2 | 2/2010 | Daniels et al. | |
| 7,703,339 B2 | 4/2010 | Sulouff, Jr. et al. | |
| 7,730,793 B2 | 6/2010 | Speldrich | |
| 7,747,319 B2 | 6/2010 | Freeman | |
| 7,775,126 B2 | 8/2010 | Eckhardt et al. | |
| 7,798,016 B2 | 9/2010 | Bonassa | |
| 7,878,980 B2 | 2/2011 | Ricciardelli | |
| 8,006,571 B2 | 8/2011 | Hersch et al. | |
| 8,025,052 B2 | 9/2011 | Matthews et al. | |
| 8,091,436 B2 | 1/2012 | Eckhardt et al. | |
| 8,104,340 B2 | 1/2012 | Speldrich | |
| 8,113,046 B2 | 2/2012 | Speldrich et al. | |
| 8,181,648 B2 | 5/2012 | Perine et al. | |
| 8,192,367 B2 | 6/2012 | Myklebust et al. | |
| 8,225,814 B2 | 7/2012 | Igarashi | |
| 8,230,857 B2 | 7/2012 | Cewers | |
| 8,251,914 B2 | 8/2012 | Daniels et al. | |
| 8,286,506 B2 | 10/2012 | Speldrich | |
| 8,312,774 B2 | 11/2012 | Bentley et al. | |
| 8,333,194 B2 | 12/2012 | Lewis et al. | |
| 8,364,427 B2 | 1/2013 | Berkcan et al. | |
| 8,381,729 B2 | 2/2013 | Freitag et al. | |
| 8,403,908 B2 | 3/2013 | Jacobson et al. | |
| 8,418,549 B2 | 4/2013 | Speldrich et al. | |
| 8,459,261 B2 | 6/2013 | Ricciardelli et al. | |
| 8,479,733 B2 | 6/2013 | Mashak | |

(56) References Cited

U.S. PATENT DOCUMENTS

| | | | |
|---|---|---|---|
| 8,485,031 B2 | 7/2013 | Speldrich et al. | |
| 8,522,782 B2 | 9/2013 | Lewis et al. | |
| 8,561,611 B2 | 10/2013 | Shissler et al. | |
| 8,725,253 B2 * | 5/2014 | Johnson | G09B 23/288 607/7 |
| 8,756,990 B2 | 6/2014 | Speldrich | |
| 8,874,389 B2 | 10/2014 | Berkcan et al. | |
| 2007/0131279 A1 | 6/2007 | Thakre et al. | |
| 2007/0151366 A1 | 7/2007 | McDonald et al. | |
| 2008/0053445 A1 * | 3/2008 | Kroupa | A61M 16/0084 128/204.23 |
| 2008/0302363 A1 * | 12/2008 | Kroupa | A61M 16/202 128/204.21 |
| 2010/0186745 A1 | 7/2010 | Mashak | |
| 2010/0242622 A1 | 9/2010 | Weckstrom | |
| 2011/0067704 A1 | 3/2011 | Kooij et al. | |
| 2012/0192642 A1 | 8/2012 | Speldrich et al. | |
| 2012/0211008 A1 * | 8/2012 | Perine | A61M 16/085 128/204.23 |
| 2012/0302910 A1 | 11/2012 | Freeman et al. | |
| 2012/0318266 A1 | 12/2012 | Chou | |
| 2013/0184600 A1 | 7/2013 | Tan et al. | |
| 2014/0150795 A1 * | 6/2014 | Milne | A61M 16/0057 128/205.23 |
| 2014/0180138 A1 * | 6/2014 | Freeman | A61B 5/0836 600/536 |
| 2014/0360501 A1 | 12/2014 | Guiducci et al. | |
| 2015/0238722 A1 * | 8/2015 | Al-Ali | A61M 16/085 128/205.13 |
| 2018/0154102 A1 * | 6/2018 | Selander | A61M 16/024 |
| 2018/0160970 A1 * | 6/2018 | Khoury | A61B 5/746 |
| 2022/0111167 A1 * | 4/2022 | Khoury | A61M 16/0051 |

OTHER PUBLICATIONS

Bird et al., "Reducing the contact time of a bouncing drop", Nature, 2013, 13 pgs., 503, Macmillan Publishers Limited.

Cassie et al., "Wettability of Porous Surfaces.", Trans. Faraday Soc., 1944, pp. 546-551, 40.

Latsios et al., "Successful primary PCI during prolonged continuous cardiopulmonary resuscitation with an automated chest compression device (AutoPulse)", International Journal of Cardiology, 2016, pp. 258-259, 225, Elsevier Ireland Ltd.

Liu et al., "Pancake bouncing on superhydrophobic surfaces", Nature Physics, 2014, pp. 515-520, 10, Macmillan Publishers Limited.

Nguyen, "Micromachined flow sensors—a review", Flow Meas. Instrum., 1997, pp. 7-16, 8:1, Elsevier Science Ltd.

Oosterbroek et al., "A micromachined pressure/flow-sensor", Sensors and Actuators, 1999, pp. 167-177, 77, Elsevier Science S.A.

Pauldine et al., "Closed-Loop Strategies for Patient Care Systems", J. Trauma., 2008, pp. S289-S294, 64:4, Lippincott Williams & Wilkins.

Richard et al., "Contact time of a bouncing drop", Nature, 2002, p. 811, 417, Nature Publishing Group.

Smith et al., "Droplet mobility on lubricant-impregnated surfaces", Soft Matter, 2013, pp. 1-11, 9:6, The Royal Society of Chemistry.

Wang et al., "MEMS-based gas flow sensors", Microfluid Nanofluid, 2009, pp. 333-346, 6, Springer-Verlag.

Wenzel, "Resistance of Solid Surfaces to Wetting By Water", Ind. Eng. Chem., 1936, pp. 988-994, 28:8.

Yuan et al., "Preparation and characterization of self-cleaning stable superhydrophobic linear low-density polyethylene", Sci. Technol. Adv. Mater., 2008, 5 pgs., 9, National Institute for Materials Science.

\* cited by examiner

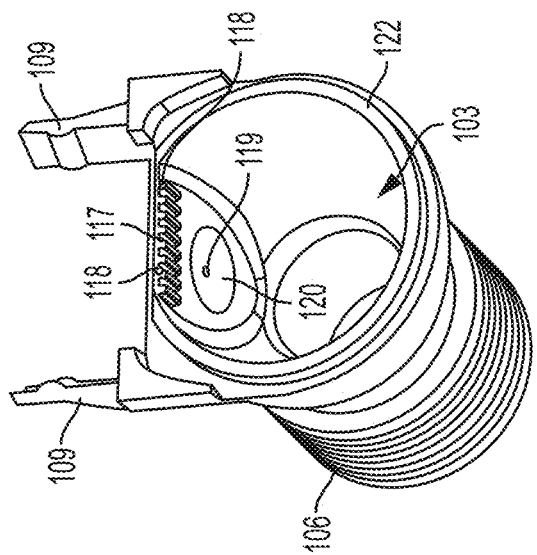
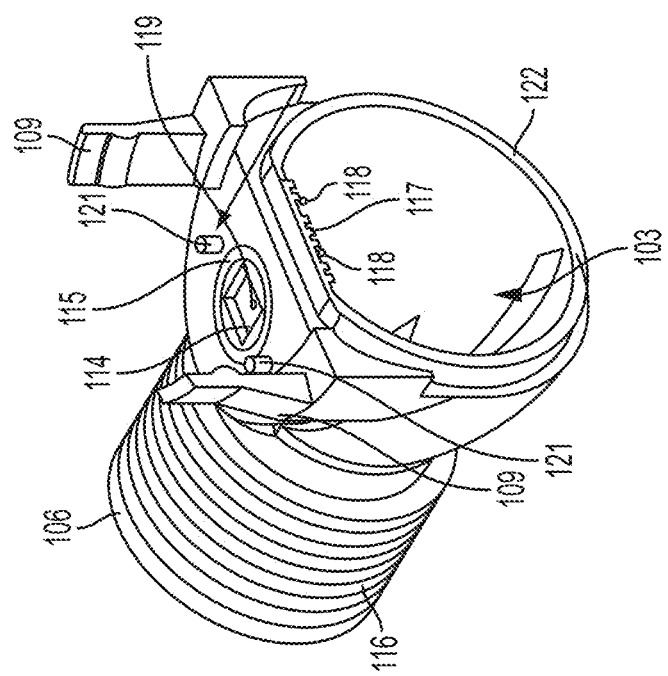
FIG. 11(b)
FIG. 11(a)

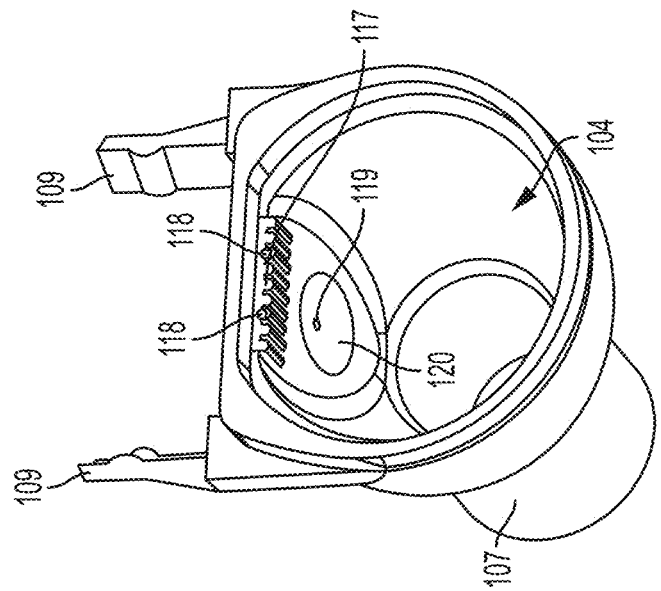
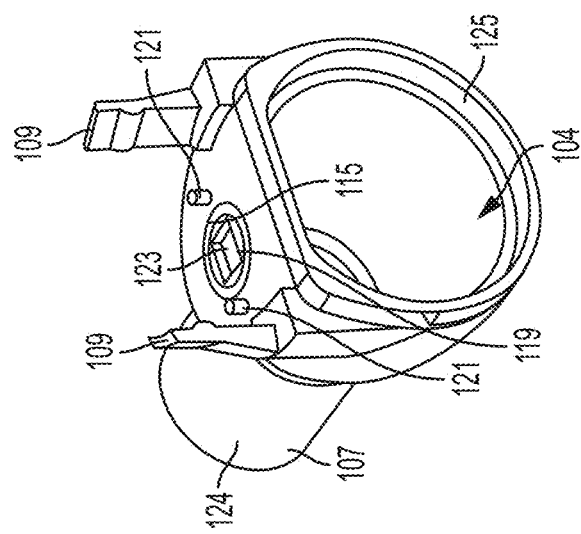

FLOW SENSOR FOR VENTILATION

CROSS-REFERENCE TO RELATED APPLICATION

This application is a continuation application of U.S. patent application Ser. No. 15/461,684, filed Mar. 17, 2017, which claims priority to U.S. Provisional Patent Application No. 62/309,784, filed on Mar. 17, 2016, each of which is incorporated herein by reference in their entireties.

BACKGROUND

Field

The present disclosure is related to a flow sensor device for use in providing ventilation therapy to a patient, for example, flow sensor devices that measure flow rate and/or volume of gas delivered to a patient during ventilation therapy which may be useful to provide feedback to an operator and/or system to adjust the delivery of gas to the patient based on the measured flow rate and/or volume of gas.

Description of Related Art

Ventilation systems and assemblies are commonly used in the art to deliver gas, such as air or oxygen, to a patient as part of an ongoing treatment or medical emergency when the patient requires assistance in breathing. Commonly during medical emergencies, an emergency medical technician (EMT), nurse, or doctor manually ventilates the patient using a manually actuatable bag ventilator system. During cardiac arrest, over-bagging of the patient is common and reduces the patient's chances of survival because rescuers may be prone to hyper-ventilate the patient beyond recommended levels.

Prior solutions to this problem have involved providing the rescuer with a measurement of the patient's end-tidal $CO_2$ (ETCO$_2$) or $SpO_2$ or to instruct the rescuer to listen to lung sounds and count the respiratory rate manually. These solutions offer several drawbacks. For instance, ETCO$_2$ measurements are reflective of several factors, including the patient's metabolism, circulation and ventilation, and do not necessarily reflect the flow rate or volume of gas being delivered to the patient to give the rescuer an indication that the ventilation therapy is being performed correctly. In addition, there is a significant time delay between when a patient may experience reduced ventilation and when the $SpO_2$ of the patient is noticeably affected. Also, the rescuer may not be able to adequately detect the patient's respiration by ear or may be overburdened with the number of tasks necessary for resuscitation, and so might not be able to manually count the patient's respirations.

Typical flow sensors associated with a manual or automatic ventilation system commonly utilize a single differential pressure sensor, which is large and expensive. Such flow sensors may be prone to the accumulation of moisture, fluid, and debris on the sensor or within the sensor system, which disrupts operation of the sensor. Conventional flow sensors may also require substantial tubing to carry air to a larger system or monitor, which may be cumbersome, for example, in emergency situations where kinking of tubes and extra lines connected to the patient may increase risk of further complications. Accordingly, such sensors are typically only used in a hospital or clinical setting where they can be regularly maintained and sterilized and where transportation of the sensor is not an issue. Use of such sensors in emergency medical settings, particularly in the field, is limited.

SUMMARY

According to one particular aspect of the present disclosure, a flow sensor system for assisting resuscitative treatment is provided. The flow sensor system comprises a flow conduit configured to be placed in a patient airway and having a lumen that accommodates gas flow between a first region and a second region; a flow restrictor disposed within the lumen of the flow conduit between the first region and the second region; and at least one pressure sensor configured to measure gas pressure of at least one of the first region and the second region of the flow conduit. A sensitive region of the flow sensor system exhibits a greater level of hydrophobicity than a neighboring region adjacent to the sensitive region.

In one example, the sensitive region includes at least a portion of the flow restrictor. Or, the sensitive region may include a portion of the flow conduit configured to accommodate substantially laminar flow through the lumen. Alternatively, the sensitive region may include at least a portion of a barrier that protects or separates the pressure sensor(s) from the lumen of the flow conduit. The neighboring region may include a reservoir configured to collect water arising from gas flowing through the lumen. The neighboring region may be configured to wick away water from the sensitive region.

In one example, the at least one pressure sensor includes a first absolute pressure sensor configured to measure gas pressure at the first region of the flow conduit and a second absolute pressure sensor configured to measure gas pressure at the second region of the flow conduit.

In one example, the at least one pressure sensor includes a differential pressure sensor configured to measure differential gas pressure between the first and second regions of the flow conduit.

In one example, the flow sensor system further comprises a processor in communication with the at least one pressure sensor, the processor being configured to generate a signal for determining at least one of a peak inspiratory pressure, a flow rate and a volume of gas flowing through the lumen of the flow conduit based on the pressure measurements in the first and second regions of the flow conduit. The processor may be configured to output signals relating to the measured gas pressure at the first and second regions of the flow conduit. The processor may be configured to send a signal displaying physiological data of the patient (e.g., vitals information) and resuscitative information to a user (e.g., feedback to adjust the gas flow through the lumen of the flow conduit, or other instructions) based on at least one of peak inspiratory pressure, the determined flow rate and the determined volume of gas flowing through the lumen. The resuscitative information may include at least one of feedback for instructing a user to adjust placement of an intubation tube, an alert that overventilation has occurred, a countdown of at least one of a number of chest compressions and time until a subsequent ventilation is to be applied, a number of chest compressions applied based on at least one of the first and second signals, a determination of whether a detected breath is due to spontaneous breathing, manually applied ventilation or automatically applied ventilation, an indication of whether ROSC (Return of Spontaneous Circulation) may have occurred, and at least one of the determined peak inspiratory pressure, flow rate and volume of gas flowing through the lumen of the flow conduit, or other instructive information. The physiological data may include at least one of ECG (Electrocardiography) data, SpO2 data, EtCO2 data, blood pressure, heart rate, temperature, SmO2 and muscle pH of the patient, or other physiological information. The processor may be configured to generate a signal for compensating for effects of altitude and/or temperature in determining the at least one of the flow rate and the volume of gas flowing through the lumen of the flow conduit.

In one example, the at least one pressure sensor is further configured to measure a temperature of gas flowing through the lumen of the flow conduit. The processor may be configured to generate a signal for determining at least one of the flow rate, a direction of flow and volume of gas flowing through the lumen based on the pressure measurements and the temperature measurement.

In one example, the flow sensor system further comprises a connector removably coupled with the flow conduit, the connector being configured to place the at least one pressure sensor in communication with the processor. The connector may be configured to be rotatably coupled to the flow conduit while maintaining electrical communication between the at least one pressure sensor and the processor. The connector may comprise the at least one pressure sensor. The connector may comprise the processor. The connector may be configured to provide at least one of audio feedback, visual feedback and haptic feedback to adjust the gas flow through the lumen of the flow conduit based on at least one of the determined flow rate and volume of gas flowing through the lumen.

In one example, the flow restrictor is configured to interrupt the flow of gas through the lumen to create a pressure drop in the lumen between the first region and the second region and the processor is configured to determine the pressure drop based on the pressure measurements of the at least one pressure sensor and to determine at least one of the flow rate, a direction of flow and volume of gas flowing through the lumen based on the determined pressure drop. The processor may comprise a memory that incorporates a flow pressure look up table comparing measured pressure drops with calculated flow rates and/or volumes and the processor determines the flow rate and/or volume of the gas flowing through the lumen by referencing the flow pressure look up table. The processor may be configured to generate a signal for outputting the determined peak inspiratory pressure, flow rate and/or volume of gas flowing through the flow conduit.

In one example, the flow sensor system further comprises at least one additional sensor configured to measure at least one of the following: a temperature of the gas flowing through the flow conduit, a concentration of gas flowing through the conduit, a humidity of the gas flowing through the conduit, and an ambient atmospheric pressure.

In one example, the processor is configured to generate a signal for determining at least one of the flow rate, a direction of flow and volume of gas flowing through the lumen based on the pressure measurements and at least one of the following: the temperature measurement, the humidity measurement, and the ambient atmospheric pressure measurement. The processor may be configured to generate a signal for detecting whether a leak exists in the flow conduit. The system may be configured to be placed in communication with a mask open to ambient conditions.

In one example, the system is configured to be placed in communication with a ventilation assembly for delivering gas through the lumen of the flow conduit. The ventilation assembly may comprise a manual bag ventilation system. The ventilation assembly may comprise an automated ventilation system.

In one example, the at least one pressure sensor is a microelectromechanical systems (MEMS) device.

In one example, the flow sensor system further comprises a circuit board disposed on the flow conduit, the at least one pressure sensor being connected to the circuit board. The circuit board may comprise at least one heating element configured to be energized to prevent or limit fluid accumulation near the at least one pressure sensor.

In one example, the flow restrictor is configured to create a pressure drop in the flow conduit between the first region and the second region that is substantially linearly variable based upon the flow of gas through the lumen. The flow restrictor may comprise a body comprising a hydrophobic material configured to be disposed in the lumen of the flow conduit, the body comprising: an outer portion surrounding an opening and at least one flap disposed in the opening. The at least one flap is coupled to the outer portion at a side of the opening. The at least one flap is configured to deflect from the opening due to gas flow through the flow restrictor. The sensitive region may include the at least one flap and the neighboring region includes the outer portion. The sensitive region may include at least a portion of the body of the flow restrictor and the neighboring region includes at least a portion of the flow conduit. The at least one flap may have a surface area smaller than a projected area of the opening forming a gap in the body of the flow restrictor when the at least one flap is in a non-deflected position within the opening. The at least one flap may be shaped such that a distance is provided by the gap between the outer portion and the at least one flap is non-uniform. The at least one flap may be shaped such that a distance provided by the gap between the outer portion and the at least one flap is substantially uniform. An amount of deflection of the at least one flap from the opening is variable based upon the flow of gas through the lumen to create the linearly variable pressure drop. The outer portion of the body of the flow restrictor may comprise a mechanical reinforcement. The mechanical reinforcement may comprise at least one laminate layer applied to the outer portion. The mechanical reinforcement may comprise a stiffener coating. The body may be formed from at least one of polytetrafluoroethylene and polyethylene terephthalate.

In one example, the flow conduit comprises a body extending from a first end to a second end, the body of the flow conduit having a hollow interior defining the lumen for the gas flow. The body of the flow conduit may comprise at least one chamber configured to house and support the at least one pressure sensor. The at least one chamber may include a first chamber and a second chamber in separate fluid communication with the lumen via respective openings defined in the body of the flow conduit.

In one example, the flow sensor system further comprises at least one barrier for protecting the at least one chamber. The at least one barrier may be configured to allow passage of gas and obstruct passage of moisture and debris therethrough. The at least one barrier may comprise at least two barriers, each of the at least two barriers configured to protect a respective one of two chambers from moisture and debris. The at least one barrier may comprise a breathable hydrophobic material. The breathable hydrophobic material may comprise at least one of the following: polytetrafluoroethylene, expanded polytetrafluoroethylene, and woven fabric. The at least one barrier may be coated with a breathable hydrophobic material. The breathable hydrophobic material may comprise at least one of the following: polytetrafluoroethylene and expanded polytetrafluoroethylene.

In one example, the at least one chamber is sealed from fluid communication with the lumen. The at least one barrier may include at least one diaphragm membrane configured to prevent passage of gas, moisture and debris therethrough. The at least one diaphragm membrane may be configured to equalize pressure between the lumen and the chambers. The at least one diaphragm membrane may include a textured surface that allows the at least one diaphragm membrane to flex back and forth. The at least one diaphragm membrane may include at least one rolling diaphragm configuration.

In one example, the body comprises two pieces of molded thermoplastic material that are ultrasonically welded. In another example, pieces of the body may be snap fit together. The two pieces may define a respective one of the first region and the second region of the flow conduit. Alternatively, the body may be formed as a single molded part.

In one example, the lumen of the flow conduit is shaped so as to be substantially symmetric about a longitudinal axis of the flow conduit.

According to another particular aspect of the present disclosure, a flow sensor system is provided. The flow sensor system comprises a flow conduit configured to be placed in a patient airway and having a lumen that accommodates gas flow between a first region and a second region; at least one sensor configured to measure gas flow information at the first region and/or the second region of the flow conduit; at least one chamber configured to house and support the at least one sensor; and at least one barrier separating the lumen through the gas flows and the at least one chamber. A sensitive region of the flow sensor system exhibits a greater level of hydrophobicity than a neighboring region adjacent to the sensitive region.

In one example, the at least one barrier includes the sensitive region and a portion of the flow conduit adjacent the flow restrictor includes the neighboring region. The at least one barrier may be a membrane configured to allow passage of gas and obstruct passage of moisture and debris therethrough. The chamber may be in fluid communication with the lumen via an opening defined in the body of the flow conduit.

In one example, the body of the flow conduit has two chambers defined therein configured to house and support respective sensors adjacent to and in communication with the lumen. Each of the two chambers may be in separate fluid communication with the lumen via an opening defined in the body of the flow conduit.

In one example, the at least one barrier comprises at least two barriers, each of the at least two barriers separating a respective one of the two chambers and the lumen through which gas flows.

In one example, the at least one barrier comprises a breathable hydrophobic material. The breathable hydrophobic material may comprise at least one of the following: polytetrafluoroethylene, expanded polytetrafluoroethylene, and woven fabric.

In one example, the at least one barrier is coated with a breathable hydrophobic material. The breathable hydrophobic material may comprise at least one of the following: polytetrafluoroethylene and expanded polytetrafluoroethylene.

In one example, the at least one barrier seals the at least one chamber off from the lumen. The at least one barrier may be at least one diaphragm membrane configured to prevent passage of gas, moisture and debris therethrough. The at least one diaphragm membrane may be configured to equalize pressure between the lumen and the at least one chamber. The at least one diaphragm membrane may include a textured surface that allows the at least one diaphragm membrane to flex back and forth. The at least one diaphragm membrane may include at least one rolling diaphragm configuration.

In one example, the body comprises two pieces of molded thermoplastic material that are ultrasonically welded. The two pieces may define a respective one of the first region and the second region of the flow conduit. The lumen of the flow conduit may be shaped so as to be substantially symmetric about a longitudinal axis of the flow conduit.

In one example, the flow sensor system further comprises at least one heater configured to prevent or limit fluid accumulation to adjacent the at least one barrier.

In one example, the body of the flow conduit comprises at least one tapered region adapted to funnel gas from the at least one barrier toward the at least one chamber. The at least one barrier may be disposed between the lumen and the at least one tapered region. The body may be configured to support a flow restrictor disposed in the lumen.

In one example, the flow conduit is configured to be assembled in fluid communication with a ventilation assembly.

In one example, the flow sensor system further comprises at least one rim made from a hydrophilic material disposed in the flow conduit, the at least one rim being configured to draw moisture away from the at least one chamber.

In one example, the flow sensor system further comprises a condensation element disposed in the flow conduit, the condensation element being configured to collect moisture from the gas flowing through the lumen.

According to another particular aspect of the present disclosure, a flow sensor system for assisting resuscitative treatment. The flow sensor system comprises a flow conduit configured to be placed in a patient airway and having a lumen that accommodates gas flow between a first region and a second region; a flow restrictor disposed within the lumen of the flow conduit between the first region and the second region; at least one pressure sensor configured to measure gas pressure of at least one of the first region and the second region of the flow conduit; and at least one heating element located adjacent to the at least one pressure sensor, the at least one heating element configured to be energized to prevent fluid accumulation near the at least one pressure sensor.

In one example, a sensitive region of the flow sensor system exhibits a greater level of hydrophobicity than a neighboring region adjacent to the sensitive region. The neighboring region may be configured to collect water arising from gas flowing through the lumen.

In one example, the at least one pressure sensor includes a first absolute pressure sensor configured to measure gas pressure at the first region of the flow conduit and a second absolute pressure sensor configured to measure gas pressure at the second region of the flow conduit.

In one example, the at least one pressure sensor includes a differential pressure sensor configured to measure differential gas pressure between the first and second regions of the flow conduit.

In one example, the flow sensor system comprises a processor in communication with the at least one absolute pressure sensor, the processor being configured to generate a signal for determining at least one of a peak inspiratory pressure, a flow rate and a volume of gas flowing through the lumen of the flow conduit based on the pressure measurements in the first and second regions of the flow conduit.

In one example, the flow sensor system further comprises at least one chamber configured to house and support the at least one pressure sensor. The at least one chamber may include a first chamber and a second chamber in separate fluid communication with the lumen via respective openings provided by the flow conduit.

In one example, the flow sensor system further comprises at least one barrier for protecting the at least one chamber. The at least one barrier may be configured to allow passage of gas and obstruct passage of moisture and debris therethrough. The at least one barrier may comprise a breathable hydrophobic material.

In one example, the at least one chamber is sealed from fluid communication with the lumen. The at least one barrier may include at least one diaphragm membrane configured to prevent passage of gas, moisture and debris therethrough. The at least one diaphragm membrane may be configured to equalize pressure between the lumen and the chambers.

According to another particular aspect of the present disclosure, a flow restrictor for a flow sensor system is provided. The flow restrictor comprises a body comprising a hydrophobic material configured to be disposed in a lumen of a flow conduit, the body comprising: an outer portion surrounding an opening and at least one flap disposed in the opening. The at least one flap is coupled to the outer portion at a side of the opening. The flap is configured to deflect from the opening due to gas flow through the flow restrictor.

In one example, the at least one flap has a surface area smaller than a projected area of the opening forming a gap in the body of the flow restrictor when the at least one flap is in a non-deflected position within the opening. The at least one flap may be shaped such that a distance provided by the gap between the outer support portion and the at least one flap is non-uniform. The flow restrictor may be configured to interrupt a flow of gas through a flow conduit to create a pressure drop in the flow conduit. An amount of deflection of the at least one flap from the opening may be variable based upon the flow of gas through the flow restrictor such that the pressure drop created by the flow restrictor is substantially linearly variable.

In one example, the outer portion of the body of the flow restrictor comprises a mechanical reinforcement. The mechanical reinforcement may comprise at least one laminate layer applied to the outer portion. The mechanical reinforcement may comprise a stiffener coating.

In one example, wherein the body is formed from polytetrafluoroethylene. In another example, the body is formed from polyethylene terephthalate.

In one example, the at least one flap comprises a single flap having a polygonal or substantially polygonal shape. The flap may have a plurality of sides, at least one of the sides being hingedly coupled to the outer portion. Corners of the flap defined between the sides may be rounded. The opening may have a rounded rectangular shape at an end opposite to the end to which the flap is hingedly coupled and wherein two sides of the flap are disposed opposite to respective rounded corners of the opening such that a gap formed between the flap and the outer portion is larger at the rounded corners of the opening.

In one example, the at least one flap comprises at least one substantially triangular flap. The at least one flap may comprise at least three substantially triangular flaps disposed adjacent to each other in the opening. The at least three substantially triangular flaps may have non-uniform shapes and sizes.

According to another particular aspect of the present disclosure, a resuscitation system for assisting ventilation is provided. The system comprises a flow conduit having a lumen defined therein; and a processor configured to: receive a first signal representing a first pressure at a first region of the flow conduit; receive a second signal representing a second pressure at a second region of the flow conduit; determine at least one of peak inspiratory pressure, flow rate and volume of gas flowing through the lumen of the flow conduit based on the first and second signals; and output a feedback signal to adjust gas flow through the lumen of the flow conduit based on at least one of the determined peak inspiratory pressure, flow rate and volume of gas flowing through the lumen.

In one example, the resuscitative information includes at least one of: feedback for instructing a user to adjust gas flow through the lumen, feedback for instructing a user to adjust placement of an intubation tube, an alert that overventilation has occurred, a countdown of at least one of a number of chest compressions and time until a subsequent ventilation is to be applied, a number of chest compressions applied based on at least one of the first and second signals, a determination of whether a detected breath is due to spontaneous breathing, manually applied ventilation or automatically applied ventilation, an indication of whether ROSC may have occurred, and at least one of the determined peak inspiratory pressure, flow rate and volume of gas flowing through the lumen of the flow conduit.

In one example, the physiological data includes at least one of ECG data, SpO2 data, EtCO2 data, blood pressure, heart rate, temperature, SmO2 and muscle pH of the patient.

In one example, the system further comprises a display interface having a first portion for displaying the physiological data and a second portion for displaying the resuscitative information.

In one example, the feedback signal includes prompting a user to ventilate according to the number of chest compressions applied and/or time elapsed since a prior ventilation.

In one example, the feedback signal includes informing a user that overventilation has occurred, the overventilation being from at least one of exceeding a threshold of peak inspiratory pressure, an excess volume administered and an excess rate of breaths administered.

In one example, the processor is configured to determine whether gas flow through the lumen of the flow conduit is produced by a spontaneous breath, an automated ventilation breath or a manually provided ventilation breath, and the feedback signal depends on the determined gas flow through the lumen.

In one example, the feedback resuscitative information includes at least one of visual feedback, audio feedback and haptic feedback. The visual feedback may include at least one of a series of LED (Light Emitting Diode) lights, a user interface display, a CPR (Cardiopulmonary Resuscitation) dashboard, a ventilation dashboard and a ventilation performance indicator.

According to another particular aspect of the present disclosure, a connector for establishing communication with a sensor disposed within a medical device. The connector comprises a housing configured to be removably coupled to the medical device; a plurality of signal conductors through an interior region of the housing; and a signal contact pad having a plurality of conductive elements arranged in a concentric pattern. The conductive elements are in electrical communication with the plurality of signal conducts and are configured to be placed in electrical communication with the sensor when the housing is removably coupled to the medical device, wherein the housing is configured to be rotatably coupled to the medical device while maintaining electrical communication between the conductive elements and the sensor.

In one example, the connector further comprises a processor configured to receive and process signals originating from the sensor.

In one example, the connector further comprises a feedback component configured to provide at least one of audio feedback, visual feedback and haptic feedback to adjust a resuscitation activity of a user.

In one example, the housing is configured to be removably coupled to a flow sensor and the conductive elements are configured to receive information from the sensor related to gas flow through the flow sensor.

According to another particular aspect of the present disclosure, a flow sensor system for ventilation treatment is provided. The flow sensor system comprises a flow conduit configured to allow gas flow between a first region and a second region, the flow conduit defining a lumen for the gas flow; a flow restrictor disposed within the lumen of the flow conduit between the first region and the second region; and at least one absolute pressure sensor configured to measure pressure of the gas flow at at least one of the first region and the second region of the flow conduit.

According to another aspect of the present disclosure, a flow sensor system for assisting resuscitative treatment is provided. The flow sensor system includes a flow conduit configured to be placed in a patient airway and having a lumen that accommodates gas flow between a first region and a second region; a flow restrictor disposed within the lumen of the flow conduit between the first region and the second region; at least one pressure sensor configured to measure gas pressure of at least one of the first region and the second region of the flow conduit; at least one chamber configured to house and support the at least one pressure sensor; and at least one diaphragm membrane between the lumen through which gas flows and the at least one chamber, the at least one diaphragm membrane configured to equalize pressure between the lumen and the at least one chamber.

In one example, the at least one diaphragm membrane includes a textured surface that allows the at least one diaphragm membrane to flex back and forth.

In another example, the at least one diaphragm membrane includes an opening that allows for gas exchange between the lumen and the at least one chamber.

Further details and advantages of the present disclosure will become clear upon reading the following detailed description in conjunction with the accompanying drawing figures, wherein like parts are designated with like reference numerals throughout.

BRIEF DESCRIPTION OF THE DRAWINGS

FIGS. 11(a) and (b) are perspective views of a first piece of the flow conduit of FIG. 8;

FIGS. 12(a) and (b) are perspective view of a second piece of the flow conduit of FIG. 8;

DETAILED DESCRIPTION

Figure 1:
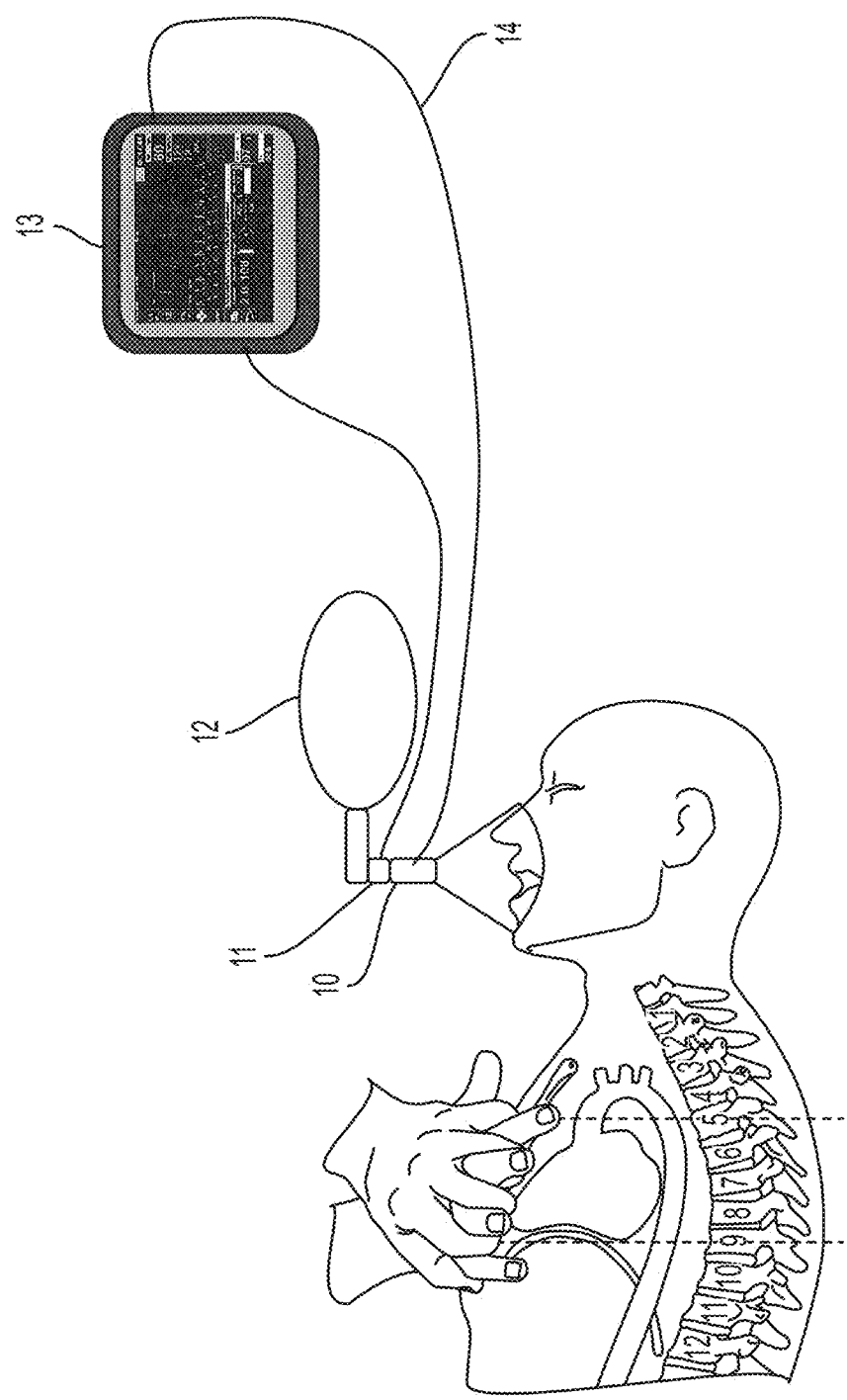
FIG. 1 is a schematic view of a ventilation assembly incorporating a flow sensor system according to an embodiment of the present disclosure.

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting. As used hereinafter, the term "substantially" is defined as "possessing wholly or largely wholly the trait that is specified."

This document relates to a flow sensor system that may be configured for use in combination with a ventilation system (e.g., manual and/or automated ventilation) that is low cost but sufficiently accurate to measure the flow rate and/or volume of gas being delivered the patient. The flow sensor system may further be resistant to the accumulation of moisture, fluid and/or debris that may impact the measurements of the sensor. For example, the flow sensor system may have sensitive regions that are more resistant (e.g., hydrophobic, oleophobic) to such accumulation so that pressure and flow readings remain sufficiently accurate. The flow sensor system may also be relatively small and convenient for transport on an ambulance, helicopter, etc., or for storage an emergency room or clinic. In various embodiments, the flow sensor system, or aspects thereof, may be constructed as a single-use/disposable assembly.

The flow sensor system determines the flow rate and/or volume of gas being provided to a patient by a ventilation assembly or system by measuring a pressure drop created by a flow restrictor between two regions of a lumen in a flow conduit of the sensor system positioned between the patient and the source of gas in the ventilation assembly. The pressure drop may be determined by independently measuring the pressure of the gas in the two regions of the lumen using two absolute pressure sensors positioned adjacent to the first and second regions of the lumen. The absolute pressure sensors may be miniature electro-mechanical systems (MEMS) devices. The flow restrictor may include a variable orifice flow restrictor (e.g., having a flexible flap), or the flow restrictor may include a rigid orifice. The flow sensor system is configured to provide the operator with feedback itself or via a remotely connected device concerning the real time measurement of breath rate, volume and/or peak inspiratory pressure (PIP) of the patient, and may also provide the operator with alerts, for example, if the rate or volume is above or below the ideal thresholds or if the peak inspiratory pressures are too high, e.g., above a certain threshold which may be harmful to the patient.

The flow sensor system may also provide the operator with a countdown to when a breath should be delivered or should stop being delivered to the patient. For instance, when ventilations are to be provided to the patient over a particular interval of time, the system may provide a countdown (e.g., via audio, visual, haptic feedback) that indicates to a rescuer how much more time is allotted during the desired interval, for example, until a subsequent resuscitation activity (e.g., ventilations and/or chest compressions) is to be performed. The flow sensor system can be used in treating a patient with ventilation therapy during cardiac arrest, traumatic brain injury, respiratory distress, and during patient intubation. The flow sensor system may be used according to systems and methods discussed in U.S. 2012/0302910, entitled "Wireless Ventilator Reporting," and U.S. Pat. No. 7,747,319, entitled "Automated Resuscitation Device with Ventilation Sensing and Prompting," each of which is hereby incorporated by reference in its entirety.

The flow sensor system may include a number of components, as discussed further herein. For example, the flow sensor system may include a conduit, flow restrictor, pressure sensor(s), along with one or more connectors (electrical and/or mechanical), processors, user interfaces, displays and/or other components that contribute to the measurement and determination of flow rate, volume of flow, etc. The flow sensor system may further include one or more apparatuses that are configured to provide feedback to a user or machine of how to adjust ventilation or other forms of resuscitative therapies (e.g., chest compressions, defibrillating shock, etc.) based on flow measurements obtained from the flow sensor.

In some implementations, the flow sensor system may include one or more pressure sensors, as discussed herein, for measuring differential pressure between separate regions of the flow sensor. The pressure sensor(s) may be positioned so as to measure differential pressure in the patient airway. For example, a small vane may be positioned between pressure sensing ports so that the pressure difference generated between the two ports is proportional to the velocity of air flow through the conduit into or out from the patient. Knowing the cross-sectional area of the air path through the conduit, allows the tidal volume to be estimated (using known differential pressure tidal volume measurement techniques).

Having calculated the ventilation rate and tidal volume, it is possible to detect whether or not the appropriate number and rate of breaths have been given as well as the proper amount of tidal volume. If the processor determines that the ventilation rate may be correct, but the tidal volume may be insufficient, a message may be generated to inform the rescuer that more air should be provided to the patient. Similar messages may also be provided to correct for incorrect ventilation rate.

With reference to FIG. 1, a ventilation assembly is shown in accordance with an embodiment of the present disclosure. The ventilation assembly incorporates a flow sensor system 10 according to any one of the following embodiments of the present disclosure. The assembly also comprises a manual bag ventilation system 12, which comprises a manual gas ventilation bag and patient mask, for delivering ventilation to a patient. The manual bag ventilation system 12 is manually operated by an operator, such as a paramedic, nurse, or doctor, to deliver breaths of a gas, such as air, to the patient in a manner known to those having ordinary skill in the art. The flow sensor system 10 and an end tidal carbon dioxide (ETCO2) sensor 11 may be disposed between the ventilation bag and the mask. The flow sensor system 10 is configured to measure at least one of a flow rate and a volume of gas being delivered to the patient by the manual bag ventilation system 12 and/or being exhaled from the patient to an exhaust. The flow sensor system 10 may be connected to a monitor device 13 by a cable connector 14 for providing the operator with feedback concerning the flow rate and/or volume of the gas being delivered to the patient. The feedback provided by the monitor device 13 may be visual, audio, and/or haptic feedback. This feedback may allow the operator to adjust the timing and/or force of the actuations of the manual bag ventilation system 12 to deliver more or less gas to the patient, as required according to the particular ventilation treatment being provided. According to an alternative embodiment, the ventilation assembly incorporates an automated ventilation system, rather than a manual bag ventilation system. In this case, the flow sensor system 10 may communicate directly with a controller of the automated ventilation system to adjust the output of the system. According to another alternative embodiment, the flow sensor system 10 may incorporate a display screen, speaker, and or vibrator device so that the flow sensor system 10 itself is configured to provide the visual, audio, and or haptic feedback to adjust the delivery of gas to the patient.

Figure 2:
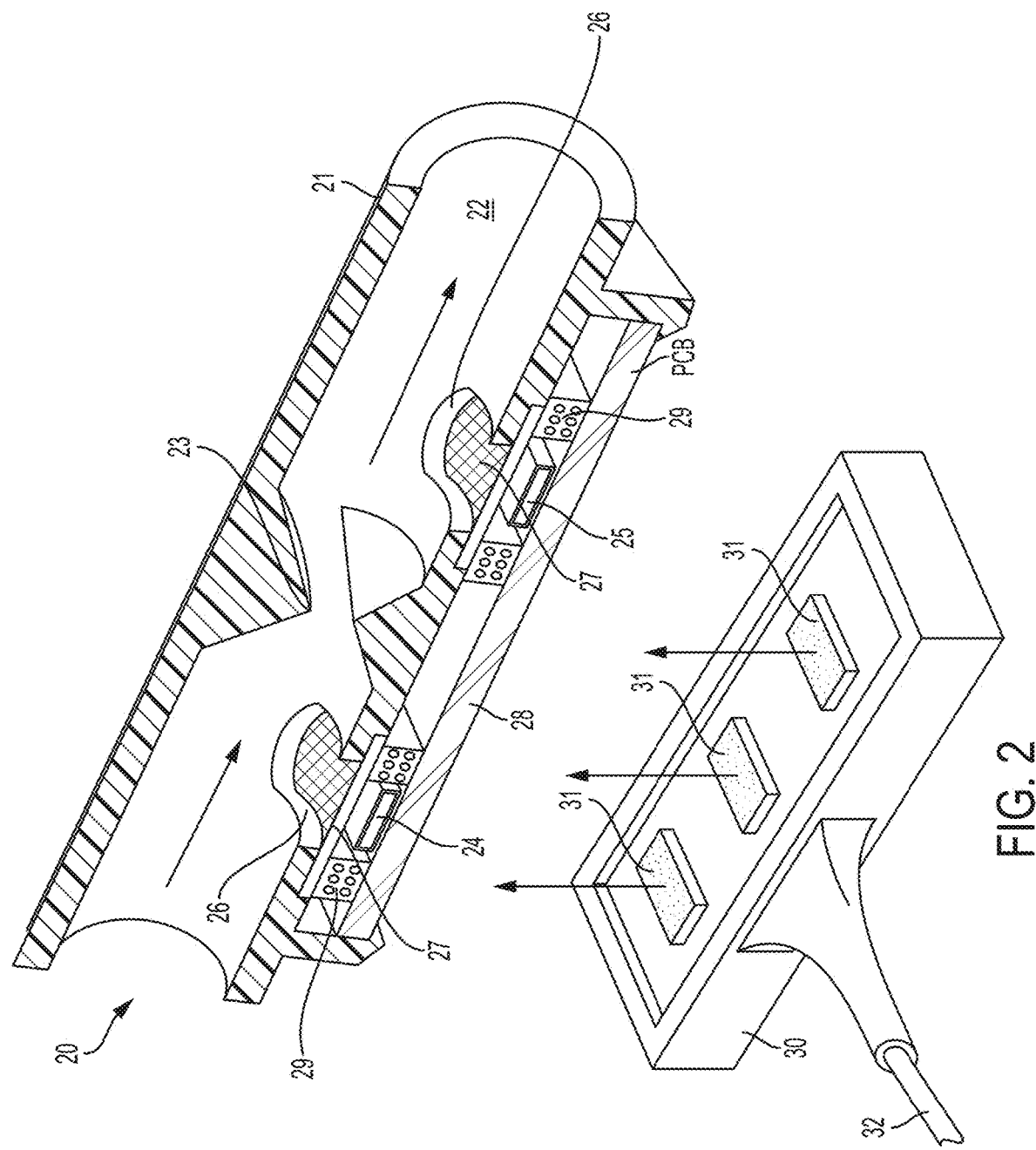
FIG. 2 is a schematic cross-sectional view of a flow sensor system according to an embodiment of the present disclosure.

With reference to FIG. 2, a flow sensor system 20 is shown in accordance with an embodiment of the present disclosure. The flow sensor system 20 comprises a flow conduit 21 that defines a lumen 22 allowing for the passage of gas through the flow conduit 21 from a ventilation source, such as a manual ventilation bag or automated ventilation system, to a patient. The flow conduit 21 comprises a flow restrictor 23 that extends into the lumen 22. The flow restrictor 23 obstructs the flow of gas through the lumen 22 in order to create a pressure drop in the flow. This differential pressure created by the flow restrictor 23 can be measured in order to calculate the flow rate and/or volume of the gas passing through the flow conduit 21. To that end, the flow sensor system 20 comprises a first absolute pressure sensor 24 and a second absolute pressure sensor 25 in communication with the lumen 22 via openings 26 defined in the flow conduit 21. According to one particular embodiment of the present disclosure, the first and second absolute pressure sensors 24, 25 are miniature electro-mechanical systems (MEMS) devices configured to sense an absolute pressure within a respective region of the lumen 22. It is to be appreciated, however, that the first and second absolute pressure sensors 24, 25 may be of any type known to be suitable to those having ordinary skill in the art for independently sensing a pressure within a region of the lumen 22.

The first and second absolute pressure sensors 24, 25 are in separate fluid communication with the lumen 22 on respective sides of the flow restrictor 23 in order to measure the absolute pressure of the gas flowing through the lumen 22 on either side of the flow restrictor 23. A processor (not expressly shown) receiving the absolute pressure measurements from the first and second absolute pressure sensors 24, 25 can thereby calculate the pressure drop created by the flow restrictor 23 from which the flow rate and/or volume of the gas flowing through the flow conduit 21 can be calculated. In various embodiments, such a processor that calculates flow rate, volume of flow, PIP, etc. may be provided as part of any component of the overall medical system. For example, the processor may be provided as part of the disposable unit (including the flow conduit and/or other components). Or, the processor may be part of the reusable cable/connector for connecting the disposable flow unit to a larger, integrated medical system (e.g., defibrillator, monitor, ventilator, diagnostic device, etc.). Or, the processor may be a part of a larger medical system; for example, pressure signals recorded from the sensors may be transmitted from the disposable unit through the reusable connector to a more central computing device (e.g., monitor, defibrillator, administrative computing device, tablet, etc.) for calculating certain key features of ventilation, such as flow rate, volume, PIP, amongst others.

The first and second absolute pressure sensors 24, 25 are mounted on a circuit board 28 disposed within the flow conduit 21. A membrane 27 is disposed between each of the openings 26 and a respective one of the first and second absolute pressure sensors 24, 25. The membrane 27 may be provided as a barrier and further may comprise a breathable, hydrophobic material, such as polytetrafluoroethylene (PTFE), of the type sold under the brand name TEFLON®, and expanded polytetrafluoroethylene (ePTFE), of the type sold under the brand name GORE-TEX®. Alternatively, the membrane 27 may be coated with the breathable, hydrophobic material. The membrane 27 is configured to allow gas to pass through from the opening 26 to a respective one of the first and second absolute pressure sensors 24, 25 but to act as a barrier to obstruct or prevent the passage of liquids and debris, such as dust, sputum, vomit, saliva, etc., from passing through to interfere with the operation or readings of the first and second absolute pressure sensors 24, 25. Alternatively, a single membrane 27 may be provided that extends across both openings 26 and over both pressure sensors 24, 25. A gasket 29 is also provided between the circuit board 28 and the flow conduit 21 around each of the first and second absolute pressure sensors 24, 25 in order to further protect the sensors 24, 25 from outside contaminants.

The flow sensor system 20 also comprises a connector 30 that comprises the processor or that is connected to the processor or to an external monitor/feedback device by a cable 32, as discussed above with reference to FIG. 1. The connector 30 comprises a plurality, in this embodiment, three contacts 31 that are configured to releasably engage the circuit board 28 on the flow conduit 21 in order to establish electronic communication between the connector 30 and the first and second absolute pressures 24, 25 such that the readings of the pressure sensors 24, 25 can be communicated to the processor and/or monitor device. By separating the processor from the flow conduit 21, the assembly of the flow conduit 21, sensors 24, 25, and the circuit board 28 can be provided as a single-use unit since the assembly can be produced relatively inexpensively. Accordingly, it is not necessary for the assembly components to be sterilized after use, which can be labor intensive, jeopardize functioning of the components, and may not completely prevent spread of infection or contaminants.

As discussed herein, the flow sensor system may include a disposable portion and reusable portion. In certain embodiments, the disposable portion of the flow sensor system includes the flow conduit, pressure sensor(s) and a circuit board, and the reusable portion of the flow sensor system includes a connector for establishing communication between the pressure sensor(s)/circuit board and another medical device or system, such as a monitor, defibrillator, ventilator, aspirator, amongst other devices, for integrating and using information gathered from the flow sensor to assist in providing resuscitative therapy.

In the illustrative embodiment shown in FIG. 2, the disposable portion of the flow sensor system 20 includes the flow conduit 21, flow restrictor 23, membrane(s) 27, gasket(s) 29, pressure sensor(s) 24, 25 and a circuit board 28, amongst other single-use components, and the reusable portion of the flow sensor system 20 includes the connector 30 with contacts 31, cable 32, and other parts intended to be reusable.

Figure 3:
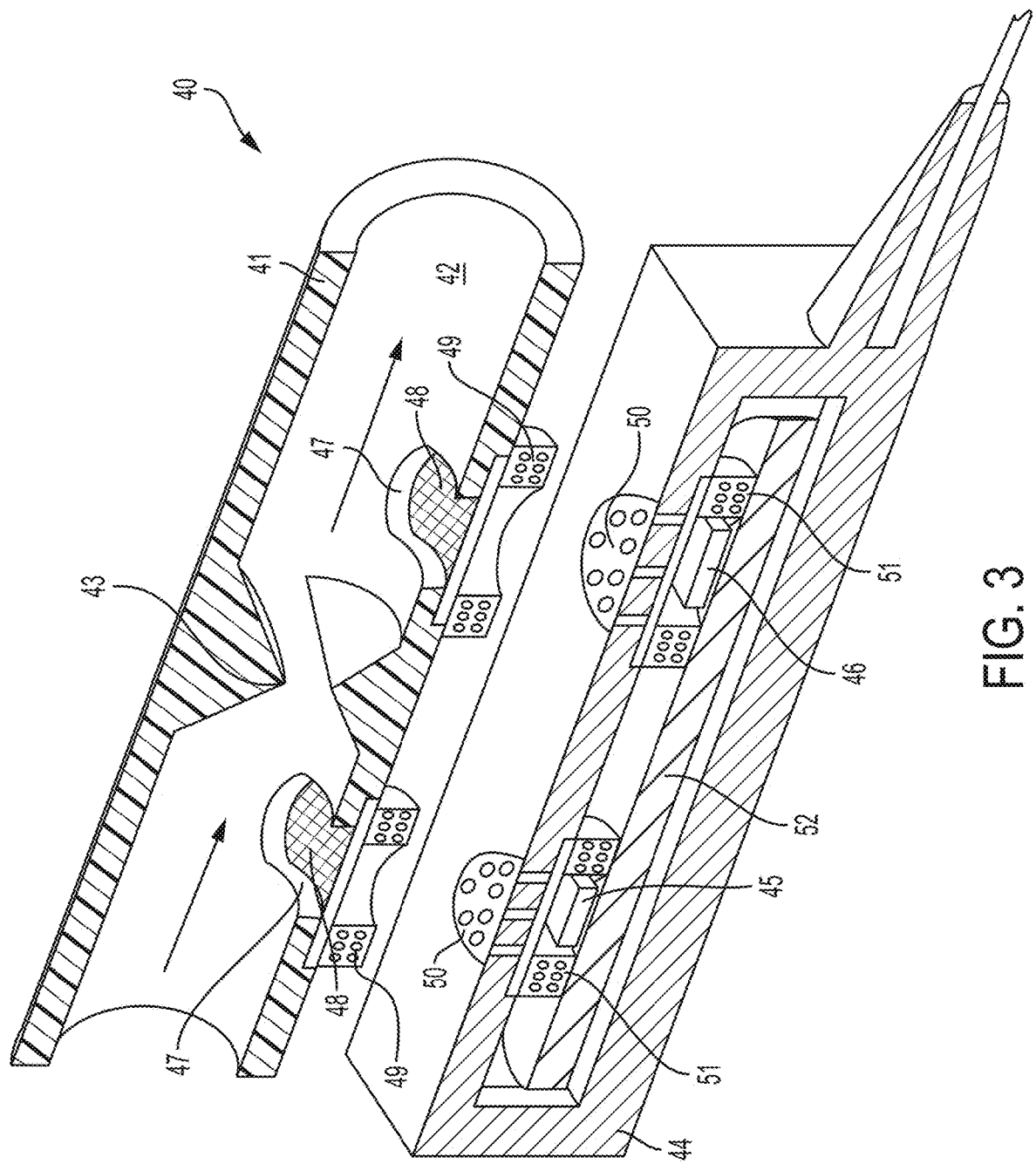
FIG. 3 is a schematic cross-sectional view of a flow sensor system according to an embodiment of the present disclosure.

With reference to FIG. 3, a flow sensor system 40 is shown in accordance with an embodiment of the present disclosure. The flow sensor system 40 comprises flow conduit 41 that defines a lumen 42 allowing for the passage of gas through the flow conduit 41 from a ventilation source, such as a manual ventilation bag or automated ventilation system, to a patient. The flow conduit 41 comprises a flow restrictor 43 that extends into the lumen 42. As discussed above with reference to FIG. 2, the flow restrictor 43 obstructs the flow of gas through the lumen 42 in order to create a pressure drop in the flow, which can be measured in order to calculate a flow rate and/or volume of the gas passing through the flow conduit 41.

The flow conduit 41 comprises openings 47 defined therein that allow for communication between the lumen 42 and a connector 44 removably associated with the flow conduit 41. The connector 44 comprises a first absolute pressure sensor 45 and a second absolute pressure sensor 46 in separate fluid communication via the openings 47 with respective regions of the lumen 42 on either side of the flow restrictor 43 so that the first and second absolute pressure sensors 45, 46 may measure the absolute pressure of the gas passing through the lumen 42 in the respective regions to determine the pressure drop in the flow of the gas through the lumen 42. According to one particular embodiment of the present disclosure, the first and second absolute pressure sensors 45, 46 are miniature electro-mechanical systems (MEMS) devices configured to sense an absolute pressure within a respective region of the lumen 42.

The first and second absolute pressure sensors 45, 46 are mounted on a circuit board 52 and disposed within an interior of the connector 44. The circuit board 52 places the pressure sensors 45, 46 with a processor and/or a monitor device, as discussed above. The connector 44 comprises openings that are filled with porous barriers 50 (e.g., plates, membranes, films, etc.), which align with the openings 47 in the flow conduit 41 so that gas from the lumen 42 may pass through to the pressure sensors 45, 46.

A membrane 48 is disposed outside of each of the openings 47 so as to be disposed between the respective opening 47 and pressure sensor 45, 46 when the connector 44 is connected to the flow conduit 41. As discussed above with reference to FIG. 2, the membrane 48 may comprise a breathable, hydrophobic material that is configured to allow gas to pass through from the opening 47 to a respective one of the first and second absolute pressure sensors 45, 46 but to act as a barrier to obstruct or prevent the passage of liquids and debris, such as dust, sputum, vomit, saliva, etc., from passing through to interfere with the operation or readings of the first and second absolute pressure sensors 45, 46. Alternatively, a single membrane 48 may be provided that extends across both openings 47. A gasket 49 is provided around each of the openings 47 to seal the engagement between the flow conduit 41 and the connector 44 around the openings 47 and prevent contaminants outside the flow sensor system 40 from entering the cavity in the connector 44 containing the pressure sensors 45, 46 and from entering the lumen 42. Additionally, gaskets 51 are also provided in the connector 44 around each of the first and second absolute pressure sensors 45, 46 to further seal and protect the pressure sensors 45, 46. By separating the pressure sensors 45, 46 and circuit board 52 from the flow conduit 41, these components may be re-used for multiple treatments. Also, the assembly of the flow conduit 41 can be provided as a single-use piece with all of the electronics removed. As discussed herein, for certain embodiments, the membrane may exhibit a greater level of hydrophobicity than neighboring regions, for example, portions of the inner surface of the flow conduit so that water or other debris may collect away from the membrane rather than on the membrane itself.

As noted above, the flow sensor system may include a disposable portion and a reusable portion. For certain embodiments, the disposable portion of the flow sensor system includes the flow conduit and chamber structures for housing the pressure sensor(s), and the reusable portion of the flow sensor system includes the pressure sensor(s), associated circuit board and connector cable that provides communication between the pressure sensor(s)/circuit board and another medical device or system (e.g., monitor, defibrillator, ventilator, aspirator, etc.), for integrating and using information gathered from the flow sensor. Accordingly, for various embodiments, the pressure sensor(s) may be provided as part of the disposable or the reusable portion of the flow sensor system.

In the illustrative embodiment shown in FIG. 3, the disposable portion of the flow sensor system 40 includes the flow conduit 41, flow restrictor 43, membrane(s) 48, gasket(s) 49, amongst other single-use components, and the reusable portion of the flow sensor system 40 includes the pressure sensor(s) 45, 46, circuit board 52, and other parts intended to be reusable.

Figure 4:
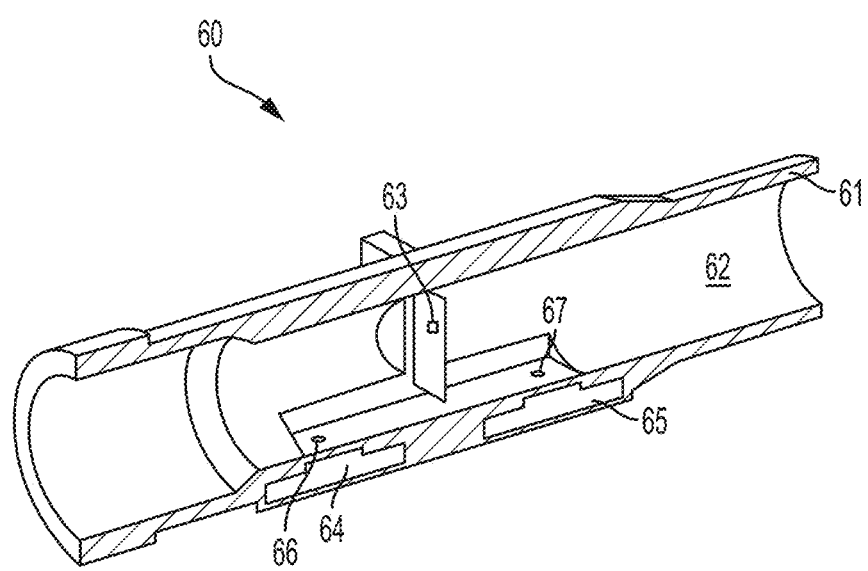
FIG. 4 is a schematic cross-sectional view of a flow sensor system according to an embodiment of the present disclosure.

With reference to FIG. 4, a flow sensor system 60 is shown in accordance with an embodiment of the present disclosure. The flow sensor system 60 comprises a flow conduit 61 that defines a lumen 62 allowing for the passage of gas through the flow conduit 61 from a ventilation source, such as a manual ventilation bag or automated ventilation system, to a patient. A flow restrictor 63 is disposed in the flow conduit 61 so as to extend across all or a portion of the of the lumen 62 in order to obstruct the flow of gas through the lumen 62 and create a pressure drop in the flow, which as discussed above, can be measured in order to calculate a flow rate and/or volume of the gas passing through the flow conduit 61.

The flow restrictor 63 comprises a thin film flap made from a polyester film, such as biaxially-oriented polyethylene terephthalate (BoPET) of the type sold under the trade name MYLAR®. The flow restrictor 63 is configured to be mounted within the flow conduit 61 to deflect under the flow of gas through the lumen 62. The amount of deflection of the flow restrictor 63 varies according to the flow of gas through the lumen 62. That is to say, the flow restrictor 63 will deflect less, thereby creating a larger obstruction in the lumen 62 and a relatively larger pressure drop, at lower flow rates of gas through the lumen 62 and will deflect more, thereby creating a smaller obstruction in the lumen 62 and a relatively smaller pressure drop, at higher flow rates of gas through the lumen 62. Accordingly, the flow restrictor 63 may be described as providing a "variable orifice" in the lumen 62 for creating the pressure drop for measuring flow. In comparison, the flow restrictor described above with reference to FIGS. 1 and 2 may be described as providing a "fixed orifice." The effects of providing a flow restrictor 63, which deflects under flow through the lumen 62, on operation of the flow sensor system 60 in comparison to providing a stationary/fixed flow restrictor of the type described above with reference to FIGS. 1 and 2 will be described in detail below with reference to later embodiments of the present disclosure.

The flow sensor system 60 comprises a first absolute pressure sensor 64 and a second absolute pressure sensor 64 in communication with the lumen 62 via respective openings 66, 67 defined in the flow conduit 61. As discussed above, the first and second absolute pressure sensors may be miniature electro-mechanical systems (MEMS) devices configured to sense an absolute pressure within a respective region of the lumen 62. The first and second absolute pressure sensors 64, 65 are in separate fluid communication with the lumen 62 on respective sides of the flow restrictor 63 in order to measure the absolute pressure of the gas flowing through the lumen 62 on either side of the flow restrictor 63. A processor (not expressly shown) receiving the absolute pressure measurements from the first and second absolute pressure sensors 64, 65 can thereby calculate the pressure drop created by the flow restrictor 63 from which the flow rate and/or volume of the gas flowing through the flow conduit 61 can be calculated. The flow sensor system 60 may incorporate other features of the flow sensor systems 20, 40 discussed above such as the circuit board, membrane(s), gaskets, and connector.

In this embodiment shown in FIG. 4, the disposable portion of the flow sensor system 60 includes the flow conduit 61, flow restrictor 63, membrane(s), gasket(s), pressure sensor(s) 64, 65, amongst other single-use components, and the reusable portion of the flow sensor system (not shown in FIG. 4) includes a connector for establishing communication between the pressure sensor(s)/circuit board and another medical device or system.

Figure 5:
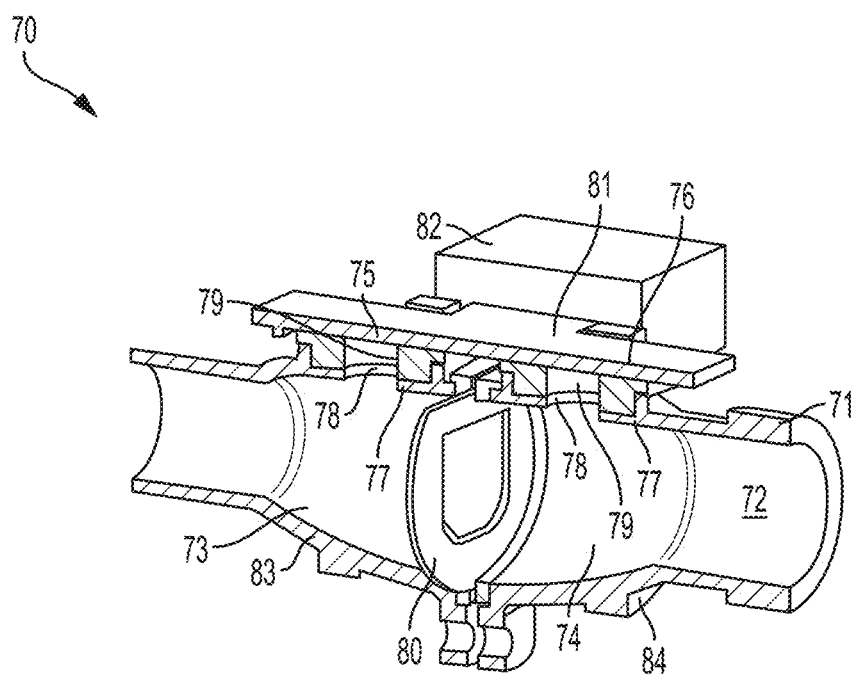
FIG. 5 is a schematic cross-sectional view of a flow sensor according to an embodiment of the present disclosure.
Figure 6:
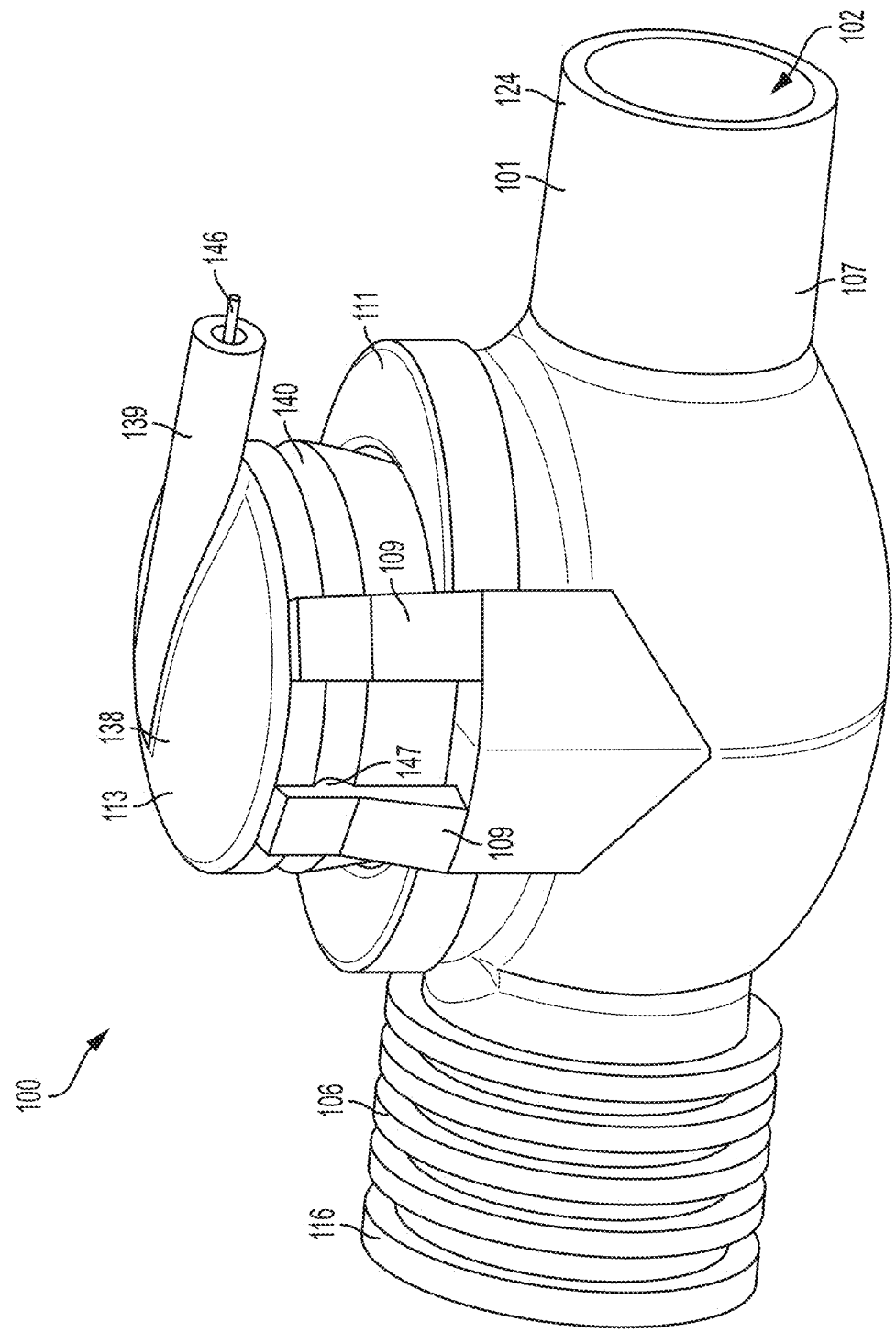
FIG. 6 is a perspective view of a flow sensor system according to an embodiment of the present disclosure.

With reference to FIG. 5, a flow sensor system 70 is shown in accordance with an embodiment of the present disclosure. The flow sensor system 70 comprises a flow conduit 71 that defines a lumen 72 allowing for the passage of gas through the flow conduit 71 from a ventilation source, such as a manual ventilation bag or automated ventilation system, to a patient. A flow restrictor 80 is disposed in the flow conduit 71 so as to extend across all or a portion of the lumen 72 in order to obstruct the flow of gas through the lumen 72 between a first region 73 and a second region 74 of the flow conduit 71 and create a pressure drop in the flow, which as discussed above, can be measured in order to calculate a flow rate and/or volume of the gas passing through the flow conduit 71. According to an embodiment of the present disclosure, the flow conduit 71 is made up of a first piece 83 and a second piece 84 molded from a thermoplastic material, which are assembled and ultrasonically welded to form the flow conduit 71. The first piece 83 defines half of the lumen 72 comprising the first region 73 and the second piece 84 defines the other half of the lumen 72 comprising the second region 74. The flow restrictor 80 is disposed between the first piece 83 and the second piece 84. The first and second pieces 83, 84 are formed such that the lumen 72 is defined symmetrically about the middle of the flow conduit 71 and the first and second regions 73, 74 have the same shape and volume. Such a symmetric structure of the lumen may provide for substantially similar flow profiles for both inspiratory and expiratory flow directions. It can be appreciated that flow conduits in accordance with the present disclosure are not required to be formed as separate components such as pieces 83, 84; for example, the flow conduit may be provided as a single unitary piece that defines the lumen through which fluid flows.

The flow restrictor 80 comprises at least one thin film flap disposed within an opening in the restrictor 80. The flow restrictor 80 is configured to be mounted within the flow conduit 71 so that the flap deflects from the opening in the flow restrictor 80 under the flow of gas through the lumen 72. The amount of deflection of the flap varies according to the flow of gas through the lumen 72. The flap of the flow restrictor 80 will deflect less, thereby creating a larger obstruction in the lumen 72 and a relatively larger pressure drop, at lower flow rates of gas through the lumen 72 and will deflect more, thereby creating a smaller obstruction in the lumen 72 and a relatively smaller pressure drop, at higher flow rates of gas through the lumen 72. Accordingly, the flow restrictor 80 may be described as providing a variable orifice in the lumen 72 for creating a pressure drop for measuring flow. Additional details concerning the flow restrictor 80 will be described below with reference to FIGS. 19(a)-21, 23, and 24.

The flow sensor system 70 comprises a first absolute pressure sensor 75 and a second absolute pressure sensor 76 in communication with the lumen 72 via openings 77 defined in the flow conduit 71. According to one particular embodiment of the present disclosure, the first and second absolute pressure sensors 75, 76 are miniature electromechanical systems (MEMS) devices configured to sense an absolute pressure within a respective region 73, 74 of the lumen 72. It is to be appreciated, however, that the first and second absolute pressure sensors 75, 76 may be of any type known to be suitable to those having ordinary skill in the art for independently sensing a pressure within a region 73, 74 of the lumen 72.

The first and second absolute pressure sensors 75, 76 are in separate communication with the lumen 72 on respective sides of the flow restrictor 80 in order to measure the absolute pressure of the gas flowing through the lumen 72 in the respective regions 73, 74 on either side of the flow restrictor 80. A processor (not shown) receiving the absolute pressure measurements from the first and second absolute pressure sensors 75, 76 can thereby calculate the pressure drop created by the flow restrictor 80 from the which the flow rate and/or volume of the gas flowing through the flow conduit 71 can be calculated.

The first and second absolute pressure sensors 75, 76 are mounted on a circuit board 81 disposed on the flow conduit 71. The circuit board 81 and the pressure sensors 75, 76 are arranged on the flow conduit 71 such that the pressure sensors 75, 76 are each disposed within a respective chamber 79 defined in the flow conduit 71 above the respective opening 77. According to one embodiment of the present disclosure, the flow conduit 71 comprises a separately molded piece in which the chambers 79 and a support surface for the circuit board 81 are defined. This piece is secured to the top of the flow conduit 71. A membrane 78 is disposed between each of the openings 77 and the respective chamber 79. The membrane 78 may comprise a breathable, hydrophobic material, such as polytetrafluoroethylene (PTFE), of the type sold under the brand name TEFLON®, and expanded polytetrafluoroethylene (ePTFE), of the type sold under the brand name GORE-TEX®. Alternatively, the membrane 78 may be coated with the breathable, hydrophobic material. The membrane 78 is configured to allow gas to pass through from the opening 77 to the respective chamber 79 in which the respective one of the first and second absolute pressure sensors 75, 76 is positioned and to act as a barrier to obstruct or prevent the passage of liquids and debris, such as dust, sputum, vomit, saliva, etc., from passing through to interfere with the operation or readings of the first and second absolute pressure sensors 75, 76. Alternatively, a single membrane 78 may be provided that extends across both openings 77 and both chambers 79. For certain embodiments, the membrane may exhibit a greater level of hydrophobicity than regions neighboring the membrane so that water or other debris may collect away from the membrane and not interfere with pressure/flow measurements.

The flow sensor system 70 also comprises a connector 82 that comprises the processor or that is connected to the processor or to an external monitor/feedback device by a cable (not shown), as discussed above. As discussed above with reference to FIG. 2, the connector 82 may comprise one or more contacts that are configured to releasably engage the circuit board 81 on the flow conduit 71 in order to establish electronic communication between the connector 82 and the first and second absolute pressure sensors 75, 76 such that the readings of the pressure sensors 75, 76 can be communicated to the processor and/or monitor device. By separating the processor from the flow conduit 71, the assembly of the flow conduit 71, sensors 75, 76, and the circuit board 81 can be provided as a single-use unit since the assembly can be produced relatively inexpensively. Accordingly, it is not necessary for the assembly components to be sterilized after use, which can be labor intensive, jeopardize functioning of the components, and may not completely prevent spread of infection or contaminants.

In the embodiment shown in FIG. 5, the disposable portion of the flow sensor system 70 includes the flow conduit 71, flow restrictor 80, membrane(s) 78, gasket(s), chamber(s) 79, pressure sensor(s) 75, 76, circuit board 81, amongst other single-use components, and the reusable portion of the flow sensor system includes a connector 82 for establishing communication between the pressure sensor(s)/circuit board and another medical device or system.

With reference to FIGS. 6-18 a flow sensor system 100 is shown in accordance with an embodiment of the present disclosure. The flow sensor system 100 comprises a flow conduit 101 that defines a lumen 102 allowing for the passage of gas through the flow conduit 101 from a ventilation source, such as a manual ventilation bag or automated ventilation system, to a patient. The flow conduit 101 is configured to allow gas flow between a first region 103 and a second region 104. The flow conduit 101 comprises a body extending from a first end to a second end of the flow conduit 101. The body has a hollow interior, which defines the lumen 102.

A flow restrictor 105 is disposed within the lumen 102 of the flow conduit 101 between the first region 103 and the second region 104 so as to extend across all or a portion of the lumen 102 in order to obstruct the flow of gas through the lumen between the first region 103 and the second region 104 and create a pressure drop in the flow, which as discussed above, can be measured to calculate a flow rate and/or volume of the gas passing through the flow conduit 101.

Figure 7:
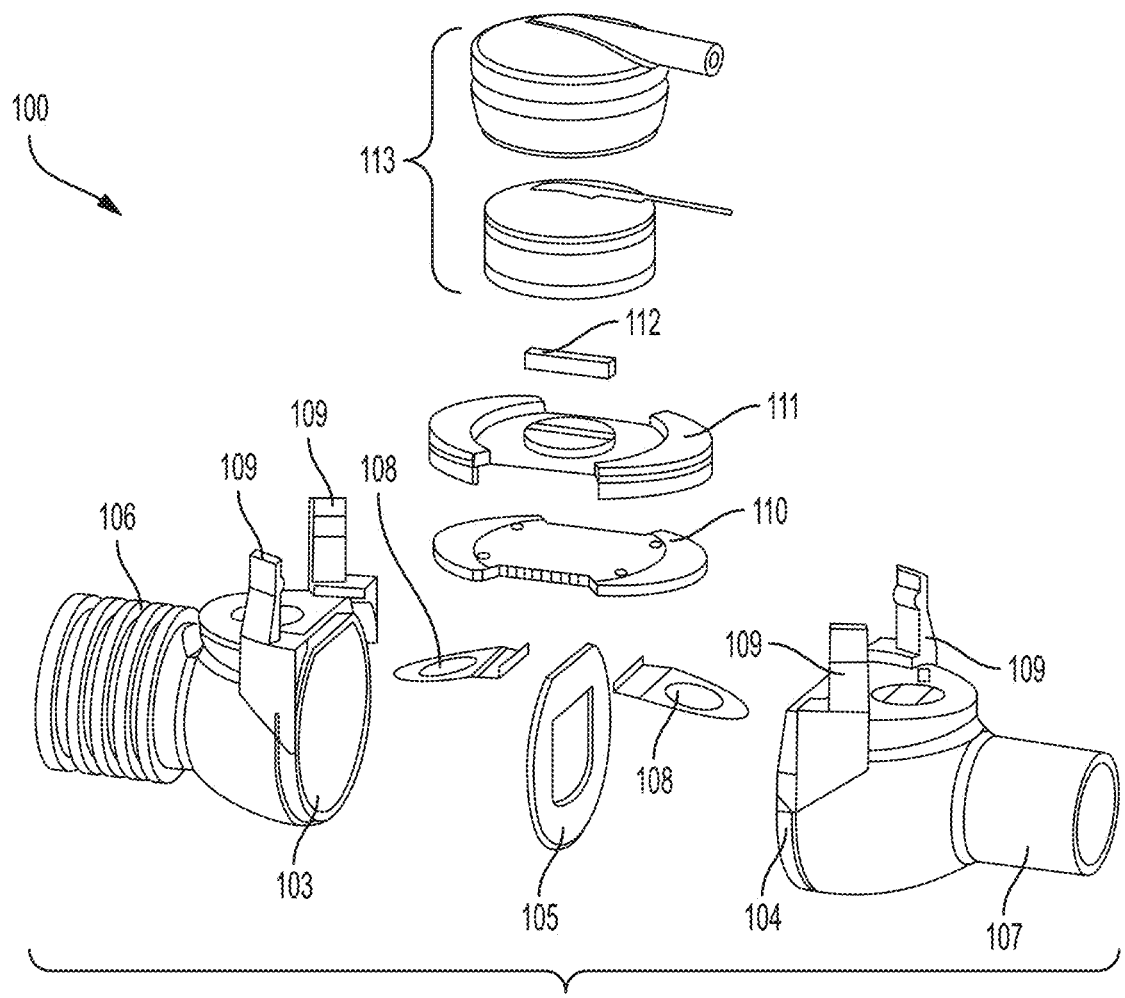
FIG. 7 is an exploded perspective view of the flow sensor system of FIG. 6.
Figure 8:
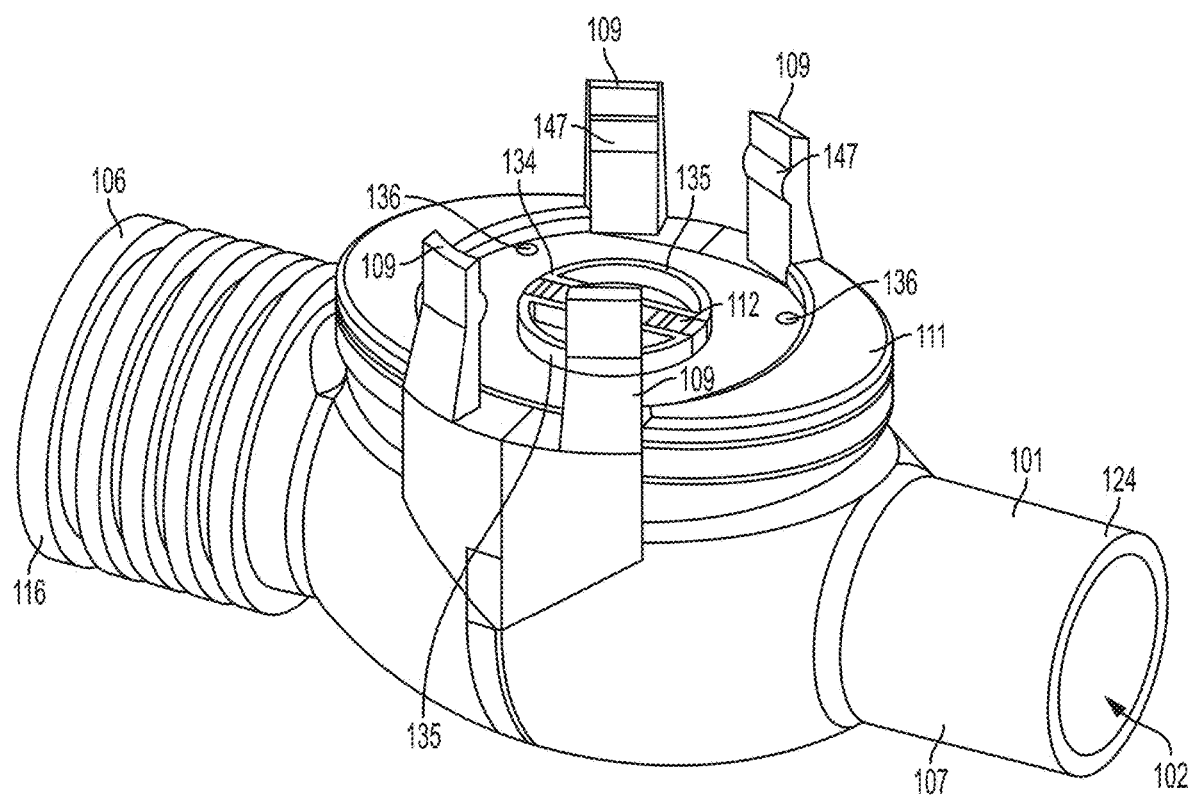
FIG. 8 is a perspective view of a flow conduit assembly of the flow sensor system of FIG. 6.
Figure 9A:
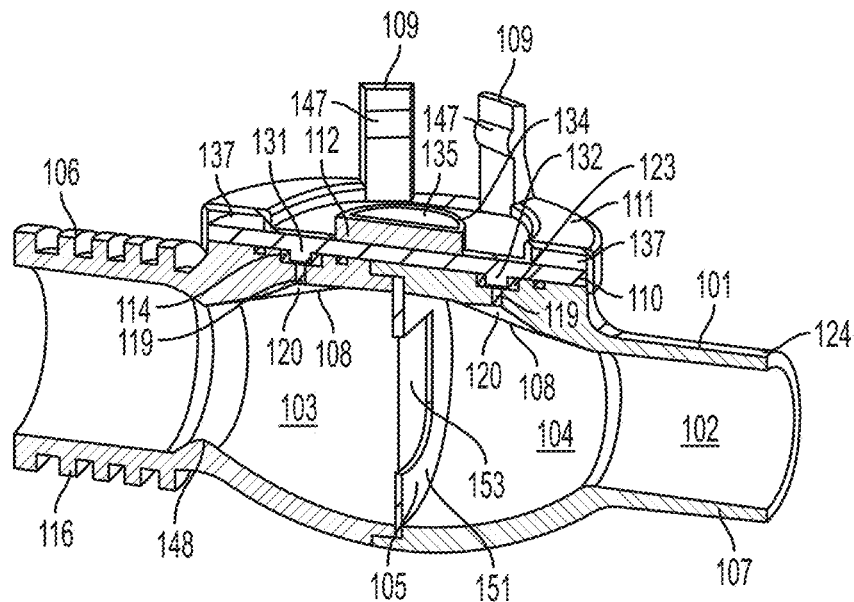
FIG. 9(a) is a cross-sectional view of the flow conduit assembly of FIG. 8.
Figure 9B:
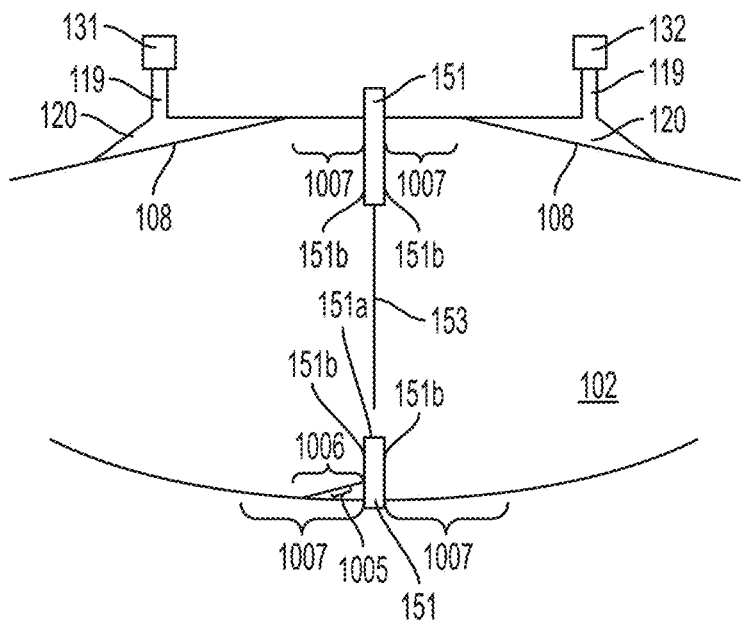
FIG. 9(b) is an enlarged area of the flow conduit assembly shown in FIG. 9(a) illustrating the regions of hydrophobicity and adjacent reservoir and hydrophilicity regions.
Figure 10:
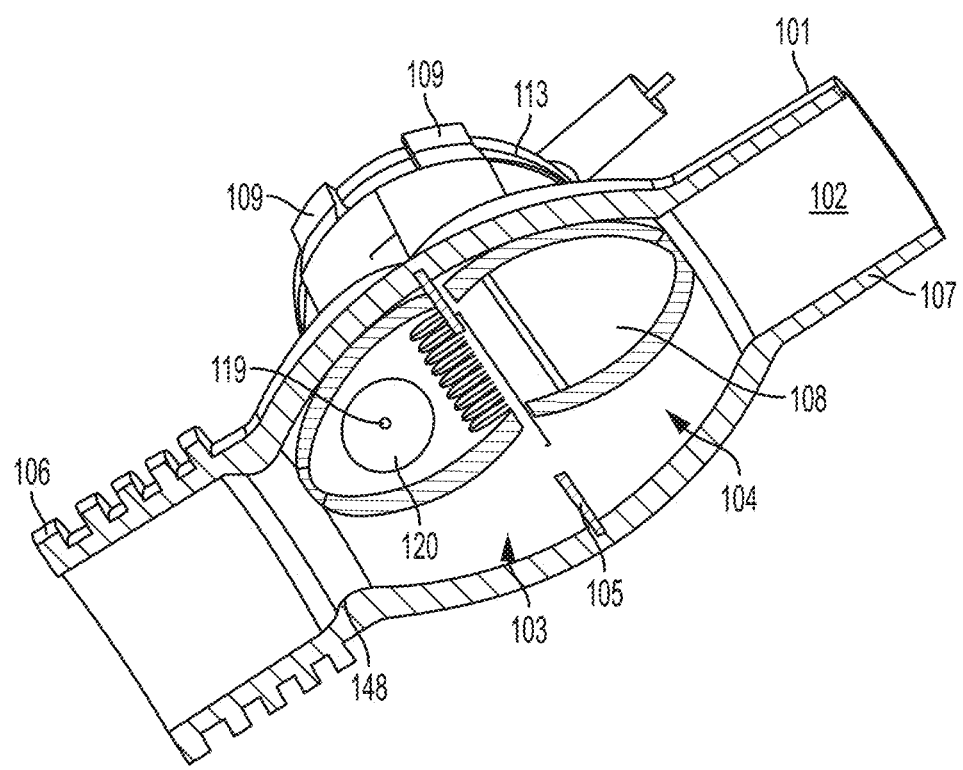
FIG. 10 is another cross-sectional view of the flow conduit assembly of FIG. 8.

According to an embodiment of the present disclosure, the flow conduit 101 is made up of a first piece 106 and a second piece 107 molded from a thermoplastic material, which are assembled and ultrasonically welded to form the flow conduit 101. The first piece 106 and the second piece 107 each comprise respective assembly indentations 122, 125 defined on the ends of the pieces 106, 107, as shown in FIGS. 11 and 12. The assembly indentations 122, 125 are configured to matingly engage each other to assist in assembly of the first and second pieces 106, 107. The first and second pieces 106, 107 may be joined by any suitable method (e.g., fastener, welding, complementary structures that couple with one another) or, as discussed above, the flow conduit may be provided as a single unitary piece defining the lumen through which fluid flows. In this embodiment, the first piece 106 defines half of the lumen 102 comprising the first region 103 and the second piece 107 defines the other half of the lumen 102 comprising the second region 104. As shown in FIGS. 7, 9, and 10, the flow restrictor 105 is disposed between the first piece 106 and the second piece 107. The first and second pieces 106, 107 are formed such that the lumen 102 in the first and second regions 103, 104 is defined symmetrically about the middle of the flow conduit 101 and the first and second regions 103, 104 have the same shape and volume. As a result, the profile of flow through the lumen is not affected by the direction of flow, for example, whether the flow is inspiratory or expiratory. To that end, the first piece 106 of the flow conduit 101, which is formed with a connection portion 116 having a larger diameter, may comprise an interior flange 148 defined at the end of the first region 103 opposite to the flow restrictor 105 so that the first region 103 has the same or similar dimensions as the second region 104. The lumen 102 in the first and second regions 103, 104 may also be defined substantially symmetrically about a longitudinal axis extending through the flow conduit 101 from the first end to the second end, for relatively consistent bi-directional flow. Accordingly, the flange 148 may contribute to consistent flow in either direction through the lumen of the conduit. In various embodiments, the respective outer structures of the connection portion 116 corresponding to the first piece 106 (or section of the fluid conduit in the case of a unitary component) and the connection portion 124 corresponding to the second piece 107 (or section of the fluid conduit) may differ due to the type of fitting(s) and/or tube(s) to which the flow sensor will be connected. For example, the connection portion 116 may be configured to couple to a ribbed fitting (e.g., for a ventilator tube or ventilation port) and the connection portion 124 may be configured to couple with a tapered fitting that slides along the surface thereof (e.g., over or under the surface of the conduit) to form a friction or interference type fit. It can be appreciated that the connection portions may have any appropriate configuration for establishing a suitable port connection with a tube or conduit.

According to one particular embodiment of the present disclosure, the flow conduit 101 has an approximate length between 5-20 cm (e.g., approximately 10-15 cm) and the approximate maximum diameter of the flow conduit 101 in the first region 103 and the second region 104 is between 2-10 cm.

With reference to FIGS. 6-12, the flow sensor system 100 is configured to be placed in communication with a ventilation assembly for delivering gas through the lumen 102 of the flow conduit 101, as discussed above with reference to FIG. 1. As discussed above, the ventilation assembly may comprise a manual bag ventilation system and/or may comprise an automated ventilation system. Accordingly, the flow conduit 101 comprises a connection portion 116 on the first piece 106 and another connection portion 124 on the second piece 107. The connection portion 116 on the first piece 106 may comprise an inner diameter having a larger diameter suitable for receiving an end of a tube or passageway of the ventilation assembly to form a standard female connection. The connection portion 116 may also comprise a ribbed outer diameter to form a standard male connection with a larger tube into which the connection portion 116 is inserted. The connection portion 124 on the second piece 107 may comprise a smooth outer diameter to form a standard male connection within another tube or passageway of the ventilation assembly. It can be appreciated that other types of connections for the flow sensor system may be possible.

As shown in FIGS. 7, 9($a$), and 10, the flow restrictor 105 comprises at least one thin film flap disposed within an opening in the flow restrictor 105. The flow restrictor 105 is configured to be mounted within the flow conduit 101 so that the flap deflects from the opening in the flow restrictor 105 under the flow of gas through the lumen 102. The amount of deflection of the flap varies according to the flow of gas through the lumen 102. The flap of the flow restrictor 105 will deflect less, thereby creating a larger obstruction in the lumen 102 and a relatively larger pressure drop, at lower flow rates of gas through the lumen 102 and will deflect more, thereby creating a smaller obstruction in the lumen 102 and a relatively smaller pressure drop, at higher flow rates of gas through the lumen 102. Accordingly, the flow restrictor may be described as providing a "variable orifice" in the lumen 102 for creating a pressure drop for measuring flow. Additional details concerning the flow restrictor 105 will be described below with reference to FIGS. 19($a$)-21, 23, and 24.

As shown in FIGS. 9($a$)-12 and 14, the flow sensor system 100 comprises a first absolute pressure sensor 131 disposed adjacent to the first region 103 of the flow conduit 101 and a second absolute pressure sensor 132 disposed adjacent to the second region 104 of the flow conduit 101. The first and second absolute pressure sensors 131, 132 are configured to measure a pressure due to gas flow at the first and second regions 103, 104 of the flow conduit 101, respectively. According to one particular embodiment of the present disclosure, the first and second absolute pressure sensors 131, 132 are miniature electro-mechanical systems (MEMS) devices configured to sense an absolute pressure within a respective region 103, 104 of the lumen 102, such as the BME 280 sensor or BMP 200 sensor manufactured by Bosch Sensortec GmbH. It is to be appreciated, however, that the first and second absolute pressure sensors 131, 132 may be of any type known to be suitable to those having ordinary skill in the art capable of independently sensing a pressure within a region 103, 104 of the lumen 102. Alternatively, for some embodiments, absolute pressure sensors are not necessary, as one or more differential pressure sensors as known to those skilled in the art may be employed. Differential pressure sensors may be configured to measure the difference between two pressures at separate locations, such as at regions on opposite sides of the flow restrictor.

With reference to FIGS. 7, 9(a)-12, and 14, the first and second absolute pressure sensors 131, 132 are in separate communication with the lumen 102 on respective sides of the flow restrictor 105 in order to measure the absolute pressure of the gas flowing through the lumen 102 in the respective regions 103, 104 on either side of the flow restrictor 105. The first and second absolute pressure sensors 131, 132 are mounted on and connected to a circuit board 110 disposed on an upper side of the flow conduit 101. The circuit board 110 and the pressure sensors 131, 132 are disposed on the flow conduit such that the first absolute pressure sensor 131 is disposed in a first chamber 114 provided in the upper surface of the first piece 106 of the flow conduit 101, and the second absolute pressure sensor 132 is disposed in a second chamber 123 provided in the upper surface of the second piece 107 of the flow conduit 101. The chambers 114, 123 are configured to house and support a respective one of the pressure sensors 131, 132 adjacent to the lumen 102 of the flow conduit 101. Each of the chambers 114, 123, and thus each of the pressure sensors 131, 132, is in fluid communication with the lumen 102 via an opening 119 defined in and extending through the flow conduit 101 between the lumen 102 and the chamber 114, 123.

A tapered/conical cavity 120 is formed in the interior surface of each of the first and second pieces 106, 107 at the top of the respective first and second regions 103, 104. The tapered/conical cavities 120 are configured to channel gas from the lumen 102, through the porous barrier 108 (permitting gas but not water or debris, as discussed below), to the openings 119 and thus to the first and second absolute pressure sensors 131, 132 in the respective chambers 114, 123 while minimizing or reducing the volume of space between the lumen 102 and the pressure sensors 131, 132 such that a minimal/small amount of gas is diverted from the lumen 102 to obtain the pressure measurements in the regions 103, 104. Hence, the cavity 120 is large enough such that the pressure sensors are exposed to a sufficient amount of gas/flow exchange between the lumen of the flow conduit and the cavity. Such a configuration allows for accurate pressure measurements to be obtained while taking up a relatively small volume of space. The interior surfaces of the first and second regions 103, 104 and the tapered/conical cavities 120 may be formed or manufactured to have a smooth finish so as to limit disruption to the flow of gas.

According to one particular embodiment of the present disclosure, the approximate total volume of space between the lumen 102 and each of the first and second absolute pressure sensors 130, 132 as defined by the respective tapered/conical cavity 120, opening 119, and chamber 114, 123 is between approximately 10 mm$^3$ and 50 mm$^3$, or between approximately 15 mm$^3$ and 40 mm$^3$, or 23.5 mm$^3$, or any other appropriate volume.

In some embodiments, specific "sensitive" regions are identified that would result in degraded performance of pressure or flow measurements were these "sensitive" regions to be contaminated with fluid or debris. Referring to FIGS. 2, 9(b), 29 and 34, in some embodiments, these sensitive areas may be the area of the flow restrictor 23, 105, 150 or 256, the permeable or impermeable membrane 27, 108, 220 or 352, the pressure sensors 24, 25, 131, 132, 254, 255 or 307, 308, the orifices 119 connecting the pressure sensor to the lumen space, the orifice of the pressure sensor itself, or regions adjacent to the orifices.

In some embodiments, a sensitive region may exhibit a greater level of hydrophobicity than regions in the immediate vicinity (e.g., neighboring regions of the flow conduit) of the sensitive region so that water or other debris may collect away from the sensitive region. Otherwise, the accumulation of such material may affect the pressure/flow readings of the flow sensor system. Referring to FIG. 9(b), the inner surface of the outer portion 151 of the flow restrictor 150 may be regarded as a sensitive region, since accumulation of fluid or debris on this surface will impair the free movement of the flap 153 which would degrade the measurement accuracy of the sensor. By having the regions adjacent to the sensitive regions be less hydrophobic (i.e. more hydrophilic), the fluids and the debris captured by the fluid can be wicked away from the sensitive region, to a region that collects the fluid 1005. We term this fluid collection region, the reservoir 1006.

There may also be regions 151b, 1007, such as on the outer portion 151 of the flow restrictor 150 or on the interior of the lumen 102 near the flow restrictor 150, adjacent to the sensitive regions of the flap 153 and the inner surface 151a of the outer portion 150, that are at intermediate levels of hydrophilicity. These wicking regions 151b, 1007 act as regions which wick away moisture and fluids from the sensitive regions 153, 151a. In some versions, the wicking regions 151b, 1007 may incorporate surface texturing or polypropylene fibers that enhance wicking action. The relative hydrophilicities of the various wicking regions 151b, 1007 can be adjusted relative to the sensitive regions (e.g. 151a, 153) such that the wicking action draws the fluid into the reservoir 1006 or simply away from the sensitive regions.

The inner surface 151a can be made more hydrophobic compared to the adjacent, more hydrophilic regions 151b by, for instance coating the inner surface 151b with a coating to make it more hydrophobic, or treating the adjacent regions 151b to make them more hydrophilic. Examples of surface treatments that increase hydrophobicity include coating with Teflon or laminating with a thin layer of Teflon or other known hydrophobic material. The surface may also be treated to create what is currently termed "ultraphobicity" or "superhydrophobicity", where the contact angles of a water droplet exceeds 150° and the roll-off angle/contact angle hysteresis is less than 10°. This is also referred to as the Lotus effect, after the superhydrophobic leaves of the lotus plant. A droplet impacting on these kind of surfaces can fully rebound like an elastic ball, or pancake. This is accomplished via microtexturing or nano-texturing the surface, such that the liquid on the surface is in the Cassie-Baxter state. Embodiments of the present disclosure may include relevant teachings from one or more of the following publications, each of which are hereby incorporated by reference in their entirety: Cassie, A B D; Baxter, S. (1944). "Wettability of Porous Surfaces". Trans. Faraday Soc. 40: 546-551), or in the Wenzel state where microtexturing amplifies the natural tendency of the surface (Wenzel, R N (1936). "Resistance of Solid Surfaces to Wetting by Water". Ind. Eng. Chem. 28 (8): 988-994; Richard, Denis, Christophe Clanet, and David Quéré. "Surface phenomena: Contact time of a bouncing drop." Nature 417.6891 (2002): 811-811; Bird, James C., et al. "Reducing the contact time of a bouncing drop." Nature 503.7476 (2013): 385-388; and Yahua Liu, Lisa Moevius, Xinpeng Xu, Tiezheng Qian, Julia M Yeomans, Zuankai Wang. "Pancake bouncing on superhydrophobic surfaces." Nature Physics, 10, 515-519 (2014).

In some embodiments, the superhydrophobic region may be created via sol-gel, plasma florination, electrospinning, template method, layer-by-layer self-assembly, or other methods known to those skilled in the art. Superhyrophobicity may also be achieved in some embodiments via a polymerization process as described by Yuan, Chen, et al. (Yuan, Zhiqing; Chen, Hong; Zhang, Jide; Zhao, Dejian; Liu, Yuejun; Zhou, Xiaoyuan; Li, Song; Shi, Pu; et al. (2008). "Preparation and characterization of self-cleaning stable superhydrophobic linear low-density polyethylene". Science and Technology of Advanced Materials), which is hereby incorporated by reference in its entirety. Using such methods, or ones similar to them, "self-cleaning" regions may be created where dirt or other contaminants deposited on the surface are easily washed away.

In some embodiments, the hydrophobicity may be enhanced by modifying the surface energy of the hydrophobic regions. In some embodiments, this modification may be achieved via lubricant-impregnated surfaces as described by Smith, Dhiman, et al. (Smith, J D; Rajeev Dhiman; Sushant Anand; Ernesto Reza-Garduno; Robert E. Cohen; Gareth H. McKinley; Kripa K. Varanasi (2013). "Droplet mobility on lubricant-impregnated surfaces". Soft Matter 19 (6): 1972-1980. See Also: http://www.rsc.org/suppdata/sm/c2/c2sm27032c/c2sm27032c.mp4), which is hereby incorporated by reference in its entirety. In some versions, a silicone oil may be utilized; other biocompatible lubricants may also be utilized. Lubricant impregnation has been shown to be effective at aiding in the mobility of viscous fluids; this is particularly applicable in the case of an airway flow sensor, which is in contact with vomit, blood, saliva and various bodily excretions during use.

DIN 55660 recommends the contact angle method for determining the SFE of a solid. The contact angle, which reflects the degree of hydrophobicity or hydrophilicity, describes the shape of a drop on the surface: the greater the hydrophilicity, the flatter the drop will be, resulting in a smaller contact angle. Young's equation holds that the contact angle is a function of the Surface Free Energy (SFE) of the solid, the surface tension of the liquid, and the interfacial tension between the two phases. In order to determine the SFE and its polar and disperse components, contact angles are measured using multiple liquids for which the interactive components of the surface tension are known. Water, which is highly polar, and diiodomethane, which is a purely dispersed liquid, are two frequently used test substances. Not only do contact angle measurements yield information on the overall surface, they also detect differences in wettability across a single sample. Thus, position-dependent measurements (mapping) reveal whether the surface has been cleaned, activated or coated uniformly. MEASUREMENT METHODS: There are a number of analytical methods that characterize the surface of plastics, and, in so doing, provide information for optimizing coatings and adhesives (e.g.): 1) Taking optical measurements of the contact angle (drop shape analysis), static and dynamic; 2) Taking mechanical measurements of the contact angle using a tensiometer; 3) Determining surface free energy and its polar and disperse components; 4) Measuring surface tension of liquids; 5) Calculating adhesion and interfacial tension; 6) Measuring the roll-off angle of drops on hydrophobic surfaces.

With reference to FIGS. 25-31, the flow sensor system 250 may include one or more impermeable diaphragm membranes 220 disposed between the flow conduit 251 and the respective chamber 252, 253 in which a corresponding pressure sensor 254, 255 is located, for the purpose of equalizing pressure between the flow conduit 251 and the respective chamber 252, 253. The diaphragm membrane(s) 220 may be provided as another type of barrier between the flow conduit 251 and the respective chamber 252, 253. The diaphragm membrane(s) 220 may be composed of a relatively thin non-porous elastic material that is impervious to gas flow therethrough. In contrast with other examples described elsewhere in this disclosure where the membrane(s) may be porous so as to allow for gas exchange between the flow conduit 251 and the respective pressure sensor(s) 254, 255, the diaphragm membrane(s) 220 may additionally form an even greater barrier, adapted to seal off gas flow to the chamber 252, 253 in which the pressure sensor 254, 255 is enclosed.

The pressure sensor 254, 255 may be permanently enclosed and, thus, protected within the chamber 252, 253 sealed by the diaphragm membrane 220, provided as a barrier. The diaphragm membrane(s) 220 may further be able to flex back and forth in such a manner that the volume within the respective chamber 252, 253 varies in order to equalize pressure between the flow conduit 251 and the space within the respective chamber 252, 253, i.e., the diaphragm membrane(s) 220 acoustically transfers pressure between the flow conduit 251 and the space within the respective chamber 252, 253. In this case, the chamber 252, 253 may provide sufficient space for the diaphragm membrane(s) 220 to freely flex inward and outward, in a manner that equalizes pressure on either side of the diaphragm membrane 220. As a result, the pressure on the flow conduit side 221 of the diaphragm membrane(s) 220 is substantially the same as the pressure on the chamber side 222 of the diaphragm member(s) 220, providing for reliable pressure measurements on either side of the flow restrictor 256. Chambers 252, 253 sealed with a diaphragm membrane 220 and enclosing a pressure sensor 254, 255 may be a part of either the disposable portion (including the flow conduit 251, flow restrictor 256 and other such components) or the reusable portion (including the cable, connector, etc.) of the flow sensor system 250.

Figure 25:
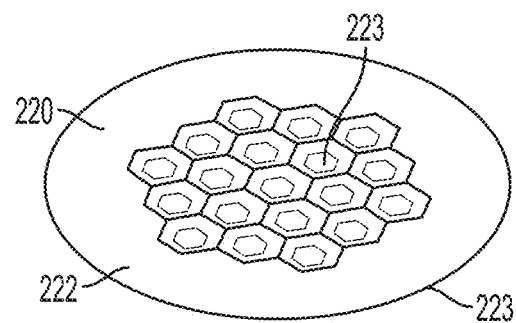
FIG. 25 is a perspective view of a diaphragm membrane according to an embodiment of the present disclosure.
Figure 26:
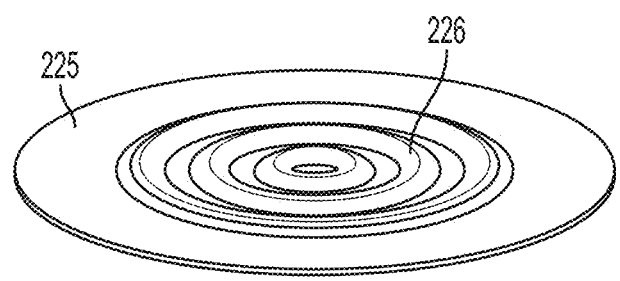
FIG. 26 is a perspective view of another diaphragm membrane according to an embodiment of the present disclosure.

FIGS. 25 and 26 show various embodiments of an impermeable diaphragm membrane 220, 225 that is relatively thin and flat, and also including a patterned structure 223, 226 that provides tolerance for the membrane 220 to oscillate without affecting the equalization of pressure on either side of the membrane 220. Accordingly, the patterned structure 223, 226 of the diaphragm membrane 220, 225 may ensure that the material of the membrane 220, 225 is not stretched under tension, which may otherwise contribute to inaccuracies in how pressure is transferred between the flow conduit 251 and the chamber 252, 253. In certain embodiments, and as shown, the diaphragm membrane 220, 225 includes a circular or ring-like pattern 223, 226 which allows for the membrane 225 to easily deflect and transfer pressure, which reduces the possibility of inaccuracies arising associated with stretching, twisting, deformation or other mechanical hindrance. Any suitable patterned structure 223, 226 may be employed. For example, as shown in FIG. 25, the patterned structure 223 may be hexagonal or polygonal in nature. Or, as shown in FIG. 26, the patterned structure 226 may involve a series of concentrically undulating waves. It can be appreciated that other patterned structures that allow for the diaphragm membrane 220, 225 to freely flex back and forth may be possible.

The diaphragm membrane(s) 220, 225 may include any suitable material. For example, the diaphragm membrane(s) 220, 225 may include an elastomer, tegaderm, rubber, silicone, polymer, or other thin elastic impermeable material able to form a seal between the chamber and the region of the lumen where gas flows.

Figure 27:
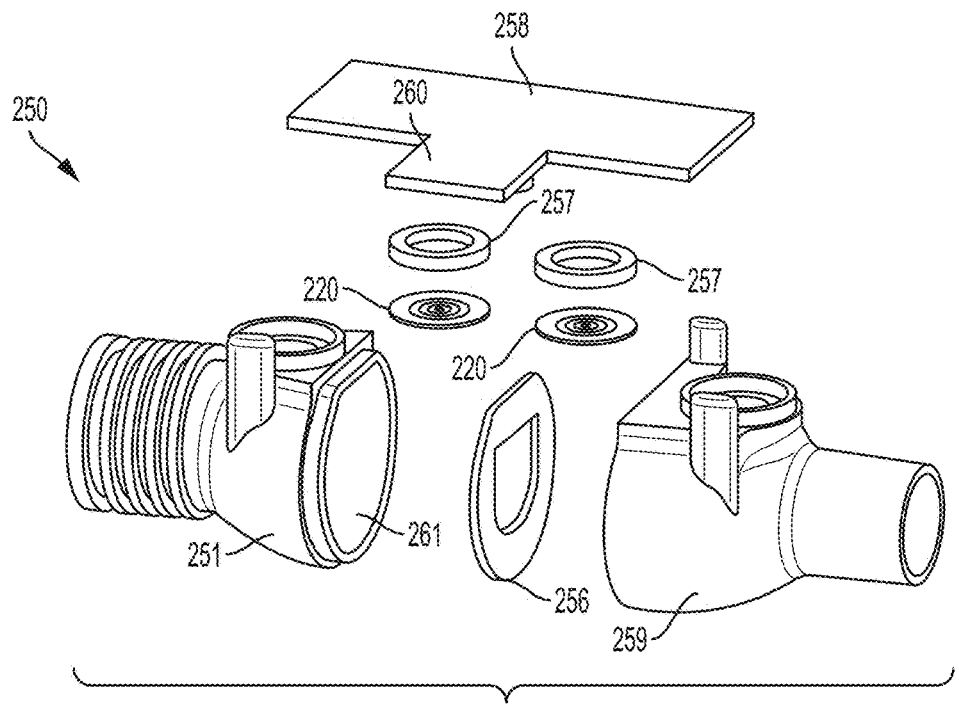
FIG. 27 is an exploded perspective view of a flow sensor system incorporating the diaphragm membrane of FIG. 25 according to an embodiment of the present disclosure.

FIG. 27 illustrates an exploded view of another embodiment of the flow sensor system 250 where the diaphragm membranes 220 are each located between the flow conduit 251 and a housing portion 257 of chambers 252, 253 in which respective pressure sensors 254, 255 are each enclosed. In this example, the diaphragm membrane 220 and the housing portion 257 of each chamber 252, 253 is structured so as to come into mutual alignment and provide an impermeable seal between the flow conduit 251 and the respective chamber 252, 253, allowing for the pressure within a lumen defined by the flow conduit 251 within the immediate vicinity of the diaphragm membrane 220 to be more accurately determined. As discussed above, the diaphragm membrane(s) 220 and associated pressure sensor(s) 254, 255 (e.g., chamber 252, 253 in which a pressure sensor 254, 255 is housed and sealed by a diaphragm membrane 220) may be provided as part of either the disposable portion or the reusable portion of the flow sensor system 250. For example, the housing portion(s) 257 and diaphragm membrane(s) 220 shown in FIG. 27 may be integrated into the reusable connector component 258, which may be connected to the flow conduit 251; or, the housing portion(s) 257 and diaphragm membrane(s) 220 may be integrated into the disposable flow conduit portion 259, to which a reusable connector component 258 may be connected.

Figure 28:
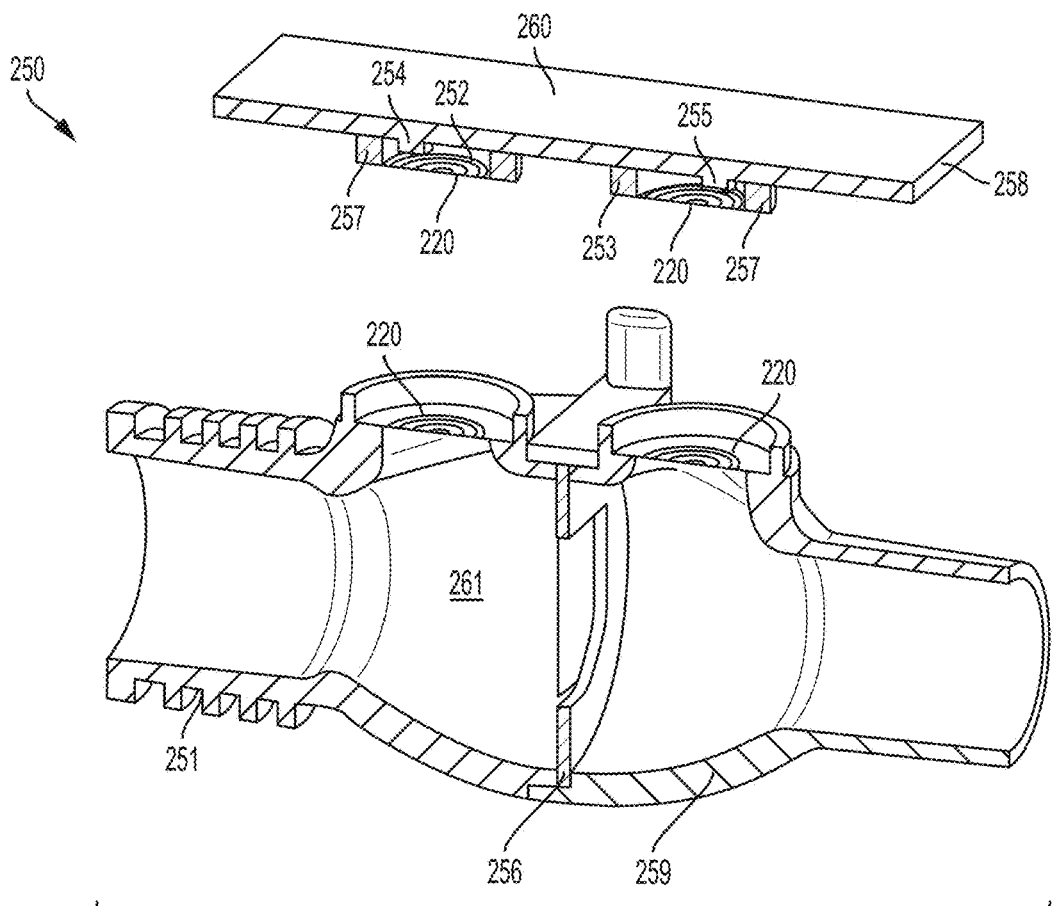
FIG. 28 is a partially exploded cross-sectional perspective view of the flow sensor system of FIG. 27.
Figure 29:
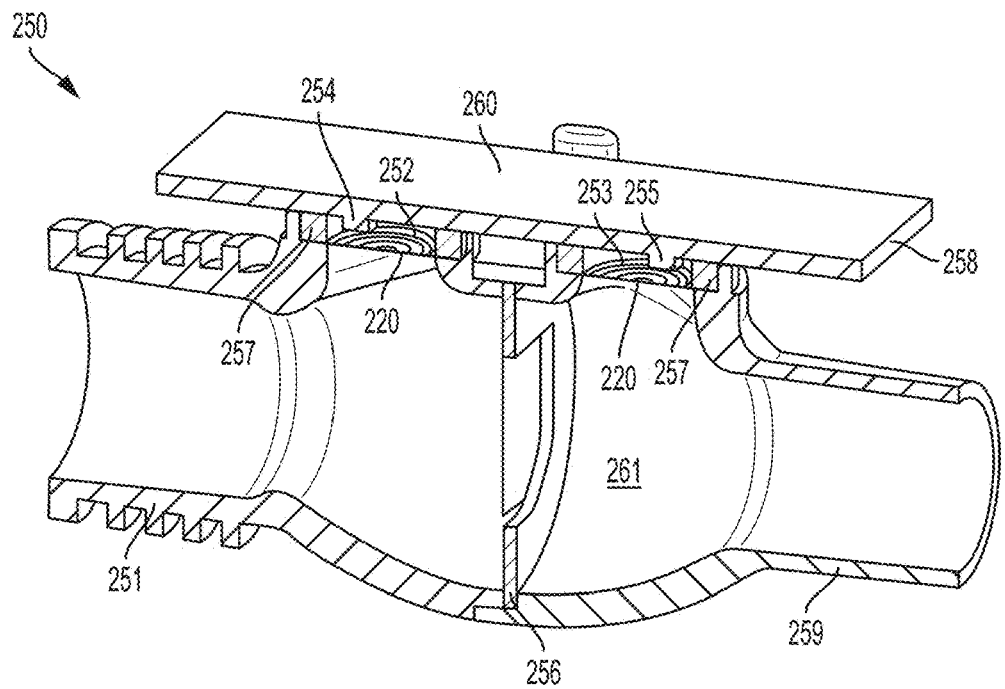
FIG. 29 is a cross-sectional perspective view of the flow sensor system of FIG. 27.
Figure 30:
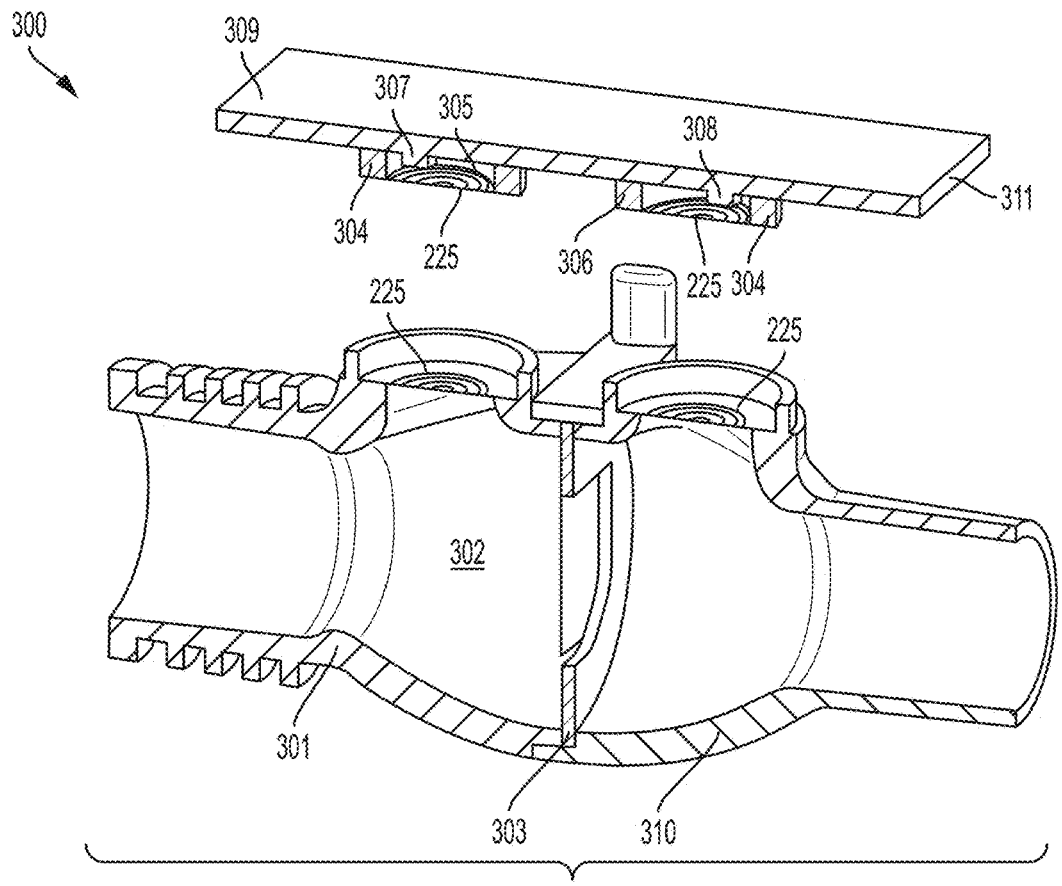
FIG. 30 is a partially exploded cross-sectional perspective view of a flow sensor system incorporating the diaphragm membrane of FIG. 26 according to an embodiment of the present disclosure.

FIGS. 28-29 and 30-31 show embodiments of an assembly of a reusable connector portion 258 and a disposable flow conduit portion 259. The reusable connector portion 258 includes a circuit board 260 (including pressure sensors 254, 255), chamber housings 257 (substantially surrounding respective pressure sensors 254, 255) and diaphragm membranes 220, 225 disposed at respective ends of the chamber housings 252, 253. Here, as shown in FIGS. 28 and 30, the circuit board 260, chamber housings 257 and diaphragm membranes 220, 225 are all part of the reusable portion 258 of the flow sensor system 250. The reusable portion 258 may include diaphragm membranes 220, 225 so that the pressure sensors 254, 255 (which are now reusable rather than single-use) may be adequately protected within the chamber 252, 253. The disposable flow conduit portion 259 includes several components similar to those described above with respect to other embodiments (e.g., flow restrictor 256, flow conduit 251, etc.), and further includes chamber housings 257 and diaphragm membranes 220, 225 that have complementary features corresponding to their reusable counterparts. That is, upon connection of the reusable 258 and disposable portions 259, the chamber housings 257 and diaphragm membranes 220, 225 of the reusable connector portion 258 may suitably engage with the corresponding chamber housings 252, 253 and diaphragm membranes 220, 225 of the disposable connector portion 259, to allow for pressure equalization between the lumen 261 of the flow conduit 251 and the space within chamber 252, 253 where the pressure sensor 254, 255 is present.

Figure 31:
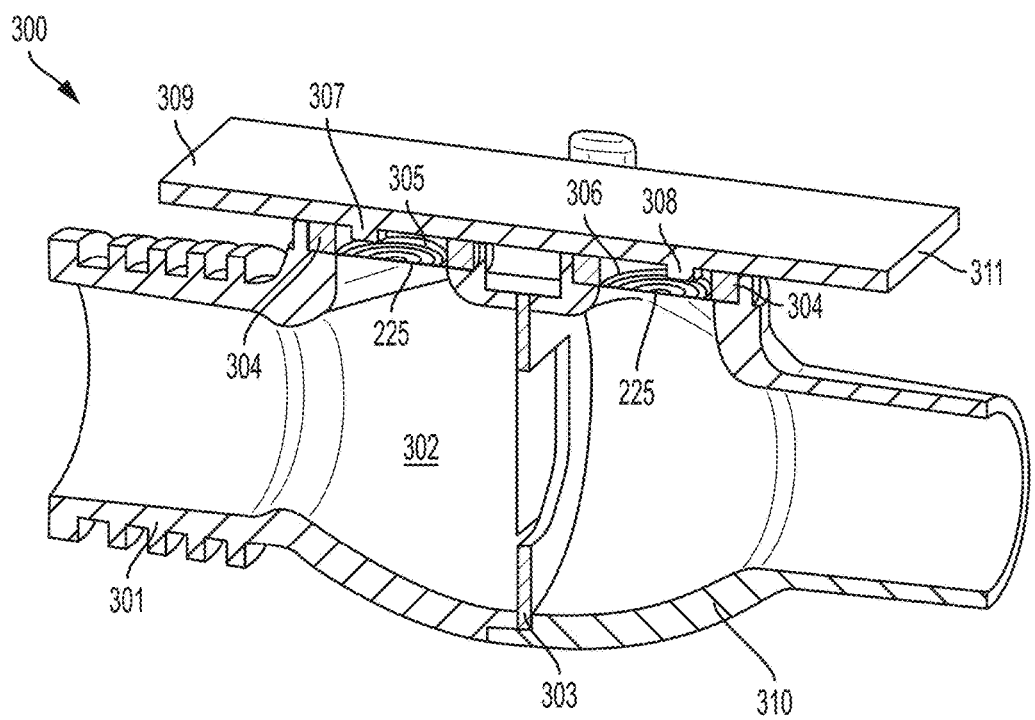
FIG. 31 is cross-sectional perspective view of the flow sensor system of FIG. 30.

As shown in FIGS. 29 and 31, when the reusable and disposable portions 258, 259 are connected, the respective chamber housings 257 may structurally engage so as to provide for appropriately sized chambers 252, 253 within which corresponding pressure sensors 254, 255 may reside. In some embodiments, the respective chamber housings 257 may engage to form a firm connection between the reusable and disposable portions 258, 259. For example, while not expressly shown in the figures, the complementary features of respective chamber housings 257 may engage via interlocking members, a friction fit, a tapered contact connection, a bayonet connection, etc. Further, as noted above, the corresponding diaphragm membranes 220, 225 may also engage in a manner that allows for accurate pressure equalization between the flow conduit 251 and chamber space. For example, the corresponding diaphragm membranes 220, 225 may have complementary patterned structures 223, 226 that are able to fit snugly together.

In FIGS. 28 and 29, the diaphragm membranes 220 have a hexagonal pattern 223, similar to that shown in FIG. 25. Similarly, in FIGS. 30 and 31, the diaphragm membranes 225 have a concentric wave pattern 226, similar to that shown in FIG. 26. In both cases, the diaphragm membranes 220, 225 of the reusable connector portion 258 complement the diaphragm members 220, 225 of the disposable flow conduit portion 259, such that upon connection of the reusable and disposable parts 258, 259, as shown in FIGS. 29 and 31, pressure equalization across the diaphragm structure 220, 225 is still able to occur, resulting in accurate pressure readings.

When subject to varying pressures (e.g., due to changing altitude), because the diaphragm membrane 220, 225 is sealed to the chamber 252, 253 in which the pressure sensor 254, 255 is located, the diaphragm membrane 220, 225 may have a tendency to bulge inward or outward, which may affect pressure readings. For example, at high altitude, the surrounding pressure may be lower than atmospheric, providing less ambient resistance to the diaphragm membrane 220, 225 as compared to atmospheric pressure. Similarly, at surrounding pressures higher than atmospheric, the ambient resistance to the diaphragm membrane 220, 225 may be greater than atmospheric pressure.

Figure 34:
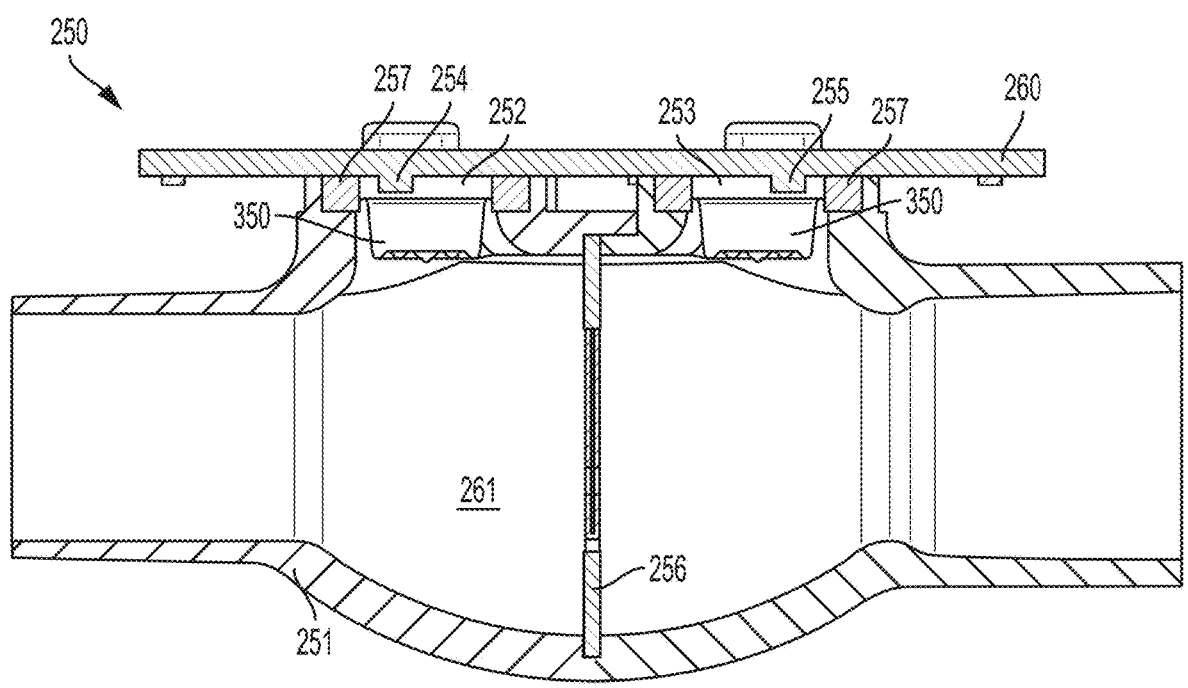
FIG. 34 is a cross-sectional view of a flow sensor system incorporating the rolling diaphragm of FIG. 32 according to an embodiment of the present disclosure when subjected to lower than normal ambient atmospheric pressure.
Figure 35:
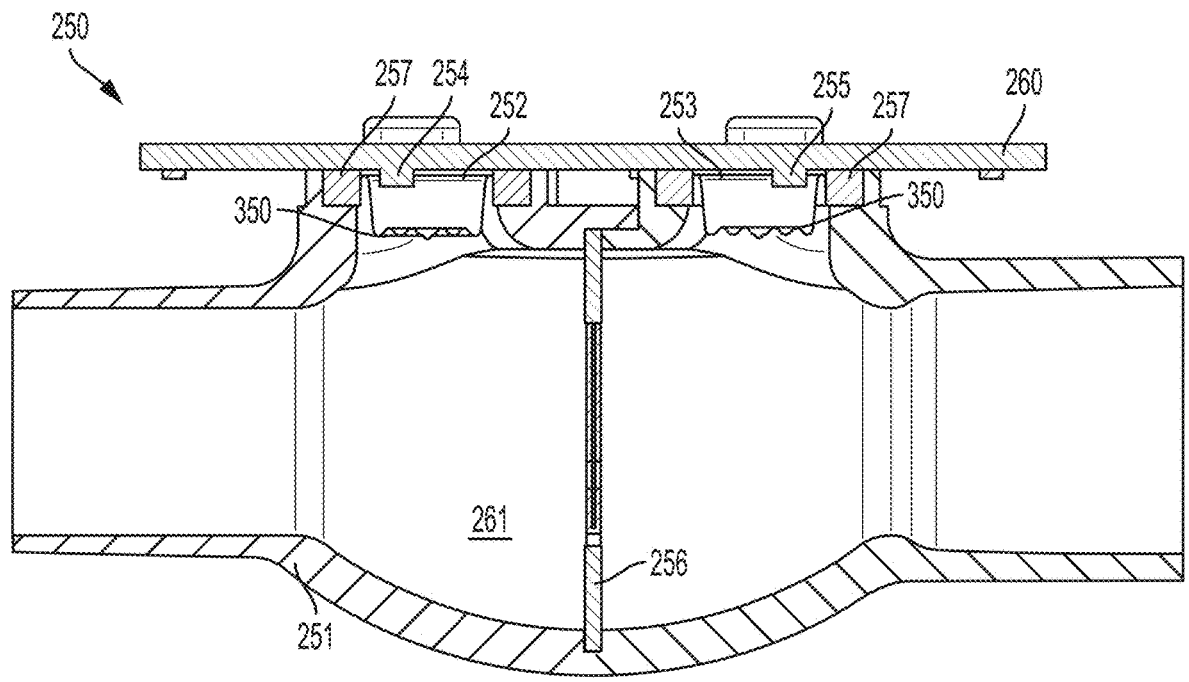
FIG. 35 is a cross-sectional view of the flow sensor system of FIG. 34 when subjected to normal ambient atmospheric pressure.

Accordingly, it may be preferable to compensate for such fluctuation in ambient pressures. In some embodiments, a rolling diaphragm configuration may be incorporated, such as that shown FIGS. 32-36, which depict a flow sensor system 300, according to an embodiment of the present disclosure, which includes a rolling diaphragm 350. As shown in FIGS. 34 and 35, the flow sensor system 300 includes a flow conduit 301, which defines a lumen 302 in which a flow restrictor 303 is disposed, as discussed above with reference to the other embodiments. Chamber housings 304 are disposed above the flow conduit 301. The chamber housings 304 define chambers 305, 306, in which are disposed first and second pressure sensors 307, 308, respectively. The pressure sensors 307, 308 are connected to a circuit board 309. The flow conduit 301 and flow restrictor 303 may form part of a disposable flow conduit portion 310 while the circuit board 309 and pressure sensors 307, 308 may form part of a reusable connector portion 311, similarly to the flow sensor system 250 discussed above with reference to FIGS. 25-31. The chamber housings 304 and rolling diaphragms 350 may be included in the disposable flow conduit portion 310 or the reusable connector portion 311, as also discussed above, though it is to be appreciated that if the chamber housings 304 form part of the reusable connector portion 311, then two rolling diaphragms 350 for each respective chamber 305, 306 and pressure sensor 307, 308 may be provided.

Figure 36:
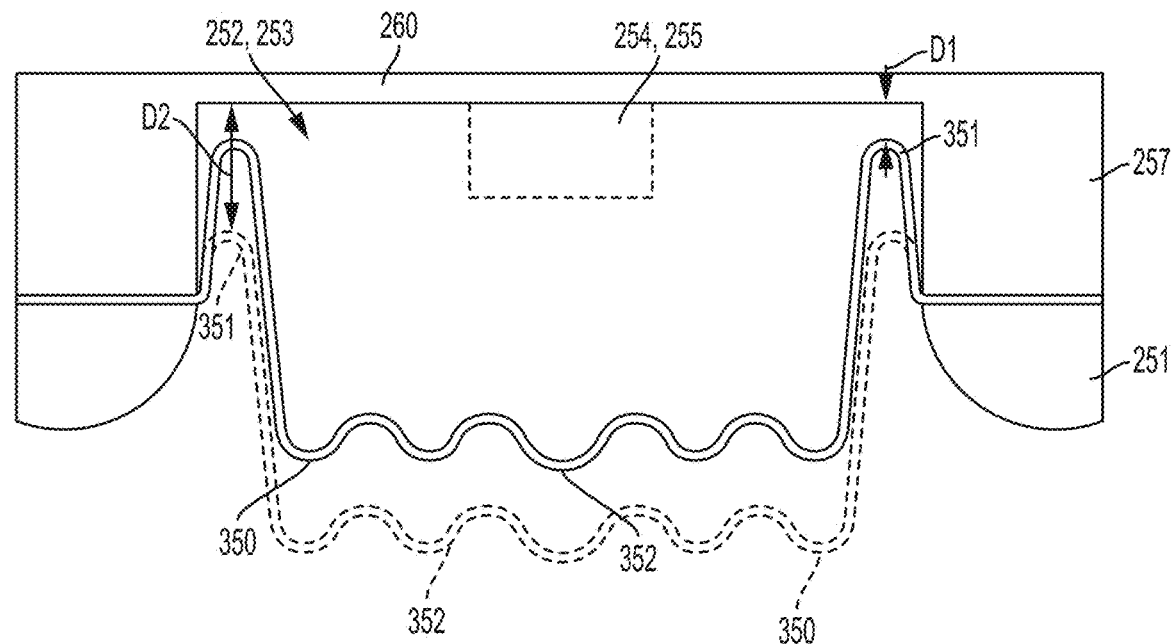
FIG. 36 is a schematic illustrating the deflection of the rolling diaphragm of FIG. 32 within the chamber housing and flow conduit of the flow sensor system of FIG. 34.

FIG. 36 provides cross-sectional representation of one of the chamber 305, 306, including a housing 304, pressure sensor 307, 308 and rolling diaphragm 350. As shown, the rolling diaphragm includes a rolling portion 351, a diaphragm membrane 352 incorporating a wavy patterned structure 353, as discussed above, and a peripheral flange 354. Here, the diaphragm membrane 352 may move up and down relative to the chamber 305, 306 to provide equilibrium between the pressure within the chamber 305, 306 and the surrounding ambient pressure. Once the rolling diaphragm 350 equilibrates, the diaphragm membrane 352 is able to accurately transfer pressure between the flow lumen 302 and the chamber 305, 306. The rolling portion 351 deflects or is manipulated according to the ambient pressure (atmospheric pressure) to allow the diaphragm membrane 351 to move up and down relative to the chamber 305, 306. The peripheral flange 354 allows for the rolling diaphragm 350 to be secured between the chamber housing 304 and the flow conduit 301.

Figure 33:
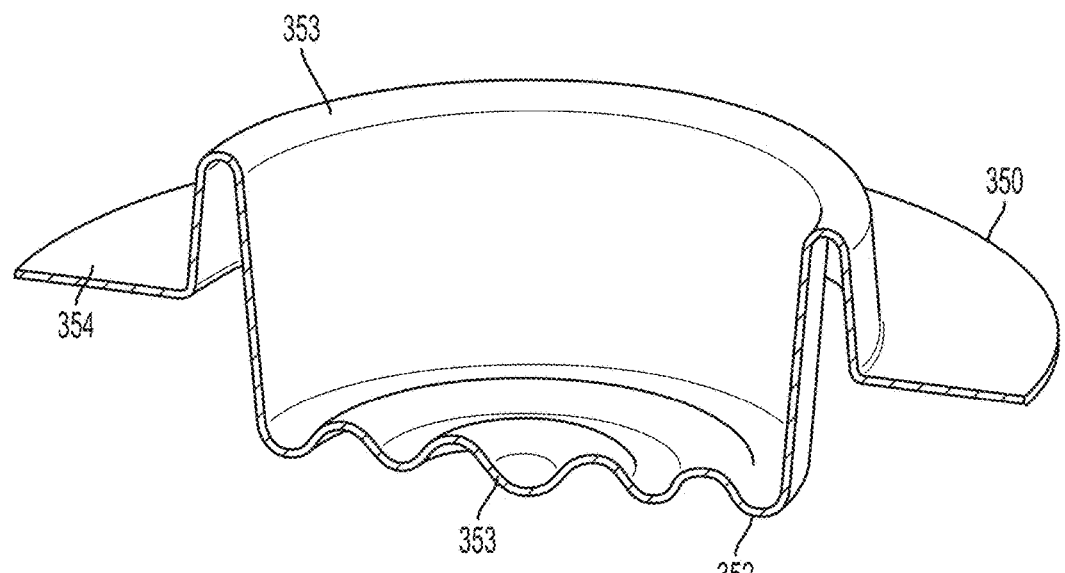
FIG. 33 is a cross-sectional perspective view of the rolling diaphragm of FIG. 32 when subjected to normal ambient atmospheric pressure.

For example, FIGS. 33, 35, and 36 (solid diaphragm) show the rolling diaphragm 350 having equilibrated with ambient pressure (atmospheric pressure) at relatively low altitude. Here, there is a sufficient distance D1 (shown in FIG. 36) between the rolling portion 351 of the rolling diaphragm 350 and the circuit board 309 so that an accurate pressure reading can be obtained. And as such, the wavy patterned structure 353 of the diaphragm membrane 352 is able to move freely back and forth to suitably transfer pressure between the flow lumen 302 and the chamber 305, 306.

Figure 32:
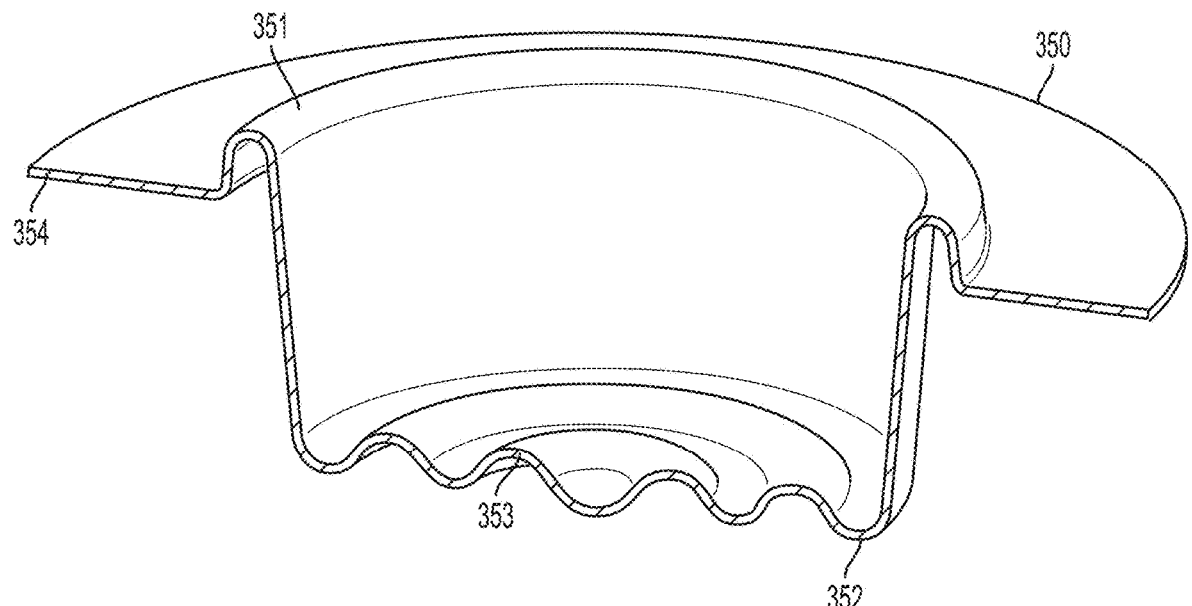
FIG. 32 is a cross-sectional perspective view of a rolling diaphragm according to an embodiment of the present disclosure when subjected to lower than normal ambient atmospheric pressure.

In FIGS. 32, 34, and 36 (dashed diaphragm), the chamber 305, 306 is exposed to higher altitude (lower than atmospheric pressure), and so instead of the diaphragm membrane 352 bulging outward, the rolling diaphragm 350 moves down with respect to the chamber 305, 306 until mechanical equilibrium is reached between the pressure within the chamber 305, 306 and the surrounding ambient pressure (lower than atmospheric pressure). Accordingly, the distance D2 between the rolling portion 351 of the rolling diaphragm 350 and the circuit board 309 (when the chamber 305, 306 is subject to lower than atmospheric pressure) is comparatively greater than the distance D1 (when the chamber is subject to atmospheric pressure). The wavy patterned structure 353 of the diaphragm membrane 352 is thus able to move back and forth unfettered, so as to be able to transfer pressure between the flow lumen 302 and the chamber 305, 306, to obtain substantially accurate readings.

Returning to FIGS. 7 and 10-13, the flow sensor system 100 comprises two membranes 108 disposed between the lumen 102 and a respective one of the two chambers 114, 123. More specifically, each membrane 108 is positioned on the interior surface of the flow conduit 101 over the respective conical/tapered cavity 120 leading to the respective opening 119 and chamber 114, 123. Each membrane 108 comprises a thin, bendable filter layer 126 that comprises a breathable, hydrophobic material that is configured to allow for the passage of gas through the membrane 108 and also act as a barrier to obstruct or prevent the passage of moisture and debris through the membrane 108. The conical/tapered cavity 120 is also shaped to allow for the surface area of the bendable filter layer 126 to be enlarged to a sufficiently large surface area so as to minimize or otherwise reduce the impedance to the flow gas to the sensors 131, 132 created by the bendable filter layer 126. According to one particular embodiment of the present disclosure, each bendable filter layer 126 has an approximate surface area of between approximately 10 mm$^2$ and 100 mm$^2$, or approximately 30 mm$^2$ and 60 mm$^2$, or 45.6 mm$^2$ or any other appropriate surface area.

According to one embodiment of the present disclosure, the filter layer 126 may comprise at least one of the following materials: polytetrafluoroethylene (PTFE), of the type sold under the brand name TEFLON®; expanded polytetrafluoroethylene (ePTFE), of the type sold under the brand name GORE-TEX®; and woven fabric. In some embodiments, the filter layer includes an oleophobic and/or hydrophobic material. The filter layer 126 may have pores between 0.1 and 1 micron (e.g., approximately 0.5 µm) with polyester/polyethylene scrim. Alternatively, the filter layer 126 may be coated with a breathable hydrophobic material that comprises one of the following materials: polytetrafluoroethylene (PTFE) and expanded polytetrafluoroethylene (ePTFE). The filter layer 126 of each membrane 108 is configured to allow gas to pass through from the lumen 102 to the respective opening 119 and chamber 114, 123 in which the respective one of the first and second absolute pressure sensors 131, 132 is positioned to obstruct or prevent the passage of liquid and debris, such as dust, sputum, or saliva, from passing through to interfere with the operation or readings of the first and second absolute pressure sensors 131, 132. Alternatively, a single membrane 108 may be provided that extends across both cavities 120 and openings 119 or more than two membranes 108 may be provided.

As shown in FIGS. 11-13, in addition to the filter layer 126 each membrane 108 may optionally include an adhesive layer 127 surrounding the filter layer 126 for applying the membrane 108 to the interior surface of the flow conduit 101 and a flap 128 for securing the membrane on the respective first and second piece 106, 107 of the flow conduit 101. The flap 128 comprises holes 129 defined therein that may receive pins 118 extending from the end of the respective first and second piece 106, 107 of the flow conduit 101 where the piece 106, 107 is attached, formed or otherwise secured to the other piece 106, 107. Each piece 106, 107 may optionally include ribs 117 provided therein on the interior surface that hold the respective membrane 108 in place. In some embodiments, the membrane(s) 108 are held in place by a structure and/or adhesive other than the depicted supporting ribs 117. During assembly, each membrane 108 is applied to the interior surface of a respective piece 106, 107 of the flow conduit 101 and against the ribs 117 in the respective piece 106, 107 such that the flap 128 is flexed to extend over the ends of the ribs 117 with the pins 118 being received in the holes 129 defined in the flap 128. The flaps 128 are thereby secured between the pieces 106, 107 when the pieces 106, 107 are fastened together. Though, it can be appreciated that the membrane(s) 108 may be coupled to the flow conduit by any other suitable method. For instance, the membrane(s) 108 and a corresponding receiving region of the flow conduit 101 may have complementary structural features which allow for the membrane(s) 108 to be coupled thereto. As an example, edges of the membrane(s) 108 may be able to slide into complementary slots/recesses of the flow conduit 101, for holding the membrane(s) 108 in place.

Certain regions of the flow sensor system may be sensitive to the accumulation of water and/or debris, for example, associated with inspiratory and expiratory flow. For example, if water or debris collects at the flow restrictor, or portions thereof, the (pre-calibrated) pressure-flow relationship may be affected. Similarly, if water or debris collects at or around the membrane (e.g., porous barrier membrane, non-porous diaphragm barrier membrane, or other membrane-type component) between the lumen of gas flow and the chamber within which the pressure sensor(s) are located, the accuracy of pressure sensing may also be affected. Accordingly, it may be preferable for water and/or debris to be diverted from the more sensitive regions of the flow sensor (e.g., regions that may contribute to the overall accuracy of flow determination) to other neighboring regions that are less sensitive to determining the accuracy of flow. Hence, one or more sensitive regions of the flow sensor (e.g., membrane between lumen of flow conduit and pressure sensor, flow restrictor) may exhibit a greater level of hydrophobicity than the neighboring region(s) adjacent to the sensitive region(s). For instance, the flow sensor may be configured such that water is less likely to condense at the sensitive region(s) but more likely to condense or otherwise collect at region(s) that neighbor the sensitive region(s).

Figure 13B:
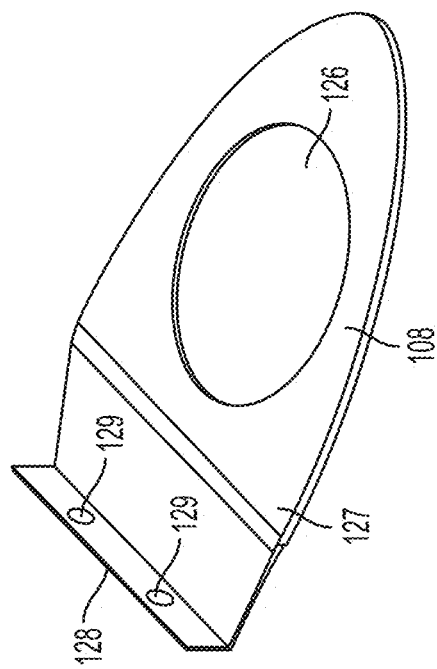
FIGS. 13(a) and (b) are perspective views of a barrier of the flow conduit assembly of FIG. 8.
FIGS. 13(c) and (d) are perspective cross-sectional views of a flow conduit showing the effects of accumulation within the lumen.
Figure 13A:
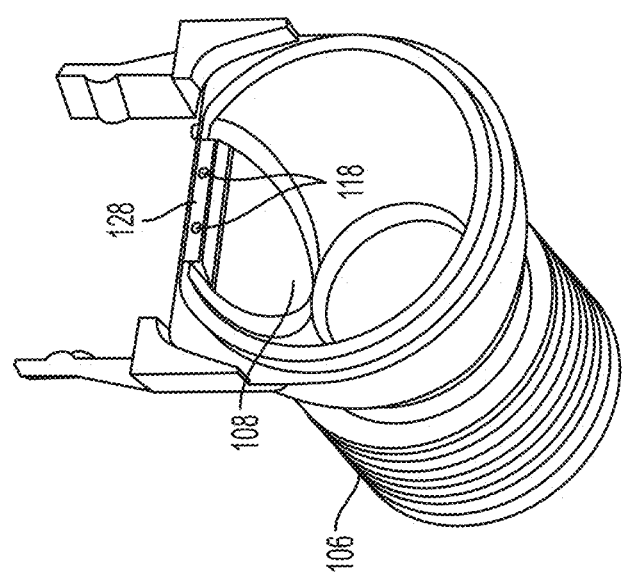

Referring to FIGS. 13(a) and 13(b), the membrane 108 may include a material (e.g., polytetrafluoroethylene) that exhibits a greater level of hydrophobicity than regions neighboring the membrane, such as the surface of the flow conduit immediately adjacent to the membrane. The more hydrophobic material may comprise the membrane, or may be coated thereon. The surface of the flow conduit neighboring the membrane may include a plastic or polymeric material that is less hydrophobic (or more hydrophilic) as compared to the membrane, resulting in water accumulation or diversion away from the membrane and toward the neighboring region. Or, the membrane itself may have regions which exhibit different levels of hydrophobicity. For example, the filter layer 126 may include a relatively hydrophobic material (e.g., polytetrafluoroethylene), and the surrounding adhesive layer 127 may be hydrophilic, or less hydrophobic, in comparison to the filter layer 126. Due to such a structure, water may tend to accumulate or be diverted away from the filter layer 126 and toward the neighboring adhesive layer 127, or even further away.

Figure 13C:
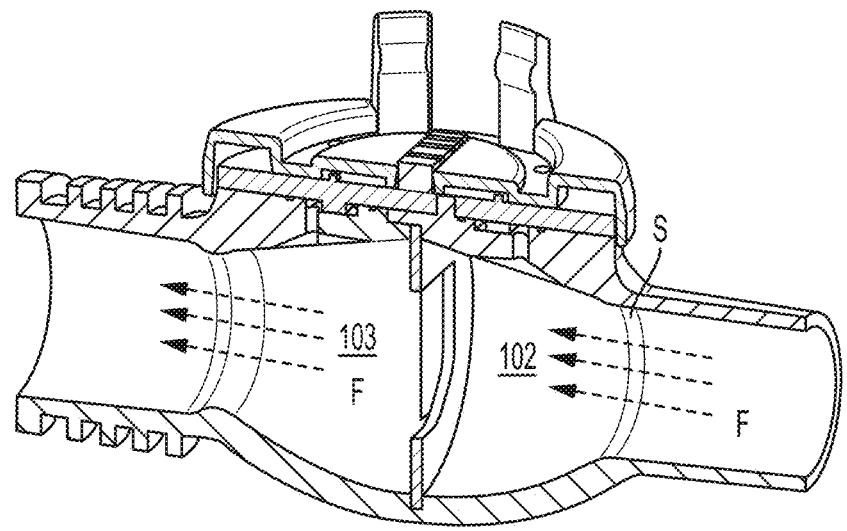
Figure 13D:
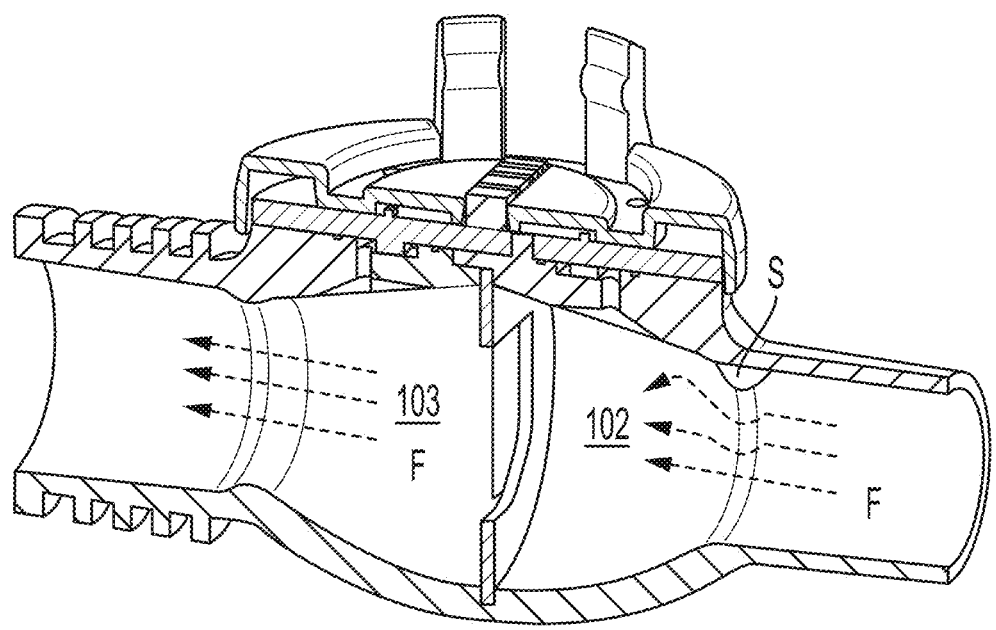

Or, referring to FIGS. 13(c) and 13(d), in some cases, other portions of the flow sensor may be sensitive to overall accuracy of the flow determination. For instance, the internal structure of the flow conduit may be shaped so that the flow through the lumen is substantially laminar. In general, such smooth flow may lead to predictable, accurate pressure/flow readings. FIG. 13(c) illustrates an example where gas flow F through the conduit is generally unimpeded. However, the accumulation of water and/or debris in certain areas of the flow conduit may affect the pressure/flow readings. For example, the buildup of water and/or debris in such areas may give rise to undesirably turbulent flow, resulting in less accurate measurements. FIG. 13(d) depicts an instance where water and/or debris is collected at a sensitive region S, in a manner where gas flow in proximity to the accumulation is affected.

Accordingly, it may be desirable for certain regions of the flow conduit to be more resistant to such accumulation than others. Similar to that of other sensitive regions of the flow sensor system, certain regions of the flow conduit may include a material (e.g., polytetrafluoroethylene) that exhibits a greater level of hydrophobicity than regions neighboring the more sensitive regions. The sensitive region(s) of the conduit may be made up of the more hydrophobic material, or the more hydrophobic may be coated thereon. Alternatively, neighboring regions around the sensitive region may include a material that is comparatively more hydrophilic than the sensitive region. For example, the surface of the flow conduit neighboring the more sensitive region(s) may include a plastic or polymeric material that is less hydrophobic (or more hydrophilic) as compared to the surface of the sensitive region(s), resulting in water accumulation or diversion away from the sensitive region(s) and toward the neighboring region(s).

Additionally, the flow conduit 101 may also incorporate a rim made from a hydrophilic material (not shown), or a material that is comparatively less hydrophobic than more sensitive regions of the flow sensor, for instance in one of the connection portions 116, 124, that is configured to collect moisture and debris from the gas flowing through the lumen 102. The flow conduit 101 may also comprise a condensation element (not shown), such as a gridded aluminum plate, that is configured to collect moisture and debris from the gas flowing through the lumen 102. Such a configuration may help to mitigate the accumulation or presence of contaminants that would otherwise contribute to inaccuracies in the flow sensing measurements.

The circuit board may be secured to the flow conduit by any suitable manner, for example, via mechanical attachment (e.g., welding, adhesive, interference fit, complementary coupling features, etc.). With reference to FIGS. 11 and 12, a ring hole 115 may be provided in the top surface of each of the first and second pieces 106, 107 around the respective chamber 114, 123. A sealant or adhesive may be placed within the ring holes 115 to secure the circuit board 110 to the upper surface of the flow conduit 101. The upper surfaces of the first and second pieces 106, 107 also comprise upwardly extending pins 121. The pins 121 are received in pin holes 130, shown in FIG. 13, extending through the circuit board 110 to assist in positioning and securing the circuit board 110 on the upper surface of the flow conduit 101.

With reference to FIGS. 6-9, 14, 15, and 18, an adapter 112 may be disposed on an upper surface of the circuit board 110 and is electronically connected to the circuit board 110. In this embodiment, the trace contacts of the circuit board to which the adapter 112 provides electrical communication with the connector 113 extend along a direction substantially parallel to the long axis of the circuit board, although other configurations may be possible. The adapter 112 is provided to establish electronic communication between the circuit board 110 and a connector 113, as will be discussed in further detail below. As shown in FIG. 14, the circuit board 110 may also incorporate at least one heating element 133, such as a resistive device (e.g., electrical resistor), that is configured to be energized to generate a small amount of heat upon the application of a current in or near the chambers 114, 123 defined in the upper surface of the flow conduit 101. The heat generated by the heating element(s) may be sufficient to prevent or otherwise limit the risk of fluid accumulation near the first and second absolute pressure sensors 131, 132. That is, while the membrane(s) 108 may act as a barrier to keep liquid water in the lumen from entering respective chambers 114, 123, the membrane(s) may allow water vapor to pass there through. In this example, the heating element(s) may raise the local temperature around the surface of the pressure sensor(s) in a manner suitable to prevent or otherwise mitigate against the risk of condensation of water vapor that may be present at the pressure sensor(s). In some cases, a single heating element may be used to prevent condensation of the pressure sensors, or multiple heating elements may be used, for example, dedicated heating elements for each pressure sensor (e.g., heating elements located adjacent to each pressure sensor).

Figure 14B:
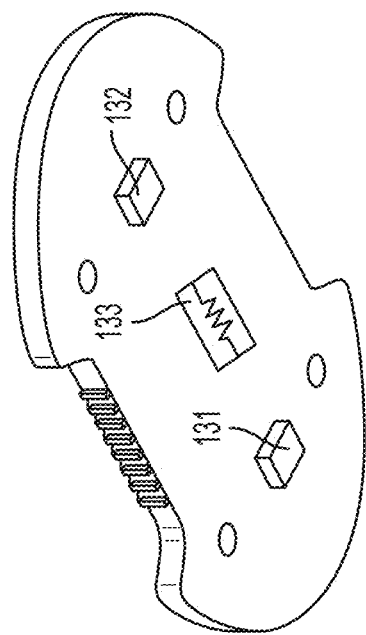
FIGS. 14(a) and (b) are perspective views of a circuit board of the flow conduit assembly of FIG. 8.
FIGS. 14(c) and 14(d) are perspective views of an alternative circuit board of the flow conduit assembly of FIG. 8
Figure 14A:
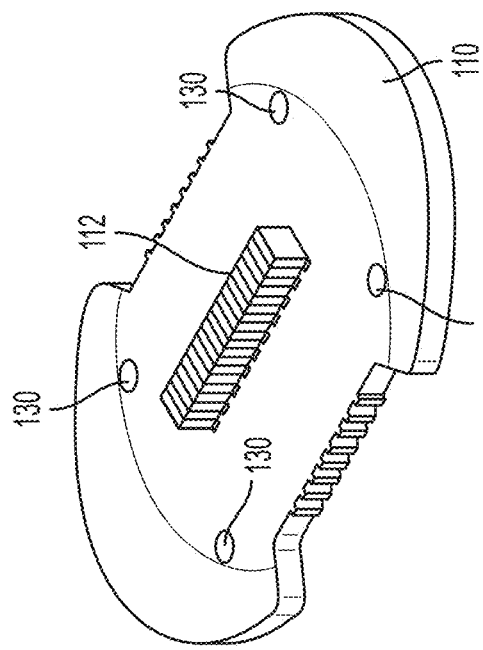
Figure 14C:
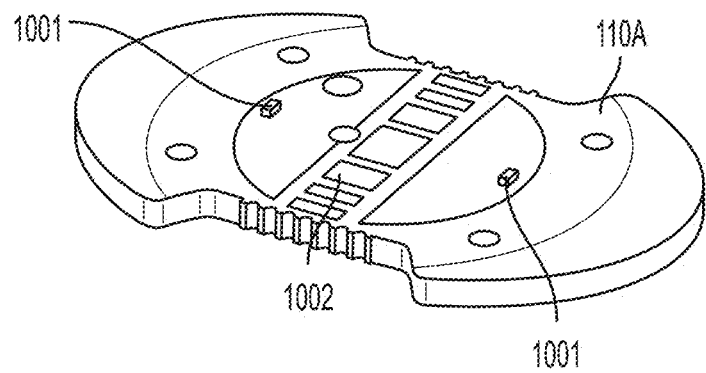
Figure 14D:
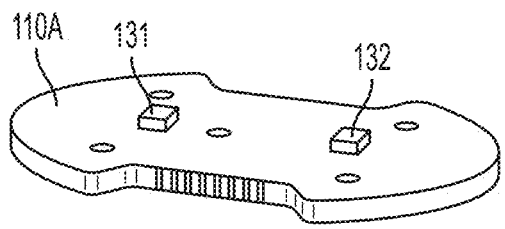

FIGS. 14(c)-14(d) depict another embodiment of a circuit board 110A wherein multiple heating elements are employed. FIG. 14(c) shows an upper perspective view of the circuit board 110A having two heating elements 1001 located on either side of the trace contacts 1002. Here, in contrast to the configuration provided above with respect to the FIG. 14, the trace contacts 1002 of the circuit board 110A, to which the adapter 112 provides electrical communication with the connector 113, extend laterally in a direction substantially perpendicular to the long axis of the circuit board 110A. Such a configuration may be preferable so that the heating elements 1001 (e.g., resistors) may be suitably placed in close proximity to the pressure sensors 131, 132. FIG. 14(d) shows a lower perspective view of the circuit board 110A, which shows the two pressure sensors 131, 132 in close proximity to respective heating elements 1001, which are located on the other side of the board 110A.

As shown in FIGS. 6-9, 15, and 18, the flow sensor system 100 also comprises a cover 111 for the circuit board 110. The cover 111 is positioned on the upper surface of the flow conduit 101 over the circuit board 110. Both the circuit board 110 and the cover 111 are shaped to correspond to the shape of the upper surface of the flow conduit 101 in order to fit on the flow conduit 101 and hold the circuit board 110 in place. The cover 111 comprises an opening and holder 134 for the adapter 112 on the circuit board 110 so that the adapter 112 may extend through the cover 111 and be supported in a position where it can establish electronic communication with the connector 113. The cover 111 also comprises an alignment disk 135 positioned on the top of the cover 111. The alignment disk 135 is configured to provide a guide for positioning the connector 113 so that the connector 113 may be electronically connected to the adapter 112 and to limit lateral movement of the connector 113 once the connector 113 is connected to the flow conduit 101. The alignment disk 135 may be recessed from the bottom for components of the circuit board 110, such as resistors and/or other electrical components. The cover 111 may also incorporate internal chambers 137 to accommodate components on the circuit board 110 and/or other features of the flow sensor system. The cover 111 comprises a plurality of pin holes 136 extending through the cover 111. The pin holes 136 are configured to receive the pins 121 extending from the upper surface of the flow conduit 101 in order to assist in positioning and securing the cover 111 on the upper surface of the flow conduit 101.

Figure 15A:
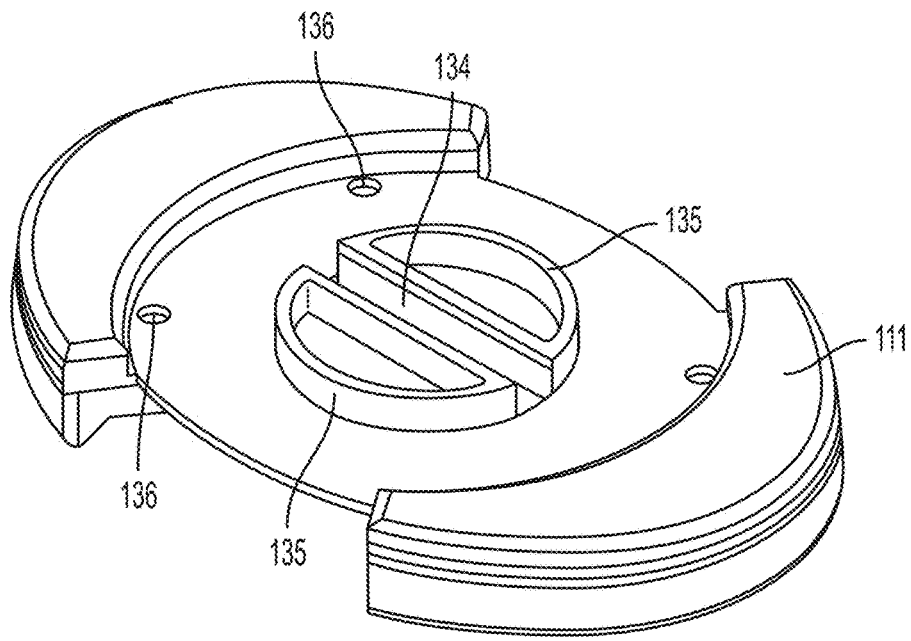
FIGS. 15(a) and (b) are perspective views of a circuit board cover of the flow conduit assembly of FIG. 8.
Figure 15B:
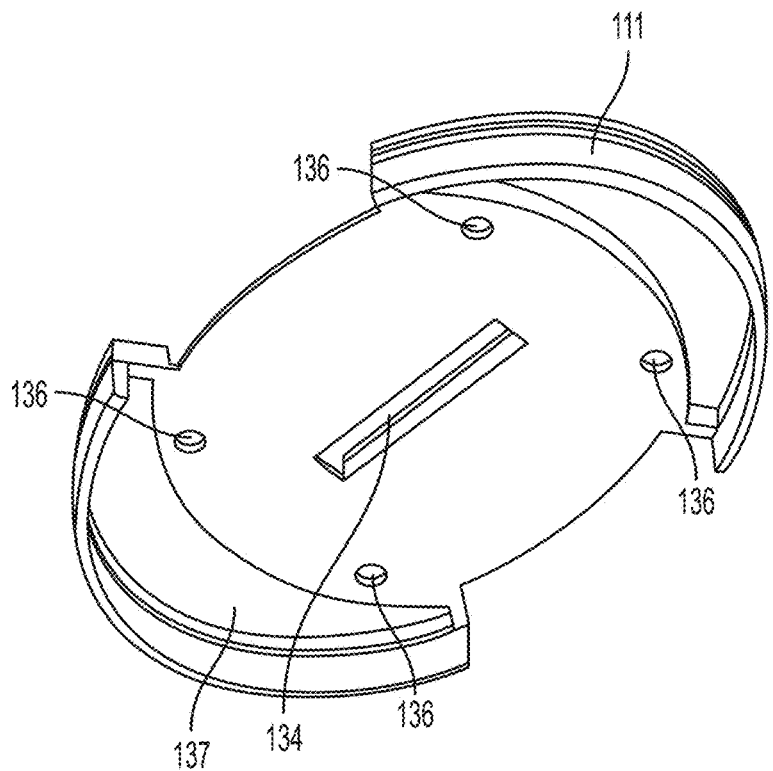
FIGS. 15(c) and 15(d) are perspective views of an alternative circuit board cover of the flow conduit assembly of FIG. 8.
FIG. 15(e) is a cross-sectional view of a region where an adapter is held in accordance with an embodiment.
Figure 15C:
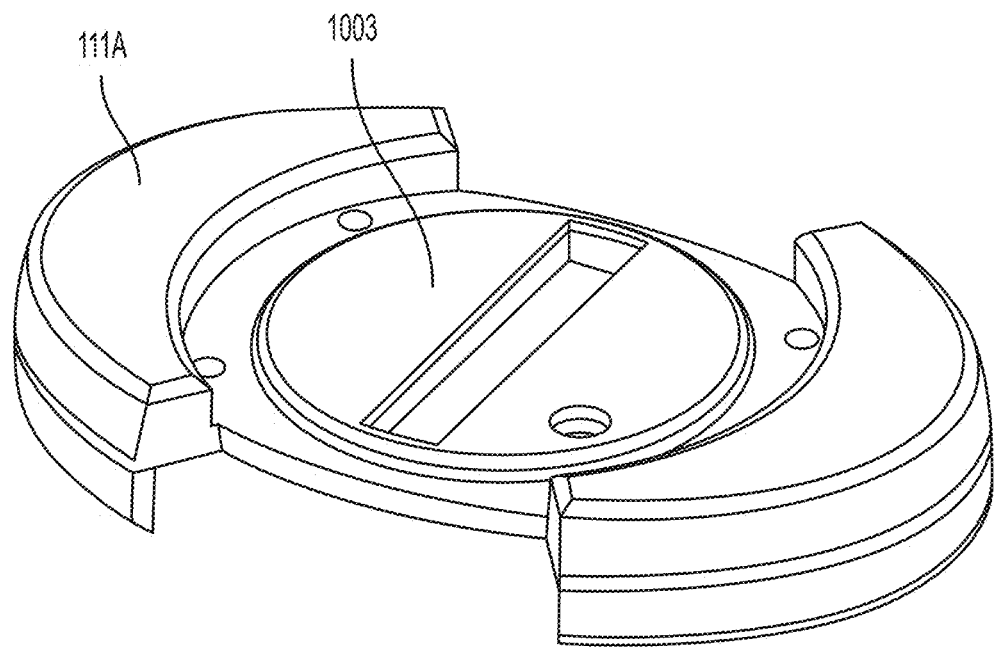
Figure 15D:
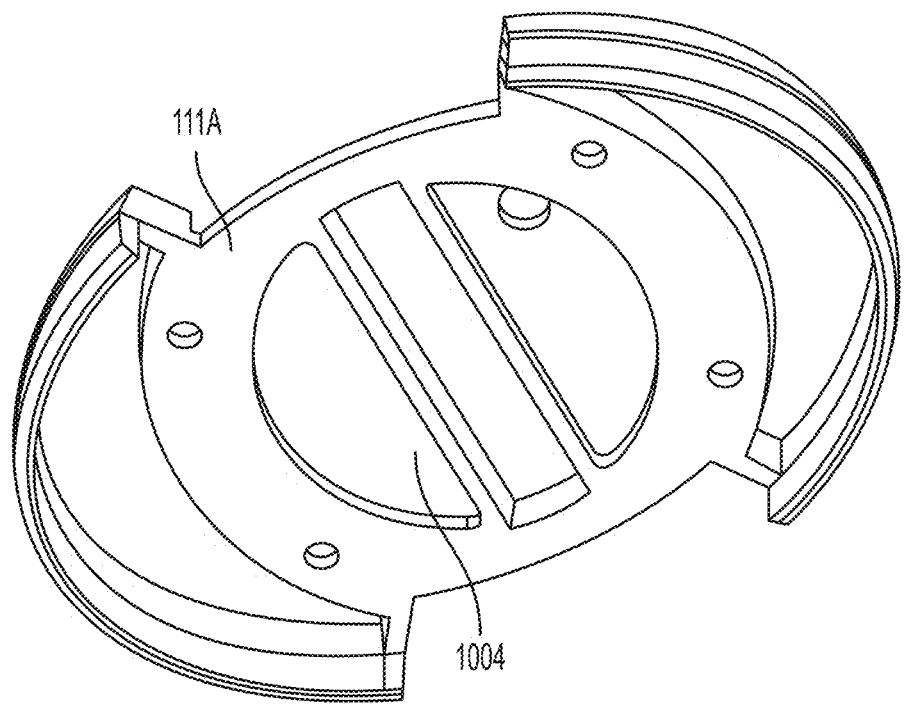
Figure 15E:
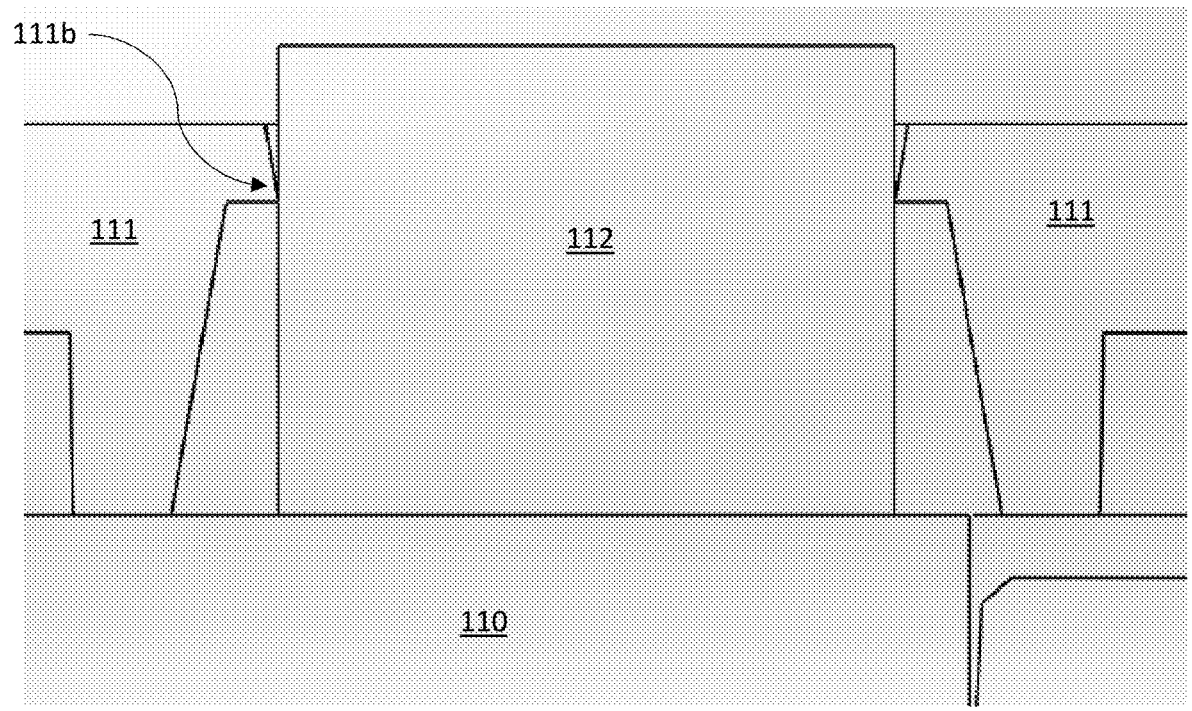

FIGS. 15(c) and 15(d) illustrate another embodiment of a cover 111A for the circuit board 110A that complements the configuration shown in FIGS. 14(c) and 14(d). FIG. 15(c) shows an upper perspective view of the cover 111A, showing an alignment disk 1003 configured to mechanically assist positioning of the connector 113, for establishing a suitable electrical connection. FIG. 15(d) shows a lower perspective view of the cover 111A that includes a recess 1004 to provide space for components of the circuit board 110A, such as resistors and/or other electrical components. FIG. 15(e) depicts an implementation where the adapter 112 is held in place by the cover 111. In this case, the cover 111 includes barbs 111b that protrude toward the adapter 112 and are tapered so as to facilitate placement of the adapter 112 on the circuit board 110, and to hold the adapter 112 securely against the circuit board 110 when placed. Accordingly, in this instance, the adapter 112 remains in firm electrical connection with the circuit board 110 without requiring further assistance (e.g., from an adhesive) to ensure that the electrical connection is maintained.

With reference to FIGS. 6, 7, and 16-18, the flow sensor system 100 also comprises the connector 113 that places the first and second absolute pressure sensors 131, 132 in electronic communication with a processor 145. The processor 145 may be configured receive the absolute pressure measurements from the first and second absolute pressure sensors 131, 132 and may determine at least one of a flow rate and a volume of gas flowing through the lumen 102 of the flow conduit 101 based on the pressure measurements in the first and second regions 103, 104 of the flow conduit 101. The processor 145 may also be configured to generate a signal outputting the determined flow rate and/or volume of gas flowing through the flow conduit 101 and/or to send a feedback signal to adjust the gas flow through the lumen 102 of the flow conduit 101 based on at least one of the determined flow rate and the volume of gas flowing through the lumen 102.

Though, it is not required for the processor 145 to perform each of the aforementioned calculations. For example, in some embodiments, the processor 145 may perform none of these calculations and simply store/transmit signals arising from the pressure sensors to another computing device for further analysis and processing. Or, the processor 145 may perform some of these calculations, such as determining the flow rate through the conduit based on the signals sent from the pressure sensor (based on a pre-calibrated pressure look up table) and may further perform a mathematical integration resulting in the flow volume. An external device (e.g., tablet, defibrillator, medical computer, etc.) may then receive those values of rate and volume and send feedback signals to the processor 145, which may be further output in an intuitive manner for guiding or otherwise encouraging a user to maintain and/or improve the overall quality of resuscitation.

It can be appreciated that each of the processes for analyzing the measurement signals produced by the pressure sensor(s) 131, 132, outputting a calculated value (e.g., flow rate, flow volume, PIP, etc.), and providing a feedback signal to adjust the manner in which gas flow is provided based on the analysis of the pressure measurement signals may be performed at any suitable part(s) and location(s) of the overall medical system. For example, each of these steps may be performed at the same location by the same processor, such as a processor 145 located in the cable head or connector 113, as discussed above. Alternatively, each of these steps may be performed at different locations of the medical system by different processors (e.g., located in the cable head connector, another part of the flow sensor, a more distantly located medical device system such as a defibrillator, monitor, tablet, computer, ventilator, etc.). For instance, the processor 145 located in the cable head connector may analyze pressure measurement signals and determine the flow rate and/or volume of flow within the lumen 102 of the flow sensor system 100. As noted above, this same processor 145, or another processor (e.g., located in a monitor, defibrillator, ventilator, amongst other suitable processing systems), may further output a feedback signal to adjust flow parameters (e.g., ventilation bagging, automated ventilation characteristics).

According to various embodiments of the present disclosure, at least one the first and second absolute pressure sensors 131, 132 may be configured to measure the absolute pressure in immediate proximity to the pressure sensors, a temperature of gas flowing through the lumen 102 of the flow conduit 101, a humidity of gas flowing through the lumen 102, and/or to measure the ambient atmospheric pressure outside of the flow sensor system 100. Alternatively, the flow sensor system 100 may incorporate sensors that are configured to measure at least one of the following other than the absolute pressure, for example, a temperature of gas flowing through the lumen 102 of the flow conduit 101, a humidity of the gas flowing through the flow conduit 101, and an ambient atmospheric pressure outside of the flow sensor system 100. In some embodiments, the pressure sensor(s) used to determine the local absolute pressure(s) may also be used to measure the local temperature, humidity, altitude, amongst other parameters. In some cases, the pressure sensor(s) and/or one or more additional sensors may be used to sense the relative concentration of gas flowing through the conduit (e.g., oxygen, carbon dioxide concentration).

Exemplary CO2 concentration sensors may include those provided in capnographs that measure infrared light absorption. Oxygen gas partial pressure may be measured by a suitable ppO2 meter such as those used in SCUBA-diving, or re-breathing apparatus. A specific example is the PSR-11-33-NMI oxygen sensor manufactured by Analytic Industries, Inc. (Pomona Calif.). This sensor works off the principle of an electro-galvanic fuel cell. Oxygen concentration sensing may also be done with an oxygen optode. In general, an oxygen optode is a sensor based on optical measurement of the oxygen concentration. In some examples of oxygen optodes, a chemical film is glued to the tip of an optical cable and the fluorescence properties of this film depend on the oxygen concentration. Fluorescence is at a maximum when there is no oxygen present. When an O2 molecule is present and collides with the film, this quenches the photoluminescence. For a given oxygen concentration there will be a specific number of O2 molecules colliding with the film at any given time, and the fluorescence properties will be stable. Thus, by observing the fluorescence properties O2 concentration can be determined.

As provided herein, the total volume of ventilation gas delivered to and from the lungs may be calculated by measuring the continuous flow rate for each individual inhalation and exhalation and then integrating the flow over time to compute volume. As concentrations may be available for each of the measured gases for each instant, the volumes delivered for each ventilation for each of the specific gases may also be calculated along with the volume delivered for all other gases not measured. In one embodiment, the measured gases are CO2 and oxygen, with the remaining gases being predominantly nitrogen. In other embodiments, gas concentrations for other gases may be provided such as additive gases that have therapeutic value such as anaesthetic gases, nitric oxide or a noble gas such as Argon.

As discussed further below, the minute-volume, as understood by those skilled in the art, for each of the measured constituent gases can be calculated. In general, minute-volume is the quantity of gas delivered to the patient, or exhaled from the patient in the case of CO2, over a one-minute period. Unlike tidal volume which is the volume delivered for a particular breath, minute volume is based on the one-minute period. The calculated minute-volume for any point in time may be calculated by summing each of the individual tidal volumes in the previous minute, or it may be estimated based on the tidal volumes of breaths occurring within some predefined time period in the immediate past.

The processor 145, or one or more processors positioned elsewhere from the connector (e.g., located at the flow sensor conduit and/or at a medical device to which the flow sensor is connected), is configured to compensate for effects of altitude, humidity of the gas flowing through the lumen 102 and/or temperature of the gas flowing through lumen 102 in determining the at least one of the flow rate and the volume of gas flowing through the lumen 102.

Figure 22A:
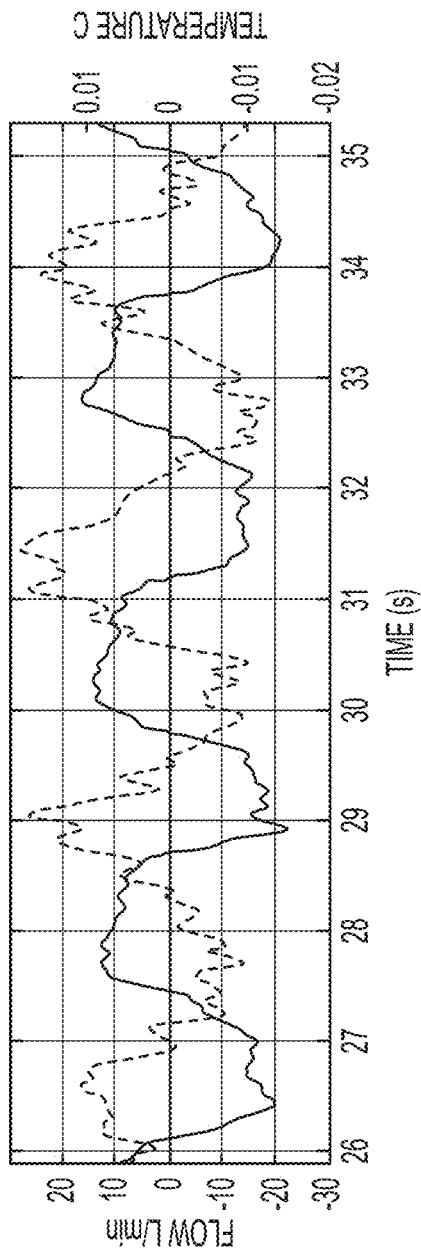
FIGS. 22(a) and (b) are charts illustrating flow and temperature versus time for a ventilation system according to an embodiment of the present disclosure.
Figure 22B:
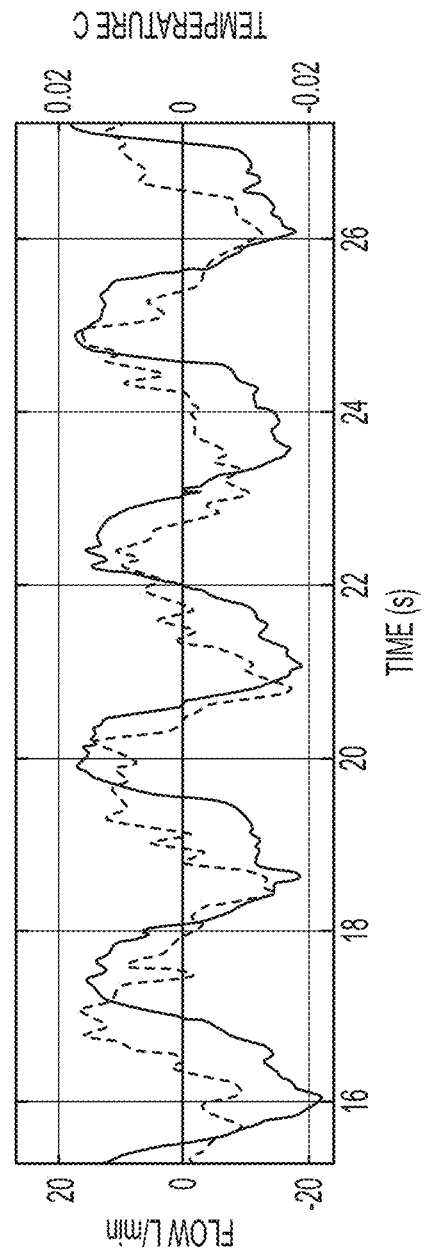

FIG. 22 illustrates the relationship between the flow of gas, the temperature of gas and time in the flow sensor conduit for a spontaneously breathing person. The solid line illustrates flow in liters/minute and the dashed line illustrates temperature in degrees Celsius. For a particular flow sensor orientation, FIG. 22(*a*) measures inspiratory flow to the patient as negative (below the 0 point of the horizontal axis) and expiratory flow from the patient as positive (above the 0 point of the horizontal axis). Here, the flow rate and temperature appear to be substantially out of phase. When the flow sensor is flipped around so as to be oriented in a reverse orientation, FIG. 22(*b*) measures inspiratory flow to the patient as positive and expiratory flow from the patient as negative. In this case, the flow rate and temperature appear to be substantially in phase. As can be appreciated from FIG. 22, the temperature of the gas within the flow sensor conduit rises in response to warm gas being exhaled by the patient into the flow sensor and correspondingly drops as cooler gas (e.g., gas at room temperature, typically lower in temperature than expired air) is inhaled by the patient. In particular, during expiration, the temperature increases and reaches a peak shortly after the end of expiration; and conversely, during inspiration, the temperature decreases and reaches a minimum shortly after the end of inspiration. Accordingly, by measuring the temperature of the gas within the flow conduit 101 in conjunction with the absolute pressures within the first and second regions 103, 104, it is demonstrated that the temperature may be used as an indicator for the direction of flow (inspiratory or expiratory) that is occurring through the flow sensor.

Based on the above discussion, the processor 145 and/or a user can determine the direction of flow through the lumen 102 based on the temperature measurement from the sensor(s) of the flow sensor system whether flows are expiratory, due to the patient exhaling gas through the flow conduit 101, or inspiratory, due to gas being delivered to the patient through the flow conduit. This may further allow the processor 145 and/or a user to determine how the flow sensor system 100 is oriented within the ventilation assembly and which of the sensors 131, 132 is oriented toward the patient and which is oriented away from the patient and provide an operator an indication of the orientation of the flow sensor system 100. The processor 145 can also use these measurements to determine inhalation and exhalation volumes separately based on the determination of whether flows are inspiratory or expiratory. Accordingly, the processor 145, or one or more processors positioned elsewhere from the connector (e.g., at the flow sensor conduit and/or at a medical), is configured to determine at least one of the flow rate, the direction of flow and volume of gas flowing through the lumen 102 based on the pressure measurements and at least one of the following: the temperature measurement, the humidity measurement, and the ambient atmospheric pressure.

As discussed herein, the flow sensor system may be able to determine both the flow rate/volume through the conduit and the direction of flow. That is, both the inspiratory and expiratory flow rate/volume may be determined. Accordingly, the system may further be able to detect the presence of a leak. For example, if there is no leak, the inspiratory and expiratory volumes will be substantially the same. Conversely, if a leak exists, the inspiratory and expiratory volumes will noticeably differ. In certain embodiments, if the difference in magnitude between inspiratory flow volume and expiratory flow volume is high enough to meet a predetermined threshold, then the system may indicate that a possible leak exists. When it is determined that a leak is present, the system may produce a signal to alert the user, for example, to check that the ventilation connection(s) are appropriately sealed.

For instances where the patient may be experiencing respiratory distress, and is not in cardiac arrest, the patient may be fitted with a non-rebreather mask (NRB) or sealed mask, which is used to assist in the delivery of oxygen therapy. A patient wearing a NRB should be able to spontaneously breathe. The NRB allows for high concentrations of oxygen to be delivered, and has one or more openings through which expired air is permitted to travel. Hence, if breaths are spontaneous and only a small amount of expiratory volume is detected, the system may detect that a NRB mask has been applied to the patient. In such cases, only inspiratory volumes may be accurate, as expiratory air is allowed to travel out of the mask through the opening(s). Thus, if it is determined that a NRB mask is being used, the flow sensor system may report inspiratory flow data, without reporting expiratory flow data.

The flow sensor system may also be useful to help determine whether an intubation tube is correctly placed. During intubation, at times, the endotracheal (ET) tube may be mistakenly misplaced into the esophagus rather than the trachea. It is also not uncommon for the ET tube to become dislodged during the course of resuscitation, or as a result of vibrations during transport by ambulance or other mode of transportation. To confirm placement of the endotracheal tube, paramedics typically rely on EtCO2 measurements. However, when patients have decreased perfusion as in cardiac arrest, the accuracy of EtCO2 may be unreliable. Hence, confirming whether there flow is present within the airway, in combination with EtCO2 and impedance measurements, may aid in the assessment of whether the tube is properly in place. When a positive pressure breath is delivered to a properly placed endotracheal tube, the EtCO2 and/or impedance would be expected to noticeably change. If the EtCO2 and/or impedance does not change, or is below a threshold value, the tube may be considered to be misplaced.

Transthoracic impedance (TTI) may also be useful for confirming endotracheal tube placement. Detection of a pressure waveform pulse may be used to initiate an analysis of either an accelerometer waveform, a TTI waveform, or both to see if the attempt to deliver respiratory gas via ventilation is delivering the gas to the lungs or to the stomach (via the esophagus). If the gas is delivered to the lungs, there will be an associated pulse waveform of the actual measured displacement of the sternal region where the accelerometer is placed (double integration of the accelerometer waveform will show a rising sternum). Alternatively, a TTI measurement can be used, as air delivered to the lungs will cause a rise in transthoracic impedance (TTI). Due to both the compressible nature of the gas as well as the fact that the lungs expand both sternally and diaphragmatically, there will be some delay following generation of the pressure pulse before the associated displacement waveform is observed from the accelerometer or the TTI measurement.

In some implementations, two pulse detection methods may be used. The first time aligns the pressure waveform pulse with the pulse waveform of the sternal displacement and TTI measurement. If the delay from the leading edge of the pressure pulse waveform to the leading edge of the displacement and TTI waveforms is less than 700 milliseconds, and the delay of the trailing edge of the pressure pulse waveform to the trailing edge of the displacement and TTI waveforms is also less than 700 milliseconds, then the displacement and TTI pulse waveforms are considered to be as a result of the ventilation cycle. The second pulse detection method uses the acceleration waveform to detect the first initial movement of the sternum due to the ventilation. The displacement waveform is calculated, and the first pulse of the acceleration signal that contributes to the displacement pulse determines the start of the sternal displacement pulse. A more accurate onset of motion of the sternum due to ventilation can oftentimes be achieved in this manner. If the displacement and TTI waveforms are found to be the result of the ventilation pressure waveform pulse, then the ET tube is considered to be in the proper location in the trachea and not in the esophagus.

If the intubation tube is placed in the esophagus, then the expired flow signal would be significantly less than the inspired flow volume. Though, if the intubation tube is correctly placed in the trachea, then the expired and inspired flows will be comparable. The shape of the inspiratory and expiratory flow waveforms would also differ depending on whether the intubation tube is placed in the esophagus versus placement in the trachea. Accordingly, for certain embodiments, in combination with EtCO2 and/or impedance measurements and/or other useful indicators of intubation tube placement, if the difference in magnitude between inspiratory flow volume and expiratory flow volume is high enough to meet a predetermined threshold, then the system may indicate that the intubation might be misplaced. In such a case, the system may produce a signal to alert (e.g., via visual, audio and/or tactile feedback) the user to check whether the intubation tube is properly placed. The system may be configured to continuously monitor placement of the intubation tube.

A visual indicator may provide visual feedback to the rescuer as to whether or not the ET tube has been properly placed. When the tube is determined to be properly placed, the system may activate a green LED at a suitable location (e.g., on the exterior of the flow conduit, on the connector, etc.). If the previous ventilation attempt resulted in the determination of an improperly placed ET tube, then the system may activate a red LED of the visual indicator. The visual indicator may also include a series of LEDs configured as a dual color bar-graph to indicate the tidal volume of each successive ventilation, with the color of the LED bars indicative of whether or not the tube is properly placed (green indicating proper placement; red-indicating improper placement). Alternatively, separate indicating lights may be provided for airway and breathing, to indicate proper ET tube placement and ventilation tidal volume, respectively. Or, an audio alarm (e.g., verbal, tone) may activated to provide feedback to the rescuer if the ET tube is placed improperly or becomes dislodged. In an embodiment, if an improperly placed ET tube is not corrected, then the alarm may escalate in intensity (e.g., increasing volume with time).

With reference to FIGS. 6-9 and 16-18, the processor 145 is incorporated in the connector 113, which is configured to be removably coupled to the flow conduit 101 to place the first and second absolute pressure sensors 131, 132 in communication with the processor 145. That is, when the connector 113 is coupled to the flow conduit 101, electrical communication is established between the pressure sensors 131, 132 and the processor 145, and other electrical components (e.g., computing device, defibrillator, tablet, monitor, etc.) to which the cable 146 extends. The connector 113 comprises a molded outer shell or housing 138 that contains the internal assembly 142 of the connector 113, comprising the processor 145. When the connector 113 is mounted on the flow conduit 101, the housing 138 is engaged by snap arms 109 extending from the upper surface of the flow conduit 101. The housing 138 comprises an indentation 140 formed therein and each of the snap arms 109 comprises a protuberance 147 formed along its length. The protuberances 147 on the snap arms 109 engage within the indentation 140 on the housing 138 to maintain the engagement between the connector 113 and the snap arms 109 while allowing the connector 113 to rotate with respect to the flow conduit 101 without becoming disengaged and allowing the connector 113 to be coupled to the flow conduit 101 from a variety of angular orientations. The snap arms 109 are flexible so that they may deflect a suitable amount to allow the connector 113 to be connected to and removed from the flow conduit 101. It can be appreciated that the complementary snap arms and protuberances are not required aspects of the present disclosure, as the flow conduit and the connector may be engaged via any suitable configuration, such as via magnetic coupling, interference fit, amongst others.

In some embodiments, as shown, when connected to the flow conduit, the connector may swivel about a transverse axis of the flow conduit, similar to that of a turret. In the configuration shown in the figures, the cable 146 extends horizontally relative to the flow conduit along the plane about which the connector 113 swivels. Though, in some embodiments (not shown), the cable may extend vertically relative to the flow conduit. For example, instead of swiveling about a two dimensional plane with a circular range of motion, the connector and flow conduit engagement may be constructed such that the cable may have a generally hemispherical or dome-like range of motion.

Figure 17A:
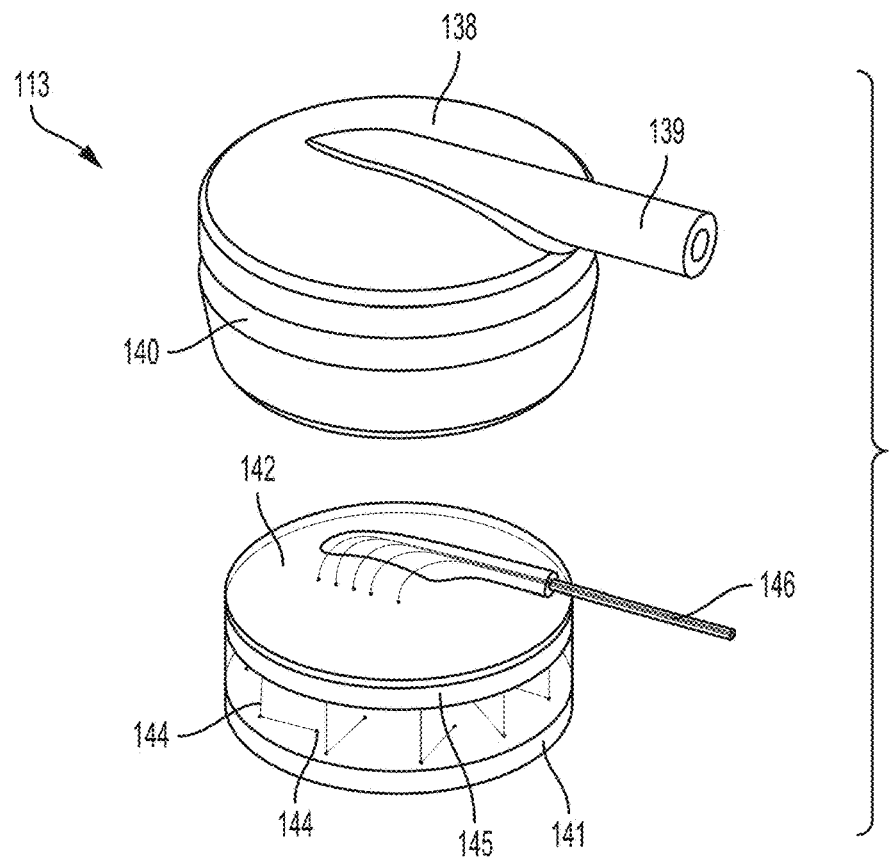
FIGS. 17(a) and (b) are exploded perspective views of the connector of FIG. 16.
Figure 17B:
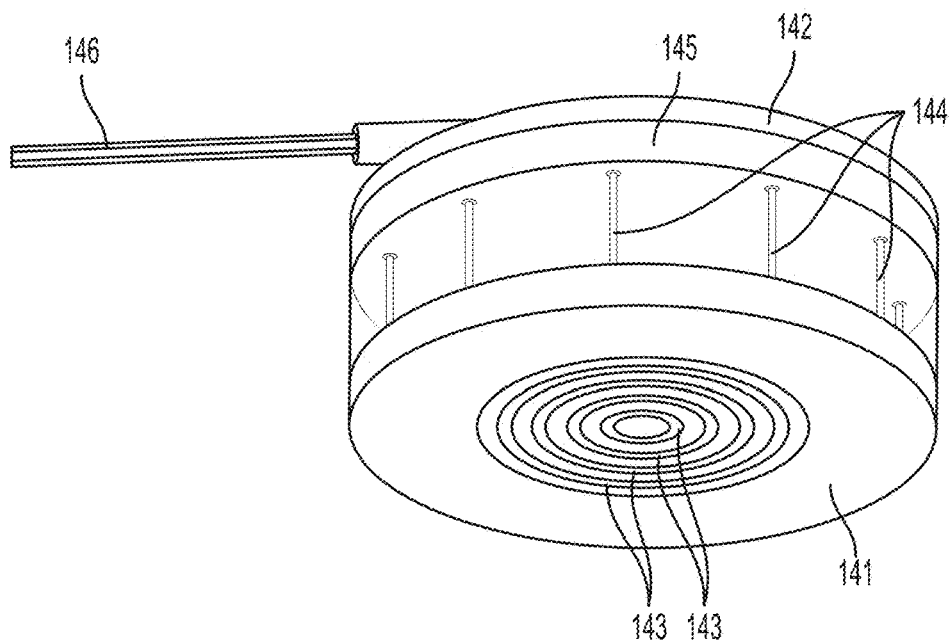
Figure 18A:
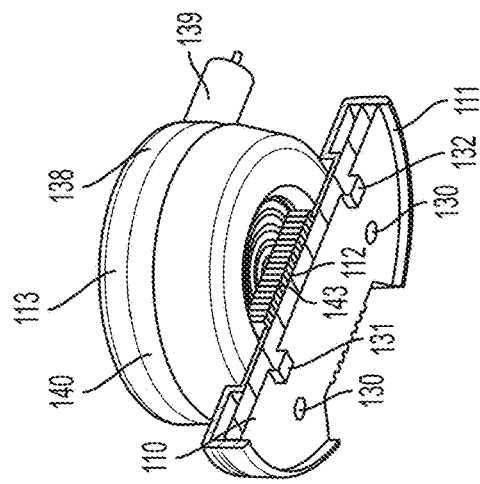
FIGS. 18(a), (b), and (c) are cross-sectional perspective views illustrating a connection between the connector and circuit board of the flow sensor system of FIG. 6.
Figure 18B:
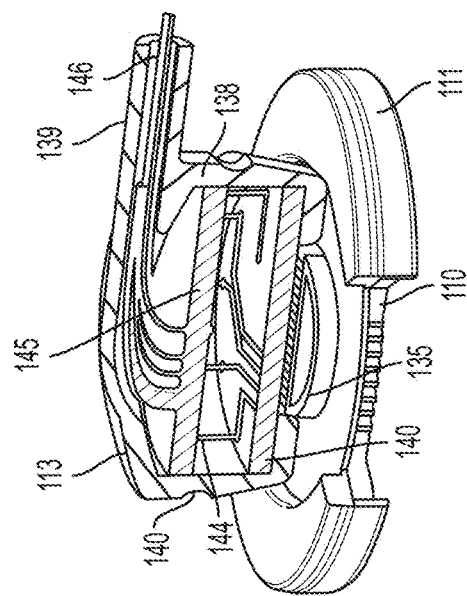
Figure 18C:
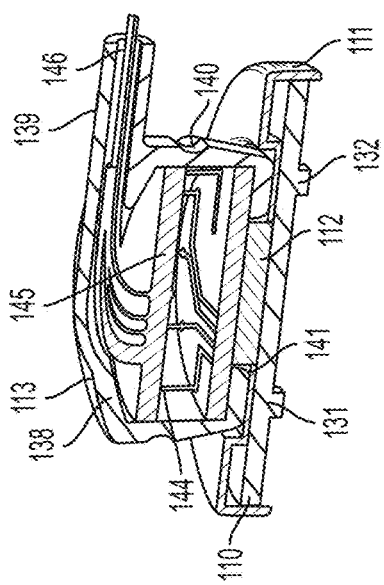

As shown in FIGS. 17 and 18, the internal assembly 142 of the connector 113 also comprises a contact pad 141 accessible through the bottom of the outer housing 138. The contact pad 141 comprises a plurality of conductive elements 143, which are arranged in concentric circles on the contact pad 141 in a bulls-eye pattern. The contact pad 141 is in communication with the processor 145 and the cable 146, which extends toward another medical device system, via a plurality of signal conductors 144 also disposed within the outer housing 138 of the connector 113. As shown in FIG. 18, the adapter 112 on the circuit board 110 comprises a plurality of alternating conductive and non-conductive layers arranged in a striped pattern ("zebra" pattern) such that the conductive layers are spaced to correspond to the radial spacing of the concentric conductive elements 143 on the contact pad 141. Accordingly, when the connector 113 is connected to the flow conduit 101, the adapter 112 can establish electronic communication with the connector 113 via contact between the conductive layers on the adapter 112 and the conductive elements 143 on the contact pad 141. Since the conductive elements 143 on the contact pad 141 are arranged in concentric circles, when the connector 113 is connected to the flow conduit 101, electronic communication may be established from all angles with respect to the flow conduit 101 within a two-dimensional plane. The connector 113 can also be rotatably coupled to or otherwise swivel about the flow conduit 101 while maintaining electrical communication between the first and second absolute pressure sensors 131, 132 and the processor 145. Also as shown in FIG. 18, the alignment disk 135 and the cavities 137 on the circuit board cover 111 engage the housing 138 to align the contact pad 141 on the connector 113 with the adapter 112 and maintain the connector 113 in a lateral and longitudinal position on the flow conduit 101 while allowing the connector 113 to rotate in place.

In some embodiments, the alternating conductive and non-conductive layers of the adapter 112 are spaced in a substantially fine manner, with a higher pitch than the example described above where the conductive layers are spaced to correspond to the radial spacing of the concentric conductive elements 143. For instance, the conductive layers may be spaced less than 0.5 mm (e.g., approximately 0.1 mm, with 230-250 conductive layers per inch) with respect to one another. That is, the conductive and non-conductive layers of the adapter 112 may be spaced substantially closer to one another than that of the spacing of the traces of the circuit boards. Such a configuration may help to ensure that matching traces on circuit boards above and below the adapter 112 are vertically connected, without horizontal misconnection(s). Accordingly, tolerances in the spacing of the traces on circuit boards above and below the adapter may be configured such that misconnections between traces are prevented. In some cases, the non-conductive layer(s) of the adapter may exhibit a suitable level of flexibility, for example, such layers may be made of a conformable material such as rubber, silicone, plastic, amongst other material, allowing for the overall adapter to be compressible (particularly if the conductive layers are composed of a rigid material). It may be preferable for the adapter to be compressible, for example, by having a relatively high pitch of alternating conductive and non-conductive layer, so as to ensure suitable connection between traces of the circuit boards positioned above and below.

The connector 113 may also comprise a cable 146 extending from the processor 145 for placing the processor 145 in communication with a monitor and/or feedback device or to the controller for an automatic ventilation system, as discussed above. The outer housing 138 of the connector 113 comprises a strain relief housing 139 that surrounds the cable 146 as it passes through the housing 138 in order to protect the connection between the cable 146 and the processor 145. As noted above, it is to be appreciated that the connector 113, the flow conduit 101, the circuit board cover 111, and the adapter 112 may be configured in such a manner as to allow for the connector 113 to be connected to the flow conduit with an additional degree of freedom, i.e., in three dimensions, so that the connector 113 may also be connected from a variety of vertical angles with respect to the flow conduit 101.

In various embodiments described herein, the connector swivels or otherwise rotates about the flow conduit, although other arrangements may be possible. It can be appreciated that connector configurations described herein may be employed for systems other than a flow sensor. For example, such connector configurations may be used for any appropriate medical connector systems, such as for chest compression sensing, pulse oximetry, carbon dioxide (e.g., end tidal CO2) sensing, ECG sensing (e.g., 12-lead, 3-lead ECGs), blood pressure, amongst others, where an electrical connection is maintained between components that are permitted to rotate, pivot, turn or otherwise move relative to one another. In various embodiments, such a connector system may be applicable for systems with disposable components. For example, the connector may be part of the reusable portion of the system, and connected to the disposable part of the system. As noted above, the disposable part of the system may include a flow conduit from which flow there through may be determined. In other examples, the disposable part of the system may include a pulse oximeter lead, ECG lead, CPR sensor lead, etc.

It is to be appreciated that by separating the processor 145 from the flow conduit 101, the assembly of the flow conduit 101, sensors 131, 132, and the circuit board 110 can be provided as a single-use disposable unit since the assembly can be produced relatively inexpensively. Accordingly, it is not necessary for the assembly components to be sterilized after use, which can be labor intensive, jeopardize functioning of the components, and may not completely prevent spread of infection or contaminants. The connector 113, on the other hand, may be used repeatedly since the connector 113 is only exposed to the patient or patient fluids to a limited degree in comparison to the disposable portion of the flow sensor system, if at all. For instances where the connector and/or other reusable components do come into contact with the patient and/or fluids, etc., the exterior surface of the connector is easy to clean, without difficult to reach openings, such as is the case for other types of connectors, for example, USB connectors. The connector and/or other reusable components may be made up of materials that are resistant to harsh or corrosive treatment(s) commonly associated with cleaning products.

The connector 113 and/or other portions of the flow sensor system may also be configured to provide at least one of audio feedback, visual feedback, and haptic feedback to the user to adjust the manner (e.g., ventilation bagging, ventilator control) in which gas flow is provided through the lumen 102 of the flow conduit 101, based on at least one of the determined flow rate and volume of gas flowing through the lumen 102. Accordingly, the connector 113 or another component may additionally incorporate a LCD screen (not shown) and/or LED light (not shown), microphone (not shown), and/or vibrator device (not shown) for providing the feedback to the user. Alternatively, the connector 113 may be connected to an external feedback device, such as a monitor device as described above with reference to FIG. 1, via the cable 146. In certain embodiments, the flow sensor system may be in communication with a defibrillator and/or monitor for assisting a user through the resuscitative process. For example, as discussed further below, based on information provided from the flow sensor system, a diagnostic system (e.g., defibrillator, monitor, etc.) may display a CPR dashboard including a chest compression dashboard and/or ventilation dashboard, as discussed further below. Or, the connector, or other part of the flow sensor system, may include an LED, or other light, audio component (e.g., speaker) and/or haptic engine that provides a signal to a user for performing various ventilation related activities. For example, the signal may assist the user in timing ventilation bagging, providing cues similar to that of a metronome. Or, the signal may provide an indication to the user to switch the type of resuscitation activity that is performed on the patient, such as switching from applying chest compressions to applying ventilations, or vice versa.

As discussed above, the flow sensor system 100 may include one or more LEDs to provide feedback to a user of the flow sensor system 100. The LED(s) may light up in a continuous and/or intermittent manner. For example, the LED(s) may blink or provide a series of flashes each time ventilation is to be provided to a victim, so as to provide a visual indication for a rescuer. The LED(s) may be located at any suitable location such that it is more likely to be seen by the rescuer, and less likely to be blocked visually by other ventilation components or physical obstacles. In some embodiments, portions of the flow sensor system 100, such as the flow conduit 101 or other components, may be made up of a light spreading material (e.g., dispersive polymer, translucent plastic). For example, when the light spreading material is exposed to a focused light source, the entire light spreading material may illuminate, making it more likely for a rescuer to notice the pattern and color of illumination of the flow sensor. Accordingly, when the light source turns on, it may appear to the user as if the entire flow conduit lights up.

Multiple modes of feedback may be provided (e.g., both rate and volume). For instance, a first LED may be provided as a backlight for a letter "R" for rate, and another LED may provide a backlight for a letter "V" for volume, and/or a pair of LEDs may be located on opposed sides of the letter, with lighting of an LED behind the letter indicating that the rate or volume being applied by the rescuer, respectively, is correct. The LEDs to the side of the letter may be lit alternatively, depending on whether the rescuer is being prompted to increase or decrease their rate or volume of ventilation.

Figure 37:
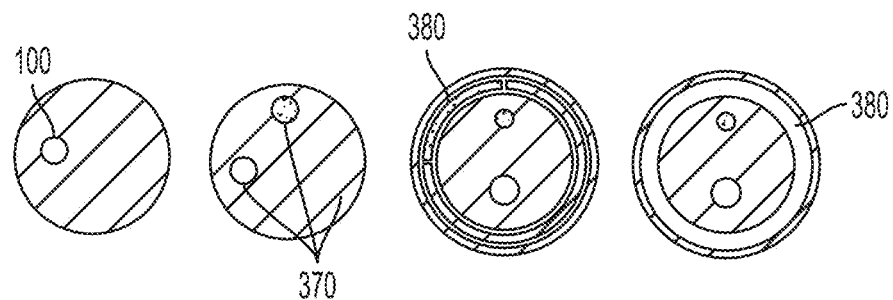
FIG. 37 is a schematic of exemplary LED displays for a flow sensor system according to an embodiment of the present disclosure.

In an embodiment, a single LED light 360, such as that shown in FIG. 37, may provide feedback according to various modes. For instance, blinking of the LED 360 may be an indication that the rescuer should ventilate. An LED 360 that is continuously lit, or blinking at a high frequency (more rapidly than if the LED 360 were blinking as a signal for the rescuer to begin ventilations), may serve as a warning indication, for example, that the patient is being over-ventilated. Such a warning indication may be triggered when the flow volume or peak inspiratory pressure has reached a preset threshold. When the LED 360 is off, no warning signal is provided, thus, indicating that the level of ventilation provided to the patient is adequately within specified parameters. In some cases, a single LED 360 may emit light of different colors, for example, red, yellow, green, etc.

In another embodiment, as further shown in FIG. 37, multiple LED lights 370 may be used. While a single LED 360 may emit multiple colors, separate multiple LED lights 370 may be configured to emit specific colors, for example, red, yellow, green, etc. The LEDs 370 may provide indication to the user of a number of warnings and/or activities. For example, at the appropriate time during the resuscitation process, the LEDs 370 may signal the user to ventilate, may indicate when the flow volume and/or peak inspiratory pressure exceeds respective thresholding. In various embodiments, a green light may indicate that the quality of ventilations are adequate and a red light may indicate that the patient is being over-ventilated. A blinking yellow light may signify that a breath should be given to the patient.

In certain embodiments, as also shown in FIG. 37, an LED ring 380 may be employed, for example, on the top of the reusable connector 113, or at any other suitable location visible to the user. When flow volume is detected and is within suitable parameters, the LED ring 380 may light up according to a suitable color (e.g., green), and when the flow volume is outside of the desired limit, the LED ring 380, or a portion thereof, may light up according to another color (e.g., yellow as a warning, red as a stronger indicator). The LED ring 380 or other LEDs may turn color, for example, from green to red, when the volume or PIP exceeds certain thresholds corresponding to when the user should be warned and when the levels are becoming significantly more harmful to the patient. In another example, the LED ring 380 may blink yellow to instruct a user that a breath should be given.

In some instances, the circumference of the LED ring 380 may provide the user with an indication of how much volume has been and provided at any given time to the patient, along with a target range. As an example, at the beginning of a breath where no volume has yet been given, the LED ring 380 may remain dim, yet as flow volume increases, the light along the LED ring 380 may be illuminated so as to track along the circumference or perimeter of the device. That is, when a quarter or half the flow volume is reached, a quarter or half the circumference of the LED ring 380 may light up, respectively, for example, as a yellow color until the flow volume is within the target range, in which case the LED ring 380 may light up as green. Though, when the target flow volume is exceeded or remains outside the target range, the LED ring 380, or other part of the display, may light up as red, indicating to the user that the flow volume is outside the desired range.

As discussed above, the flow restrictor 105 is configured to interrupt the flow of gas through the lumen 102 to create the pressure drop in the lumen 102 between the first region 103 and the second region 104 for determining flow rate/volume. The processor 145 is configured to determine the pressure drop based on the pressure measurements of the first and second absolute pressure sensors 131, 132 and to determine at least one of the flow rate, the direction of flow, and volume of gas flowing through the lumen 102 based on the determined pressure drop. The processor 145 may include a memory that incorporates a flow pressure look up table for comparing the measured pressure drops with predetermined flow rates and/or volumes. The processor may determine the flow rate and/or volume of the gas flowing through the lumen 102 by referencing the flow pressure look up table. Alternatively, the processor 145 may be connected to an external memory device that contains the flow pressure look up tables. Also as discussed above, the flow look up tables may also incorporate information accounting for the effects of temperature and/or humidity of the gas flowing through the lumen 102 and/or the altitude/ambient atmospheric pressure on the flow rate and/or volume of the gas.

With reference to FIGS. 19(a) and 20(a)-(f), various flow restrictors 150, 160, 170, 180, 190, and 200 may be used in flow sensor systems described in accordance with embodiments of the present disclosure. Each of the flow restrictors 150, 160, 170, 180, 190, and 200 is a variable orifice flow restrictor that comprises at least one flap that deflects under the flow of gas through the restrictor 150, 160, 170, 180, 190, and 200 to create the pressure drop in the flow conduit 71, 101 between the first and second regions. The relative pressure drop created by any one of the flow restrictors 150, 160, 170, 180, 190, and 200 varies according to substantially linear and/or curvilinear profiles based upon the flow of gas through the lumen 72, 102. As the overall construction of the flow restrictor contributes to the behavior of the pressure-flow relationship, it can be appreciated that the pressure-flow relationship can be tuned depending on the geometry of the flow restrictor. For example, it may be desirable for the pressure-flow relationship to exhibit linear behavior at certain flow regimes, and exhibit more curvilinear behavior at other flow regimes. For certain embodiments, the flow restrictor may be configured to give rise to a pressure drop in the flow conduit that is non-linear (e.g., parabolic, step-linear, linear-parabolic), while allowing for high resolution measurements for a wide range of flow rates (e.g., between approximately −50 L/min and approximately 50 L/min, or outside this range, such as flow rates up to 400 L/min, up to 800 L/min).

Figure 23:
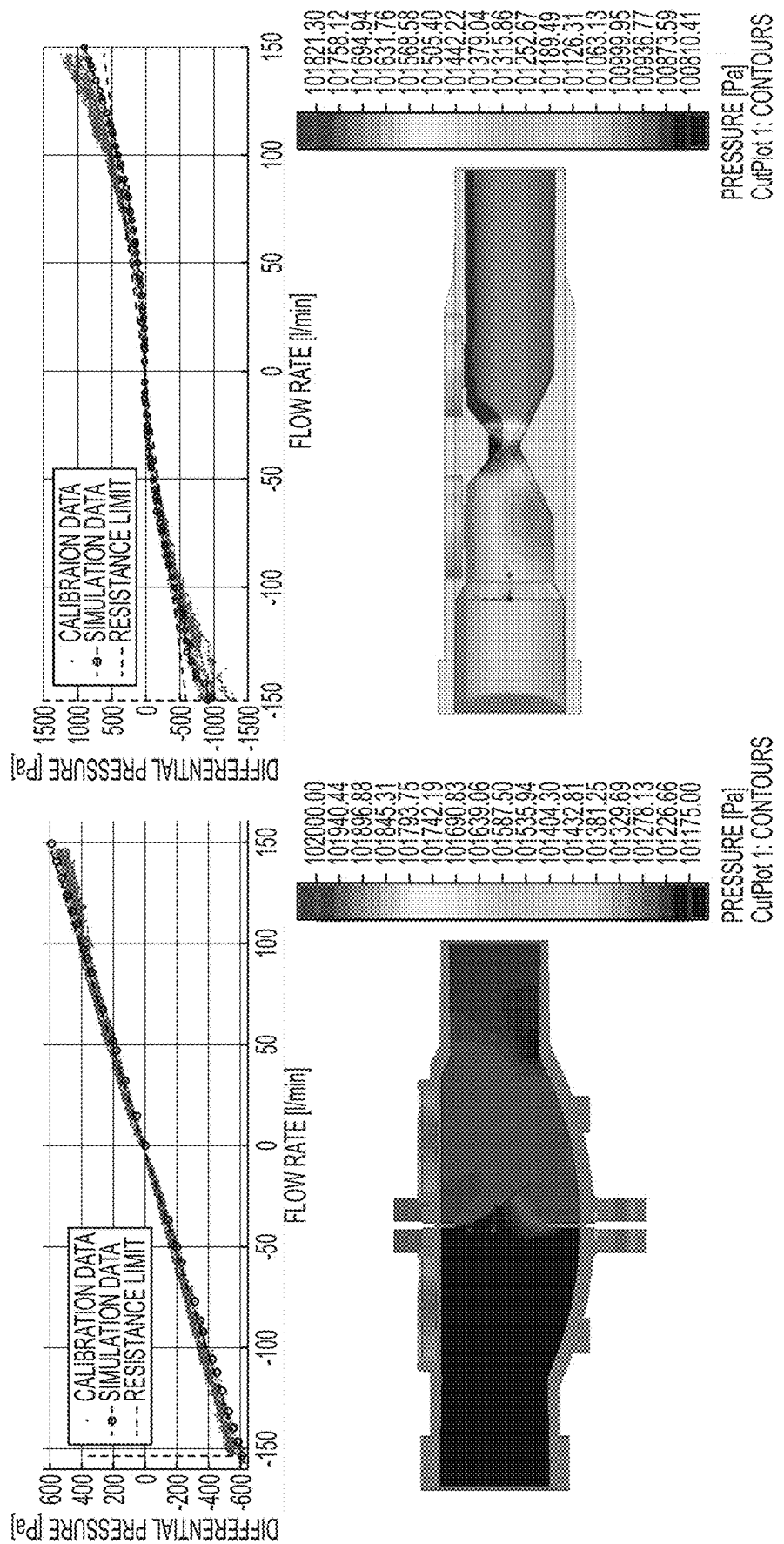
FIG. 23 is a chart illustrating pressure drop versus flow for a variable orifice flow restrictor and a fixed orifice flow restrictor.
Figure 24:
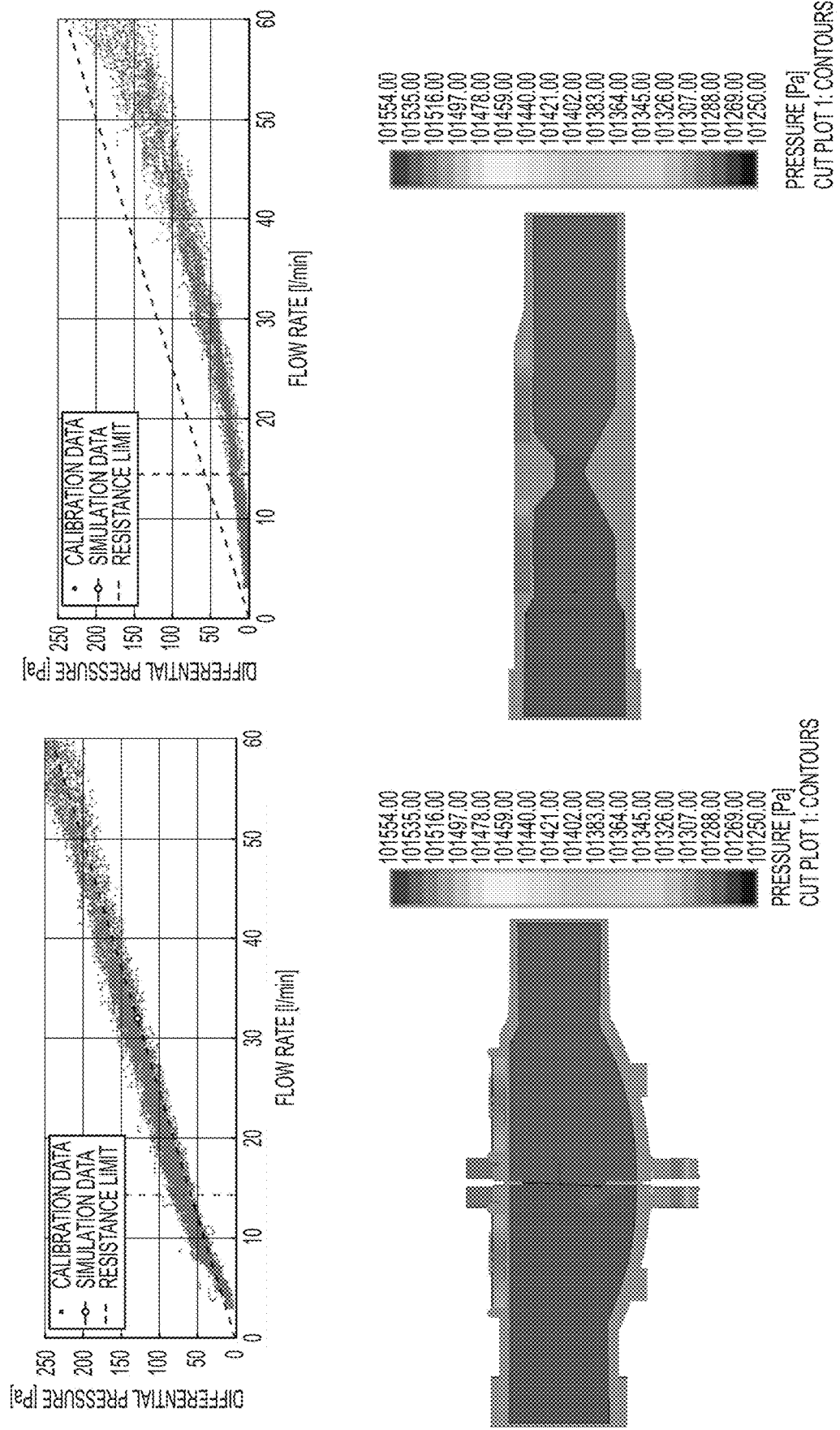
FIG. 24 is a chart illustrating pressure drop versus flow at low flow rates for a variable orifice flow restrictor and a fixed orifice flow restrictor.

FIGS. 23 and 24 illustrate the relationship between the flow of gas through a lumen and the pressure drop created by a flow restrictor within the lumen for a variable orifice flow restrictor and a fixed orifice flow restrictor. As shown, the pressure drop created by a fixed orifice flow restrictor, such as in the flow sensor systems 20, 40 discussed above with reference to FIGS. 2 and 3, varies quadratically with respect to the flow rate of the gas through the lumen. As such, the pressure drop created by a fixed orifice flow restrictor is relatively small at lower flow rates and is relatively large at higher flow rates. For example, as shown in FIGS. 23 and 24, the pressure drop created by an exemplary fixed orifice flow restrictor is approximately 10 Pa at a flow rate near 15 l/min, is approximately 40 Pa at a flow rate near 30 l/min, and is approximately 1000 Pa at a flow rate of 150 l/min. This raises potential issues with respect to measuring the pressure drop between the two regions of the lumen to accurately determine the flow rate and/or volume of the gas flowing through the lumen. The pressure drop at lower flow rates is very small, because of that the absolute pressure sensors may not be accurate enough to adequately measure the pressure drop because the pressure drop falls within the range of resolution detectable by the sensors. Additionally, the pressure drop created by the fixed flow restrictor at higher flow rates becomes increasingly large, which may result in too large of an obstruction to the flow through the lumen and inadequate delivery of gas at the desired flow rate and/or volume.

On the other hand, the variable orifice flow restrictor of the type used in the flow sensor systems 60, 70, 100 discussed above with reference to FIGS. 4-18 is configured so that a relationship between the flow rate of gas through the lumen and the pressure drop created by the restrictor is linear or substantially linear. This is because as flow rates move from −150 to +150 L/min the flap or flaps of the variable orifice flow restrictor deflect in order to change the size of the opening. Accordingly, by configuring the opening and the geometry of the flap(s) of the variable orifice flow restrictor, the pressure drop created by variable orifice flow restrictor can be controlled. In particular, the pressure drop created by the variable orifice flow restrictor can increased to be relatively large compared to the flow. More specifically, the pressure drop at lower flow rates is large enough to be adequately measured by the absolute pressure sensors, which leads to greater accuracy in determining the flow rate and/or volume of gas flowing through the lumen. For example, as shown in FIG. 24, the pressure drop created by an exemplary variable orifice flow restrictor is approximately 50 Pa at a flow rate near 15 l/min and is approximately 125 Pa at a flow rate near 30 l/min.

At higher flow rates, the pressure drop created by the variable orifice flow restrictor is relatively small so that the flow restrictor does not create too large an obstruction to the flow. For example, as shown in FIG. 23, the pressure drop created by an exemplary variable orifice flow restrictor is approximately 600 Pa at a flow rate near 150 l/min.

According to one embodiment of the present disclosure, the variable orifice flow restrictor is configured so that the relationship between the pressure drop created by the flow restrictor and the flow rate of gas flowing through the lumen extends substantially linearly along a resistance limit for the flow sensor system, as shown in FIG. 23(a). The resistance limit is the maximum rate of pressure drop that can be created in the flow conduit without detrimentally obstructing flow. The resistance limit of the flow conduits 21, 41, 61, 71, 101 described above is 4.08 Pa/l/min for flow rates between 0-50 l/min. In other words, the variable orifice flow restrictor is configured to provide the maximum pressure drop at any given flow rate between −150 to +150 L/min without detrimentally obstructing flow. It is to be appreciated that the geometry of the flap(s) and opening of the variable orifice flow restrictor may be altered to provide different relationships between the pressure drop created by the flow restrictor and the flow rate of gas. The relationship created by the variable orifice flow restrictor does not necessarily need to be linear. Other statistical relationships are possible to achieve the desired result of increasing the pressure drop to a detectable level at low flow rates while not going above the resistance limit for the flow conduit. The overall configuration of the variable orifice flow restrictor is intended to optimize the pressure versus flow relationship for a given flow conduit. Ideally, the specific configuration of the flow restrictor will result in a pressure versus flow relationship that achieves a desired statistical relationship (linearity, steepness, smoothness, symmetry between positive and negative pressures and is repeatable over multiple uses and multiple flow restrictors so that the behavior of the flow restrictor is predictable.

Figure 19A:
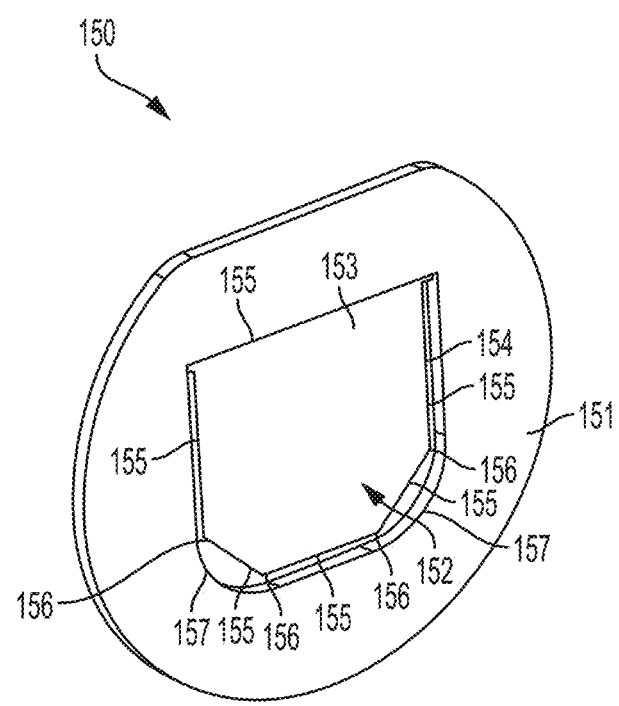
FIG. 19(a) is a perspective view of a flow restrictor according to an embodiment of the present disclosure.
Figure 20A:
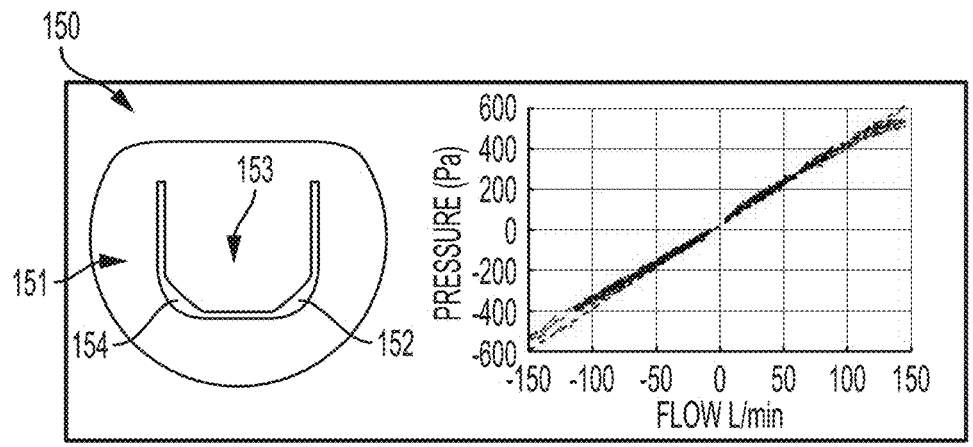
FIGS. 20 (a), (b), (c), (d), (e), and (f) are front views and charts illustrating pressure drop versus flow for several examples of a flow restrictor according to embodiments of the present disclosure.

With reference to FIGS. 19(a) and 20(a), the flow restrictor 150 according to one embodiment of the present disclosure comprises a body configured to be disposed in the lumen 72, 102 of a flow conduit 71, 101. The body comprises an outer portion 151 that surrounds an opening 152 and a flap 153 disposed in the opening 152. The outer portion 151 may provide mechanical reinforcement so that the flow restrictor 150 is firmly secured within the lumen of the flow conduit in a substantially vertical position relative to the horizontal direction of fluid flow. As shown, a single flap is provided in the opening, although for certain embodiments, the flow restrictor may include multiple flaps (e.g., flap with slits, and/or flaps having varying orientation(s) around a common central region as described further below). The flap 153 is coupled to the outer portion 151 at a side of the opening 152. As discussed above, the flap 153 is configured to deflect from the opening 152 due to gas flow through the flow restrictor 150. The amount of deflection of the flap 153 is variable based upon the flow of gas through the lumen 72, 102 to create a substantially linearly variable pressure drop and flow relationship. The flap 153 has a surface area smaller than a surface area of the opening 152, thereby forming a gap 154 in the body of the flow restrictor 150 when the flap 153 is in a non-deflected position within the opening 152. The flap 153 is shaped so that the gap 154 is non-uniform.

Figure 19B:
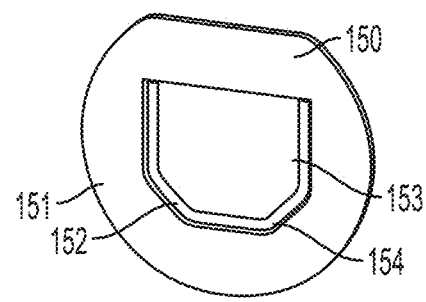
FIGS. 19(b) and 19(c) are perspective views of an alternative flow restrictor according to an embodiment of the present disclosure.
Figure 19C:
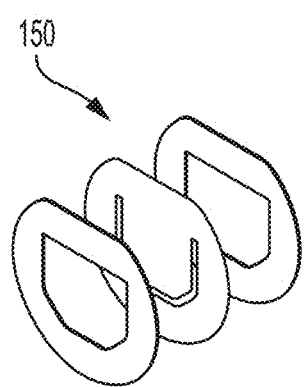

For certain embodiments, such as that shown in FIGS. 19(b) and 19(c), the flap 153 of the flow restrictor 150 may be shaped such that the gap 154 is substantially uniform. Here, the body of the flow restrictor 150 has a mechanically reinforced outer portion 151 surrounding an opening 152, with the flap 153 positioned in the opening. The flap 153 is coupled to the outer portion 151 at a side of the opening 152 and may deflect from the opening 152 due to gas flow through the flow restrictor 150. As shown, the flap 153 is shaped and sized such that the gap 154 between the outer edge of the flap 153 and the inner edge of the outer portion 151 is substantially uniform. In this case, the width of the gap 154 at the flap sides 155 is greater for the example of FIGS. 19(b)-(c) as compared to the width of the gap 154 for the example of FIG. 19(a). As further shown, the overall area or size of the gap between the flap and the outer portion along the plane of the flow restrictor is substantially similar for the examples shown in each of FIGS. 19(a) and 19(b)-(c).

Figure 19D:
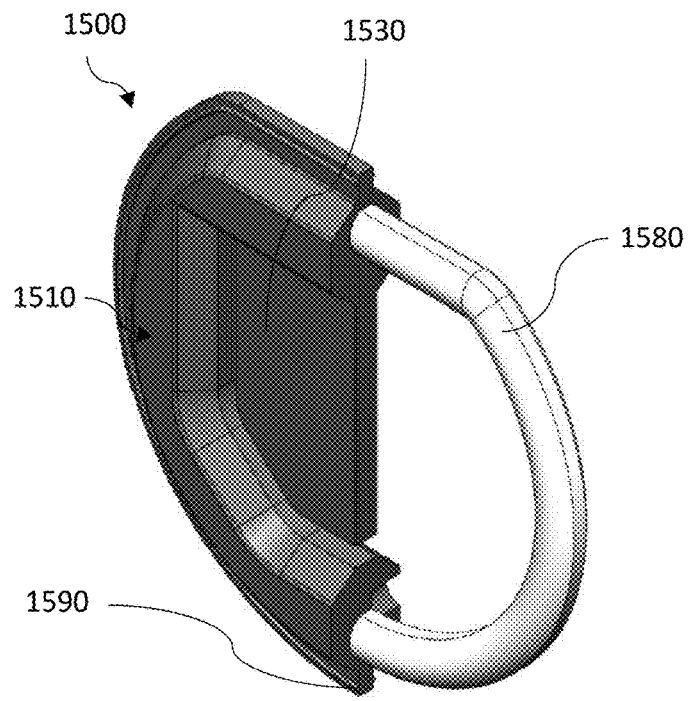
FIG. 19(d) depicts a partial perspective view of a flow restrictor in accordance with an embodiment.
Figure 19E:
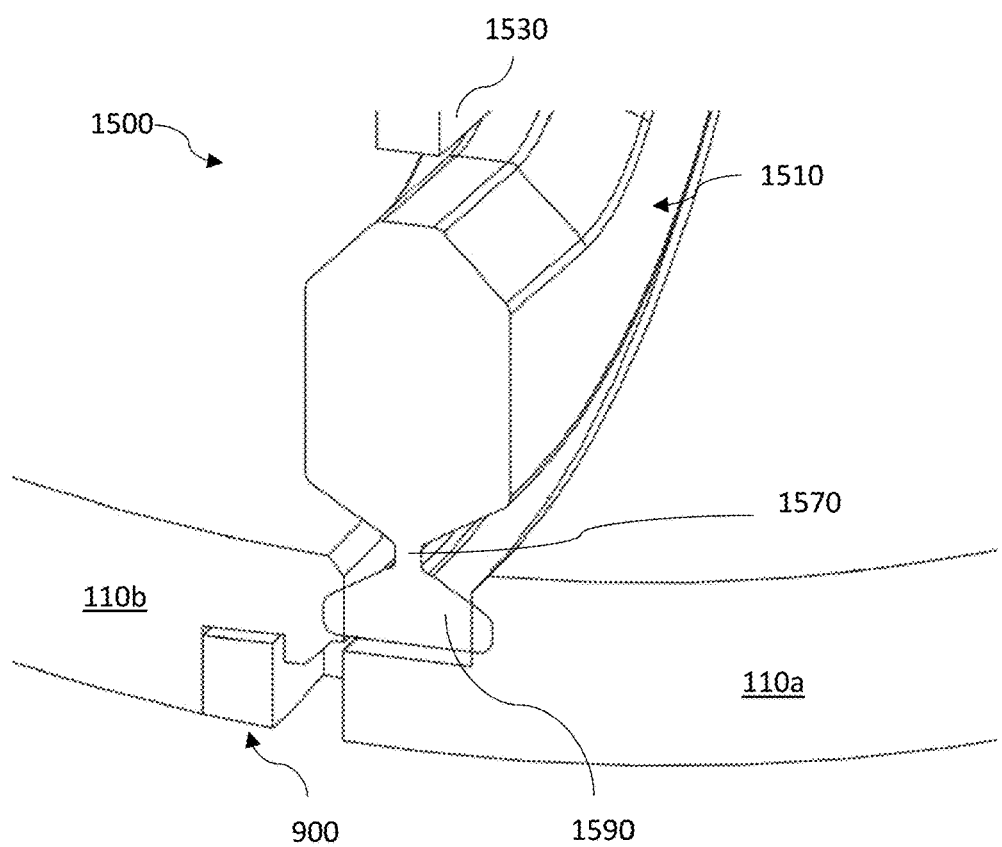
FIG. 19(e) depicts a cross-sectional view of a portion of a flow restrictor in accordance with an embodiment.

FIGS. 19(d)-(e) depict another embodiment of a flow restrictor 1500 having an outer portion 1510 surrounding a flap 1530, similar to other examples described herein. However, in this embodiment, the outer portion 1510 encapsulates an insert 1580 which may provide a suitable level of mechanical stability for the flow restrictor 1500. In particular, the insert 1580 may support the flap 1530 during assembly of the flow sensor system (e.g., where the flow conduit may be provided as a snap fit arrangement), and may prevent or reduce the possibility of bending of the flap 1530. Otherwise, when pressure is applied to the outer portion 1510 during assembly, without such increased stability, the flap 1530 may be undesirably prone to bending which may then lead to inaccuracies in flow measurements. Hence, the insert 1580 may be composed of a relatively rigid material as compared to the flap 1530 and the outer portion 1510 of the flow restrictor 1500. For example, the insert 1580 may comprise a reinforced plastic/polymer, metal, or other suitable material, and the outer portion 1510 may include a silicone rubber. Alternatively, the outer portion 1510 of the flow restrictor 1500 may be composed of a material that is substantially stiffer or more rigid than the flap 1530, without requiring an insert encapsulated therein. In certain embodiments, as shown in FIGS. 19(d)-(e), the flow restrictor 1500 further includes an outer rim 1590 that facilitates the formation of a seal upon assembly of two segments (e.g., halves) of a flow conduit that are connected together.

Accordingly, the flow conduit may be manufactured according to a snap fit configuration where two segments 110a, 110b of the flow conduit are connected together to form a larger assembly. For example, FIG. 19(e) depicts an up close view showing a connector 900 that provides a snap fit seal against an outer rim 1590 (e.g., made up on a silicone rubber or other elastomeric material) of the flow restrictor 1500 for segments 110a, 110b of the flow conduit upon assembly thereof. The flow restrictor 1500 may be substantially tapered to a thin neck region 1570 adjacent to the outer rim 1590. This thin neck region 1570 may be useful to minimize or otherwise reduce the possibility for the flap 1530 to bend during assembly of the segments of the flow conduit 110a, 110b. Such bending may be due to torsion that is transferred toward the flap 1530; a relatively thin neck region 1570 may reduce the effects of torsional transfer during assembly. In general, it may be preferable for the flap 1530 to be kept relatively straight so as to give rise to consistent bi-directional flow through the lumen 102. The outer portion 1510 may further include chamfers that are tapered toward the flap 1530. Such a tapered shape may be beneficial to help streamline air flow toward the flap, rather than for more turbulent flow patterns to develop. While not shown in the figures, the flap 1530 itself may also be chamfered, so as to allow for relatively smoother (more laminar) flow through the opening. The shape of the tapered (chamfered) surfaces of the outer portion 1510 and/or the flap 1530 may provide for comparatively less flow obstruction than if the surfaces were rectangular or more bulky in nature. Such constructions have been found to result in more linear pressure-flow rate behavior, particularly at low flow pressures (e.g., less than 75 Pa).

In particular, the flap 153 (or 1530) has a polygonal or substantially polygonal shape with a plurality of flap sides 155 and rounded corners 156 defined between at least some of the sides 155. One of the sides 155 is hingedly coupled to the outer portion 151 to allow for deflection of the flap 153. The opening 152 has a rounded rectangular shape at an end opposite to the end to which the flap 153 is hingedly coupled to the outer portion 151. Two sides 155 of the flap 153 are disposed opposite to respective rounded corners 157 of the opening 152 such that the gap 154 formed between the flap 153 and the outer portion 151 is larger at the rounded corners 157 of the opening 152. Alternatively, as shown for FIGS. 19(b)-19(c), the flap may be shaped and sized such that the outer edge of the flap and the inner edge of the outer portion extend generally parallel to one another, resulting in a substantially uniform gap. As shown in FIG. 20(a), the configuration of the opening 152 and the flap 153 results in the flow restrictor 150 creating a pressure drop that varies substantially linearly with respect to the flow rate of gas through the lumen at or near the resistance limit for the flow conduit.

As noted above, with respect to obtaining accurate flow readings, certain regions of the flow sensor system may be more sensitive to the accumulation of water and/or debris than others. The flow restrictor may be constructed so that water and/or debris are diverted away from more sensitive regions, which may contribute to the overall accuracy of flow determination, to other neighboring regions that are less sensitive to determining the accuracy of flow. Hence, one or more sensitive regions of the flow restrictor may exhibit a greater level of hydrophobicity than the neighboring region(s) adjacent to the sensitive region(s).

For example, the flow restrictor 150 may include a material (e.g., polytetrafluoroethylene) that exhibits a greater level of hydrophobicity than regions neighboring the flow restrictor, such as the surface of the flow conduit immediately adjacent to the flow restrictor. The flow restrictor itself may be made up of the hydrophobic material, or the flow restrictor may be coated with the hydrophobic material. As noted above, the surface of the flow conduit neighboring the flow restrictor may include a plastic or polymeric material that is less hydrophobic (or more hydrophilic) as compared to the flow restrictor, resulting in water accumulation or diversion away from the flow restrictor and toward the neighboring region. Or, the flow restrictor itself may have regions which exhibit different levels of hydrophobicity. For example, the flap 153 may include a relatively hydrophobic material (e.g., polytetrafluoroethylene), and the surrounding outer portion 151 may be hydrophilic, or less hydrophobic, in comparison to the flap 153. Accordingly, water may tend to accumulate or be diverted away from the flap 153 and toward the neighboring or surrounding outer portion 151, resulting in more accurate pressure/flow readings than might otherwise be the case.

Flow restrictors in accordance with the present disclosure may be formed by any suitable technique. For example, parts or the entirety of the flow restrictor may be die cut, molded, or formed by another appropriate method. In some cases, forming the flow restrictor as a molded part may have manufacturing benefits, for example, in producing relatively inexpensive parts in an accurate and precise manner.

Figure 20B:
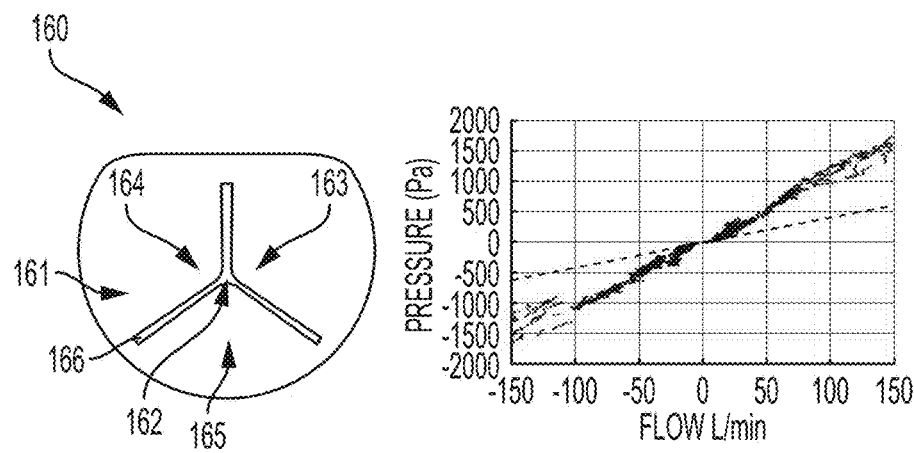

With reference to FIG. 20(b), the flow restrictor 160 according to one embodiment of the present disclosure comprises a body configured to be disposed in the lumen 72, 102 of a flow conduit 71, 101. The body comprises an outer portion 161 that surrounds an opening 162. Three similarly sized and shaped substantially triangular flaps 163, 164, 165 are disposed adjacent to each other in the opening 162 and are hingedly coupled to the outer portion 161 at respective sides of the opening 162. The flaps 163, 164, 165 are sized to have a collective surface area smaller than the surface area of the opening 162 so as to leave a gap 166 between each other when the flaps 163, 164, 165 are in a non-deflected position. The gap 166 is substantially uniform and has three equally spaced legs. The flaps 163, 164, 165 are configured to deflect from the opening 162 due to gas flow through the restrictor 160. The amount of deflection of the flaps 163, 164, 165 is variable based upon the flow of gas through the lumen 72, 102. As shown in FIG. 20(b), the configuration of the opening 162 and the flaps 163, 164, 165 results in the flow restrictor 160 creating a pressure drop that varies somewhat linearly with respect to the flow rate of gas through the lumen 72, 102, but above the preferred resistance limit for the flow conduit.

Figure 20C:
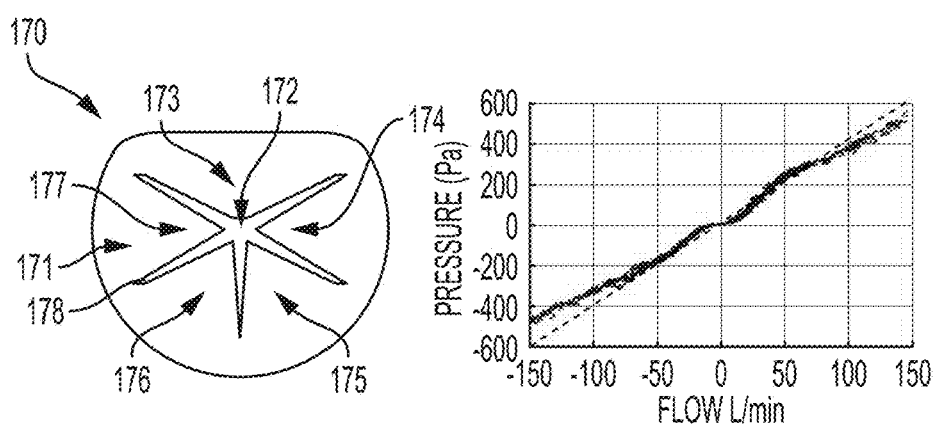

With reference to FIG. 20(c), the flow restrictor 71, 101 according to one embodiment of the present disclosure comprises a body configured to be disposed in the lumen 72, 102 of a flow conduit 71, 101. The body comprises an outer portion 171 that surrounds an opening 172. Five differently sized and shaped substantially triangular flaps 173, 174, 175, 176, 177 are disposed adjacent to each other in the opening 172 and are hingedly coupled to the outer portion 171 at respective sides of the opening 172. In particular, the top flap 173 is broader and shorter while the other four flaps 174, 175, 176, 177 are similarly sized and shaped. The flaps 173, 174, 175, 176, 177 are sized to have a collective surface area smaller than the surface area of the opening 172 so as to leave a gap 178 between each other when the flaps 173, 174, 175, 176, 177 are in a non-deflected position. The gap 178 is non-uniformly shaped and has five differently sized and shaped legs configured in the manner of a five pointed star. The flaps 173, 174, 175, 176, 177 are configured to deflect from the opening 172 due to gas flow through the flow restrictor 170. The amount of deflection of the flaps 173, 174, 175, 176, 177 is variable based upon the flow of gas through the lumen 72, 102. As shown in FIG. 20(c), the configuration of the opening 172 and the flaps 173, 174, 175, 176, 177 results in the flow restrictor 170 creating a pressure drop that varies substantially linearly with respect to the flow rate of gas through the lumen at or near the preferred resistance limit for the flow conduit.

Figure 20D:
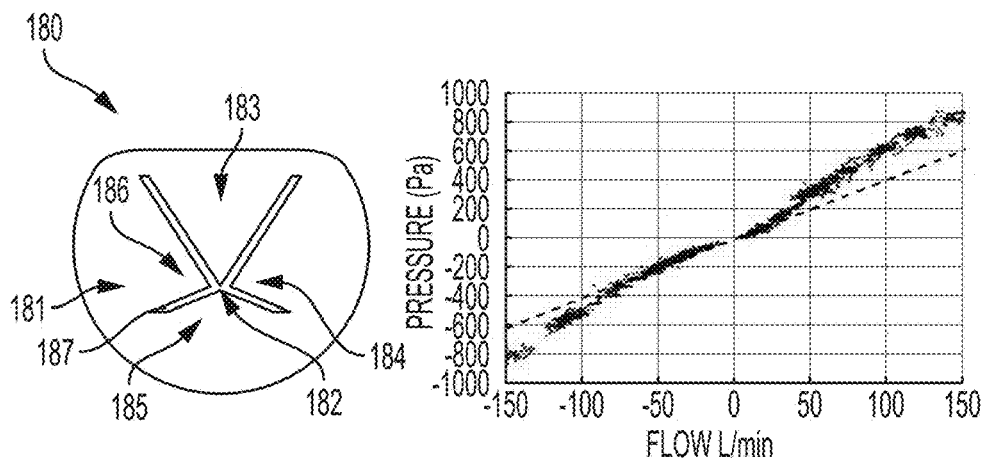

With reference to FIG. 20(d), the flow restrictor 180 according to one embodiment of the present disclosure comprises a body configured to be disposed in the lumen 72, 102 of a flow conduit 71, 101. The body comprises an outer portion 181 that surrounds an opening 182. Four differently sized and shaped substantially triangular flaps 183, 184, 185, 186 are disposed adjacent to each other in the opening 182 and are hingedly coupled to the outer portion 181 at respective sides of the opening 182. The flaps 183, 184, 185, 186 are sized to have a collective surface area smaller than the surface area of the opening 182 so as to leave a gap 187 between each other when the flaps 183, 184, 185, 186 are in a non-deflected position. The top flap 183 is longer while the bottom flap 185 is correspondingly shorter. The side flaps 184, 186 are similarly shaped in a manner complementary to the top and bottom flaps 183, 185. The gap 187 is non-uniform and has four non-equally spaced and sized legs arranged in opposing large and small substantially V-shapes. The flaps 183, 184, 185, 186 are configured to deflect from the opening 182 due to gas flow through the flow restrictor 180. The amount of deflection of the flaps 183, 184, 185, 186 is variable based upon the flow of gas through the lumen 72, 102. As shown in FIG. 20(d), the configuration of the opening 182 and the flaps 183, 184, 185, 186 results in the flow restrictor 180 creating a pressure drop that varies somewhat linearly with respect to the flow rate of gas through the lumen, yet slightly above a preferred resistance limit for the flow conduit.

Figure 20E:
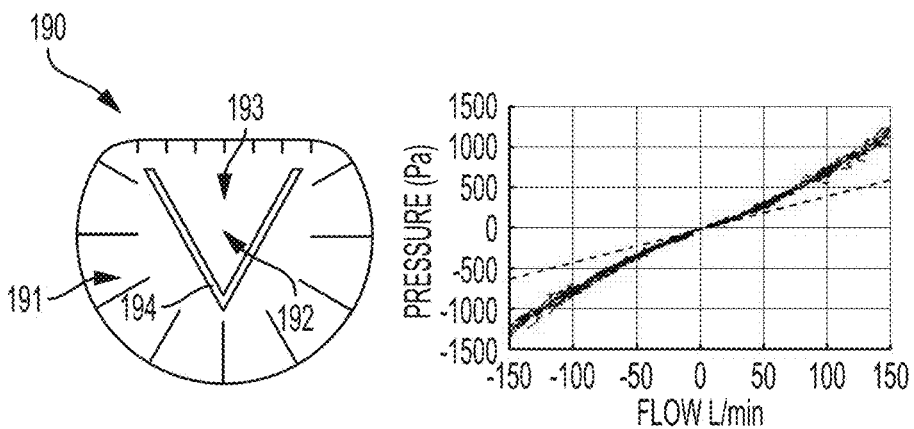

With reference to FIG. 20(e), the flow restrictor 190 according to one embodiment of the present disclosure comprises a body configured to be disposed in the lumen 72, 102 of a flow conduit 71, 101. The body comprises an outer portion 191 that surrounds an opening 192. A single substantially triangular flap 193 is disposed in the opening 192 and is hingedly coupled to the outer portion 191 at the top side of the opening 192. In some embodiments, the flap may incorporate slits to allow for multiple flap segments. The flap 193 is sized to have a surface area smaller than the surface area of the opening 192 so as to leave a gap 194 between the flap 193 and the outer portion 191 when the flap 193 is in a non-deflected position. The gap 194 is substantially V-shaped and has a substantially uniform thickness. The flap 193 is configured to deflect from the opening 192 due to gas flow through the flow restrictor 190. The amount of deflection of the flap 193 is variable based upon the flow of gas through the lumen 72, 102. As shown in FIG. 20(e), the configuration of the opening 192 and the flap 193 results in the flow restrictor 190 creating a pressure drop that varies non-linearly, somewhat curvilinearly, with respect to the flow rate of gas through the lumen 72, 102, yet above a preferred resistance limit for the flow conduit.

Figure 20F:
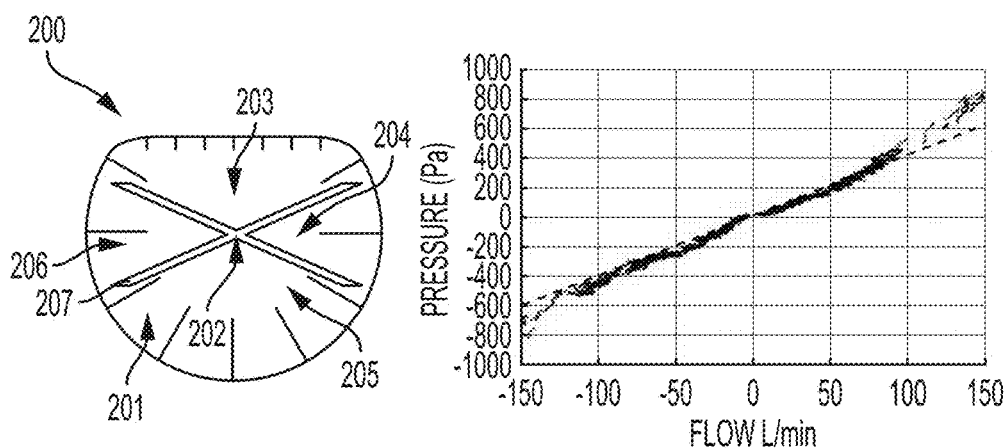

With reference to FIG. 20(f), the flow restrictor 200 according to one embodiment of the present disclosure comprises a body configured to be disposed in the lumen 72, 102 of a flow conduit 71, 101. The body comprises an outer portion 201 that surrounds an opening 202. Four differently sized and shaped substantially triangular flaps 203, 204, 205, 206 are disposed adjacent to each other in the opening 202 and are hingedly coupled to the outer portion 201 at respective sides of the opening 202. The flaps 203, 204, 205, 206 are sized to have a collective surface area smaller than the surface area of the opening 202 so as to leave a gap 207 between each other when the flaps 203, 204, 205, 206 are in a non-deflected position. The gap 207 is substantially uniform and has a substantially X-shape. The top and bottom flaps 203, 205 are symmetrically shaped with each other and are comparatively shorter and broader and the right and left flaps 204, 206 are symmetrically shaped with each other and are comparatively longer and narrower. The flaps 203, 204, 205, 206 are configured to deflect from the opening 202 due to gas flow through the flow restrictor 200. The amount of deflection of the flaps 203, 204, 205, 206 is variable based upon the flow of gas through the lumen 72, 102. As shown in FIG. 20(*f*), the configuration of the opening 202 and the flaps 203, 204, 205, 206 results in the flow restrictor 200 creating a pressure drop that varies substantially linearly with respect to the flow rate of gas through the lumen 72, 102 at or near the preferred resistance limit for the flow conduit 71, 101.

According to one embodiment of the present disclosure, the body of the flow restrictor 150, 160, 170, 180, 190, 200 comprises a hydrophobic material in order to limit or prevent the accumulation of moisture and debris on the body of the flow restrictor 150, 160, 170, 180, 190, 200. In particular, the body is formed from polytetrafluoroethylene (PTFE) of the type sold under the brand name TEFLON®. Alternatively, the body may be made from polyethylene terephthalate (BoPET) of the type sold under the trade name MYLAR®. It is to be appreciated that the flow restrictor 150, 160, 170, 180, 190, 200 may be formed from any material known to be suitable to those having ordinary skill in the art. The outer portion 151, 161, 171, 181, 191, 201 comprises a mechanical reinforcement to prevent deflection of the body outside of the at least one flap, maintain the flow restrictor 150, 160, 170, 180, 190, 200 in a secure position, and facilitate rigid and repeatable assembly of the flow conduit 71, 101. The mechanical reinforcement may comprise at least one laminate layer applied to the outer portion 151, 161, 171, 181, 191, 201 and/or a stiffener coating.

In accordance with aspects of the present disclosure, as noted above, the flow restrictor 150, 160, 170, 180, 190, 200 may be tune-ably constructed so as to exhibit a preferred relationship (e.g., linear, non-linear, curvilinear, quadratic, etc.) between pressure drop and flow. It can be appreciated that a number of factors contribute to how the pressure drop and flow may vary with respect to one another, such as the shape(s), size(s) and material(s) from which the flow restrictor 150, 160, 170, 180, 190, 200 is constructed. In the case of the flow restrictor 150 of FIGS. 19(*a*)-(*c*), the height of the flap 153, the width of the flap 153, the size of the gap 154, and other factors may contribute to the overall pressure-flow relationship of the flow sensor. For example, a flap 153 having an approximately similar height and width and a gap 154 of sufficient size may result in a substantially linear pressure-flow relationship. In some cases, the number of flaps may contribute to the curvature in the relationship between pressure drop and flow, for example, less flaps may give rise to a more linear response. The type of material(s) from which the flow restrictor 150, 160, 170, 180, 190, 200 is composed of may also contribute to the overall pressure-flow relationship. For example, for a given flow rate through the lumen 101, use of a flow restrictor 150, 160, 170, 180, 190, 200 made up of a more rigid material may result in a greater pressure drop as compared to use of a flow restrictor 150, 160, 170, 180, 190, 200 made up of a more flexible material. Or, in some instances, the shape of the flap(s) may contribute to the manner in which pressure drop varies with flow. For instance, the example flow restrictor 190 of FIG. 20(*e*) resulted in a relatively quadratic, non-linear pressure-flow profile, whereas the example flow restrictor 150 of FIG. 20(*a*) resulted in a substantially linear pressure-flow profile. Accordingly, by adjusting various aspects of the flow restrictor 150, 160, 170, 180, 190, 200 (e.g., shape, size, material, thickness, amongst others), the pressure-flow response profile may be appropriately configured to desired specifications.

Figure 21B:
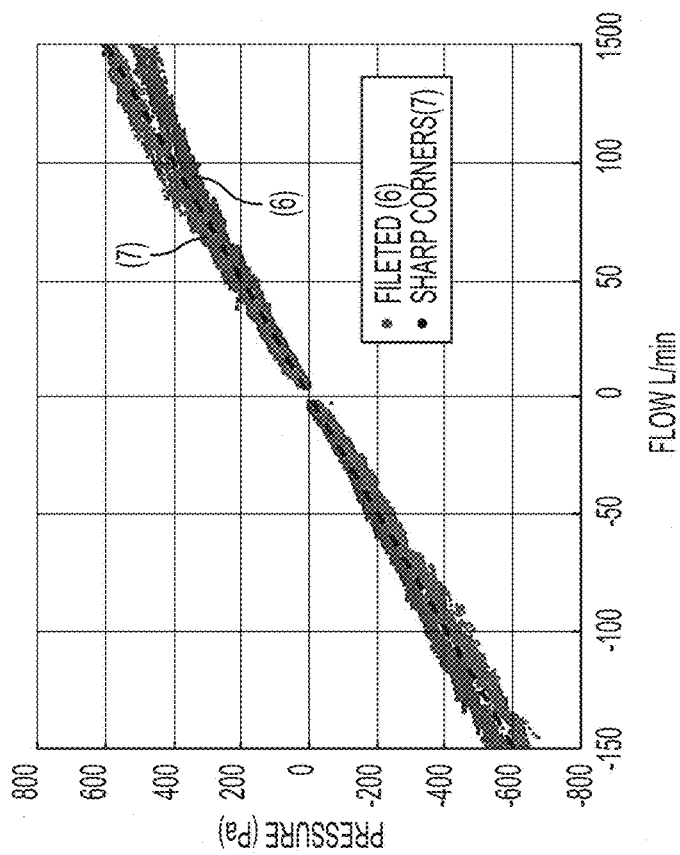
FIGS. 21 (a) and (b) are charts illustrating pressure drop versus flow for several examples of a flow restrictor according to embodiments of the present disclosure.
Figure 21A:
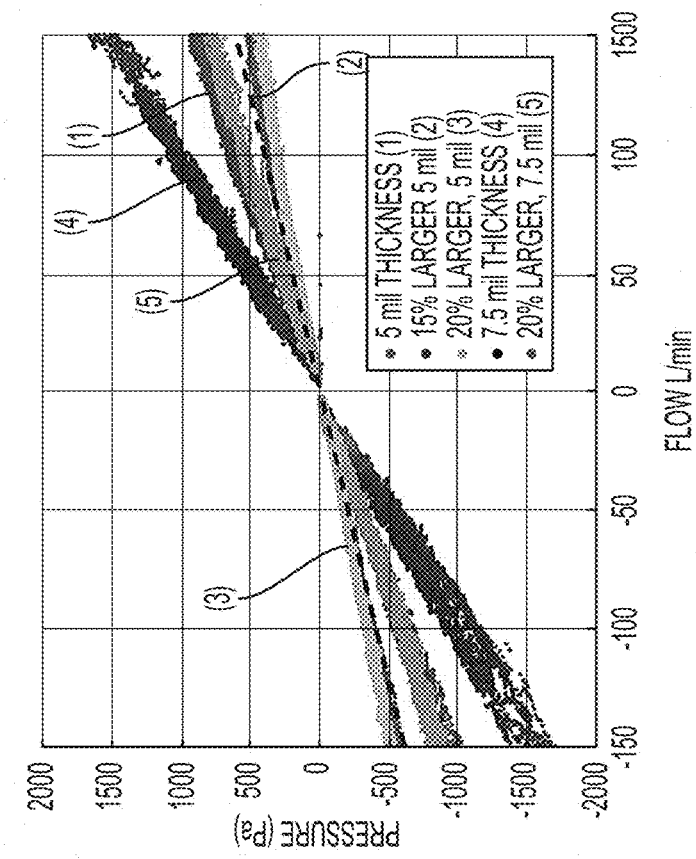

FIG. 21(*a*) illustrates the effects of changing the thickness of the variable orifice flow restrictor and the size of the opening on the relationship between the pressure drop created by the flow restrictor and the flow rate of gas through the lumen. As shown, adding thickness (hence, further mechanical reinforcement) to the flap tends to increase the pressure drop created by the flow restrictor to a level past the resistance limit of the flow conduit. This effect can be ameliorated by increasing the size of the opening by a suitable degree. Accordingly, certain flow restrictors with an enlarged opening may perform better at achieving pressure drops at or near the resistance limit of the flow conduit for a given flow rate of gas regardless of material thickness. In various embodiments, flow restrictors may be constructed so as to vary in thickness along their length, so suit the desired pressure-flow relationship. FIG. 21(*b*) illustrates the effects of providing sharp corners or rounded or fileted corners on the flap on the relationship between the pressure drop created by the flow restrictor and the flow rate of gas through the lumen. As shown, fileting the corners of the flap slightly reduces the pressure drop created by the flow restrictor at a given flow rate, which can be helpful in achieving a pressure drop within the resistance limit of the flow conduit.

According to one particular embodiment of the present disclosure, the flow restrictor 150, 160, 170, 180, 190, 200 is appropriately sized to extend across the lumen 72, 102 of the flow conduit 71, 101 and has a material thickness of approximately 5-7 mil. The approximate surface area of the opening 152, 162, 172, 182, 192, 202 through the flow restrictor 150, 160, 170, 180, 190, 200 is between approximately 0.01-0.1 square inches (e.g., 0.2-0.06 square inches) and the approximate surface area of the single flap or combined surface areas of the multiple flaps is between approximately 0.01-0.5 square inches (e.g., 0.1-0.3 square inches).

With reference to FIGS. 1-18, according to an embodiment of the present disclosure a resuscitation system for assisting ventilation is provided. The system comprises a flow conduit 21, 41, 61, 71, 101 having a lumen 22, 42, 62, 72, 102 defined therein and a processor 145. The processor 145 (optionally located in the cable connector and/or other portions of the resuscitation system) is configured to receive a first signal representing a first pressure at a first region of the flow conduit 21, 41, 61, 71, 101, receive a second signal representing a second pressure at a second region of the flow conduit 21, 41, 61, 71, 101, determine at least one of flow rate and volume of gas flowing through the lumen 22, 42, 62, 72, 102 of the flow conduit 21, 41, 61, 71, 101 based on the first and second signals, and output a feedback signal for a user and/or machine to adjust gas flow through the lumen 22, 42, 62, 72, 102 of the flow conduit 21, 41, 61, 71, 101 based on at least one of the determined flow rate and volume of gas flowing through the lumen 22, 42, 62, 72, 102.

Figure 16A:
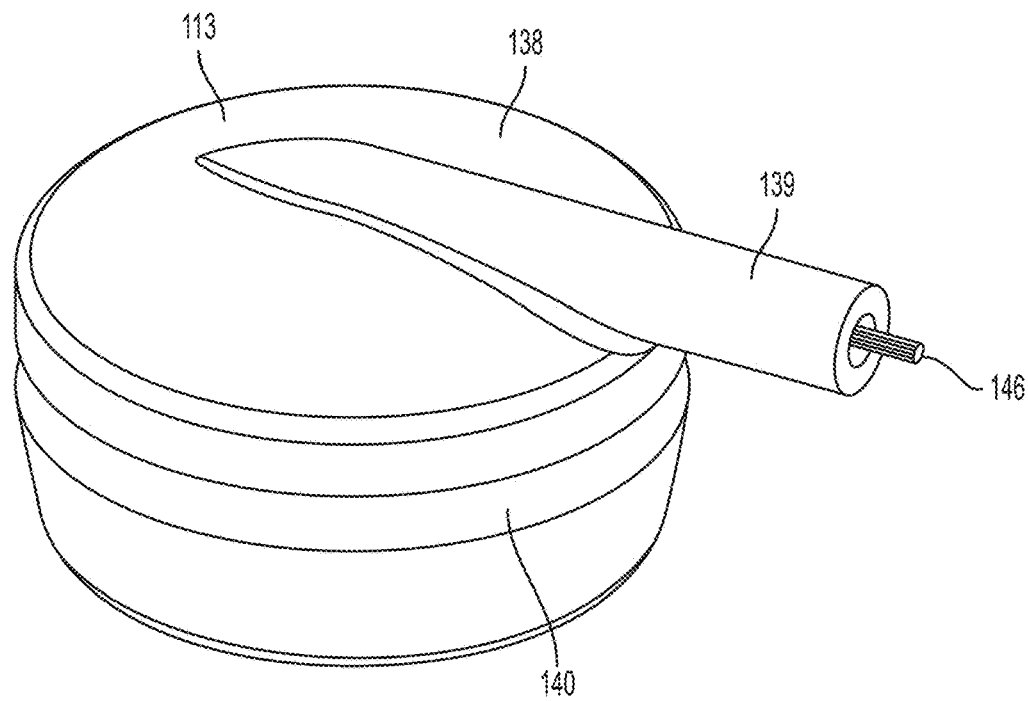
FIGS. 16(a) and (b) are perspective views of a connector of the flow sensor system of FIG. 6.
Figure 16B:
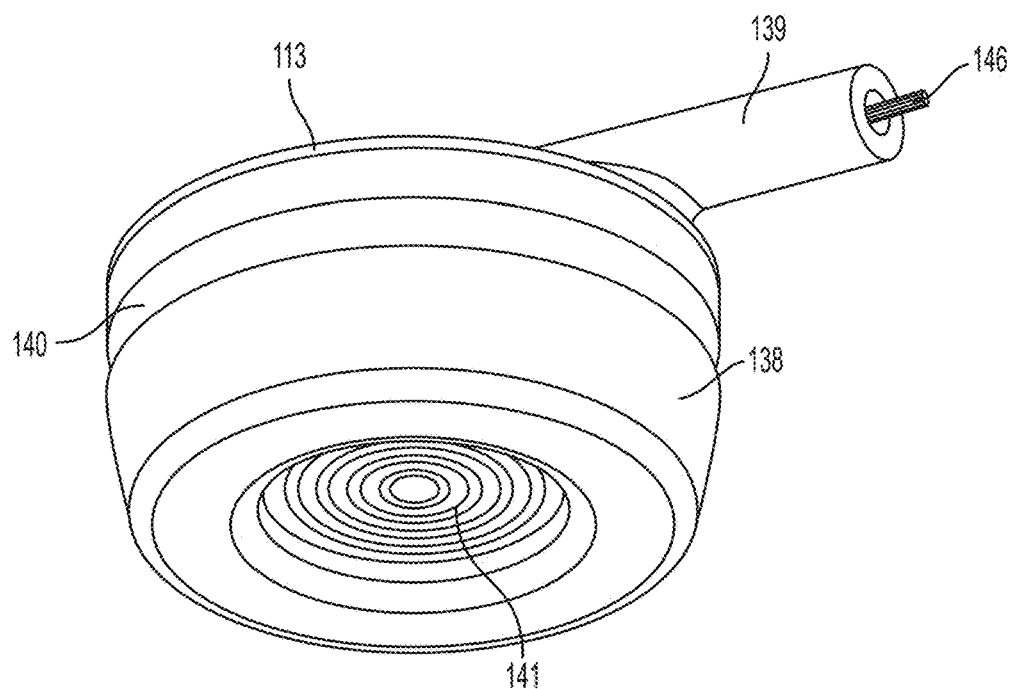

With reference to FIGS. 16-18, according to an embodiment of the present disclosure a connector 113 for establishing communication between any suitable medical devices (e.g., between a sensor and a patient monitor) is provided. The connector 113 comprises a housing 138 configured to be removably coupled to a medical device, a plurality of signal conductors 144 through an interior region of the housing 138, and a signal contact pad 141 having a plurality of conductive elements 143 arranged in a concentric pattern. The conductive elements 143 are in electrical communication with the plurality of signal conductors 144 and are configured to be placed in electrical communication and removably coupled to the medical device. As discussed above, for various embodiments, the connector is provided as a reusable component connected to a medical device monitor, where the reusable connector is configured to be removably coupled to a sensor provided as a disposable component, to establish electrical communication between the medical device monitor and the sensor. While the connector may be used to establish electrical communication between a flow sensor and a ventilation flow monitor, in accordance with embodiments described herein, the connector may be used for other appropriate sensors and/or devices, such as for example, pulse oximeter, muscle pH sensor, carbon dioxide sensor, blood pressure sensor, ECG sensor, chest compression sensor, etc.

Flow sensor systems described herein may be used not only with automated mechanical ventilation systems and manual ventilation (bagging) systems, but also may be used with spontaneously breathing patients. For example, the patient may have a mask to which the flow sensor may be coupled and exposed to the ambient atmosphere. In such cases, because the flow sensor is used in an open system that is exposed to ambient air, the flow sensor does not require two separate absolute pressure sensors. That is, the pressure at the region within the lumen of the flow conduit exposed to the ambient atmosphere is already known to be approximately atmospheric pressure (which can be determined when the flow sensor system is turned on prior to use with a patient or by calculating the pressure value upon which the pressure readings oscillate). Accordingly, a single absolute pressure sensor is provided to determine the pressure on the other region within the lumen of the flow conduit on the opposite side of the flow restrictor. As a result, flow sensor systems in accordance with the present disclosure may employ only a single pressure sensor for measuring the absolute pressure at a patient side region of the lumen within the flow conduit.

Figure 38:
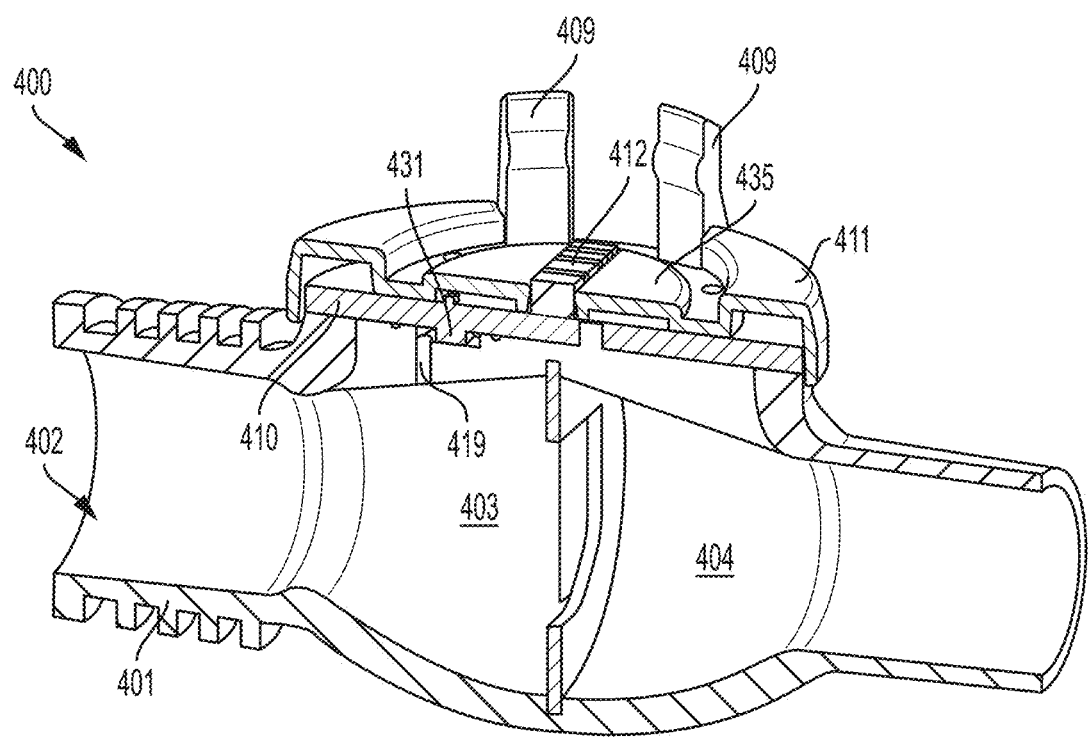
FIG. 38 is a perspective cross-sectional view of a flow sensor system according to an embodiment of the present disclosure.
Figure 39:
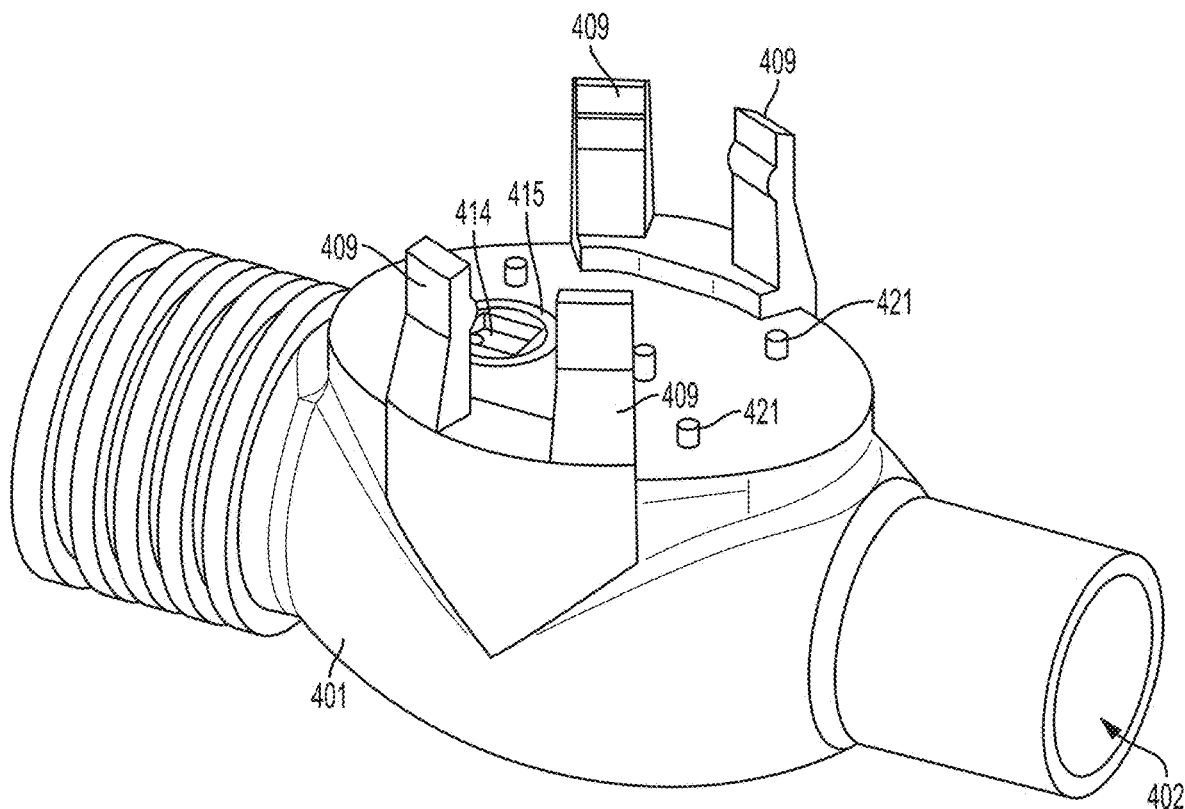
FIG. 39 is a perspective view of a flow conduit of the flow sensor system of FIG. 38.

For instance, FIGS. 38 and 39 illustrate a flow sensor system 400 in accordance with an embodiment of the present disclosure that incorporates a single absolute pressure sensor 431 for measuring the absolute pressure in a first, patient side, region 403 of the lumen 402 within the flow conduit 401. The flow sensor system 400 comprises the flow conduit 401 that defines the lumen 402 allowing for the passage of gas through the flow conduit 401 from a ventilation source, such as a manual ventilation bag or automated ventilation system, to a patient. The flow conduit 401 is configured to allow gas flow between the first, patient side, region 403 and a second region 404. The flow conduit 401 comprises a body extending from a first end to a second end of the flow conduit 401. The body has a hollow interior, which defines the lumen 402.

A flow restrictor 405, which can be a flow restrictor according to any of the above-described embodiments, is disposed within the lumen 402 of the flow conduit 401 between the first region 403 and the second region 404 so as to extend across all or a portion of the lumen 402 in order to obstruct the flow of gas through the lumen between the first region 403 and the second region 404 and create a pressure drop in the flow, which can be measured to calculate the absolute pressure of the gas passing through the flow conduit 401 in the first, patient side, region 403 of the lumen 402.

As shown, the flow sensor system 400 comprises a single absolute pressure sensor 431 disposed adjacent to the first region 403 of the flow conduit 401. The single absolute pressure sensor 431 is configured to measure a pressure due to gas flow in the first region 403 of the flow conduit 401. According to one particular embodiment of the present disclosure, the absolute pressure sensor 431 is a miniature electro-mechanical systems (MEMS) devices configured to sense an absolute pressure within the respective region 403 of the lumen 402, such as the BME 280 sensor or BMP 200 sensor manufactured by Bosch Sensortec GmbH. It is to be appreciated, however, that the absolute pressure sensor 431 may be of any type known to be suitable to those having ordinary skill in the art capable of sensing a pressure within the region 403 of the lumen 402. Or, as further provided herein, rather than absolute pressure sensors, differential pressure sensors may be employed for determining the pressure drop between regions on opposing sides of the flow restrictor.

The absolute pressure sensor 431 is in communication with the lumen 402 in the first, patient side, region 403 in order to measure the absolute pressure of the gas flowing through the lumen 402 in the region 403. The absolute pressure sensor is mounted on and connected to a circuit board 410 disposed on the flow conduit 401 such that the absolute pressure sensor 431 is disposed in a chamber 414 provided in the upper surface of the flow conduit 401. The chamber 414 is configured to house and support the pressure sensor 431 adjacent to the lumen 402 of the flow conduit 401. The chamber 414, and thus the pressure sensor 431, is in fluid communication with the lumen 402 via an opening 419 defined in and extending through the flow conduit 401 between the lumen 402 and the chamber 414. A membrane, diaphragm membrane, or a rolling diaphragm as discussed above with respect to various other embodiments of the present disclosure may be provided to prevent moisture, debris, and possibly gas from passing to the chamber 414 from the lumen 402.

The circuit board 410 may be secured to the flow conduit 401 by any suitable manner, for example, via mechanical attachment (e.g., welding, adhesive, interference fit, complementary coupling features, etc.). With reference to FIG. 39, a ring hole 415 may be provided in the top surface of each of the flow conduit 401 around the chamber 414. A sealant or adhesive may be placed within the ring hole 415 to secure the circuit board 410 to the upper surface of the flow conduit 401. The upper surface of the flow conduit 401 also comprises upwardly extending pins 421. The pins 421 are received in pin holes (not shown) extending through the circuit board 410 to assist in positioning and securing the circuit board 410 on the upper surface of the flow conduit 401.

An adapter 412, which may be the same as the adapter discussed above with reference to the embodiment of FIGS. 6-18, may be disposed on an upper surface of the circuit board 410 and is electronically connected to the circuit board 410. The flow sensor system 400 also comprises a cover 411 for the circuit board 410. The cover 411 is positioned on the upper surface of the flow conduit 401 over the circuit board 410. Both the circuit board 410 and the cover 411 are shaped to correspond to the shape of the upper surface of the flow conduit 401 in order to fit on the flow conduit 401 and hold the circuit board 410 in place. The cover 411 is configured to hold the adapter 412 and allow the adapter 412 to extend therethrough so that the adapter 412 can establish electronic communication with a connector, such as the connector 113 discussed above with reference to the embodiment of FIGS. 6-18. The cover 411 comprises an alignment disk 435 positioned on the top of the cover 411. As discussed above, the alignment disk 435 is configured to provide a guide for positioning the connector so that the connector may be electronically connected to the adapter 412 and to limit lateral movement of the connector once the connector is connected to the flow conduit 401. Snap arms 409 may extend from the upper surface of the flow conduit 401 to engage the connector to maintain the connector in a connected position with the cover 411 and the adapter 412, as discussed above. Though, the connector may be engaged with the conduit by any other suitable method, for example, interference fit, magnetic coupling, etc.

In another embodiment of the present disclosure, as shown in FIGS. 57-59(a)-(b), the flow sensor system 100 includes chamber inserts 600 and membranes 640 disposed within respective recesses 650 on either side of the flow restrictor 105, so as to form corresponding chambers 610 for each pressure sensor. It is noted that, for this embodiment, the pressure sensors are provided on the lower side of the circuit board 110 and, hence, are not expressly shown in FIGS. 57-59(a)-(b). Also not expressly shown in these figures are optional heating elements (e.g., electrical resistors) located adjacent to the pressure sensors. Similar to other filter layers described herein, the membranes 640 may be made up of a gas permeable, breathable, hydrophobic material that allow for the passage of gas through the membrane 640 while also providing a barrier that prevents or otherwise obstructs the passage of liquid moisture and debris through the membrane 640. The body of the flow conduit 101 is shaped so as to include reservoirs 630 on either side of the flow restrictor 105, for trapping and collection of water, particulate matter and/or other debris.

Figure 59A:
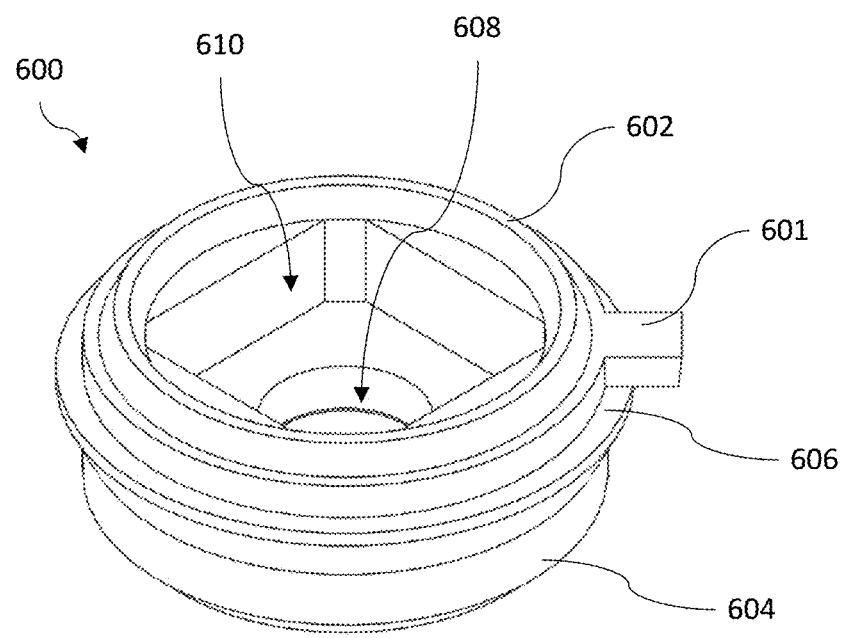
FIGS. 59(a)-(b) depict a perspective view and a cross-sectional view of a chamber insert for the flow sensor of FIG. 57.
Figure 59B:
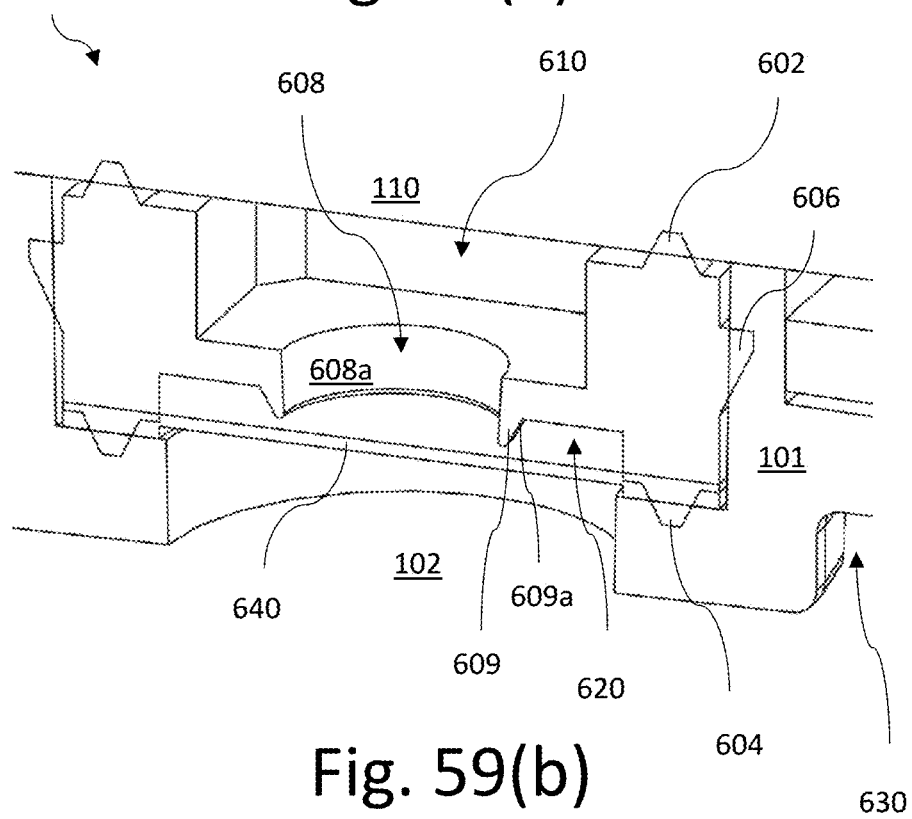
Figure 60:
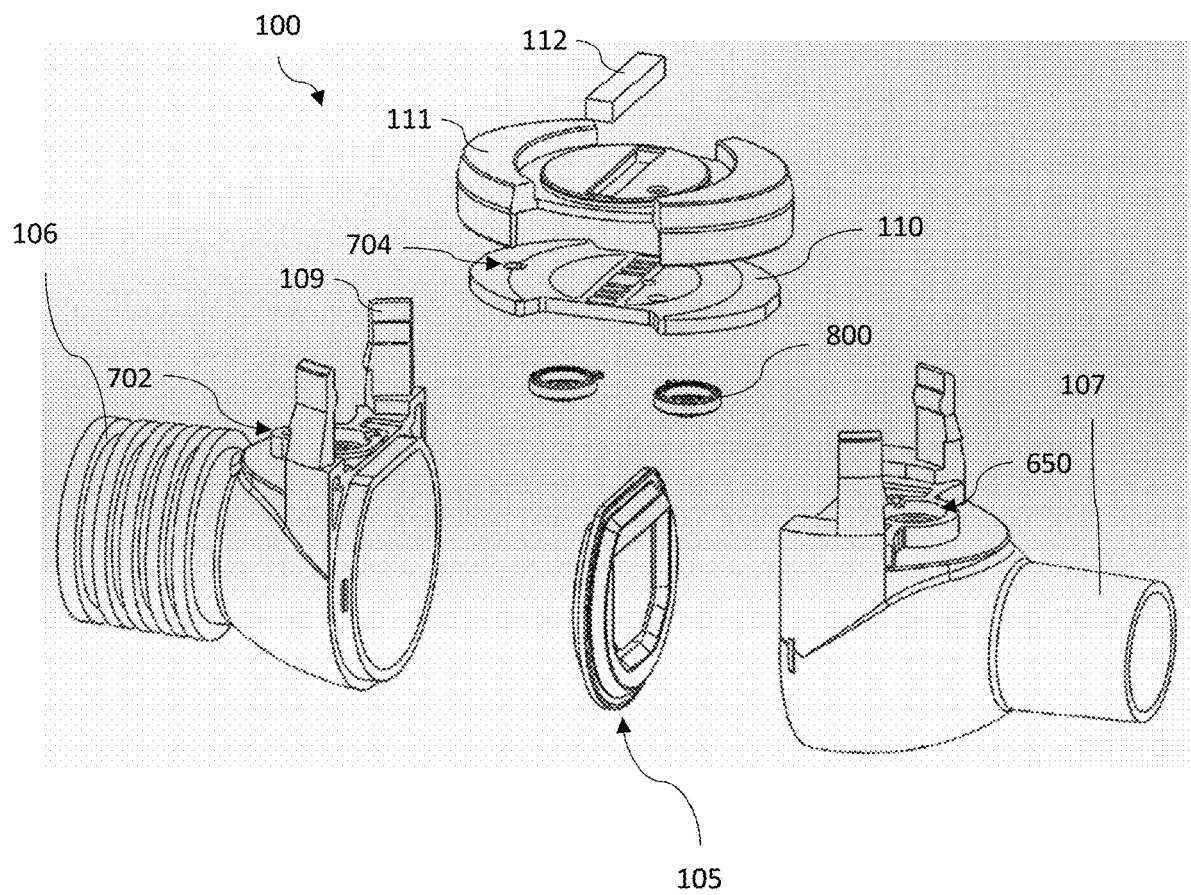
FIG. 60 depicts an exploded perspective view of another flow sensor system in accordance with an embodiment.
Figure 61:
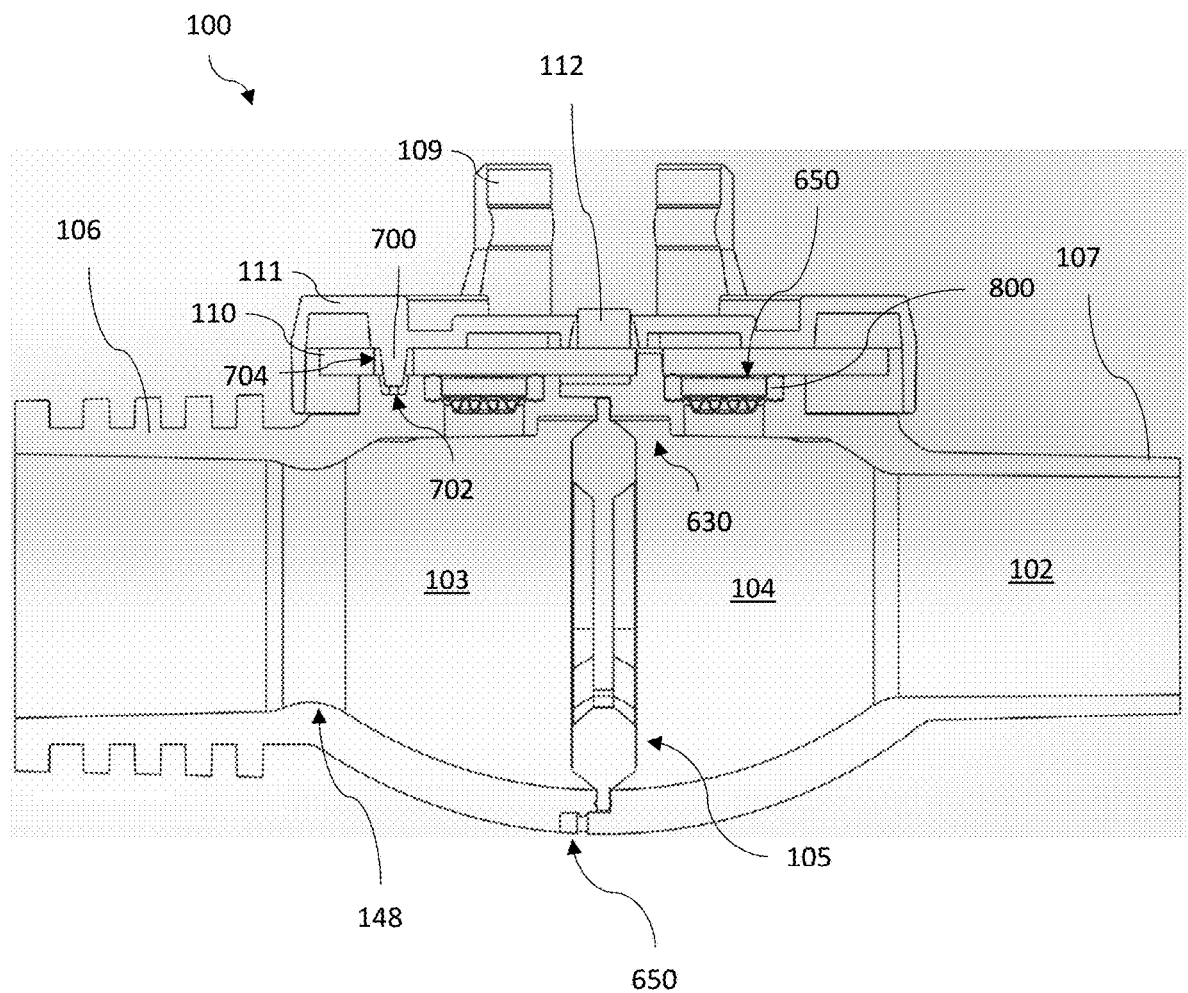
FIG. 61 is a cross-sectional view of the assembled flow sensor system of FIG. 60.

FIG. 59(a) shows a closer view of the chamber insert 600, and FIG. 59(b) depicts a cross-sectional view of the chamber insert 600 positioned within a corresponding recess 650 of the flow sensor system. When suitably positioned within the recess 650, a chamber 610 is formed around the respective pressure sensor of the circuit board 110. While not expressly shown in FIG. 59(b), the pressure sensor is located within the chamber 610 and mounted on the circuit board 110 so as to face in a downward direction, toward the opening 608. The opening 608 allows for gas to pass there through having traveled across the gas permeable membrane 640 between the lumen 102 of the flow conduit 101 and the chamber 610. Further, the chamber 610 may be shaped so as to allow a snug fit for the pressure sensor therein, with little air volume between the pressure sensor and the surface of the chamber insert 600. By sizing the chamber 610 to approximate that of the pressure sensor (e.g., minimizing the amount of excess chamber volume), the total amount of air for the heating elements to transfer heat is reduced, leading to an overall enhanced heating effect as compared to instances where the chamber is sized to enclose larger volumes of air.

In this embodiment, the opening 608 has a ribbed portion 609 that is structured so as to form another reservoir 620 adjacent to the opening 608 and the membrane 640. This reservoir 620 provides a small pocket for trapping and collecting liquid, debris and/or other potential sources of contamination that might otherwise interfere with pressure sensor readings. For instance, the reservoir 620 may serve as a destination for water vapor having traveled from the flow lumen 102 and passed through the membrane 640 to condense or settle. Salt or other particulates that are able to pass through the membrane 640 may also collect at the reservoir 620. The ribbed portion 609 is slightly tapered in a manner that directs liquid or other debris from the opening 608 toward the reservoir 620.

In some embodiments, to encourage water and/or other sources of contamination away from the chamber 610 within which the pressure sensor is located and, for example, toward the reservoir 620, certain portions of the chamber insert 600 may exhibit varying levels of hydrophobicity. As an example, the inner surface 608a of the opening 608 may include a material and/or coating that exhibits a greater level of hydrophobicity as compared to the outer surface 609a of the reservoir 620. For instance, the outer surface 609a of the ribbed portion 609 and/or the reservoir 620 may include a material and/or coating that is hydrophilic in nature (e.g., contact angle less than 90 degrees). As noted above, heating elements may be provided within or adjacent to the chambers 610 (e.g., next to the pressure sensors), further reducing the possibility of condensation which could otherwise give rise to measurement errors.

As illustrated, the chamber insert 600 includes additional ribbed portions 602, 604, 606 formed as rings around the body of the chamber insert and that protrude therefrom so as to provide an enhanced seal and/or mechanical stability in engagement between the chamber insert 600 and other portions of the flow sensor system. In particular, the chamber insert 600 includes an upper ribbed portion 602 that protrudes upward from the body of the chamber insert 600 in a manner that sealingly engages with the lower surface of the circuit board 110. The chamber insert 600 also includes a lower ribbed portion 604 that protrudes downward from the body of the chamber insert 600 to sealingly engage with a corresponding region of the flow conduit 101. And further, the chamber insert 600 includes a lateral ribbed portion 606 that protrudes laterally from the chamber insert body to sealingly engage with another corresponding region of the flow conduit 101.

Figure 57:
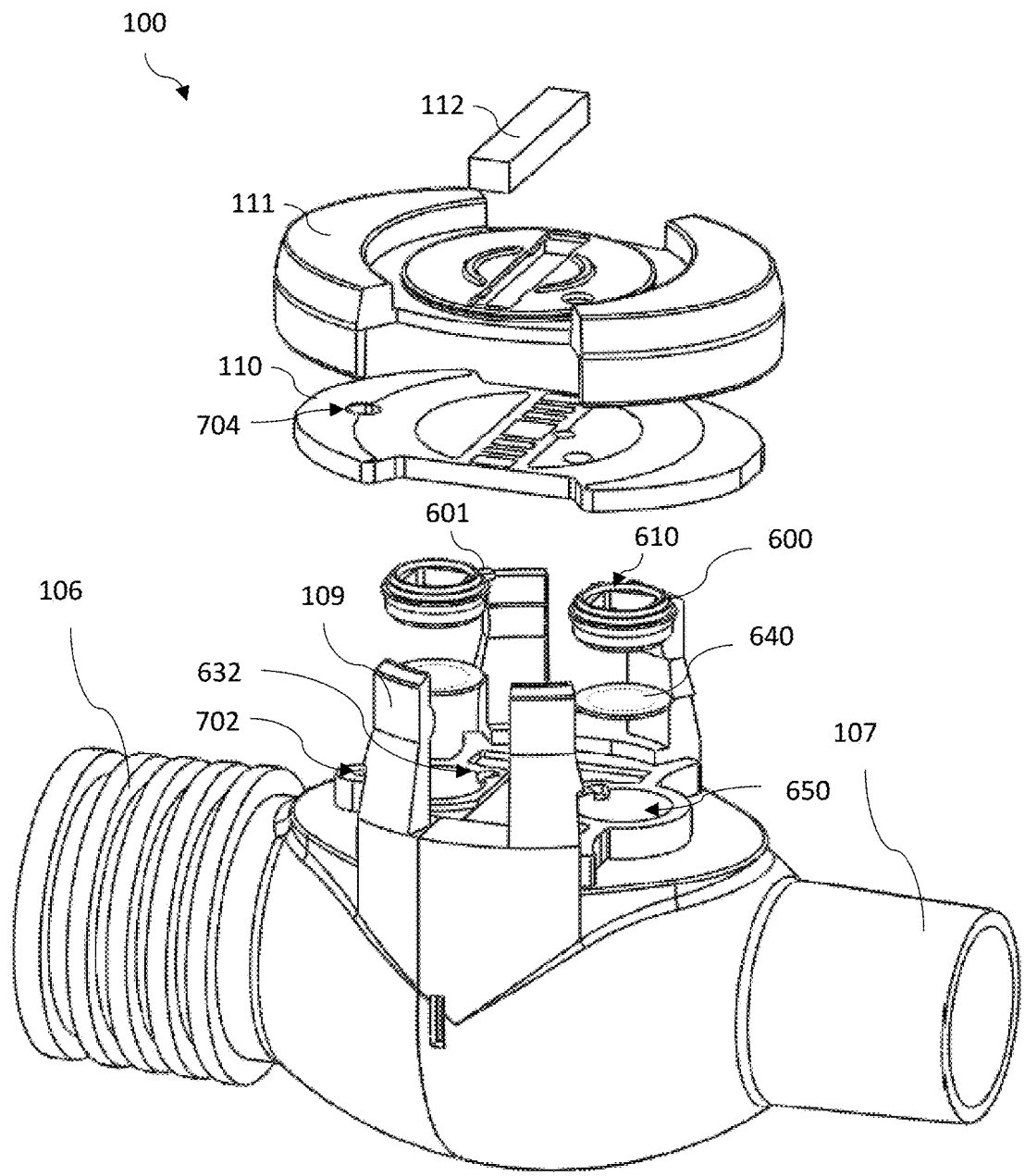
FIG. 57 depicts an exploded perspective view of a flow sensor system in accordance with an embodiment.
Figure 58:
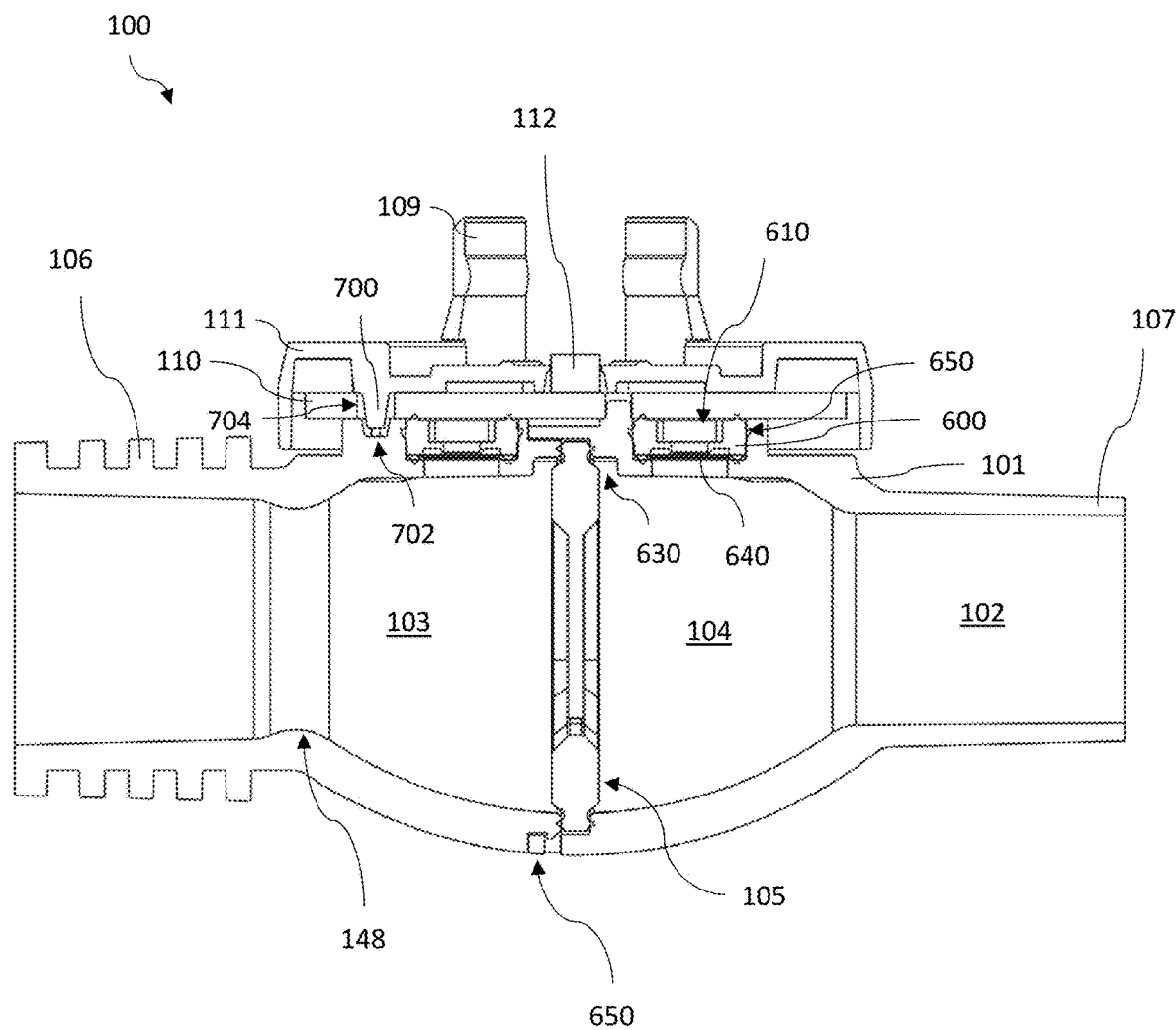
FIG. 58 is a cross-sectional view of the assembled flow sensor system of FIG. 57.

For convenient and proper assembly of the flow sensor, similar to other embodiments described herein, various parts may include appropriately positioned protrusions and recesses for insertion/assembly thereof. For example, as shown in FIG. 58, the cover 111 includes a pin 700 that inserts into a hole 704 of the circuit board 110, and further inserts into a hole 702 of the flow conduit 101. Further, as shown in FIGS. 57 and 59(a), the chamber insert 600 may include a keying arm 601, which is constructed for insertion in a corresponding recess 632 of the flow conduit 101. The combined keying arm 601 and recess 632 assists a user in proper assembly of the flow sensor system, for example, so that the insert 600 is not inserted upside down.

Figure 62A:
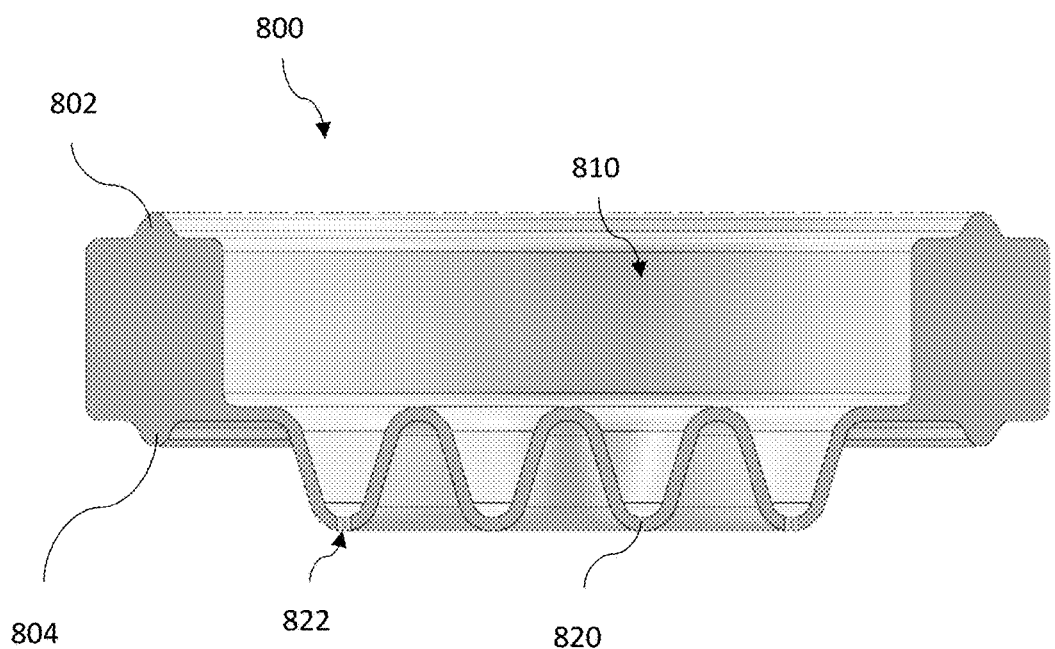
FIGS. 62(a)-(b) depict a perspective view and a cross-sectional view of a chamber insert for the flow sensor of FIG. 60.
Figure 62B:
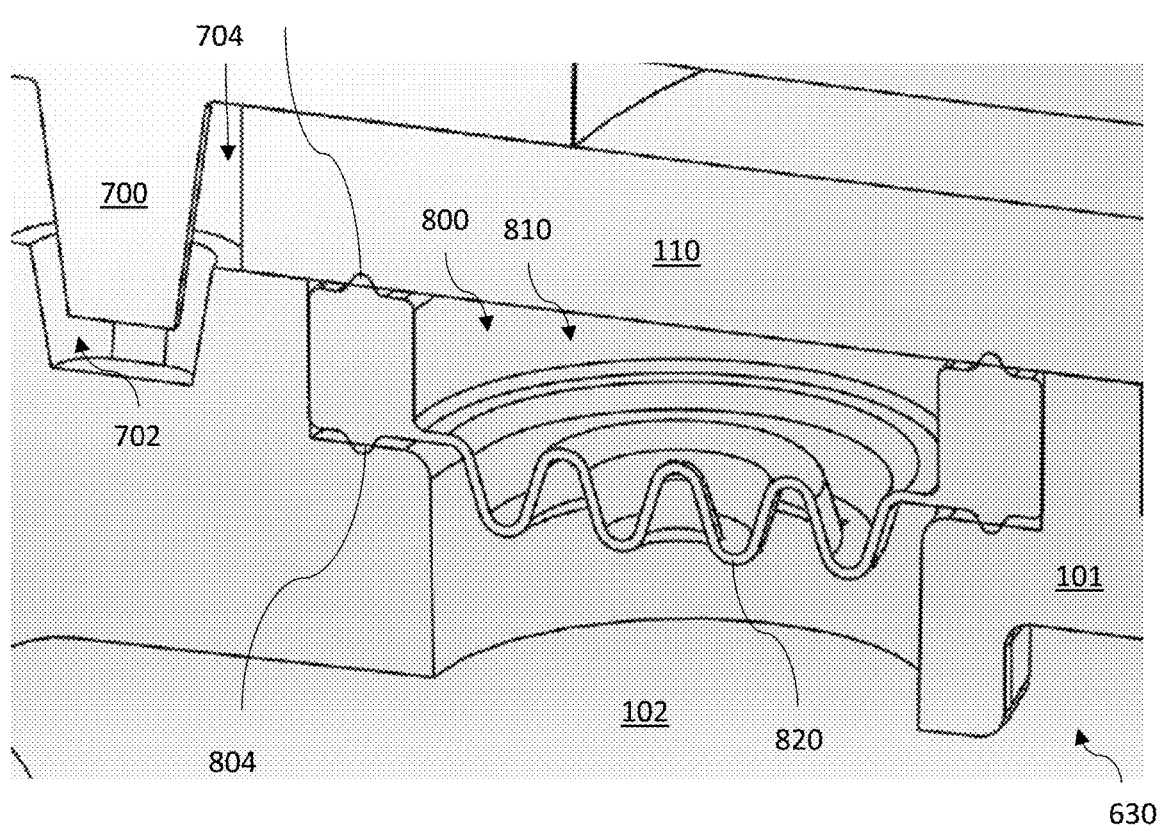

FIGS. 60-62(a)-(b) depict another embodiment of a flow sensor system 100 having chamber inserts 800 that include diaphragm membranes 820 similar to those of other embodiments described herein. It is noted that, for this embodiment, the components of the flow conduit 101, circuit board 110, cover 111 and adapter 112 are the same as that described for the embodiment of FIGS. 57-59(a)-(b), with the exception of the chamber inserts 800 and absence of the gas permeable membranes 640. In particular, the chamber inserts 800 of this embodiment have replaced the chamber inserts 600 and membranes 640 of FIGS. 57-59(a)-(b). Indeed, the respective chamber inserts 600 and 800 may be interchangeable. Accordingly, upon assembly of the flow sensor, the chamber inserts 800 are disposed within respective recesses 650 on either side of the flow restrictor 105 so as to form corresponding chambers 810 for each pressure sensor. In this example, the diaphragm membrane 820 provides a substantial barrier between the flow conduit 101 and the respective chamber 810, allowing for pressure changes within the lumen 102 within the immediate vicinity of the diaphragm membrane 820 to be suitably determined. In various embodiments, the diaphragm membrane 820 is composed of a material that is impermeable to gas. Also, the body of the flow conduit 101 is shaped so as to include reservoirs 630 on either side of the flow restrictor 105, for trapping and collection of water, particulate matter and/or other debris. FIG. 62(*a*) shows a closer view of the chamber insert 800, and FIG. 62(*b*) depicts a cross-sectional view of the chamber insert 800 positioned within a corresponding recess 650 of the flow sensor system 100. When suitably positioned within the recess 650, a substantially sealed chamber 810 is formed around the respective pressure sensor of the circuit board 110. The diaphragm membrane 820, formed of an impermeable material and equipped with a suitably patterned structure, then allows for pressure equalization between the lumen 102 of the flow conduit 101 and the space within chamber 810 where the pressure sensor is located. Accordingly, pressure changes of the region of the lumen 102 immediately outside of the chamber 810 can be suitably determined by the pressure sensor located within the chamber 810, while at the same time minimizing or otherwise reducing the travel of water vapor and/or other gases into the chamber in a manner that would introduce unwanted error in the pressure measurements. By sufficiently protecting the pressure sensor from significant exposure to the external environment, other methods for averting water accumulation (e.g., via condensation) within the chamber and, hence, ensuring accuracy of pressure sensor measurements, such as implementation of the resistive heating element(s) (which uses a small amount of power output from the system) may not be required.

As discussed above, it may be desirable for the flow sensor system 100 to be used in environments of varying pressure, for example, low altitude and high altitude. However, if the chamber 810 is completely sealed, the flow sensor system may succumb to inaccurate pressure-flow readings when subjected to large variations in environmental pressure. The rolling diaphragm configuration described above may be employed, though, another method of compensating for such situations is by incorporating a slight opening 822 within the diaphragm membrane 820, as illustrated in FIG. 62(*a*). The presence of this opening 822 allows for slow travel of gas between the chamber 810 and the lumen 102. Accordingly, when the flow sensor 100 system moves from a high pressure system to a low pressure system, or vice versa, the pressure between the chamber 810 and the lumen 102 can come to a suitable equilibrium, without detrimental effect to flow sensor operation. However, the size of the opening 822 is small enough such that immediate pressure fluctuations due to flow through the sensor will still be captured in a reliable and suitably accurate manner. As a result, the flow sensor system 100 may be effective in its usage both at sea level (i.e., high pressure environment) and at high altitudes (i.e., low pressure environment).

The chamber insert 800 may include ribbed portions 802, 804, similar to that discussed above with respect to other embodiments. Such ribbed portions may provide an enhanced seal and/or mechanical stability in engagement between the chamber insert 800 and other portions of the flow sensor system 100, such as the circuit board 110 and the flow conduit 101.

In addition to processing pressure signals to determine particular flow parameters, such as flow rate and flow volume, flow sensor systems in accordance with certain embodiments may be used to provide additional patient information to assist other aspects of the resuscitation process. For example, the pressure signal recorded by the pressure sensor(s) may be used to detect or otherwise estimate the rate and/or depth of chest compressions. When CPR chest compressions are applied to a patient, a small amount of airflow is generated due to the force of compressions on the chest of the patient. This airflow can be measured by the flow sensor system and, hence, can be used to determine whether chest compressions are being applied, the rate at which chest compressions are occurring, and the relative depth or force of CPR compressions.

Figure 40:
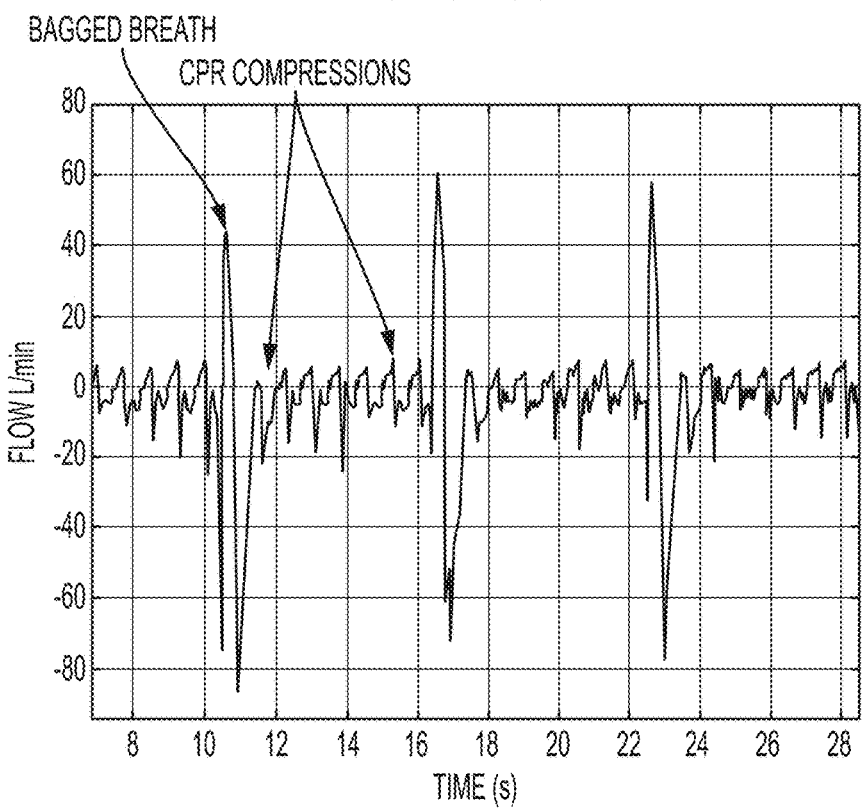
FIG. 40 is a graph that plots how flow rate changes with time as chest compressions are applied to the patient.

FIG. 40 depicts a graph that plots how flow rate changes with time as chest compressions are applied to the patient. Flow rates generated from CPR chest compressions can be clearly distinguished from flow rates generated from bagged breaths given to the patient. Thus, the number of chest compressions applied can be easily counted by the system and/or user. In some cases, the overall minute ventilation provided to be patient may be characterized from compressions, which may indicate that fewer ventilation breaths may be required. As shown in FIG. 40, chest compressions produce a rate of airflow that is readily apparent and measurable by the flow sensor system. Further, the flow rate produced from chest compressions, while easily observable, is substantially smaller than the flow rate produced from a bagged breath. Hence, it is possible to determine the rate of chest compressions applied to the patient. Accordingly, the number of chest compressions may also be counted or otherwise tracked by a user and/or system, for example, to ensure that the rescue process is in adherence to preferred resuscitation protocols. In some embodiments, an accelerometer may be used to detect CPR chest compressions and/or ventilation rate. Sternal displacement due to compressions has a high frequency leading edge and is initially negative (compression), while the ventilation cycle has a leading edge that is approximately an order of magnitude lower in frequency (0.5 Hz vs. 5 Hz) than the compression cycle, and is positive (chest rising due to lung inflation). Thus, ventilations can be distinguished from compressions, e.g., using a bandpass filter in the software detection algorithm. In situations where compressions are given to the patient during the course of a ventilation, the system may be able to distinguish between flows that have arisen due to ventilation versus compression. Such a distinction may be beneficial so that flow arising due to a compression is not mistakenly counted as an additional ventilation when determining ventilation rate. For example, in counting the number of ventilations that have occurred, there may be a requirement for the flow volume to meet a particular threshold (e.g., 100 mL) for a positive ventilation detection to be registered, otherwise, the system may be configured such that flow volumes below the threshold are not sufficient enough to be counted as "true" ventilations, but may simply be due to other activities (e.g., chest compressions, movement of the patient).

A common protocol employed by emergency services during resuscitation is a 30:2 protocol, where 30 chest compressions are applied for every 2 positive ventilation breaths. An alternative protocol is for a patient to be ventilated continuously at a rate of 8-10 positive breaths per minute concurrently with synchronized chest compressions (e.g., applying a positive ventilation breath during the upstroke phase of chest compression), for example, when the airway is in place. Thus, depending on the resuscitation protocol employed, the system may provide an indication of the number of chest compressions that have been applied so as to guide/coach the user in applying ventilations at the appropriate time(s), and/or to coordinate timing of positive pressure breaths provided by an automated ventilation system. For example, if a 30:2 compressions to ventilations protocol is employed, the flow sensor system, optionally in combination with a chest compression sensor (e.g., accelerometer, motion sensor), may be used to detect whether chest compressions are applied. The system may further count the number of applied compressions (e.g., based on pressure data collected from the flow sensor and/or accelerometer data collected from a chest compression sensor) and then alert the rescuer to give breaths at the appropriate times. Alternatively, in another example, if a continuous ventilation protocol is employed, a countdown timer and/or a count up timer based on elapsed time may be used to continuously prompt the user and/or ventilation apparatus to give a breath every 6-8 seconds or another rate, according to whatever target rate is provided by the protocol. Or, the system may simply prompt the user to apply a ventilation according to a timed schedule (e.g., every 15-20 seconds, approximately every 18 seconds for 30 compressions at 100 compressions/minute).

The system may have a user interface that allows the preferred ventilation protocol to be applied. For example, a button or other control may be actuated so as to toggle or otherwise select between ventilation protocols so that the rescuer is appropriately guided through the ventilation portion of the resuscitation process. Though, it is not required for a user to actively select which ventilation protocol is applied. For example, in some embodiments, because the flow sensor system may detect both ventilations and chest compressions, the ventilation protocol may be automatically detected and, hence, be automatically selected without need for an express user selection. That is, once ventilations are detected, a ventilation dashboard or other feedback mechanism (e.g., visual, audio, haptic) configured to provide guidance to the user in administering proper ventilations (according to the appropriate ventilation protocol) may be launched.

In some embodiments, it can be beneficial to time the CPR compressions such that the CPR compression does not occur at the same time as a ventilation. The system may time compressions provided by manual or automated CPR compressions via the pressure signal and/or an accelerometer. Based on information from the accelerometer or pressure signal in combination with data from the ventilation assembly, the system determines whether a timing for a ventilation overlaps with a timing for a CPR compression cycle and provides an indication to the rescuer if a ventilation is being delivered during a compression cycle so the rescuer can delay either the compression or the ventilation so that they do not overlap. As noted above, the system may guide the rescuer in providing a positive pressure breath during the chest recoil phase of compressions so that air is more easily able to travel into the lungs due to the negative intrathoracic pressure induced by chest wall recoil.

In some embodiments, artifacts produced due to chest compressions may be filtered out of the flow rate and/or volume signal, allowing chest compressions to continue while also observing or determining an estimated, substantially error-free flow/volume signal. For example, since the rate of chest compressions may be determined via an accelerometer and/or pressure signal, the system may be configured to filter out artifacts due to the compressions so as to calculate and/or display a filtered representation of the flow rate and/or flow volume. In various embodiments, systems and methods for filtering out chest compressions from a flow signal may be similar to those described in US2013/0184600, entitled "Systems and Methods for Filtering ECG Artifacts," which is hereby incorporated by reference in its entirety.

The filtering algorithm may be a time domain filter. Additionally, the filtering algorithm may be adaptive such that it identifies the different artifacts created by different rescue workers applying chest compressions, or different artifacts resulting from rescue worker fatigue, and adjusts the filter accordingly. In various examples, the filter may be a time domain filter, a Kalman filter, an autoregressive moving average (ARMA) filter, an adaptive notch filter, or a template-based filter. In one example, a Kalman filter may be used to predict the artifact to be subtracted from the flow data in a continuously adaptive process. According to one embodiment, a heterodyne process is used to filter out the compression artifact by filtering the compression artifact in time with a carrier signal. The carrier signal is created by a local oscillator and set to be close in frequency to the frequency of the compression rate. The heterodyne process may be used to modulate the amplitude of the artifact.

In certain embodiments, a continuous filter may be used to filter out artifacts from the flow data. The continuous filter may be synchronized to the chest compressions. In one example, one or more notch filters are used to filter out artifacts from ECG data. When multiple notch filters are used to remove the compression artifacts, the center frequency of the notch filter can correspond to the chest compression rate or two or more times that chest compression rate (e.g., harmonics of the chest compression rate). The chest compression rate may be determined using sensor data (including, but not limited to pressure sensors, impedance sensors, accelerometers, motion sensors, or other types of sensors), data provided by an automatic electro-mechanical chest compression device, or data derived from a calculation of compression rate based on the incoming raw pressure data. In one example, two filters are set to the compression frequency, two filters are set to the first harmonic of the compression frequency (where the first harmonic is equal to two times the compression frequency), and one filter is set to the second harmonic of the compression frequency (where the second harmonic is equal to three times the compression frequency). Optionally, additional filters may be used to filter out higher harmonics of the compression frequency. In another example, the center frequency of the notch filter corresponds to the most prominent frequency of the artifact.

In some embodiments, the flow sensor system may be used to detect the type of ventilations that are applied to the patient, or whether the patient is breathing spontaneously. Based on the profile of pressure and/or flow, it can be determined whether the type of ventilation is due to manually applied bagged breaths, automatically applied ventilator breaths or spontaneous breaths by the patient. For example, information provided from the flow sensor system may be used to determine whether breaths are generated via positive or negative pressure ventilation. Positive pressure ventilation involves breaths provided from automatic ventilators and manual bag valve masks, which supply a positive pressure at the airway opening to push air into the lungs. Negative pressure ventilation occurs in spontaneously breathing patients where the diaphragm creates a negative intrathoracic pressure to draw air into the lungs.

Figure 41:
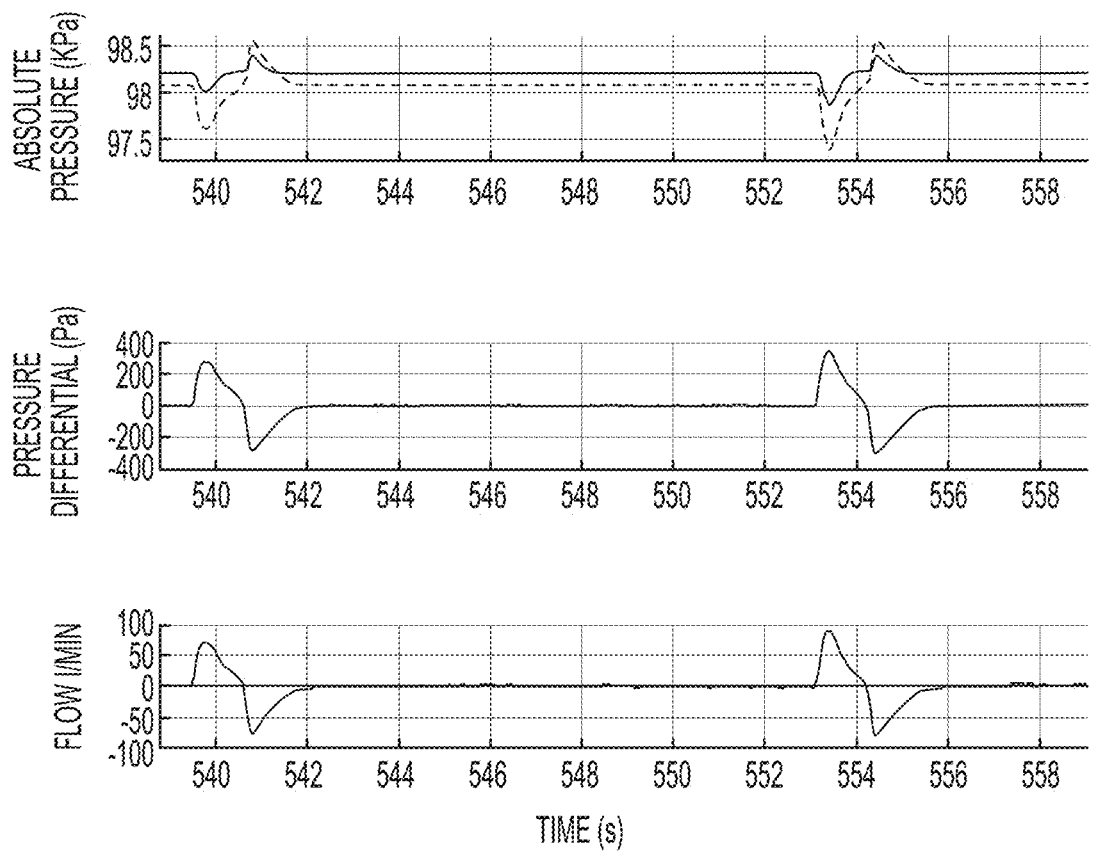
FIG. 41 depicts a series of graphs that show the absolute pressure, pressure differential and flow rate detected over time by the flow sensor system for a spontaneously breathing patient.

FIG. 41 depicts a series of graphs that show the absolute pressure, pressure differential and flow rate detected over time by the flow sensor system for a spontaneously breathing patient. Such a flow profile may also be indicative of a patient who is experiencing agonal respiration, which is generally characterized by an abnormal pattern of breathing and may include gasping, labored breathing, accompanied by irregular vocalization and/or myoclonus. In a spontaneous breath, because air is drawn in due to negative pressure generated by downward movement of the diaphragm, the absolute pressure senses an initial decrease during inspiration, followed by an increase in pressure during expiration.

In some cases, mere detection of a negative pressure may not be conclusive that spontaneously breathing is occurring; for example, incidental jostling or movement of nearby equipment may cause a negative pressure signal to be detected. Hence, to provide greater confidence of spontaneous breathing, it may be useful to set a minimum threshold of flow rate/volume (e.g., flow volume thresholds of at least 50 L, at least 100 mL, at least 150 L, etc. and/or flow rates of at least 5 L/min, at least 10 L/min, etc.), in combination with a negative pressure change. For example, when the system detects an initial negative pressure change and a threshold level of flow rate or volume, the system may provide an indication to the rescuer or other device that the patient may be undergoing spontaneous breathing. This information, while not conclusive, may be further useful in providing a rescuer with an indication that the patient may be experiencing return of spontaneous circulation (ROSC). For example, the system may provide a display to the rescuer of "Possible ROSC" and/or may provide appropriate instructions/guidance. To determine whether ROSC has actually occurred, other parameters may need to be considered, such as ETCO2, ECG signal, pulse detection, pulse oximetry, etc.

Figure 42:
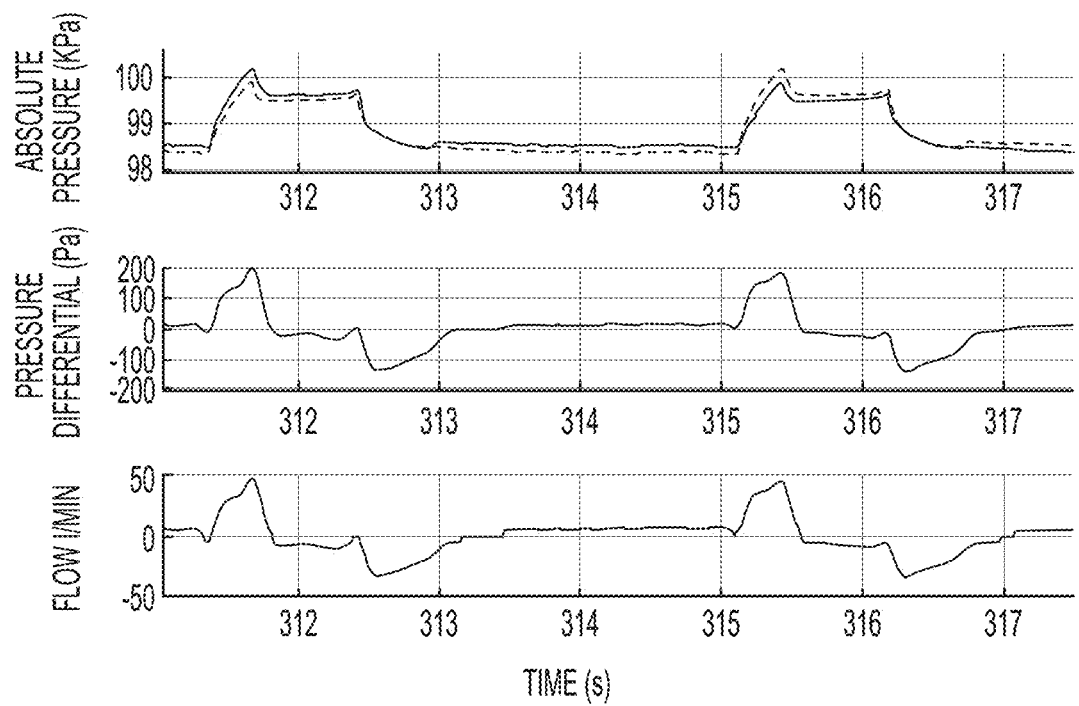
FIG. 42 depicts a series of graphs that show the absolute pressure, pressure differential and flow rate detected over time by the flow sensor system for a patient receiving positive pressure ventilation with a ventilator.

FIG. 42 depicts a series of graphs similar to that shown in FIG. 41, yet for a patient receiving positive pressure ventilation with a ventilator. Here, both absolute pressure sensors are increased above atmospheric pressure for both inspiration and expiration. The pressure waveform is further characterized by a plateau at the height of the ventilator breath, which is distinct from a positive pressure breath given by manual ventilation.

Figure 43:
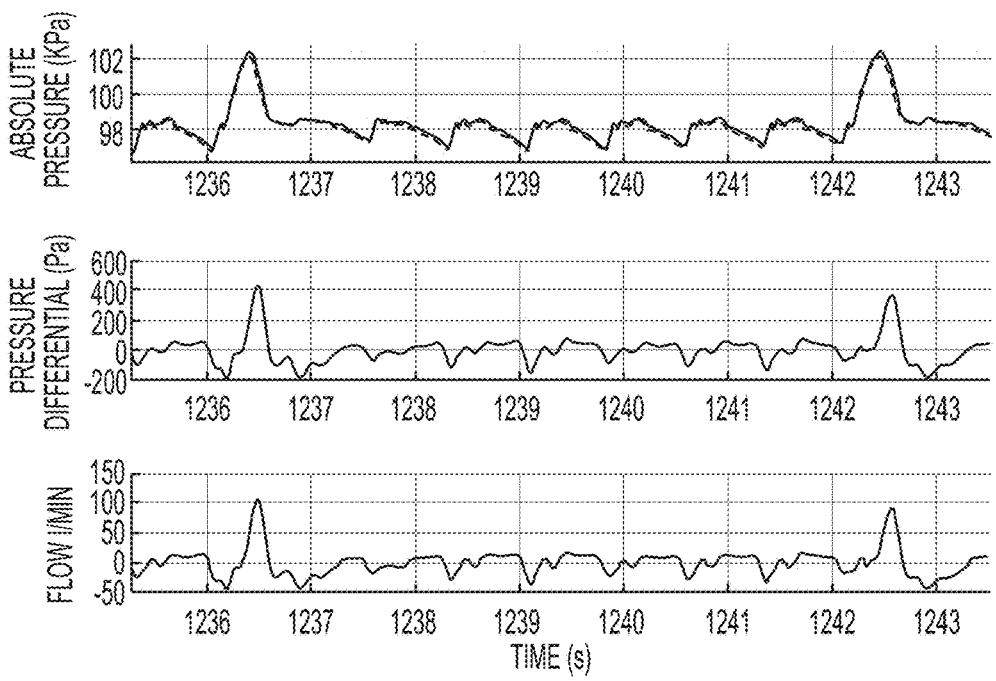
FIG. 43 depicts a series of graphs that show the absolute pressure, pressure differential and flow rate detected over time by the flow sensor system for a patient receiving manual (bagged) ventilation breaths.

Similarly, FIG. 43 shows similar graphs for a patient receiving manual (bagged) ventilation breaths. In this particular graph, interposed between the two large manual ventilation peaks are a number of smaller peaks indicative of chest compressions. In bagged breathing, both pressure signals are increased above atmospheric pressure for both inspiration and expiration. In this respect, both manual and automated ventilation breaths are easily distinguishable from spontaneous breaths in that they are positive pressure breaths. Though, it can be appreciated that the shape of the manually administered breath is substantially different than that for a breath given by a typical automated ventilator. For example, the automated ventilator breath shows a more regular pressure/flow profile, including a plateau in pressure, which is not the case for the administered breath, which is more irregular in nature.

By determining the type of breath that is occurring, rescuers can be alerted whether the patient has begun spontaneous breathing and adjust the treatment protocol accordingly. For instance, for a spontaneously breathing patient, the rescuer may adjust how much additional ventilator support is necessary to give above what the patient is generating on their own. That is, when the patient is spontaneously breathing, the amount of pressure support assisted by manual or automated ventilation may be appropriately reduced. For example, the better the patient is able to breathe, the less pressure support may be required by positive pressure ventilation.

Further, as noted above, spontaneous breathing, while not fully conclusive, may be helpful evidence in determining whether the patient has achieved ROSC. Such information may be considered during an analysis of whether or not to administer a defibrillating shock to the patient. For example, if spontaneous breathing is detected, the rescuer or system may be triggered to perform a series of checks to determine if the patient has achieved or is likely to achieve ROSC. If ROSC has been achieved, then it may be decided that a shock should not be given. Such information may also be relevant for code review in evaluating whether rescuers were performing quality CPR. EMS rescuers are typically evaluated for how well they each performed CPR, whether or not ROSC has occurred. However, when ROSC has occurred in a patient, it may be determined that CPR may no longer be needed, hence, it may be preferable that EMS rescuers not be evaluated for their quality of CPR during ROSC. Thus, using techniques described herein, evidence of ROSC may be considered for determining whether EMS rescuers are evaluated for quality of CPR during the time period in which ROSC may have occurred. When ROSC is likely to have occurred, the code review may reflect that possibility and, in some cases, the score of EMS rescuers during the time in which ROSC may have occurred may be withheld from the overall evaluation.

Additionally, when a patient is experiencing spontaneous and/or agonal breathing, yet still receiving positive pressure breaths, the flow signal for the positive pressure breath may be inaccurate. Hence, when a spontaneous breath is detected at or around the time in which a positive pressure breath is administered, the flow parameters for that particular breath may be omitted or otherwise removed from the display or report provided to a user interface or other device associated with the resuscitative effort.

Figure 44:
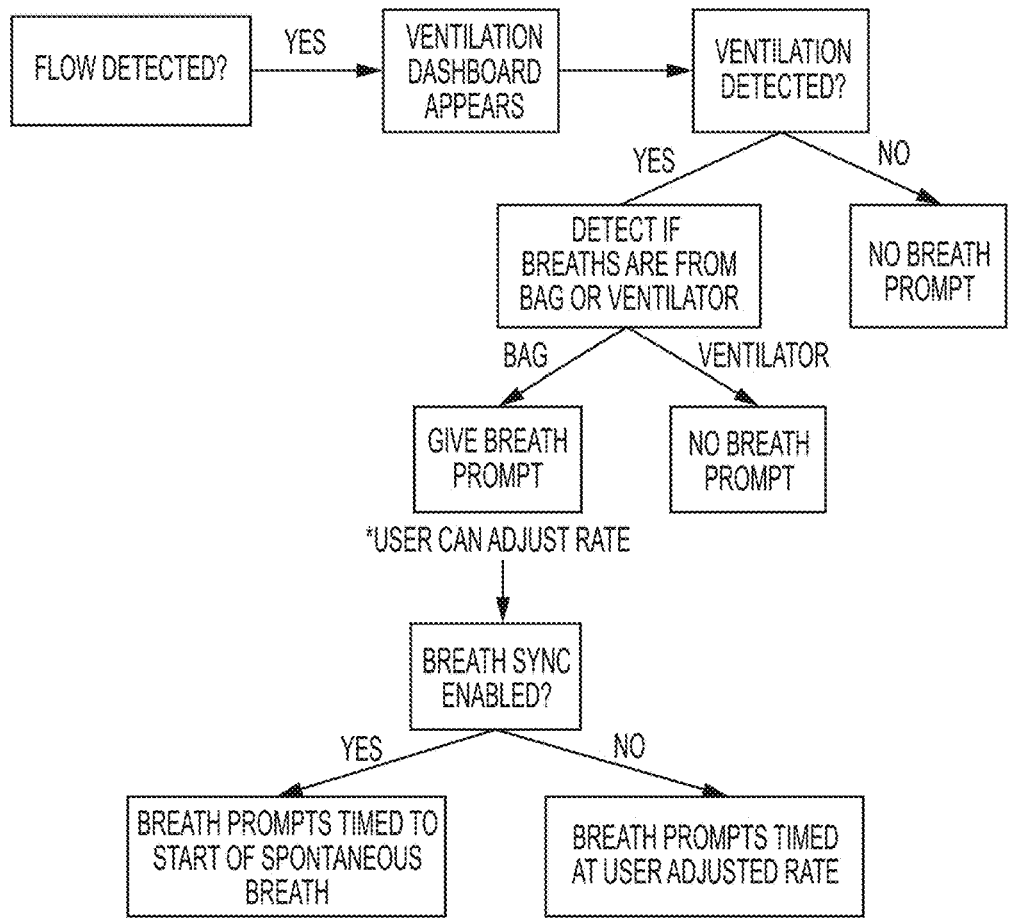
FIG. 44 depicts a flow chart illustrating a process through which a system may utilize information provided from the flow sensor according to an embodiment of the present disclosure.

FIG. 44 provides a flow chart illustrating an embodiment of the process through which a system may utilize information provided from the flow sensor. As shown, the system may detect whether flow is occurring through the conduit based on whether a threshold flow rate or volume has been met. If flow has been detected, then a user interface or display provided by a device of the system or monitor thereof, may enter into a mode that accounts for ventilation parameters. For example, in response to flow detection, the device may produce a ventilation dashboard displayed on a screen thereof. In some embodiments, an overall CPR dashboard may be displayed, which has a chest compression dashboard portion and a ventilation dashboard portion, as appropriate for the type of treatment(s) to be provided.

The ventilation dashboard may display a number of parameters, such as indicia showing the flow rate and/or volume detected from a breath. The system may further determine what type of breath is being provided, for example, spontaneous or by positive pressure ventilation (e.g., manually given or automated breath). If ventilations are not detected, the system infers that manual ventilations are not being given to the patient, so then the system refrains from providing prompts to administer manual ventilation breaths. Though, if ventilations are detected, then the system determines whether the ventilation breaths are generated manually (e.g., from bag ventilation) or mechanically (e.g., from an automated ventilator). If the system determines that the breaths are being administered mechanically, then the system refrains from providing prompts for a user to administer manual ventilation breaths. Though, if the system determines that the breaths are produced manually, then the system then continues to prompt the rescuer to administer breaths according to the appropriate treatment protocol.

In certain embodiments, as further shown in FIG. 44, for patients who are able to breathe spontaneously, the system may be configured to cause positive pressure breaths to be synchronized with spontaneous breaths. It may be preferable for a positive pressure breath to be administered to a patient simultaneously during the beginning of an inspiratory breath, so that the gas more readily enters the lungs, for example, in contrast to expiratory flow during exhalation. Accordingly, when manual ventilations are detected, the system may sense when the patient is just beginning a spontaneous inspiratory breath, and immediately prompt the rescuer to administer a manual ventilation so that the positive pressure breath is provided as air is being pulled into the lungs. This breath synchronization protocol may be provided as a mode to the system, and requires vigilance on the part of the system and the rescuer to determine when a spontaneous breath is occurring. Or, the system may further provide a notification to the rescuer of the effectiveness of the breath synchronization, particularly if the attempted breath synchronization is ineffective or even harmful to the patient. If the breath synchronization protocol is disabled, ventilation prompts may be provided according to a timed rate such as in the case of a continuous breath protocol, or ventilation prompts may be provided according to the number of chest compressions that have been administered; for example, based on the 30:2 protocol, the system may countdown the number of chest compression that have occurred and prompt the rescuer to vent when the countdown has finished.

Figure 45A:
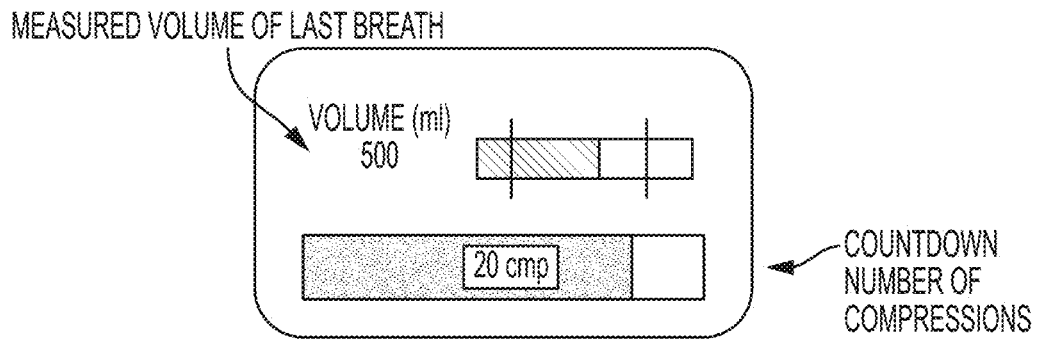
FIGS. 45(a)-(c) depict exemplary display dashboards for providing feedback according to an embodiment of the present disclosure.
Figure 45B:
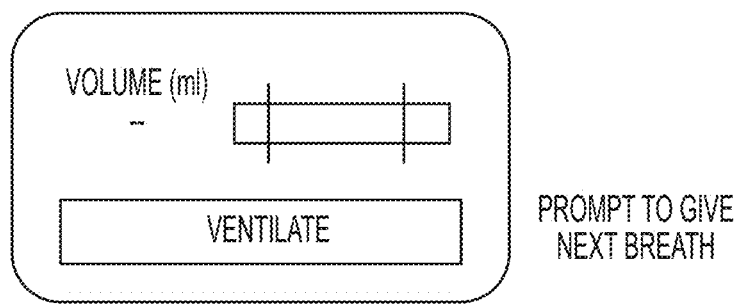

As noted above, a number of treatment protocols may be employed for manually ventilating a patient, such as the 30:2 protocol, providing 2 positive pressure breaths for 30 chest compressions. In this protocol, the system may display a ventilation dashboard (e.g., within an overall CPR dashboard, which may further include a chest compression dashboard, or simply having separate dashboards for ventilation and chest compressions) that shows an indication of how many chest compressions are remaining before a ventilation is to be administered. For example, as shown in FIG. 45(a), the dashboard may include a countdown bar that decrements with each detected chest compression. In this case, when a chest compression is detected, the number of compressions remaining decrements by 1 and the light-colored bar is slightly reduced in size. When the number of chest compressions reaches 0, or another value that provides an indication for a breath to be applied, the system prompts the user to ventilate, as shown in FIG. 45(b). Or, in another embodiment, the dashboard may include a displayed number (e.g., number provided within a circled area), or other suitable indicator for counting down to ventilation prompt.

For this manual ventilation technique, the dashboard further shows the volume of air provided to the patient for a given bagged breath. The dashboard depicted in FIG. 45(a) shows a numerical value of the ventilation volume (shown as 500 mL) and a bar graph providing a visual indication of the ventilation volume. The bar graph includes hashmarks which indicate to the user the preferred range of volume per breath that the patient should receive. Any suitable upper and lower limits for this range may be chosen, depending on the desired volume to be administered to the patient (e.g., 400 mL, 500 mL, 600 mL). In another embodiment, a circular region fills based on the detected flow volume and rate, and changes color based on whether the volume and rate are or are not within desired limits. For example, if the circular region turns green, then flow volume and rate are within the prescribed range. If the circular region turns yellow or red, then the flow volume is above or below the prescribed range. An incomplete or partial filling of the circular region may be an indication that the volume delivered is insufficient. In general, the ventilation breath should include a sufficient amount of air to the lung that supplies enough of a source of oxygen for gas exchange and circulation to the body. Conversely, the ventilation breath should not be excessive, otherwise lung damage may occur. The lower limit for the volume per breath given to the patient may be approximately 100 mL, approximately 200 mL, approximately 250 L, approximately 300 mL, approximately 350 L, approximately 400 mL, etc.; conversely, the upper limit for the volume per breath given to the patient may be approximately 1500 mL, approximately 1200 mL, approximately 1000 mL, approximately 900 mL, approximately 800 mL, approximately 750 mL, approximately 700 mL, approximately 650 L, approximately 600 mL, etc. The desired ventilation volume may depend on patient characteristics, such as patient size, condition, age, weight, lung capacity, amongst others.

As noted above, the ventilation feedback provided may be customized for the particular victim, or alternatively may follow a set (default) protocol that does not differ from victim to victim. For example, the rate and volume of ventilation to provide a victim may depend on how long the victim has been suffering from a current condition. Thus, a rescuer may try to ascertain how long the victim has been down, or a time stamp from the time at which an emergency was called in may be used as a proxy. Also, various states of the victim may be relevant to the treatment protocol (e.g., rate and volume of ventilation) to be provided to the victim, including, for example, whether the patient is pediatric or adult; patient condition (e.g. traumatic brain injury, cerebral herniation, cardiac arrest); ECG characteristics that suggest different ventilation requirements (e.g., patients with ventricular fibrillation may have lower ventilation requirements than patients with asystole or PEA; etiology of disease (e.g., cardiac arrest due to drowning vs. presumed myocardial infarction; duration of patient downtime for cardiac arrest; presence/absence of (effective) bystander CPR (compressions and/or ventilations) prior to arrival of EMS; ETCO2 levels (e.g., recommendations to titrate ventilation rate to achieve a particular end tidal CO2 value; SpO2 levels (e.g., adjust ventilation rate to achieve optimal peripheral oxygen saturation); and impact of SmO2 (muscle oxygenation) and/or tissue pH levels. Depending on what input parameters are provided to the system, an appropriate treatment protocol may be selected and/or adjusted, and ultimately communicated to the user. Though, in certain situations, such as those where the patient condition is rapidly deteriorating (e.g., sudden oxygen desaturation, patient becomes extremely hypotensive, etc.) it may be preferable that any changes in protocol not be displayed or otherwise communicated to the user, e.g., it may be better to maintain the current the current target ventilation parameters, rather than adjusting them.

Figure 45C:
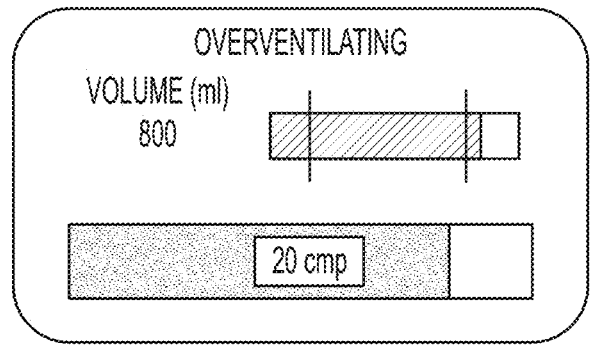

When a positive pressure breath is provided, the bar graph on the dashboard may fill so as to show the instantaneous volume of air provided to the patient. Hence, a manual bagger may view the bar graph to determine whether the total volume administered to the patient is within desired limits. As shown in FIG. 45(a), the 500 mL ventilation volume falls within the specified limits. As also shown, when the positive pressure breath is completed and chest compressions are to be administered, the ventilation dashboard may continue to show information regarding the previously provided ventilation breath during the current set of chest compressions, until the next ventilation breath is administered. The user should then provide a positive pressure breath similar to the previous breath. As further shown in FIG. 45(b), when the dashboard prompts the user to ventilate, the volume indication (numerical value and bar graph) resets and provides the ventilation volume when the breath is applied. FIG. 45(c) shows the ventilation volume to be 800 mL, which falls outside of the specified range. Accordingly, the dashboard provides an indication to the user that the patient has been overventilated. This may provide a signal to the user to lessen the ventilation volume of the next positive pressure breath.

Figure 46A:
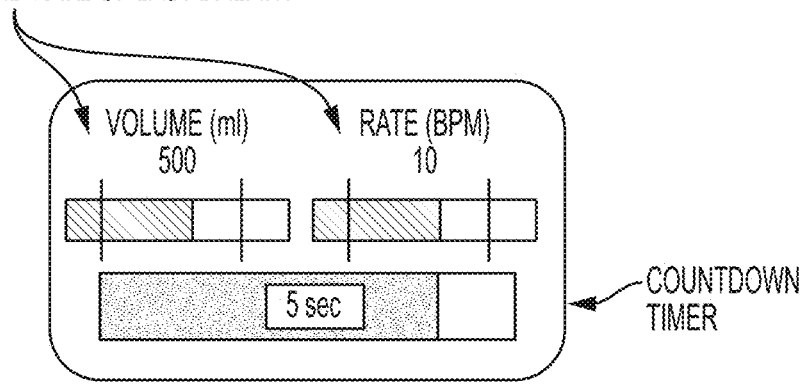
FIGS. 46(a)-(c) depict exemplary display dashboards for providing feedback according to an embodiment of the present disclosure.
Figure 46B:
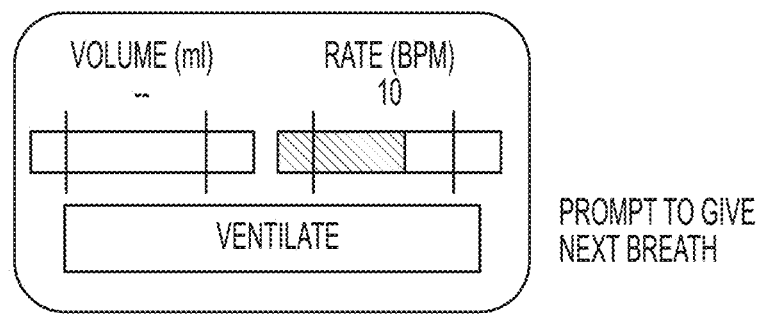
Figure 46C:
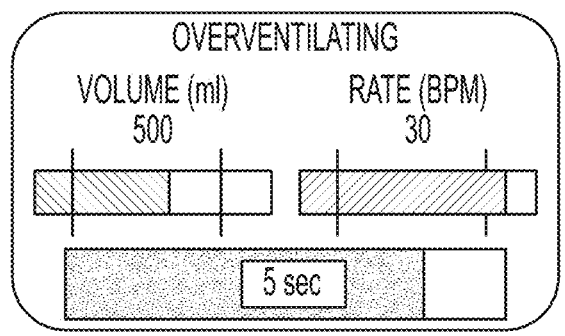

FIGS. 46(a)-(c) show a ventilation dashboard appropriate for a continuous ventilation protocol, which may involve providing a breath prompt every 6-8 seconds during CPR. In this protocol, the ventilation dashboard may show an indication of how much time is left a ventilation is to be administered. For example, as shown in FIG. 46(a), the dashboard may include a countdown bar by seconds, with the light-colored bar steadily or discretely decreasing in size, until it reaches 0, and the user is then prompted to ventilate. The dashboard further shows relevant information, such as the numeric ventilation volume and rate in breaths per minute, from which the minute volume may be determined. Similar to the bar graph for ventilation volume, the bar graph corresponding to ventilation rate includes hashmarks which indicate to the user the preferred range of rate in breaths per minute that the patient should receive. Appropriate upper and lower limits for this range may be chosen, depending on the desired ventilation rate (e.g., 6 bpm, 8 bpm, 10 bpm). The lower limit for the rate given to the patient may be approximately 4 bpm, approximately 6 bpm, approximately 8 bpm, approximately 10 bpm, etc.; conversely, the upper limit for the rate given to the patient may be approximately 16 bpm, approximately 15 bpm, approximately 14 bpm, approximately 12 bpm, approximately 10 bpm, approximately 8 bpm, etc.

FIGS. 46(a) and 46(b) show the ventilation volume and rate to fall within specified limits. Though, FIG. 46(c) shows the ventilation rate to be 30 bpm, which falls outside of the specified range. Hence, the dashboard provides an indication to the user that the patient has been overventilated. This may provide a signal to the user to lessen the rate at which positive pressure breaths are given to the patient.

Figure 47A:
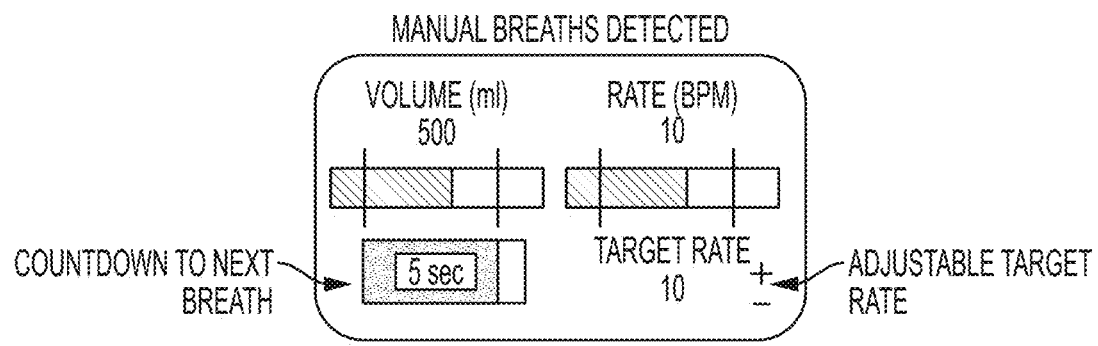
FIGS. 47(a) and (b) depict exemplary display dashboards for providing feedback according to an embodiment of the present disclosure.
Figure 47B:
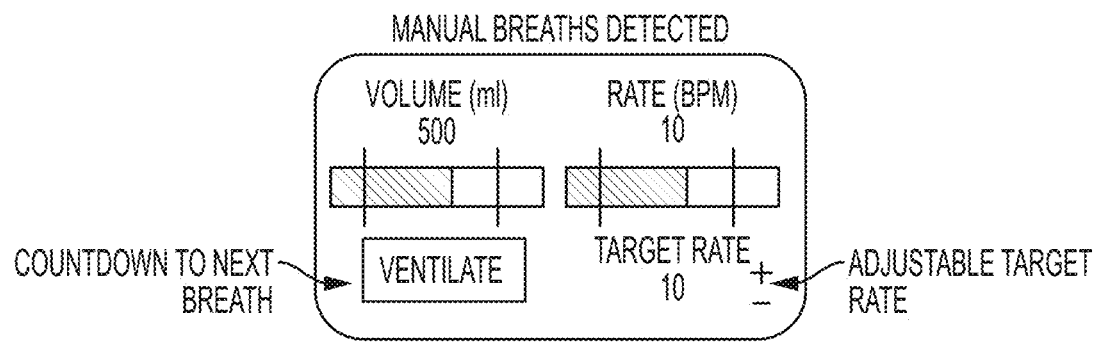

FIGS. 47(a) and 47(b) show similar information as that provided above with respect to ventilation volume, breath rate and countdown information to the next breath, with the addition of an option to manually adjust the target parameters. As shown in these figures, the target rate may be adjusted, for example via touch screen interface on the dashboard. While not shown, other parameters may also be adjusted, for example, the target ventilation volume and the limits for rate and volume. In some cases, the size of the target range may be set such that when a specified target volume or rate is input, the upper and lower limits (e.g., shown as hashmarks) adjust accordingly. Or, the individual upper and lower limits may be adjusted independently of one another.

Figure 48:
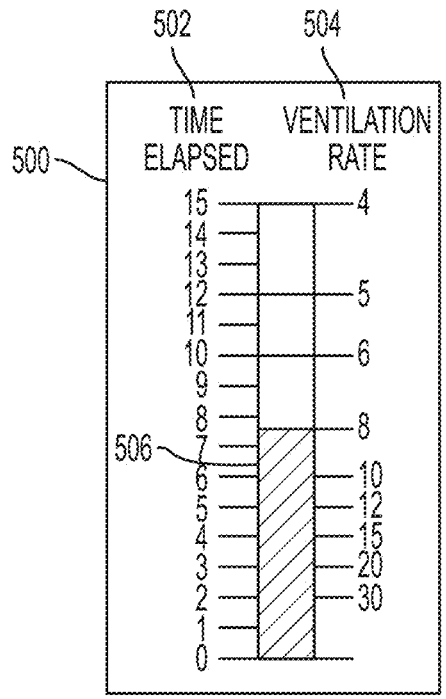
FIG. 48 depicts a ventilation timer display according to an embodiment of the present disclosure.

FIG. 48 shows another embodiment that provides exemplary information, e.g., a ventilation timer 500, displayed on a display device to a rescuer during the administration of ventilation to a patient. The ventilation timer 500 provides information to the rescuer to help the rescuer control the rate of ventilation provided to the patient. The ventilation timer 500 can include a bar 506 (or other shape) that fills as time elapses between breaths. The bar 506 can include scaling information (e.g., tick marks on the graph) that provide information about the elapsed time 502 and/or ventilation rate 504. The elapsed time 502 provides an indication of the amount of time that has passed since the last ventilation event and the ventilation rate 504 provides the number of breaths per minute (e.g., 5 seconds between breaths=12 breaths/minute).

The information displayed on the ventilation timer 500 is based on ventilation related data received from a device that detects when a ventilation has been delivered (e.g., a flow meter, capnography, thoracic impedance). The ventilation related information is used by a computer to provide an input indicating when to re-start the timer such that the elapsed time can be determined.

In some examples, the information presented on the ventilation timer 500 can be color coded or otherwise supplemented by a visual indicator of ranges that indicate adequate ventilation versus sub-optimal ventilation. In one example, the color of the bar 506 in the ventilation timer can change based on the adequacy of the ventilation. For example, the bar could be colored green when proper ventilation is being provided and yellow or red when the ventilation falls outside the desired range of respiration rates. Additionally, in some examples, an indication of whether the user should increase or decrease the rate of respiration could be provided. Additionally, in some examples, an indication of the optimal elapsed time/ventilation rate could be provided such as by overlaying a line or other indicator at the desired level so the rescuer can attempt to have the bar 506 match the displayed optimal timing indicator.

In some additional examples, the information presented in the ventilation timer 500 can be color coded or otherwise supplemented by other visual indicator based on the nature of the underlying condition being treated, e.g. respiratory distress vs cardiac arrest vs TBI. Additionally, the range that is indicated as an optimal or an acceptable respiration rate can change based on information from one or more physiologic monitoring sensors and estimate from those sensor(s) of the underlying status of the patient's cardiopulmonary status. Such physiologic monitoring can be based, for example on information about EtCO2 (e.g., the partial pressure or maximal concentration of carbon dioxide, CO2 at the end of an exhaled breath, which is expressed as a percentage of CO2 or mmHg) and/or information about oxygen saturation from a pulse oximeter, a medical device that indirectly monitors the oxygen saturation of a patient's blood. Such physiologic monitoring can also include information from a tissue CO2 sensor that can be used to calculate the blood oxygen concentration, for example, based on the ventilation/perfusion ratio (or V/Q ratio) which provides a measurement used to assess the efficiency and adequacy of the matching of the amount air reaching the alveoli to the amount of blood reaching the alveoli (sometimes reported as the VQ mismatch which is used to express when the ventilation and the perfusion of a gas exchanging unit are not matched).

Minute-volume CO2 measures may be helpful during ventilation because ETCO2 measures are dependent on the actual volume of gas delivered to the patient. The physiologic measure that the clinician is titrating to is the amount of CO2 gas exhaled from the patient, which is a helpful overall measure of the patient's physiologic state. Increasing the ventilation rate or tidal volume will cause ETCO2 values to decrease for a fixed CO2 gas elimination rate from a patient; this is not the case for minute-volume CO2 measures. Thus, minute-volume measures of CO2 may be a useful parameter in situations where ventilation is being delivered in a manual fashion with a rescuer squeezing a ventilation bag where both ventilation rates and tidal volumes have been shown in multiple studies to be completely uncontrolled in the clinical environment.

Figure 49A:
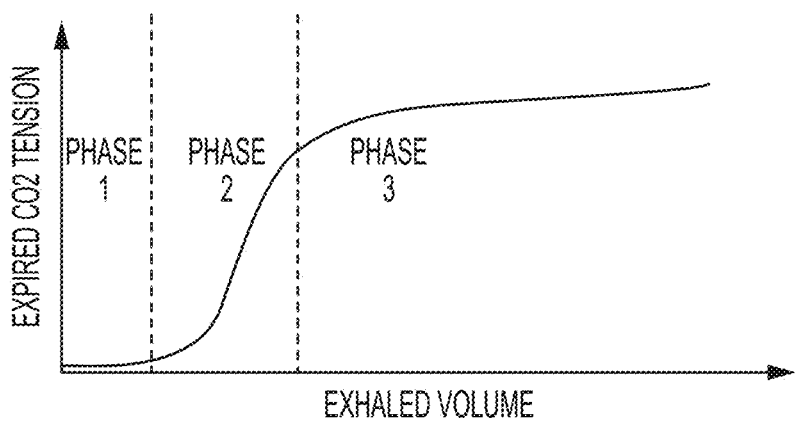
FIGS. 49(a) and (b) depict exemplary line graphs showing expired $CO_2$ tension versus exhaled volume.
Figure 49B:
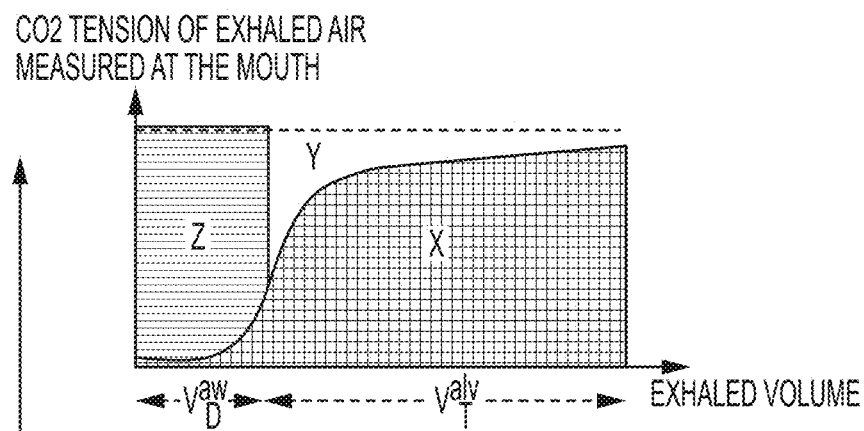

CO2 concentration as a function of expired volume may be plotted such as in the form of a single-breath CO2 analysis (SBCO2), known to those skilled in the art. The SBCO2 curve has three phases: phase 1 made up of non-alveolar gas, or ventilatory dead-space gas, that is essentially free of CO2; phase 2 that is a transition phase with a characteristic S-shape that contains some amount CO2; and phase 3 that is the alveolar gas bearing the predominant quantity of exhaled CO2. Because the x-axis of the SBCO2, or expirogram as it is sometimes called, has units of volume, calculations can be made to determine both alveolar as well as non-alveolar deadspace based on techniques known to those skilled in the art. For example, FIGS. 49(*a*) and 49(*b*) (from IEEE TRANSACTIONS ON INFORMATION TECHNOLOGY IN BIOMEDICINE, VOL. 6, NO. 4, December 2002), each show the expired CO2 tension versus exhaled volume. The non-alveolar deadspace is the area of 'Z' in FIG. 49(*a*), and the alveolar deadspace is the area of 'Y'. The sum of these two deadspaces does not produce any gas exchange in the patient, so this sets the minimum ventilation volume for each patient. Additionally, including dynamic lung compliance in the calculation of overall lung volume using SBCO2 curves may enhance the accuracy produced by SBCO2-based calculations.

Figure 50:
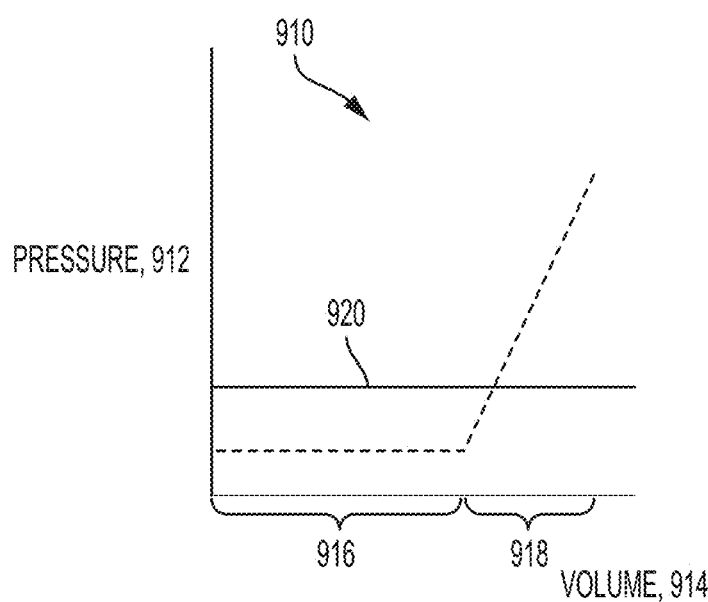
FIG. 50 depicts an exemplary graph of pressure versus volume during manual ventilation.

FIG. 50 is an exemplary graph 910 of pressure 912 versus volume 914 during manual ventilation. Indications of pressure versus volume can be used as a guide for determining an optimal tidal volume for manual ventilation of victims. In general, for adult patients and older children tidal volume (Vt) is calculated in milliliters per kilogram and values in the range of 6 to 8 mL/kg are often used. Hence a patient weighing 70 kg would get a Vt of 420-480 mL. However, in the field, a rescuer often will not have access to patient weight to calculate a desired tidal volume. Thus, it can be beneficial to provide feedback to the rescuer on an appropriate tidal volume without performing calculations based on patient specific weight or age parameters.

In some cases, the height may be used as an estimate for weight and/or size of the patient. For example, Broselow pediatric emergency tape may be used as such as estimator. Broselow tape, generally speaking, has a scale provided as a color-coded measure for pediatric emergencies. The Broselow scale relates the height of a child (up to approximately 12 years in age) as measured by the tape to his/her weight (up to approximately 36 kg or 80 lbs), which is useful to provide medical treatment instructions, such as medication dosages, the size of the equipment that should be used, the level of defibrillation shock voltage, amongst others. Particular to children is the need to calculate the relevant therapies for each child individually, primarily based on size. And in an emergency, the time required to make such calculation(s) may detract from valuable time needed to evaluate, initiate, and monitor patient treatment. A similar Broselow-type scale may be used to determine the ventilation parameters that would apply for pediatric or adult patients. That is, ventilation parameters may vary based on the size of the patient, whether pediatric or adult. For example, the estimated tidal volume, breath volume/rate, etc. may be provided as targets to the rescuer administering the therapy. Tidal volume may generally be determined based on predicted body weight (not necessarily actual body weight because overweight people generally have similarly sized lungs as thinner people of the same height), estimated from gender and height. For example, the predicted body weight (kg) for females is generally (50+2.3 (height (in)–60); and for males is generally (45.5+2.3 (height (in)–60). In some embodiments, the system may be configured to estimate size/weight of the patient and, hence, select an appropriate therapy based on an input (e.g., via a user interface) of patient height or other size information. The feedback information provided to the rescuer may then be adjusted based on the selected therapy.

In manual ventilation, as shown in FIG. 50, as the volume 914 of air administered to the victim increases, initially the pressure remains low and substantially constant (portion 916) as the lungs inflate. As the lungs near full inflation, the pressure required to administer additional volume is increased (portion 918). As the pressure rises above 45 cm H2O (4.4 kPa) for adults, the risk of barotrauma is increased and efforts should be made to try to reduce the peak airway pressure. In infants and children, even lower levels of peak pressure may cause damage. In general, keeping peak pressures below 30 cm H2O (2.9 kPa) (denoted by line 920) may be desirable. Thus, by observing changes in the peak pressure or by observing changes in pressure per changes in volume, a determination can be made of when a desirable tidal volume has been administered to the victim.

The change in volume divided by change in pressure is sometimes referred to as a compliance measurement. Compliance is a measure of the "stiffness" of the lung and chest wall. The mathematical formula for compliance (C) is change in volume divided by change in pressure. The higher the compliance, the more easily the lungs will inflate in response to positive pressure. Compliance values can be calculated and used to provide feedback on tidal volume to the rescuer.

The ventilation dashboard may be provided as a stand-alone display or as a portion of a CPR dashboard or larger display, for example, on the user interface display of a hospital or EMS monitor, such as the E Series®, M Series®, R Series® and X Series®, provided by ZOLL Medical Corporation. The ventilation and CPR dashboard may also be provided as part of displays described in U.S. Pat. No. 8,725,253, entitled "Defibrillator Display Including CPR Depth Information," which is hereby incorporated by reference in its entirety.

For example, a general display may include a wide variety of physiological data of the patient, such as ECG, EtCO2, SpO2, blood pressure, muscle oxygenation, muscle pH, diagnostic information, heart rate, temperature, etc. The general display may also include a CPR dashboard, which may provide the user with resuscitative information useful for assisting a user in providing resuscitative treatment to the patient, for example, in maintaining the quality of CPR, including chest compressions and/or ventilations. Accordingly, the CPR dashboard may include a chest compression dashboard, for tracking parameters useful for providing quality chest compressions, such as depth, rate and/or release. The CPR dashboard may also include a ventilation dashboard, for tracking parameters useful for providing quality ventilations, such as ventilation rate, volume, minute volume and/or ventilation timing.

Other resuscitative information for assisting the user in providing resuscitative treatment may be provided, for example, based on a number of embodiments described herein. For instance, such resuscitative information may include feedback for instructing a user to adjust gas flow (e.g., flow rate, flow volume, minute volume) through the lumen, feedback for instructing a user to adjust placement of an intubation tube, alerts to a user and/or machine that overventilation has occurred or may occur, a countdown of the number of chest compressions until a subsequent ventilation is to be applied, a countdown of the time until a subsequent ventilation is to be applied, a number of chest compressions applied based on pressure and/or flow rate signals, a determination of whether a detected breath is due to spontaneous breathing, manually applied ventilation or automatically applied ventilation, instructions to the user to check the patient based on an indication of whether ROSC may have occurred, an indication of the determined peak inspiratory pressure, flow rate and/or volume of gas flowing through the lumen of the flow conduit, amongst others in accordance with embodiments discussed herein.

The physiological data of the patient and the resuscitative information may be provided on a display interface of a defibrillator and/or monitor. In some embodiments, the physiological data of the patient may be provided on a first portion of the display and the resuscitative information of assisting the user in providing resuscitative treatment may be provided on a second portion of the display. That is, depending on what information may be most relevant in treating the patient, the display may provide both physiological data of the patient and resuscitative information for assisting the user.

Figure 51:
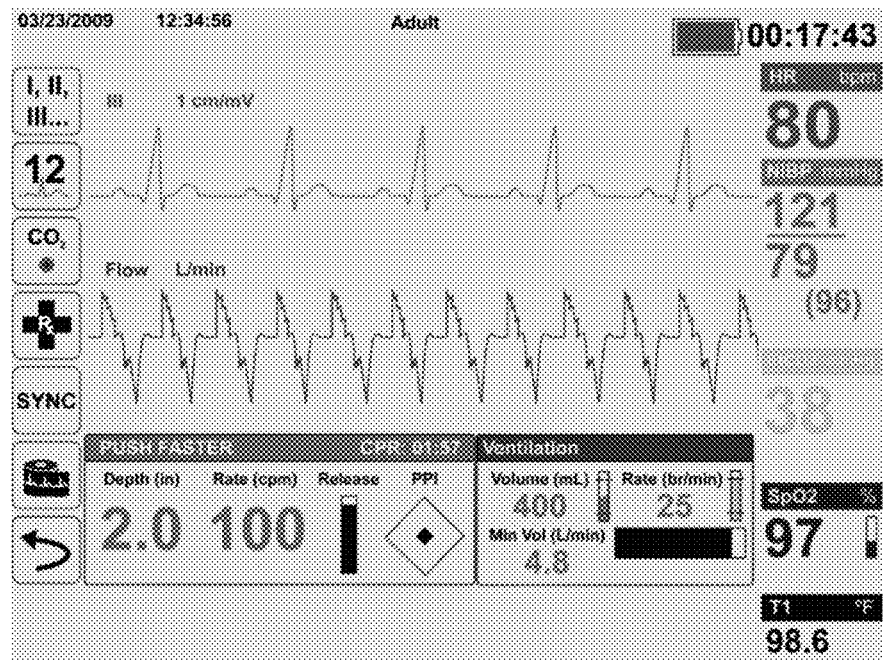
FIGS. 51-53 depict exemplary screen shots of feedback displays, each of which includes additional information other than the ventilation dashboard according to different embodiments of the present disclosure.
Figure 52:
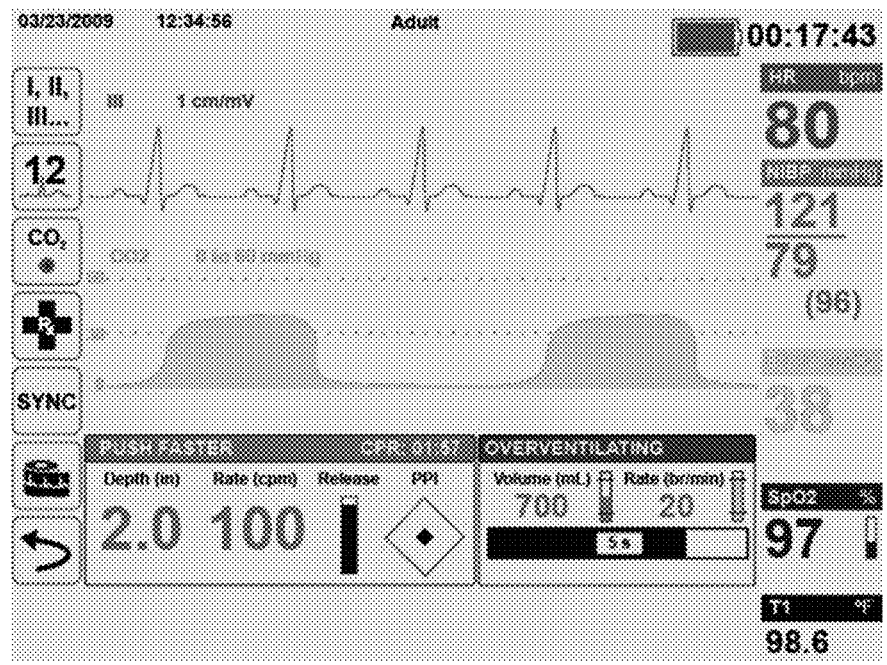
Figure 53:
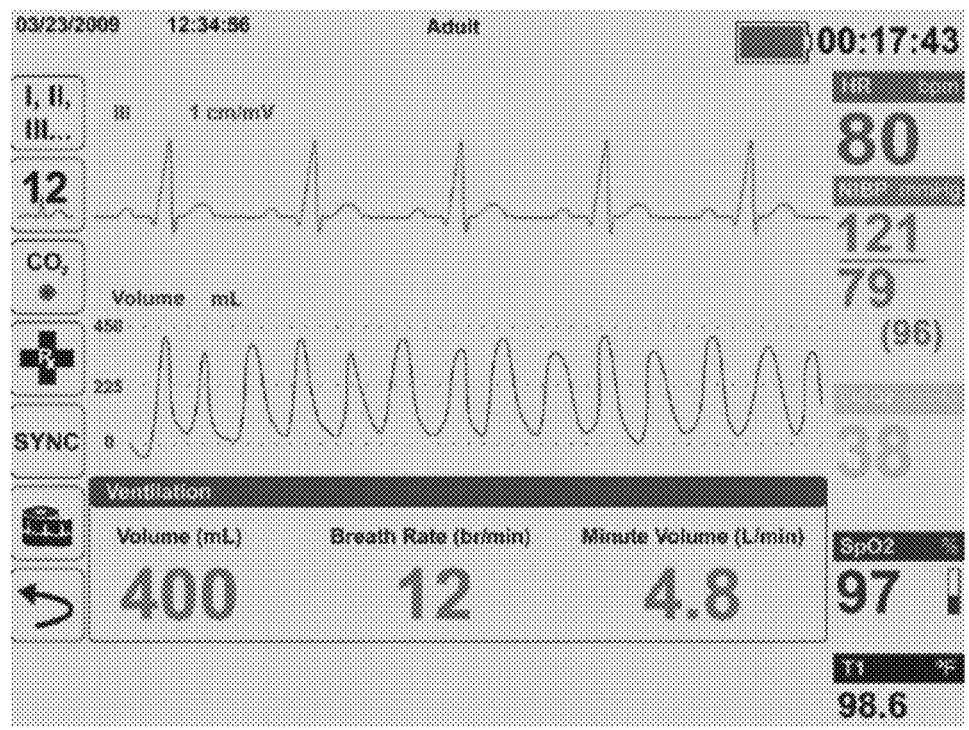

FIGS. 51-53 also show various embodiments of screen shots of such displays, each of which includes additional information other than the CPR dashboard (which may include a chest compression dashboard and/or ventilation dashboard), such as physiological data, for example, the heart rate, blood pressure, ETCO2, SpO2, temperature, etc. The CPR dashboard may include a chest compression dashboard providing feedback on the depth, rate, release of chest compressions, and/or a ventilation dashboard, which shows the breath volume, breath rate, minute volume and a countdown to when the patient should be ventilated.

The display interface of FIG. 51 depicts the CPR dashboard and a graph showing trends in flow volume over time, as provided via the flow sensor system. This CPR dashboard may be relevant for a patient suffering from cardiac arrest, where both chest compressions and ventilations are provided. This display interface further shows other physiological data, including ECG data, heart rate, NIBP, EtCO2, SpO2 and temperature of the patient.

The ventilation portion of the CPR dashboard of FIG. 52 shows the breath volume and rate to have exceeded their preferred ranges, respectively, and so displays a message to the user that the patient has been overventilated. Similar to the embodiment of FIG. 51, this CPR dashboard may also be relevant for a patient suffering from cardiac arrest. The display interface of FIG. 52 further shows other physiological data, such as ECG data, heart rate, NIBP, EtCO2, SpO2, a capnogram and temperature of the patient.

FIG. 53 shows an example of a display interface including the ventilation dashboard, without showing the chest compression portion of the CPR dashboard, which may be preferable for a patient experiencing respiratory distress or traumatic brain injury, rather than cardiac arrest. That is, there is no need to provide chest compression feedback if no chest compressions are being applied to the patient. The display interface of FIG. 53 further provides a graph that shows trends in flow volume for each breath. As shown, each ventilation volume provided to the patient is between 225 mL and 450 L. The display interface of FIG. 53 also shows other physiological data, such as ECG data, heart rate, NIBP, EtCO2, SpO2 and temperature of the patient.

Similar to the above, FIGS. 63-66 depict additional embodiments of screen shots 1000 of a display monitor showing a variety of resuscitation related data, including a ventilation dashboard. The display system may be configured such that when air flow is detected through the sensor, the ventilation dashboard 1010 automatically appears along with ventilation history 1014, which provides a bar that shows the ventilation volume at specific time points. As shown in FIGS. 63-66, the ventilation dashboard 1010 includes a numerical ventilation volume indicator 1011, a numerical ventilation rate indicator 1013 and a ventilation performance indicator 1012. The display may also show numerical values for inspiratory volume 1016 and expiratory volume 1018 for each positive pressure breath ventilation.

In this embodiment, the ventilation performance indicator 1012 is provided as a graphic of a circular region that fills as inspiratory air is detected by the flow sensor system. After the breath is over, the circular region may change color depending on whether the ventilation rate or volume is within a pre-specified target range. For example, the circular region may display a green color, or another appropriate color, if both the measured ventilation rate and volume fall within the target range. Though, if either of the ventilation volume or ventilation rate falls outside of the target range, the circular region may display a different color, such as yellow, orange, red, or another color, indicating that one of more parameters are out of range. For example, if the patient is under-ventilated (i.e., given a volume lower than the lower bound of the target range) or over-ventilated (i.e., given a volume that exceeds the upper bound of the target range), then the circular region of the ventilation performance indicator 1012 may depict a yellow warning color or other suitable color, and the numerical ventilation volume indicator 1011 may also change to a similar color (e.g., yellow). Similarly, if the measured ventilation rate does not fall within the pre-specified target range, then the circular region of the ventilation performance indicator 1012 may illuminate a yellow warning color or other suitable color, and the numerical ventilation rate indicator 1013 may also exhibit a similar change in color.

Figure 63:
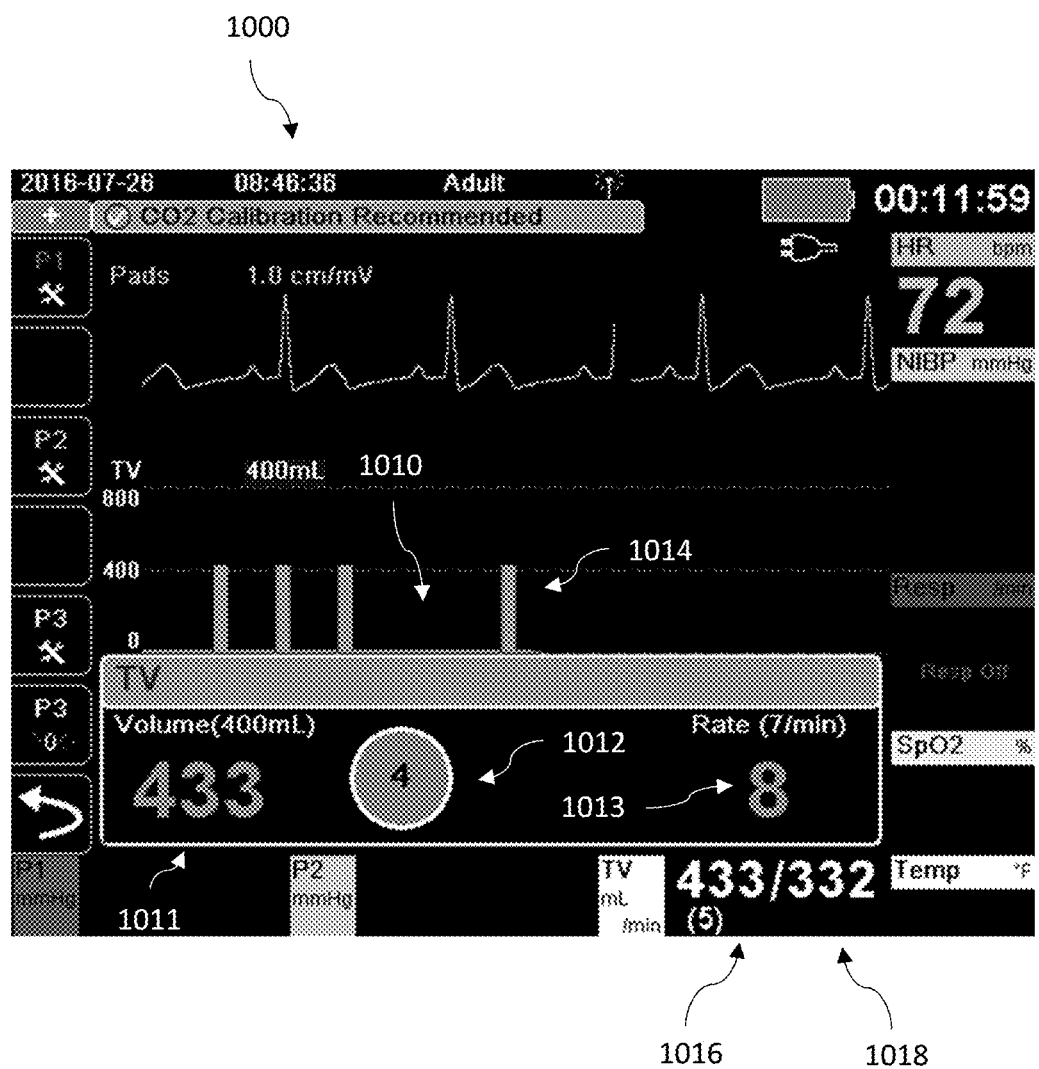
FIGS. 63-66 depict exemplary screen shots of feedback displays according to various embodiments of the present disclosure.
Figure 64:
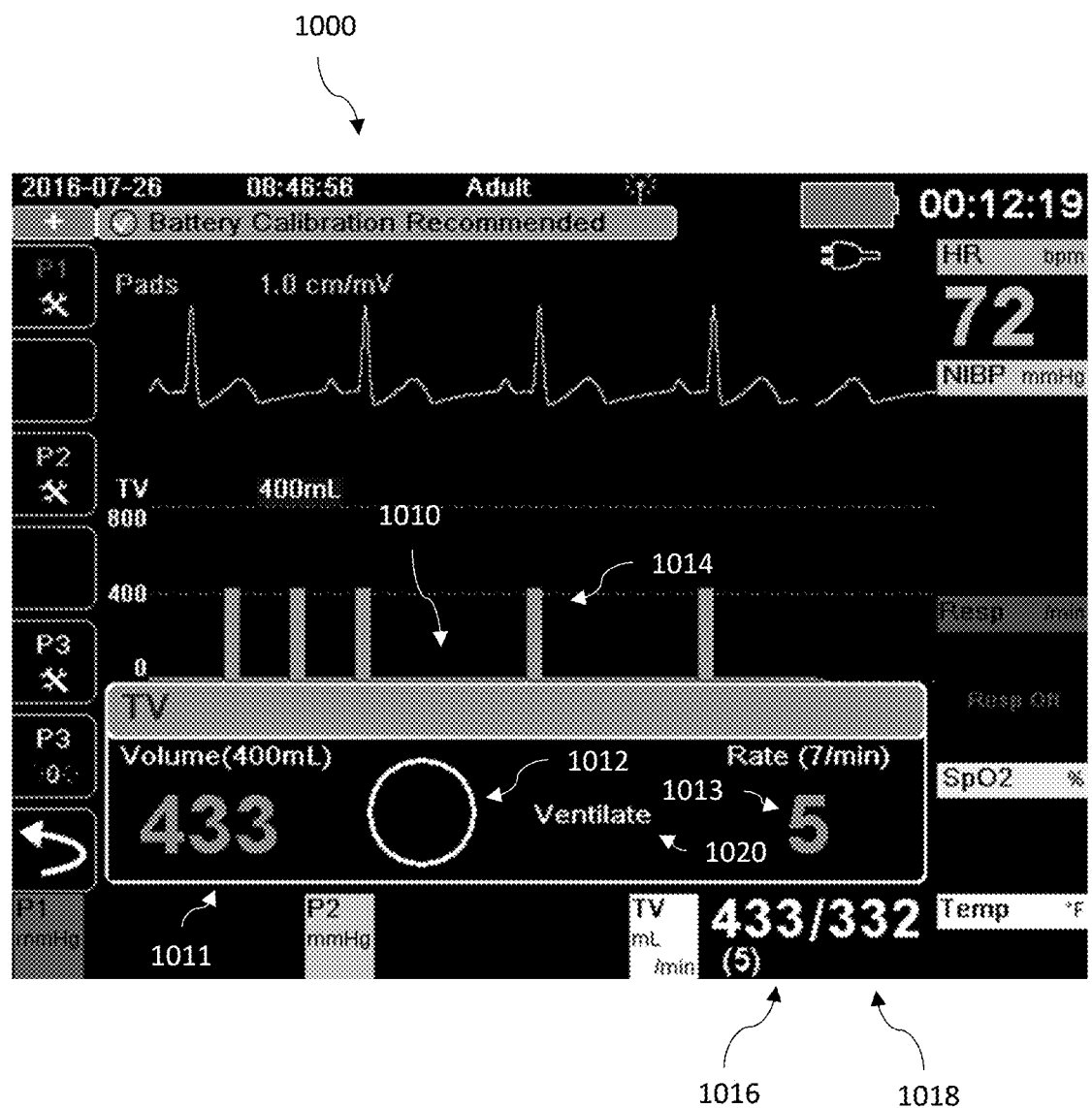

As shown in FIG. 63, the ventilation performance indicator 1012 may include a numerical countdown timer located within the circular region. Once the numerical countdown timer counts down to 0 (e.g., counting down by seconds or another time period), then, as shown in FIG. 64, the circular region empties and a "Ventilate" prompt 1020 appears. This is to instruct a user to apply a positive pressure ventilation to the patient (e.g., by squeezing an attached bag valve mask). If no breath is detected after a period of time (e.g., 3-5 seconds), then the "Ventilate" prompt 1020 begins to flash. If no breath is detected after a subsequent period of time (e.g., another 3-5 seconds), then the circular region itself flashes and optionally changes color to warn the user that a ventilation should be given. Or, alarms (e.g., audible, visual, tactile) may be further triggered to warn the user that a ventilation action should be taken. It can be appreciated that other methods and displays for providing ventilation information and prompting to the user may be employed.

Figure 65:
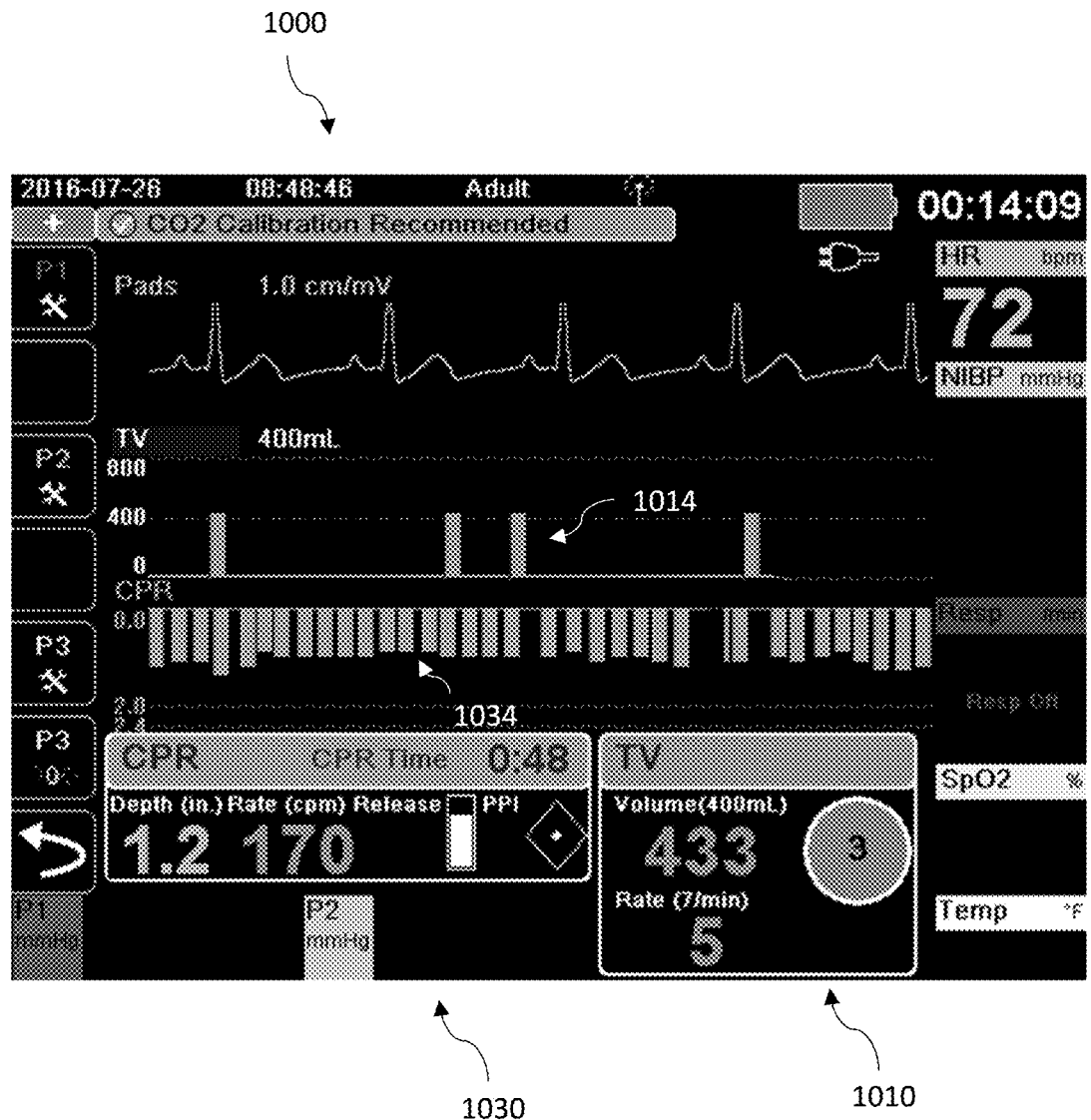

FIG. 65 illustrates a screen shot of the ventilation dashboard 1010 along with a chest compression dashboard 1030, which provides chest compression feedback for the user in compressing the chest within an appropriate target depth and rate. Similar to the ventilation history indicator 1014, the chest compression history indicator 1034 shows a bar for the depth of each chest compression during a CPR interval.

Figure 66:
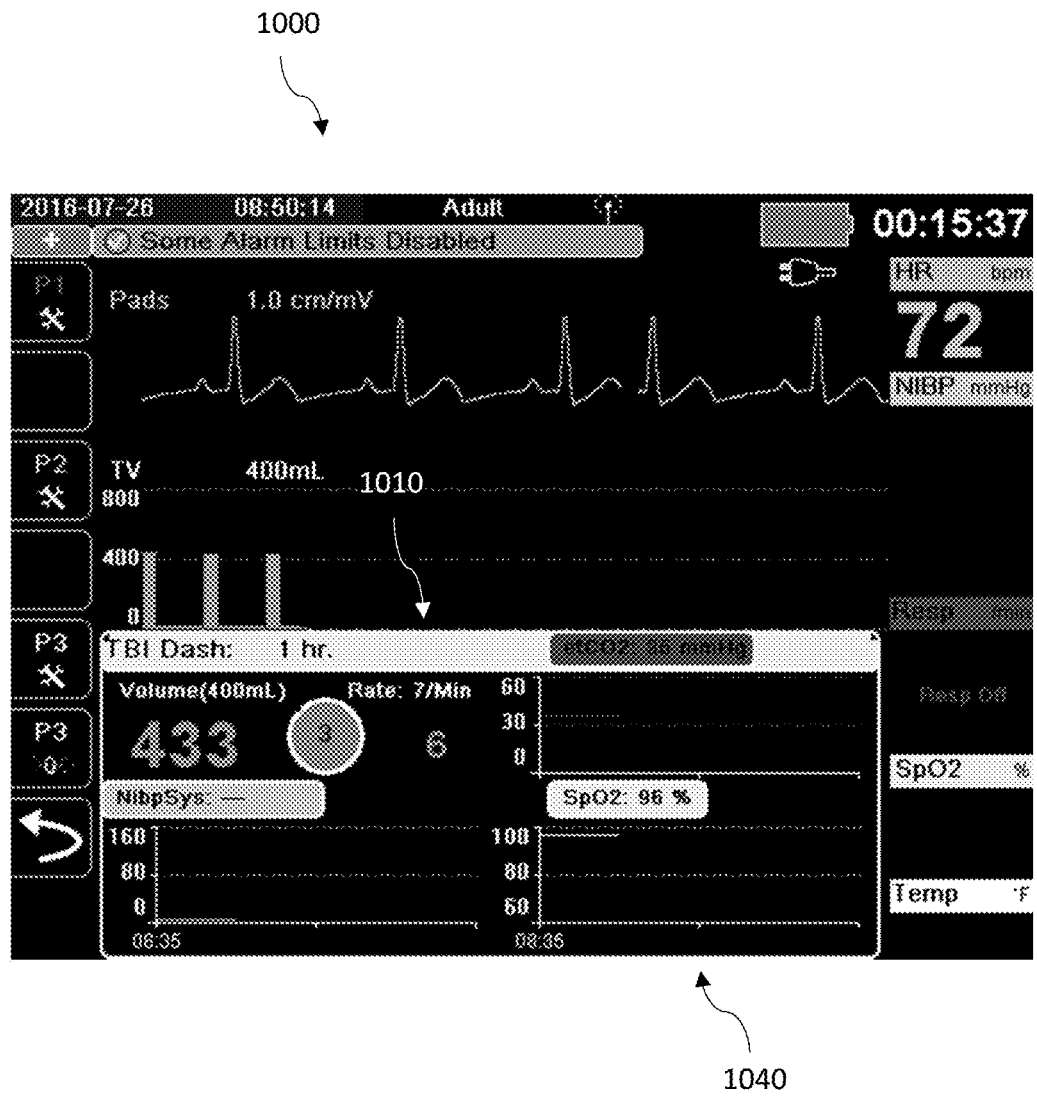

FIG. 66 shows a screen shot of the ventilation dashboard 1010 along with a traumatic brain injury (TBI) dashboard 1040, which provides parameters useful for monitoring a patient who has suffered from a traumatic brain injury. Accordingly, in addition to the ventilation dashboard 1010, the TBI dashboard 1040 includes trending graphs for NIBP, EtCO2 and SpO2 over appropriate time intervals.

Figure 54:
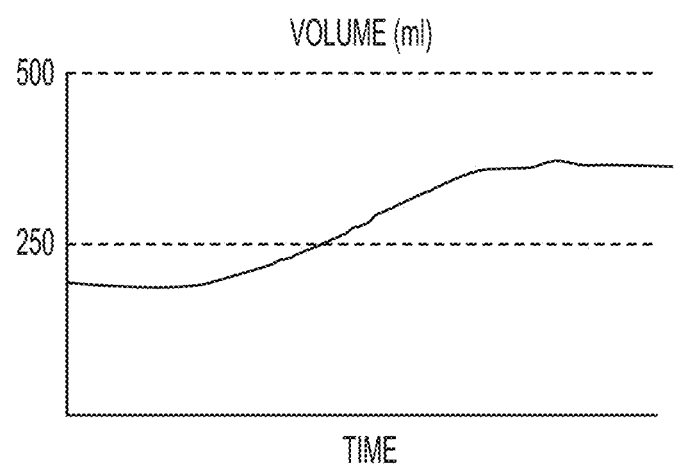
FIGS. 54 and 55 depict graphs that show examples of the ventilation volume over time and the ventilation rate over time, respectively.
Figure 55:
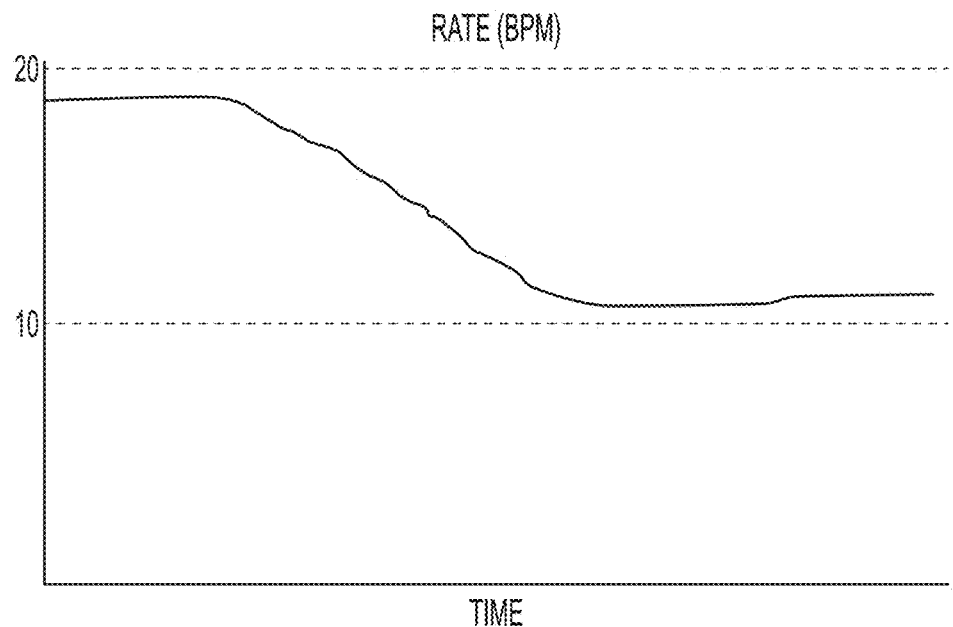
Figure 56A:
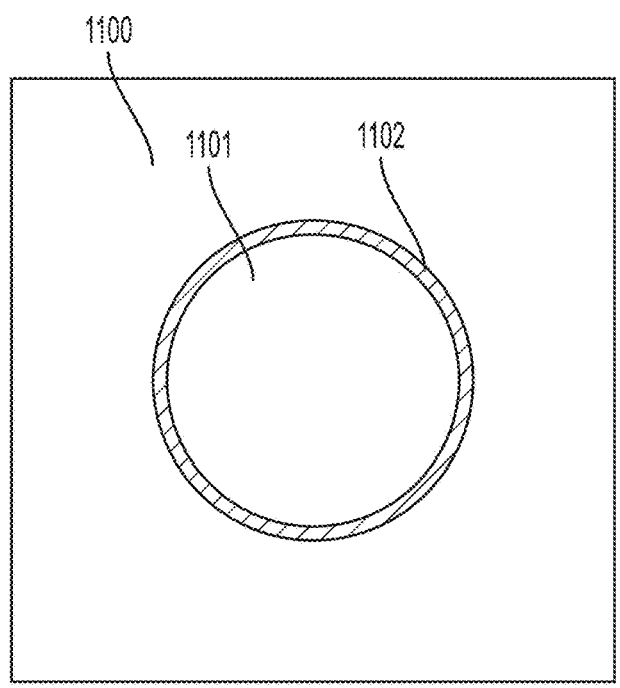
FIGS. 56(a)-(e) depict various display graphics for providing feedback to indicate the quality of ventilations according to an embodiment of the present disclosure.
Figure 56B:
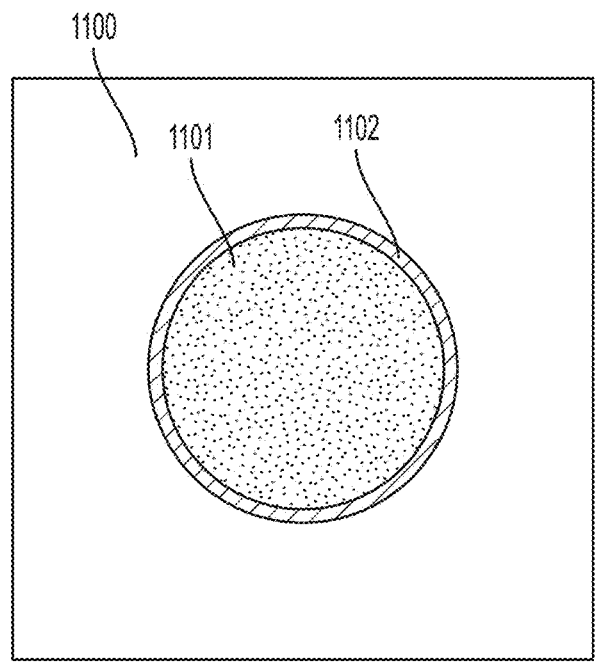
Figure 56C:
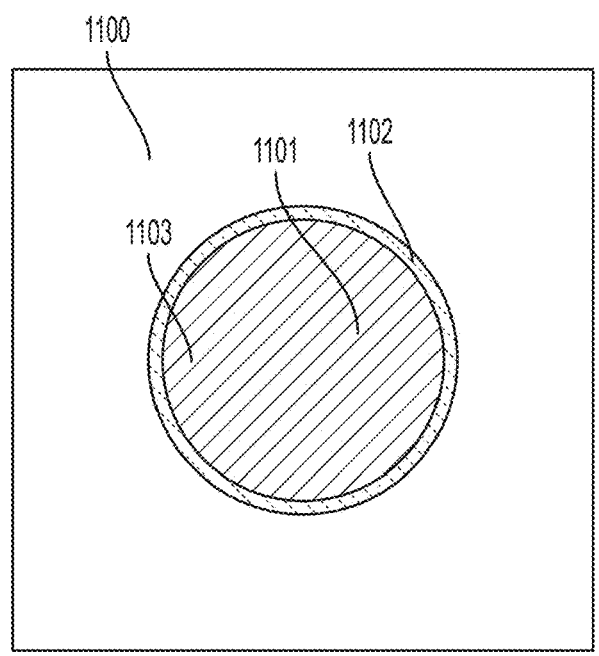
Figure 56D:
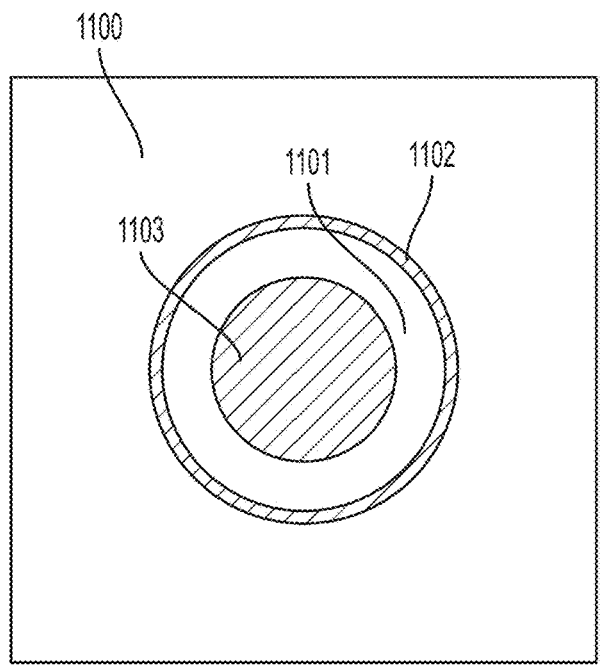
Figure 56E:
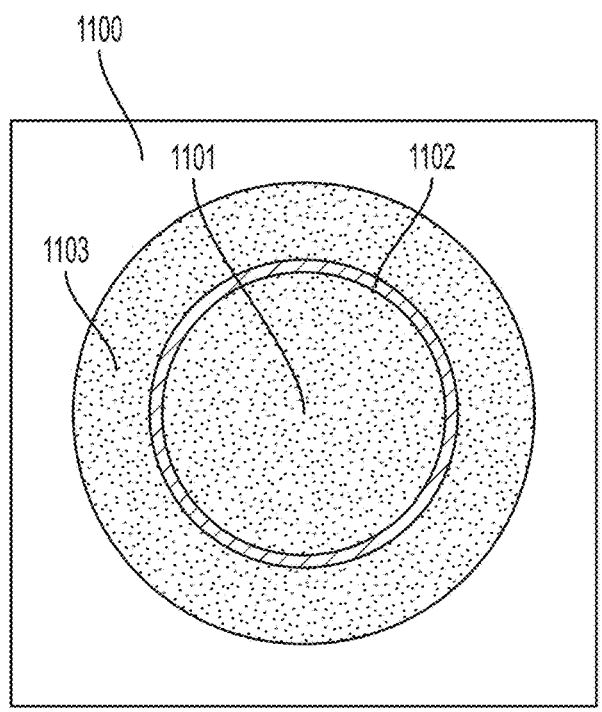

In some embodiments, the flow sensor system may report trends of ventilation volume and rate over time, which can provide signs of increasing difficulty of breathing for the patient or how the patient is responding to treatment. For instance, such trends may assist in determining whether the provided treatment is working. If, prior to treatment, the patient is experiencing rapid and shallow breathing, but after treatment the metrics have improved to normal ranges, then it may be determined that the treatment is working within desired parameters. If the trends remain unchanged, then this may indicate that either another dose needs to be given to the patient or a different treatment should be provided. FIGS. 54 and 55 depict graphs that show examples of the ventilation volume over time and the ventilation rate over time, respectively. These values may be reported as averages over pre-set time intervals (e.g., 30 seconds, 1 minute, 2 minutes, etc.).

In another embodiment of an interface display for use with flow sensor systems described herein, an interactive tool may be used to aid in users attempts to administer the proper volume of air to a patient at the proper times and at the proper pressures. The interactive tool may involve a simple graphical symbol, icon or other visual indicia, provided as a ventilation performance indicator, which varies over time in a manner that encourages the user to perform manual ventilations within preferred parameters. In this example, by responding to the changing symbol, the user may be able to perform high quality therapy (e.g., manual ventilations) without having to know specific numbers or protocols.

In certain embodiments, as shown in FIGS. 56(*a*)-(*e*), the graphic 1100 used for helping to indicate the quality of ventilations may include a simple filled circle or any other suitable shape (e.g., square, polygon, ellipse, etc.) with a solid colored core region 1101 and a perimeter 1102 of contrasting color that is easily seen. The perimeter 1102 of the circle (or other shape) may provide a boundary that the user may reference in administering manual ventilations to the patient. For example, as the user administers a ventilation breath, which adds volume to the patient's lungs, the inner core region 1101 of the circle may begin to fill up, and the boundary 1102 may provide a visual indication of the preferred ventilation volume to the patient. In this regard, exceeding the boundary limit may be an indication to the user that the patient is being overventilated.

As an example, when the interactive program for ventilation starts, the ventilation performance indicator 1100 may be provided as a circle (or other intuitive shape) that is filled according with a certain color, indicating that the patient is not yet in need of ventilations. FIG. 56(*a*) shows an example of the interactive tool in a rest state, where the administration of ventilations is not yet recommended. In some cases, when it is determined that the user should receive ventilations, the ventilation performance indicator 1100 may provide a visual communication of that determination to the user. For instance, immediately before the user is supposed to start applying air to the patient (bagging), the filled core 1101 of the circle may change colors, as shown in FIG. 56(*b*), or may flash with a contrasting color, alerting the user that they should apply bagging therapy. Other indications that the user should ventilate may be provided, for example, the graphic may optionally provide flashing or steady text (e.g., "ventilate") inside or outside the circle.

Upon the start of ventilation, as shown in FIG. 56(*c*), the entire core 1101 of the circle (or other shape) is filled with an interactive ("living") object 1103 having a third contrasting color that may immediately begin to shrink in size. FIG. 56(*d*) depicts an example of the interactively shrinking object 1103, which had previously filled the inner core 1101 of the circular outer boundary 1102. Depending on the recommended rate and volume of flow, this interactive object 1103 may shrink at a rate that is intended to simulate the depletion of oxygen from the lungs. When an appropriate amount of air is provided to the patient, the interactive object 1103 then increases in size (e.g., radius); in this example, upon the application of each manual bagging, the radius of the interactive object increases toward the outer boundary 1102 of the graphic.

Such an interactive tool provides an indication of ventilation quality by effectively encouraging the person administering manual ventilations to compensate for the shrinkage of the interactive object by squeezing or otherwise manipulating the bag in attempting to make the interactive object substantially match the shape of the outer boundary. Hence, in this example of a circular ventilation performance indicator, the objective of the user is to keep the circle full. The manner in which the size of the interactive object 1103 changes (e.g., decreasing due to oxygen depletion and increasing due to manual bagging) may be controlled by an algorithm that simulates gas exchange (e.g., oxygen and/or CO2 exchange) and flow rate/volume. Thus, when oxygen is removed from the lungs and replaced with CO2, the interactive object 1103 may shrink in size, and when fresh air is provided to the lungs, the size of the interactive object may increase.

When the size of the interactive object 1103 increases so as to exceed the outer boundary 1102 of the graphic, it may be determined that overventilation may be occurring. FIG. 56(*e*) depicts an example where the graphic 1100 indicates the bagger to be overventilating, for example, the size of the interactive object 1103 overflows past the outer boundary 1102. In some cases, if overventilation is detected, the color of the interactive object 1103 and/or a substantial portion of the entire graphical simulation 1100 may change, for example, to red or yellow, denoting to the user that ventilation flows are beyond specified parameters.

When manual ventilations are finished, the ventilation performance indicator 1100 may return back to the rest state, for example, as shown in FIG. 56(*a*). When ventilations are to be administered again (e.g., as indicated by a countdown/count up timer and/or chest compression counter), the ventilation performance indicator 1100 may then activate so as to provide appropriate guidance to the user. This interactive tool may be provided to the user as a simple game that assists the user to deliver appropriate quantities of air according to recommended times and rates. In certain embodiments, the objective of the game may be to "keep the circle full." While the user is presented with this simple task, in the background, the system performs calculations and adjustments to correlate the behavior of the ventilation performance indicator, including the interactive object, with the rate volume of air to be therapeutically administered to the patient, at appropriate timing intervals.

Although a flow sensor system has been described in detail for the purpose of illustration based on what is currently considered to be the most practical examples, it is to be understood that such detail is solely for that purpose and that the subject matter of this disclosure is not limited to the disclosed examples, but, on the contrary, is intended to cover modifications and equivalent arrangements. For example, it is to be understood that this disclosure contemplates that, to the extent possible, one or more features of any example can be combined with one or more features of any other example.

As used herein, the singular form of "a", "an", and "the" include plural referents unless the context clearly dictates otherwise.

As used herein, the terms "right", "left", "top", "bottom", and derivatives thereof shall relate to the subject matter of this disclosure as it is oriented in the drawing figures. However, it is to be understood that the subject matter of this disclosure can assume various alternative orientations and, accordingly, such terms are not to be considered as limiting. Also, it is to be understood that the subject matter of this disclosure can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

The invention claimed is:

1. A ventilation assembly for assisting resuscitative treatment of a patient comprising delivery of manual ventilations to the patient by at least one rescuer, the ventilation assembly comprising:
   a monitor device comprising a display interface; and
   a flow sensor in communication with the monitor device and configured to generate a measurement signal corresponding to at least one flow parameter of a first ventilation breath of the manual ventilations delivered to the patient,
   wherein the monitor device is configured to receive the measurement signal generated by the flow sensor and display ventilation feedback on the display interface for guiding the at least one rescuer in performing the manual ventilations to the patient, and
   wherein the ventilation feedback comprises a ventilation performance indicator comprising a shape that fills as the ventilation breath of the manual ventilations is delivered to the patient, and the ventilation feedback further comprising a countdown timer provided in anticipation of a second ventilation breath, which is configured to count down an interval time until the second ventilation breath of the manual ventilations should be delivered to the patient.

2. The ventilation assembly according to claim 1, wherein at least a portion of the ventilation performance indicator is configured to change color when the monitor device determines that the ventilation breath of the manual ventilations should be delivered.

3. The ventilation assembly according to claim 2, wherein at least a portion of the ventilation performance indicator is configured to flash when the monitor device determines that the second ventilation breath of the manual ventilations should be delivered.

4. The ventilation assembly according to claim 1, wherein the ventilation performance indicator comprises a boundary and an inner core region.

5. The ventilation assembly according to claim 4, wherein the boundary and the inner core region are of contrasting colors when the monitor device determines that the second ventilation breath should be delivered.

6. The ventilation assembly according to claim 1, wherein the ventilation performance indicator is configured to fill with a first color when the monitor device determines that ventilation flow is within a pre-specified target range.

7. The ventilation assembly according to claim 6, wherein the ventilation performance indicator is configured to fill with a second color different from the first color when the monitor device determines that ventilation flow is outside the pre-specified target range.

8. The ventilation assembly according to claim 1, wherein the ventilation performance indicator is configured to change color when the monitor device determines that no second ventilation breath has been delivered within the interval time until the second ventilation breath should be delivered to the patient as required by a predetermined manual ventilation protocol.

9. The ventilation assembly according to claim 1, wherein the ventilation feedback further comprises a numerical ventilation volume indicator displaying a numerical value of a ventilation volume delivered to the patient.

10. The ventilation assembly according to claim 9, wherein the numerical ventilation volume indicator is displayed in a first color when the monitor device determines that the ventilation volume is within a pre-specified target range.

11. The ventilation assembly according to claim 10, wherein the numerical ventilation volume indicator turns a second color different from the first color when the monitor device determines that the ventilation volume is outside the pre-specified target range.

12. The ventilation assembly according to claim 1, wherein the ventilation feedback further comprises a numerical ventilation rate indicator displaying a numerical value of a ventilation rate at which ventilation breaths of the manual ventilations are delivered to the patient.

13. The ventilation assembly according to claim 12, wherein the numerical ventilation rate indicator is displayed in a first color when the monitor device determines that the ventilation rate is within a pre-specified target range.

14. The ventilation assembly according to claim 13, wherein the numerical ventilation rate indicator turns a second color different from the first color when the monitor device determines that the ventilation rate is outside the pre-specified target range.

15. The ventilation assembly according to claim 1, wherein the ventilation performance indicator comprises an interactive object configured to shrink at a rate simulating depletion of oxygen from the patient's lungs, which is determined according to an algorithm that simulates gas exchange based on flow rate and/or flow volume sensed by the flow sensor.

16. The ventilation assembly according to claim 1, wherein the display interface further comprises a CPR dashboard.

17. The ventilation assembly according to claim 1, wherein the flow sensor comprises:
   a flow conduit configured to be placed in a patient airway and having a lumen that accommodates gas flow between a first region and a second region;
   a flow restrictor disposed within the lumen of the flow conduit between the first region and the second region; and
   at least one pressure sensor configured to measure gas pressure of at least one of the first region and the second region of the flow conduit.

18. The ventilation assembly according to claim 17, wherein a sensitive region of the flow sensor exhibits a greater level of hydrophobicity than a neighboring region adjacent to the sensitive region.

19. The ventilation assembly according to claim 1, further comprising a manual ventilation bag and patient mask for delivering the ventilation breath of the manual ventilations to the patient, wherein the flow sensor is positioned between the manual ventilation bag and the patient mask for sensing gas expelled from the manual ventilation bag towards the patient.

20. The ventilation assembly according to claim 1, wherein the ventilation performance indicator comprises the countdown timer.

21. The ventilation assembly according to claim 1, wherein the countdown timer is configured to count down a time between completion of the first ventilation breath and when the second ventilation breath of the manual ventilations should be delivered to the patient.

22. The ventilation assembly according to claim 1, wherein the shape of the ventilation performance indicator is configured to flash when the monitor device determines that no ventilation breath was delivered within the interval time as required by the predetermined manual ventilation protocol.

* * * * *